(12) United States Patent
Schreiter et al.

(10) Patent No.: US 11,598,792 B2
(45) Date of Patent: Mar. 7, 2023

(54) VOLTAGE INDICATORS

(71) Applicant: HOWARD HUGHES MEDICAL INSTITUTE, Chevy Chase, MD (US)

(72) Inventors: Eric R. Schreiter, Ashburn, VA (US); Ahmed Abdelfattah, Ashburn, VA (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 310 days.

(21) Appl. No.: 16/872,188

(22) Filed: May 11, 2020

(65) Prior Publication Data
US 2020/0363455 A1 Nov. 19, 2020

Related U.S. Application Data

(60) Provisional application No. 62/845,643, filed on May 9, 2019.

(51) Int. Cl.
*G01R 15/22* (2006.01)
*G01R 19/00* (2006.01)
*C07K 14/435* (2006.01)
*G01N 21/64* (2006.01)

(52) U.S. Cl.
CPC ......... *G01R 15/22* (2013.01); *G01R 19/0084* (2013.01); *C07K 14/43504* (2013.01); *C07K 2319/60* (2013.01); *G01N 21/6486* (2013.01)

(58) Field of Classification Search
CPC .............. C07K 2319/60; C07K 14/195; C07K 14/43504; C07K 2319/03; C07K 2319/33; C07K 2319/61; G01N 21/6486; G01R 15/22; G01R 19/0084; C12Y 308/01015
See application file for complete search history.

(56) References Cited

U.S. PATENT DOCUMENTS

| | | | |
|---|---|---|---|
| 9,933,417 B2 | 4/2018 | Lavis et al. | |
| 10,018,624 B1 | 7/2018 | Lavis et al. | |
| 10,161,932 B2 | 12/2018 | Lavis et al. | |
| 10,495,632 B2 | 12/2019 | Lavis et al. | |
| 2014/0324138 A1* | 10/2014 | Wentz | A61N 5/0622 607/90 |
| 2015/0369740 A1* | 12/2015 | Cohen | C07K 14/705 536/23.5 |
| 2020/0025769 A1* | 1/2020 | Schreiter | C07K 14/405 |
| 2020/0123218 A1 | 4/2020 | Cohen et al. | |

OTHER PUBLICATIONS

Bedbrook et al. Chem. Biol. (2015) 22: 1108-1121 (Year: 2015).*
Abdelfattah, A.S., et al. "A general approach to engineer positive-going eFRET voltage indicators," bioRxiv; doi: https://doi.org/10.1101/690925, printed Jul. 3, 2019.
Abdelfattah, A.S., et al. "A general approach to engineer positive-going eFRET voltage indicators," Nature Communications, (2020) 11:3444, https://doi.org/10.1038/S41467-020-17322-1.
Grimm, J., et al. "A general method to fine-tune fluorophores for live-cell and in vivo imaging," Nat Methods 14, 987-994 (2017). https://doi.org/10.1038/nmeth.4403.
Xu, Y., et al. "Voltage imaging with genetically encoded indicators," Science Direct, Current Opinion in Chemical Biology, (2017) vol. 39, pp. 1-10, ISSN 1367-5931, https://doi.org/10.1016/j.cbpa.2017.04.005.
Grimm, J., et al. "A general method to improve fluorophores for live-cell and single-molecule microscopy," Nat. Methods 12, 244-250 (2015). https://doi.org/10.1038/nmeth.3256.
Abdelfattah, A.S., et al. "Bright and photostable chemigenetic indicators for extended in vivo voltage imaging," bioRxiv 436840; doi: https://doi.org/10.1101/436840, printed Oct. 6, 2018.

* cited by examiner

*Primary Examiner* — Susan M Hanley
(74) *Attorney, Agent, or Firm* — Stites & Harbison, PLLC; Mandy Wilson Decker

(57) ABSTRACT

A voltage indicator includes a polypeptide sequence comprising a voltage-sensitive opsin domain and a capture protein domain arranged and disposed to capture a fluorescent dye ligand. When the fluorescent dye ligand is captured and the voltage indicator is bound to a cell membrane, an increase in voltage across the cell membrane causes an increase in fluorescent emission.

18 Claims, 58 Drawing Sheets

Specification includes a Sequence Listing.

FIG. 4

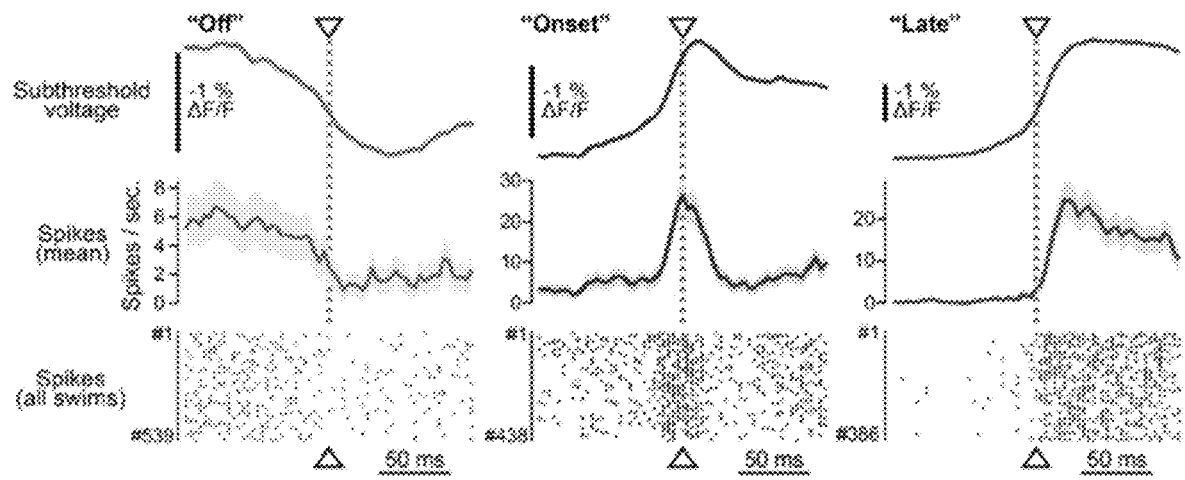
FIG. 8D
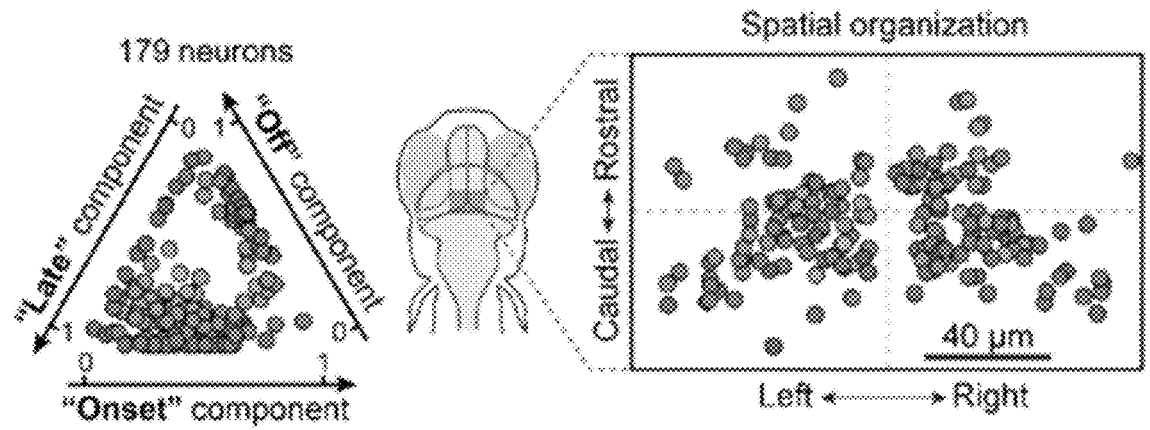
FIG. 8E
FIG. 8F
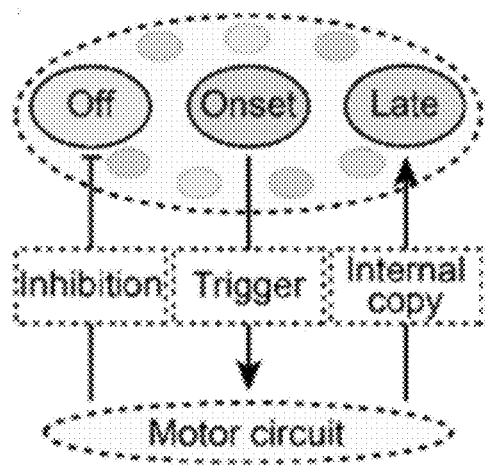
FIG. 8G

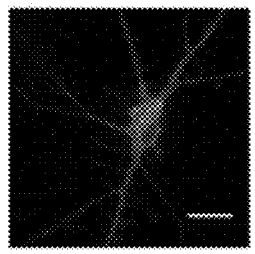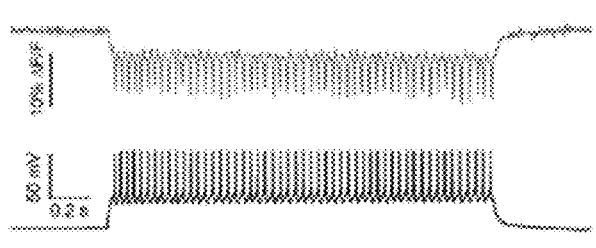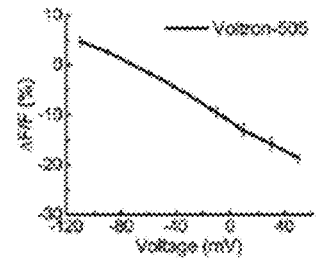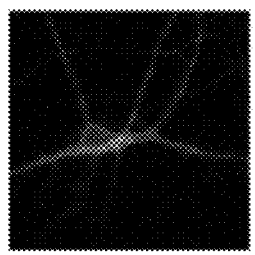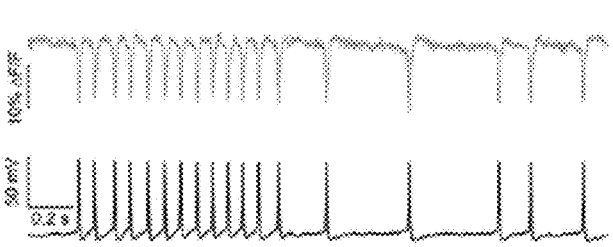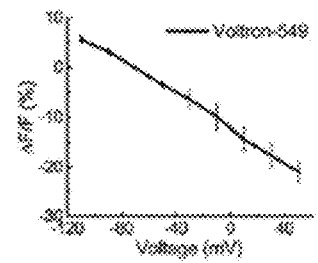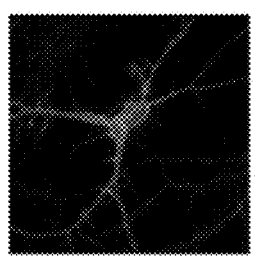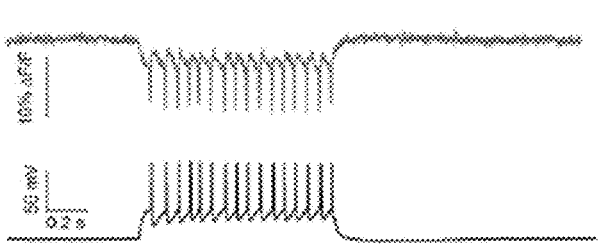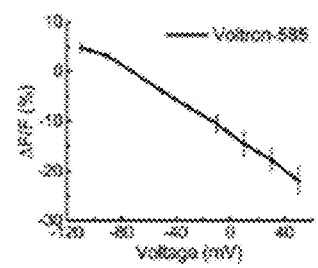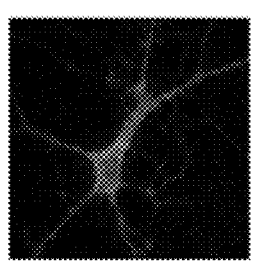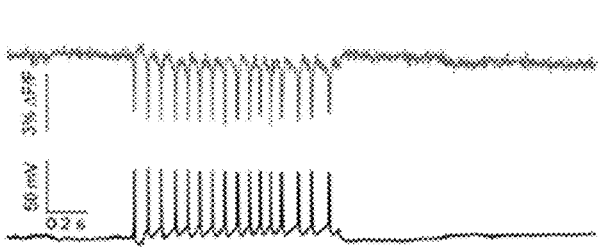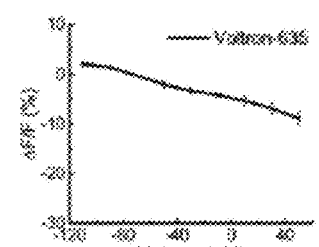
FIG. 13A  FIG. 13B  FIG. 13C

VOLTAGE INDICATORS

RELATED APPLICATIONS

This application claims priority from U.S. Provisional Application Ser. No. 62/845,643 filed May 9, 2019, the entire disclosure of which is incorporated herein by this reference.

TECHNICAL FIELD

The presently-disclosed subject matter generally relates to voltage indicators and methods of use thereof. More specifically, the presently-disclosed subject matter relates to chemigenetic voltage indicators and methods of measuring voltage using chemigenetic voltage.

INTRODUCTION

Imaging changes in membrane potential using genetically encoded fluorescent voltage indicators (GEVIs) has great potential for monitoring neuronal activity with high spatial and temporal resolution.

Animal behavior is produced by patterns of neuronal activity that span a wide range of spatial and temporal scales. To understand how neural circuits mediate behavior thus requires high-speed recording from ensembles of neurons for long periods of time. Although the activity of large numbers of neurons can now be routinely recorded using genetically encoded calcium indicators (GECIs) (1), the slow kinetics of calcium signals complicate the measurement of action potentials, and sub-threshold voltage signals are missed entirely (1-3).

Voltage imaging using genetically encoded voltage indicators (GEVIs) can overcome these challenges, enabling imaging of fast spikes and subthreshold dynamics in genetically defined neurons (4, 5). The high imaging speed and excitation intensity required for voltage imaging, combined with the smaller volume of the cellular membrane, place increased demands on voltage indicators relative to GECIs.

Extant GEVIs rely on fluorescence from either microbial rhodopsins (6-8, 19) or fluorescent proteins (FPs) (9-13). These fluorophores lack the brightness and photostability to allow in vivo voltage imaging from large fields of view over timescales of many behavioral events, precluding the millisecond-timescale interrogation of neural circuits. Although the intrinsic fluorescence from rhodopsin domains is low, making them difficult to image, it has been possible to attach bright fluorophores, such as fluorescent proteins or rhodamine dyes, to rhodopsin domains to facilitate imaging (10, 11, 18).

These indicators function via electrochromic fluorescence resonance energy transfer (eFRET), and fluorescence from the bright fluorophore is decreased as the absorbance of the rhodopsin is increased. This results in a decrease in fluorescence with increasing membrane potential, and voltage signals, such as action potentials in neurons, take on a downward-going shape.

Upward-going fluorescence signals can be advantageous in microscopic imaging because, for example, background fluorescence from non-responsive regions is low and signals stand out above the background, increasing signal-to-noise, and, for another example, the fluorophore spends more time in the low-fluorescence state, which can decrease photobleaching.

Accordingly, there is a need in the art for improved voltage indicators that allow for the benefits associated with upward-going fluorescence signals.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

As disclosed herein, a unique electrochromic fluorescence resonance energy transfer (eFRET) genetically encoded voltage indicator (GEVIs) was engineered, which uses bright and photostable synthetic dyes instead of protein-based fluorophores, extending the combined duration of imaging and number of neurons imaged simultaneously by more than tenfold relative to existing GEVIs.

Recent development of improved rhodamine dyes such as the Janelia Fluor® (JF) dyes enable their use in complex biological experiments due to their high brightness and photostability (14), compatibility with self-labeling protein tags (15, 16), and the ability to traverse the blood-brain barrier for in vivo delivery (17).

Described herein is a 'chemigenetic' GEVI scaffold, referred to herein as "Voltron," which incorporates such synthetic fluorophore dyes. Voltron provides an increased photon yield that enables in vivo imaging of neuronal spiking and sub-threshold voltage signals in model organisms with order-of-magnitude improvement in the number of neurons imaged simultaneously over substantially longer durations.

Furthermore, through mutagenesis, an inversion of the direction of fluorescence change in rhodopsin eFRET GEVIs to an "upward-going" fluorescence signal was achieved, such that an increase in membrane potential lead to an increase in fluorescence.

The presently-disclosed subject matter includes a voltage indicator including a polypeptide sequence comprising a voltage-sensitive opsin domain including one, two, three, or four amino acid mutations relative to a wild type polypeptide sequence, and a capture protein domain arranged and disposed to capture a fluorescent dye ligand. When the fluorescent dye ligand is captured and the voltage indicator is bound to a cell membrane, an increase in voltage across the cell membrane causes an increase in fluorescent emission. In some embodiments, the response time between the increase in voltage and the increase in fluorescent emission is less than about a millisecond.

In some embodiments of the voltage indicator, the voltage-sensitive opsin domain is a microbial opsin domain. In some embodiments, the voltage-sensitive opsin domain is a microbial rhodopsin domain. In some embodiments, the microbial rhodopsin domain is selected from the group consisting of QuarsAr1, QuarsAr2, Ace2N, and combinations thereof.

In some embodiments, the voltage-sensitive opsin domain is Ace2N including an amino acid mutation at one or more of residue 81, 92, and 199.

In some embodiments, the voltage-sensitive opsin domain comprises the polypeptide of SEQ ID NO: 9, 15, 16, or 17, having one, two, three, or four amino acid mutations.

In some embodiments, the voltage-sensitive opsin domain comprises the amino acid sequence of SEQ ID NO: 9 having an amino acid mutation at one or more of residue 81, 92, and 199.

In some embodiments, the voltage indicator comprises an amino acid sequence selected from the group of amino acid sequences of SEQ ID NOS: 2, 4, 6, 8, 20, 22, 24, and 26.

In some embodiments, the voltage indicator comprises an amino acid sequence encoded by a nucleotide sequence selected from the group of nucleotide sequences of SEQ ID NOS: 1, 3, 5, 7, 19, 21, 23, and 25.

In some embodiments of the voltage indicator, the capture protein is a non-covalent capture protein. In some embodiments, the non-covalent capture protein is selected from the group consisting of TMP-tag®, biotin-avidin, and a combination thereof. In some embodiments, the capture protein domain is a self-labeling protein tag. In some embodiments, the capture protein domain is selected from a HaloTag® and a SNAP-Tag®. In some embodiments, the capture protein is a covalent capture protein selected from the group consisting of HaloTag®, SNAP-tag®, TMP-tag®,βLac-tag, CLIP-tag®, or a combination thereof. In some embodiments, the capture protein domain comprises an amino acid sequence selected from the amino acid sequence of SEQ ID NOS: 10 and 11. In some embodiments, 1, 2, 3, 4, 5, 6, 7, 8, 9, or 10 amino acids are removed from the junction between the opsin domain and the capture protein.

In some embodiments, the voltage indicator also includes a targeting sequence. In some embodiments, the targeting sequence is a soma targeting sequence. In some embodiments, the targeting sequence comprises the amino acid sequence of SEQ ID NO: 12. In some embodiments, the voltage-sensitive domain and the capture protein are provided as a fusion protein. In some embodiments, the capture protein is positioned at the c-terminal end of the voltage-sensitive domain.

In some embodiments of the voltage indicator, the fluorescent dye ligand is an azetidine-containing dye. For example, the fluorescent dye ligand can be a Janelia Fluor™ dye, such as, for example, Janelia Fluor™$_{505}$, Janelia Fluor™$_{525}$, Janelia Fluor™$_{549}$, Janelia Fluor™$_{585}$, Janelia Fluor™$_{646}$, and combinations thereof. In some embodiments, the fluorescent dye ligand is a fluorescent protein. For example, the fluorescent dye ligand can be a florescent protein such as sfGFP or mNeonGreen.

When the fluorescent dye ligand is captured by the capture protein domain, and when the voltage indicator is bound to a cell membrane, an increase in voltage across the cell membrane causes an increase in fluorescent emission from the fluorescent dye ligand. The cell membrane can be, for example, a cell membrane of a neuron. When there is an increase in voltage, in some embodiments, the increase in voltage includes a spike in voltage and a subthreshold voltage signal. In some embodiments, the response time between the increase in voltage and the increase in fluorescent emission is less than about a millisecond. In some embodiments the response time between the increase in voltage and the increase in fluorescent emission is less than about a millisecond.

The presently-disclosed subject matter includes a method of measuring voltage, which involves administering or contacting the voltage indicator as described herein and determining changes in fluorescence of the fluorescent dye ligand. In this regard, the indicator can be contacted with a cell, such as, for example, a neuron. When the fluorescent dye ligand is captured by the capture protein domain, and when the voltage indicator is bound to a cell membrane, an increase in voltage across the cell membrane causes an increase in fluorescent emission from the fluorescent dye ligand. In some embodiments, the increase in voltage is a spike in voltage or a subthreshold voltage signal. In some embodiments, the response time between the increase in voltage and the increase in fluorescent emission is less than about a millisecond. In some embodiments, the response time between the increase in voltage and the increase in fluorescent emission is less than about a millisecond. In some embodiments of the method, the changes in fluorescence are observed with a microscope.

In some embodiments, the voltage indicator further comprises a linker between the voltage-sensitive domain and the capture protein domain, and the method further involves modifying a length of the linker. In some embodiments, modifying the length of the linker includes removing at least one amino acid residue. In some embodiments, between 1 and 22 amino acid residues are removed. In some embodiments, modifying the length of the linker modifies the size of a fluorescence response. In some embodiments, the method also includes determining changes in voltage based upon changes in fluorescence. In some embodiments, an increase in membrane potential leads to an increase in fluorescence.

BRIEF DESCRIPTION OF THE SEQUENCE LISTING

SEQ ID NO: 1 is the nucleotide sequence encoding an exemplary voltage indicator according to the presently-disclosed subject matter.

SEQ ID NO: 2 is the polypeptide sequence an exemplary voltage indicator according to the presently-disclosed subject matter.

SEQ ID NO: 3 is the nucleotide sequence encoding an exemplary voltage indicator according to the presently-disclosed subject matter.

SEQ ID NO: 4 is the polypeptide sequence of an exemplary voltage indicator according to the presently-disclosed subject matter.

SEQ ID NO: 5 is the nucleotide sequence encoding an exemplary voltage indicator according to the presently-disclosed subject matter.

SEQ ID NO: 6 is the polypeptide sequence of an exemplary voltage indicator according to the presently-disclosed subject matter.

SEQ ID NO: 7 is the nucleotide sequence encoding an exemplary voltage indicator according to the presently-disclosed subject matter.

SEQ ID NO: 8 is the polypeptide sequence of an exemplary voltage indicator according to the presently-disclosed subject matter.

SEQ ID NO: 9 is the polypeptide sequence of an exemplary voltage-sensitive domain according to the presently-disclosed subject matter.

SEQ ID NO: 10 is the polypeptide sequence of an exemplary capture protein domain according to the presently-disclosed subject matter.

SEQ ID NO: 11 is the polypeptide sequence of an exemplary capture protein domain according to the presently-disclosed subject matter.

SEQ ID NO: 12 is the polypeptide sequence of an exemplary targeting sequence according to the presently-disclosed subject matter.

SEQ ID NO: 13 is the polypeptide sequence of an exemplary targeting sequence according to the presently-disclosed subject matter.

SEQ ID NO: 14 is the polypeptide sequence of an exemplary targeting sequence according to the presently-disclosed subject matter.

SEQ ID NO: 15 is the polypeptide sequence of an exemplary voltage-sensitive domain according to the presently-disclosed subject matter.

SEQ ID NO: 16 is the polypeptide sequence of an exemplary voltage-sensitive domain according to the presently-disclosed subject matter.

SEQ ID NO: 17 is the polypeptide sequence of an exemplary voltage-sensitive domain according to the presently-disclosed subject matter.

SEQ ID NO: 18 is the polypeptide sequence of an exemplary capture protein domain according to the presently-disclosed subject matter.

SEQ ID NO: 19 is the nucleotide sequence as set forth in FIG. 4.

SEQ ID NO: 20 is the polypeptide sequence as set forth in FIG. 4.

SEQ ID NO: 21 is the nucleotide sequence as set forth in FIG. 10.

SEQ ID NO: 22 is the polypeptide sequence as set forth in FIG. 10.

SEQ ID NO: 23 is the nucleotide sequence as set forth in FIG. 11.

SEQ ID NO: 24 is the polypeptide sequence as set forth in FIG. 11.

SEQ ID NO: 25 is the first nucleotide sequence as set forth in FIG. 12.

SEQ ID NO: 26 is the first polypeptide sequence as set forth in FIG. 12.

SEQ ID NO: 27 is the second nucleotide sequence as set forth in FIG. 12.

SEQ ID NO: 28 is the second polypeptide sequence as set forth in FIG. 12.

SEQ ID NO: 29 is the third nucleotide sequence as set forth in FIG. 12.

SEQ ID NO: 30 is the third polypeptide sequence as set forth in FIG. 12.

SEQ ID NO: 31 is the fourth nucleotide sequence as set forth in FIG. 12.

SEQ ID NO: 32 is the fourth polypeptide sequence as set forth in FIG. 12.

SEQ ID NO: 33 is the fifth nucleotide sequence as set forth in FIG. 12.

SEQ ID NO: 34 is the fifth polypeptide sequence as set forth in FIG. 12.

SEQ ID NO: 35 is the sixth nucleotide sequence as set forth in FIG. 12.

SEQ ID NO: 36 is the sixth polypeptide sequence as set forth in FIG. 12.

SEQ ID NO: 37 is the seventh nucleotide sequence as set forth in FIG. 12.

SEQ ID NO: 38 is the seventh polypeptide sequence as set forth in FIG. 12.

SEQ ID NO: 39 is the eighth nucleotide sequence as set forth in FIG. 12.

SEQ ID NO: 40 is the eighth polypeptide sequence as set forth in FIG. 12

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 4 includes a nucleotide sequence (SEQ ID NO: 19) and amino acid sequence (SEQ ID NO: 20) of "Voltron," an exemplary rhodopsin electrochromic fluorescence resonance energy transfer (eFRET) genetically encoded voltage indicators (GEVIs), with sequence features annotated. To localize the indicator to the neuron soma, a targeting sequence from Kv2.1 was added to the C-terminus of the sequence.

FIG. 5A: Schematic of Voltron sequence: A rhodopsin (Ace2) is fused to a self-labeling tag domain (HaloTag) with additional sequences added to improve or localize membrane targeting: endoplasmic reticulum export sequence (ER), Golgi export trafficking sequence (TS), and somatic targeting sequence (ST). FIG. 5B: Model of Voltron mechanism. The HaloTag domain of the transmembrane Voltron protein (grey cylinders) covalently binds a small molecule fluorophore such as JF525 (green glow) with an appended HaloTag ligand. Membrane depolarization reversibly decreases JF525 fluorescence via increased FRET to the rhodopsin domain. FIG. 5C: Left panel: cultured rat hippocampal neuron expressing Voltron and labeled with JF525. Scale bar: 20 µm. Right panel: single-trial recording of action potentials and sub-threshold voltage signals from current injections in primary neuron culture using imaging (top, fluorescence) or electrophysiology (bottom, membrane potential). FIG. 5D: Fluorescence emission spectra of different JF dyes overlaid with the absorbance spectrum of Ace2N. FIG. 5E: Fluorescence change as a function of membrane voltage with different JF dye-Voltron conjugates. FIG. 5F: Relative fluorescence of ASAP2f, Ace2N-mNeon, Voltron$_{525}$ and Voltron$_{549}$ in cultured neurons (n=70, 68, 48 and 62 measurements from five independent transfections for each construct). Illumination intensity ~10 mW/mm$^2$ at imaging plane. *$P<0.001$, one-way analysis of variance (ANOVA) followed by Bonferroni's test on each pair. Fluorescence was normalized to ASAP2f mean intensity. FIG. 5G: Relative single molecule brightness of Ace2N-mNeon and Voltron$_{549}$. *$P<0.001$, two-tailed Student's t-test. FIG. 5H: Bleaching curves for ASAP2f, Ace2N-mNeon, Voltron$_{525}$, and Voltron$_{549}$ in primary neuron culture. Illumination intensity ~23 mW/mm$^2$ at imaging plane. Bleaching curves were normalized to mean cellular fluorescence from FIG. 5F or normalized to the zero-time value (inset). FIG. 5I: Mean time to bleach of Ace2N-mNeon and Voltron$_{549}$ during single-molecule imaging, 100 ms frames. ***$P<0.001$, two-tailed Student's t-test. FIGS. 5J and 5K: Simultaneous in vivo Voltron imaging and electrophysiology in larval zebrafish (extracellular) and adult *Drosophila* (whole cell), respectively.

and visual cortex pyramidal neurons (FIGS. 6A-6L) of mice using Voltron. (FIGS. 6C-6E) Voltron$_{525}$ raw $\Delta F/F_0$ traces showing spontaneous spikes of a PV neuron (FIG. 6B) located at a depth of 60 μm in hippocampal CA1 region imaged at 3858 frames per second. Boxes indicate intervals shown at expanded time scales. Scalebar: 20 μm. (FIG. 6F) Overlay of 177 spikes detected during a 15 s period (gray) and their average (black). (FIG. 6G) Spike shape of 11 PV neurons. (FIG. 6H) Schematic of imaging of mouse primary visual cortex during display of drifting grating visual stimuli. (FIG. 6I) Example trace showing Voltron fluorescence during one trial of a sequence of visual stimuli. Arrows below represent the direction of movement of the drifting grating. (FIGS. 6J-6L) Top left, images of a pyramidal cell at a depth of 148 μm, imaged three times over a period of four weeks on the indicated weeks after virus injection. Scalebar: 10 μm. Top right, average of all spikes in session (black) and standard deviation (grey). Middle, raw $\Delta F/F_0$ trace for five repetitions in each session, showing two orthogonal orientations (indicated with arrows below) from the neuron pictured on the top left. Bottom, orientation tuning to full-frame drifting gratings of the neuron pictured on the top left, displayed from number of spikes during trials (blue), number of spikes during preceding inter-trial intervals (grey), and subthreshold $\Delta F/F_0$ (right y-axis) after low-pass filtering traces using a 10-point median filter. For each orientation, response is calculated by averaging the low-pass filtered trace between 100-400 ms after trial onset, and baseline is calculated by averaging the low pass filtered trace from 80 ms preceding trial onset to 20 ms after trial onset. Displayed as response minus baseline. Error bars represent standard error of the mean (s.e.m.) (20-22 repetitions per session).

(FIG. 7A) Schematic of the imaging setup. (FIG. 7B) Image of two neurons expressing ST-Voltron$_{525}$ in layer 1 of visual cortex of an NDNF-Cre mouse. Scalebar: 10 μm. (FIG. 7C) $\Delta F/F_0$ traces from neurons in FIG. 7B, recorded over 15 minutes. (FIG. 7D) Color-coded zooms of indicated regions of the traces in FIG. 7C with detected action potentials indicated by black dots above the fluorescence traces. (FIG. 7E) Average of all spikes in session (black) and standard deviation (grey). (FIG. 7F) Left panel: Fluorescence image of a cranial window over primary visual cortex (V1) in an NDNF-Cre mouse showing Cre-dependent expression of ST-Voltron$_{525}$ (bright spots). Scalebar: 1 mm. Right panel: zoomed image of FIG. 7F in the area indicated by the white rectangle, with neurons labels corresponding to fluorescence traces in FIG. 7G. Scalebar: 100 μm. (FIG. 7G) Left panel: $\Delta F/F_0$ traces during 3 min. recording from neurons pictured in FIG. 7F, in decreasing order of signal-to-noise ratio. Right panel: zooms of $\Delta F/F_0$ traces from color-coded regions of FIG. 7G with detected action potentials represented as black dots above, illustrating representative traces with high (top), medium (middle), and low (bottom) SNR. Traces have been background-subtracted, which removes shared subthreshold membrane potential fluctuations (Compare vs. FIG. 27 without subtraction).

FIGS. 8A-8G illustrate millisecond-timescale neural dynamics during swimming behavior in zebrafish. (FIG. 8A) Schematic illustration of the setup. An immobilized zebrafish is placed under the light-sheet microscope and the motor signals (inset) from its tail are recorded during the imaging session using a pair of electrodes. Visual stimuli (forward drifting gratings) for triggering swimming responses are presented below the fish. (FIG. 8B) Left panel: anatomical location of the imaged brain region (midbrain nucleus; see FIG. 42A). Center, a representative field of view of the imaged region expressing Voltron. Scale bar, 20 μm. Right, the position of neurons analyzed in FIG. 8C. (FIG. 8C) Left panel: periods of visual motion (pink) and swim signals (grey) are plotted above Voltron fluorescence traces (black) simultaneously recorded from 11 neurons shown in FIG. 8B. Right panel: zoom of swimming signals (top) and Voltron fluorescence traces from two representative neurons (bottom) are expanded from the dashed box in the left panel. Dots on the top of each trace represent spikes recognized by the algorithm described in FIG. 42B-C. Downward triangles and dotted gray lines indicate initiation of each swim bout. (FIG. 8D) Mean subthreshold signal (top), mean spiking frequency (middle) and spike raster plots (bottom) near the initiation of swim bouts from three representative neurons: "Off" (green), "Onset" (red) and "Late" (blue) neuron. Shadows in the top and middle panels represent s.e.m. across swim events. (FIG. 8E) Classification of recorded neurons by their mean subthreshold signals near the initiation of swim bouts. 179 neurons recorded from 43 fish were classified using non-negative matrix factorization and colored according to the weights for three factors: "onset" (red), "off" (green) and "late" (blue). The details of this classification are described in the Methods. (FIG. 8F) Spatial organization of the same population of neurons as in FIG. 8E. Neurons from multiple fish are superimposed to a single map based on the distance from the center of this midbrain nucleus. (FIG. 8G) Hypothetical model of neural activity modulation in this midbrain nucleus. "Onset" neurons send motor commands to downstream motor circuits to trigger swim bouts, while activity of "off" neurons is inhibited. "Late" neurons receive internal copy signals of ongoing swim bouts from the motor circuit.

(FIG. 9A) Bar graph shows number of residues truncated from 0-22 amino acids. (FIG. 9B) Chemical structure of $_{JF549}$. (FIG. 9C) Image of primary neuron cells expressing Voltron labeled with $_{JF549}$. Scale bar: 20 μm (FIG. 9D) Imaging of spontaneous activity in neuron culture with QuasAr2-HaloTag-16 labeled with JF$_{549}$.

FIG. 10 includes the nucleotide sequence (SEQ ID NO: 21) and amino acid sequence (SEQ ID NO: 22) of QuasAr2-HaloTag, with sequence features annotated.

FIG. 11 includes the nucleotide sequence (SEQ ID NO: 23) and amino acid sequence (SEQ ID NO: 24) of QuasAr2-SNAP-Tag, with sequence features annotated.

FIG. 13A-13C include (from top to bottom: JF505, JF549, JF585, JF635) FIG. 13A: images of neurons expressing Voltron and labeled with different JF-HaloTag dye conjugates, Scale bar: 20 μm; FIG. 13B: Single-trial recording of action potentials and subthreshold voltage signals from current injections. Raw fluorescence traces, colored by dye emission, are shown on the top of each panel. Membrane potential, recorded with a patch pipette, is shown at the bottom of each panel in black; and FIG. 13C: Voltron fluorescence change as a function of membrane voltage with different JF dye conjugates.

FIG. 21A: A schematic drawing showing the configuration of the experiment and the location of the images in the subsequent panels. FIG. 21B: A single plane of two-photon image of the patched cell expressing Voltron (yellow) in the background of scanned Dodt gradient contrast (grey). FIG. 21C: A widefield image showing the location of the region of interest used to extract Voltron signal in the following panels. FIG. 21D: Traces of Voltron fluorescence (above) and whole-cell recording (below). Spikes are indicated by asterisks. FIG. 21E: Traces of denoised Voltron fluorescence (above) and whole-cell recording (below). A small subthreshold event is indicated by an arrow.

FIG. 22A: Infrared image of fly brain overlaid with Voltron549 florescence in a dopamine neuron. Voltron expression was driven by a split-Gal4 driver (MB058B-Gal4) that labels a pair of PPL1-α'2/α2 dopamine neurons, one on each brain hemisphere. FIG. 22B: PPL1-α'2/α2 neurons receive dendritic input from the ipsilateral hemisphere, and send axonal output bilaterally to form patch-like innervations in both the ipsilateral (ipsi.) and contralateral (contra.) mushroom body lobes. Consequently, each projection zone in the mushroom body contains axonal terminals of both cells, although each cell body contributes more extensive arbor to the projection zone in the same hemisphere. FIG. 22C-22E: Voltron imaging in different neuronal compartments. Left, single-trial recordings of fluorescence traces and cell membrane potential from concurrent whole-cell recording. Circles mark action potential spikes detected in the Voltron traces. In dendrites, there was a perfect match between spikes detected from Voltron and from whole-cell recording. In axons, about half of spikes on the Voltron traces were contributed by the sister cell whose soma is in the opposite hemisphere. When these spikes were segregated (see methods), the remaining events aligned with whole-cell recording with marginal error (3 false positive from 447 Voltron spikes, 7 false negative from 451 whole-cell recording spikes). Note that Voltron traces from the soma could not be imaged while recording in whole-cell mode. Right, spike waveforms aligned to their peaks. For axon, both Voltron spike waveforms were from the ipsilateral traces. FIG. 22F: Signal-to-noise ratios (SNRs) in different neuronal compartments, calculated as Voltron spike peak amplitude over standard deviation of the spike-free zones of the trace.

FIG. 28A: Spike triggered averages calculated from traces shown in FIG. 27B. For each pair of neurons, estimated spike times of the first neuron (cell-pre, rows) were used to calculate the average membrane potential of the second neuron (cell-post, columns) in a window of 400 ms around the spike times. Diagonal line shown in red is the average spike shape of each neuron. FIG. 28B: Schematic to illustrate calculation of spike triggered average. FIG. 28C: Zoom-in of spike triggered average for cell 15 (pre) to cell 19 (post). Gray bar: standard deviation of shuffled spike triggered average. FIG. 28D: Estimated optical cross talk between a pair of neurons. For neurons very close to each other, there was apparent optical cross-talk between the neurons which makes the spike triggered average calculated in this way unreliable. Blue line: distance threshold based on which pairs of neurons were excluded in FIG. 28A. Excluded neuron pairs are shown as white squares in FIG. 28A.

FIG. 42A: Left, anatomical location of the midbrain nucleus imaged in this study. The image was taken from plane 81 of image stacks from Tg(eval3:H2B-RFP) (gray) and Tg(vglut2:GFP) (green) transgenic zebrafish in the Z-brain atlas (33). Right, a representative image of the same nucleus in a Tg(vglut2: Gal4); Tg(UAS:GFP) transgenic zebrafish. FIG. 42B: Flow chart of the data processing pipeline for the acquired data. FIG. 42C: An example of pixel weight optimization for a representative neuron. Traces from the initial pixel weights (middle) and the final pixel weights (bottom) of the same neurons are plotted on the right. FIG. 42D: Schematic of averaging procedure of neural activity at the onset of first bout of the swimming for each trial for the analysis in FIG. 42E. FIG. 42E: Average firing rates (top) and raster plots across trials (bottom) at the onset of the first bout for each trial plotted for 3 representative neurons on a long timescale (−3 seconds to 3 seconds). The example 'Off' neuron shows suppression of firing at the onset of swimming (following a brief increase in firing rate just before swimming). The 'Ramp' neuron shows a gradual increase in activity starting about 1.5 seconds before the onset of swimming, and a decay in activity after swim onset. 'Motor'-type neurons (subdivided into 'Onset' and 'Late' neurons in FIG. 8) show increased firing at the onset of swimming. Shadows represent standard error of the mean (s.e.m.) across multiple trials.

DESCRIPTION OF EXEMPLARY EMBODIMENTS

Figure 1A:
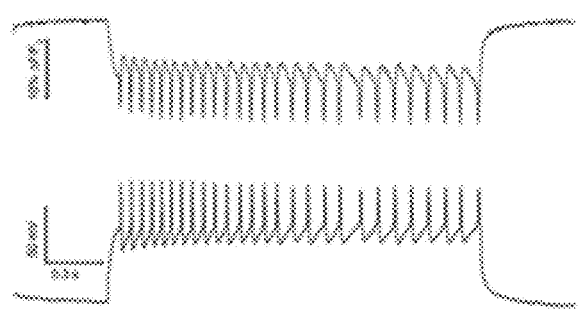
FIGS. 1A-1D includes fluorescence response (top) and membrane potential changes in neutrons (bottom) for GEVIs including Voltron (FIG. 1A), Voltron D92N (FIG. 1B), Voltron N81D D92N (FIG. 1C), and Voltron N81D D92N E199V (FIG. 1D).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes a genetically encoded voltage indicators (GEVI) with a direction of fluorescence change such that an increase in membrane potential leads to an increase in fluorescence.

The presently-disclosed subject matter includes voltage indicators and methods of measuring voltage. In some embodiments, the voltage indicators include membrane-localized voltage-sensitive protein and a capture protein engineered to capture a fluorescent dye ligand. These voltage indicators combine the brightness and photostability of robust fluorescent dyes with the targetability of proteins. In this regard, the voltage indicators of the presently-disclosed subject matter include amino acid sequences to improve/localize membrane targeting, such that membrane potential/membrane voltage can be assessed. When the voltage indicator is targeted to a cell membrane, an increase in voltage across the cell membrane causes an increase in fluorescent emission from a fluorescent dye ligand associated with the voltage indicator.

As described herein, the voltage indicators of the presently-disclosed subject matter are uniquely designed to provide a number of benefits that allow for a rapid increase in a robust fluorescent signal in response to spikes in voltage across the membrane. It is also notable that, for example in the case of a neuron, the voltage indicators provide for a rapid increase in a robust fluorescent signal in response to spikes, as well as in response to subthreshold voltage signals. Embodiments of the indicators have sub-millisecond response times between an increase in voltage and an increase in florescent emission. As will be appreciated by those of ordinary skill in the art, the ability to rapidly assess voltage increases with an increase in fluorescence is of particular utility, for example, to reduce noise and enhance sensitivity.

The presently-disclosed subject matter includes a voltage indicator, which comprises a voltage-sensitive protein including amino acid mutations, and a capture protein domain arranged and disposed to capture a fluorescent dye ligand. Beneficially, when the fluorescent dye ligand is captured by the capture protein domain, and when the voltage indicator is bound to a membrane, an increase in voltage across the membrane causes an increase in fluorescent emission from the fluorescent dye ligand. In some embodiments, the membrane is a membrane of a neuron. In this regard, the increase in voltage, whether a spike in voltage or a subthreshold voltage signal, results in an increase in fluorescent emission correlating to the voltage. In some embodiments, the response time between the increase in voltage and the increase in fluorescent emission is less than about a millisecond.

Suitable voltage sensitive proteins include, but are not limited to, one or more opsins, one or more other molecules including a voltage-sensing domain, or a combination thereof, and including amino acid mutations. For example, in some embodiments, the voltage-sensitive protein is a voltage-sensitive opsin domain. In some embodiments, the voltage-sensitive opsin domain is a microbial opsin domain. In some embodiments, the voltage-sensitive opsin domain is a microbial rhodopsin domain.

"Microbial rhodopsins" are a large class of proteins characterized by seven transmembrane domains and a retinilydene chromophore bound in the protein core to a lysine via a Schiff base. Over 5,000 microbial rhodopsins are known, and these proteins are found in all kingdoms of life. Microbial rhodopsins serve a variety of functions for their hosts: some are light-driven proton pumps (bacteriorhodopsin, proteorhodopsins), others are light-driven ion channels (channelrhodopsins), chloride pumps (halorhodopsins), or serve in a purely photosensory capacity (sensory rhodopsins). The retinilydene chromophore imbues microbial rhodopsins with unusual optical properties. The linear and nonlinear responses of the retinal are highly sensitive to interactions with the protein host: small changes in the electrostatic environment can lead to large changes in absorption spectrum. These electro-optical couplings provide the basis for voltage sensitivity in microbial rhodopsins.

In some embodiments, the microbial rhodopsin domain is selected from the group consisting of QuarsAr1, QuarsAr2, Ace2N, and combinations thereof. In another embodiment, the voltage sensitive protein includes a Ciona intestinalis voltage-sensing domain (CiVSD), *Danio rerio* voltage-sensing domain (DrVSD), *Gallus gallus* voltage-sensing domain (GgVSD), or a combination thereof.

In some embodiments, the microbial rhodopsin domain comprises an amino acid sequence having at least 90, 95, 98, or 99% sequence identity to SEQ ID NO: 9, SEQ ID NO: 15, SEQ ID NO: 16, or SEQ ID NO: 17.

In some embodiments, the voltage-sensitive opsin domain is Ace2N including an amino acid mutation at one or more of residue 81, 92, and 199. In some embodiments, the voltage-sensitive opsin domain comprises the polypeptide of SEQ ID NO: 9 having one, two, three, or four amino acid mutations. In some embodiments, the voltage-sensitive opsin domain comprises the amino acid sequence of SEQ ID NO: 9 having an amino acid mutation at one or more of residue 81, 92, and 199.

In some embodiments, the voltage indicator includes an amino acid sequence selected from SEQ ID NOS: 2, 4, 6, 8, 20, 22, 24, and 26. In some embodiments, the voltage indicator includes an amino acid sequence encoded by a nucleotide sequence selected from the group of nucleotide sequences of SEQ ID NOS: 1, 3, 5, 7, 19, 21, 23, and 25.

Suitable capture proteins include any protein configured to bind a desired ligand. For example, in one embodiment, the capture protein includes a covalent capture protein. In some embodiments, the capture protein of the voltage indicator is a non-covalent capture protein. In some embodiments, the non-covalent capture protein is selected from the group consisting of TMP-tag, biotin-avidin, and a combination thereof. In some embodiments, the capture protein domain is selected from a HaloTag and a SNAP-Tag. In some embodiments, the capture protein is a covalent capture protein. In some embodiments, the covalent capture protein is selected from the group consisting of HaloTag, SNAP-tag, TMP-tag, βLac-tag, CLIP-tag, or a combination thereof. In some embodiments, the capture protein domain comprises an amino acid sequence selected from the amino acid sequence of SEQ ID NOS: 10 and 11.

In some embodiments, 1, 2, 3, 4, 5, 6, 7, 8, 9, or 10 amino acids are removed from the junction between the opsin domain and the capture protein.

In some embodiments, in addition to the voltage-sensitive protein domain and the capture protein domain, the voltage indicator also includes a targeting sequence. In some embodiments, the targeting sequence is a soma targeting sequence for directing the indicator to a neuron. In some embodiments, the targeting sequence comprises the amino acid sequence of SEQ ID NO: 12.

In some embodiments, the mutated voltage-sensitive microbial opsin domain and the capture protein are provided as a fusion protein. In some embodiments, the capture protein is positioned at the c-terminal end of the voltage-sensitive microbial opsin domain. In some embodiments, the indicator also includes a targeting sequence that is positioned at the c-terminal end of the capture protein.

As noted herein above, the voltage indicator includes a capture protein domain arranged and disposed to capture a fluorescent dye ligand. Suitable fluorescent dye ligands include, but are not limited to, one or more fluorophore dyes.

In one embodiment, the fluorophore dye includes a fluorophore containing one or more cyclic amine substituents. In another embodiment, the fluorescent dye ligand is an azetidine-containing Janelia Fluor™ dyes. For example, the fluorescent dye ligand can be Janelia Fluor™$_{505}$, Janelia Fluor™$_{525}$, Janelia Fluor™$_{549}$, Janelia Fluor™$_{585}$, Janelia Fluor™$_{646}$, or combinations thereof. In some embodiments, the fluorescent dye ligand is a fluorescent protein. For example, the fluorescent dye ligand can be sfGFP or mNeonGreen.

The presently-disclosed subject matter also includes methods of measuring voltage, and in particular, methods of measuring voltage across a membrane. The voltage indicators as described herein are used to perform the method.

In some embodiments, the method involves administering the voltage indicator and determining changes in fluorescence of the fluorescent dye ligand. When the fluorescent dye ligand is captured by the capture protein domain, and when the voltage indicator is bound to a cell membrane, an increase in voltage across the cell membrane causes an increase in fluorescent emission from the fluorescent dye ligand. In this regard, the method can involve determining changes in voltage based on changes in fluorescence. In some embodiments, an increase in membrane potential leads to an increase in fluorescence.

The method can be used to measure voltage across the membrane of a cell, such as a neuron. Florescent emission will increase with an increase in voltage, which can be a spike in voltage or a subthreshold voltage signal. In some embodiments, the response time between the increase in voltage and the increase in fluorescent emission is less than about a millisecond.

The changes in fluorescence may be measured through any suitable method such as, but not limited to, observation with a microscope, image capture, video recording, or a combination thereof.

In some embodiments, the voltage indicator includes a linker between the voltage-sensitive domain and the capture protein domain. Embodiments of the indicator and method can include modifying a length of the linker. For example, modifying the length of the linker can include removing at least one amino acid residue. In some embodiments, about 1, 2, 3, 4, 5, 6, 7, 8, 9, 10, 11, 12, 13, 14, 15, 16, 17, 18, 19, 20, 21, or 22 amino acid residues can be removed. In some embodiments, the modification of the length of the linker can modify the size of a fluorescence response.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

Example 1

Through mutagenesis, the present inventors inverted the direction of fluorescence change in exemplary rhodopsin electrochromic fluorescence resonance energy transfer (eFRET) genetically encoded voltage indicators (GEVIs) such that an increase in membrane potential lead to an increase in fluorescence. Several different single amino acid substitutions inverted the fluorescence change of an exemplary eFRET GEVI (i.e., an amino acid substitution relative to the sequence of FIG. 4).

Figure 1B:
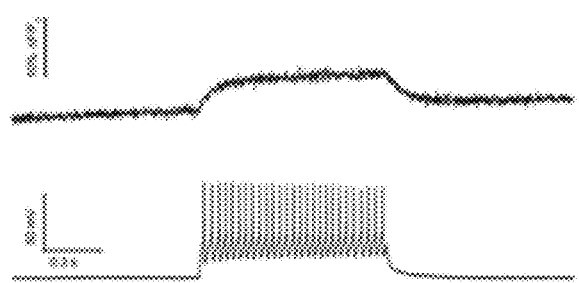
Figure 4:
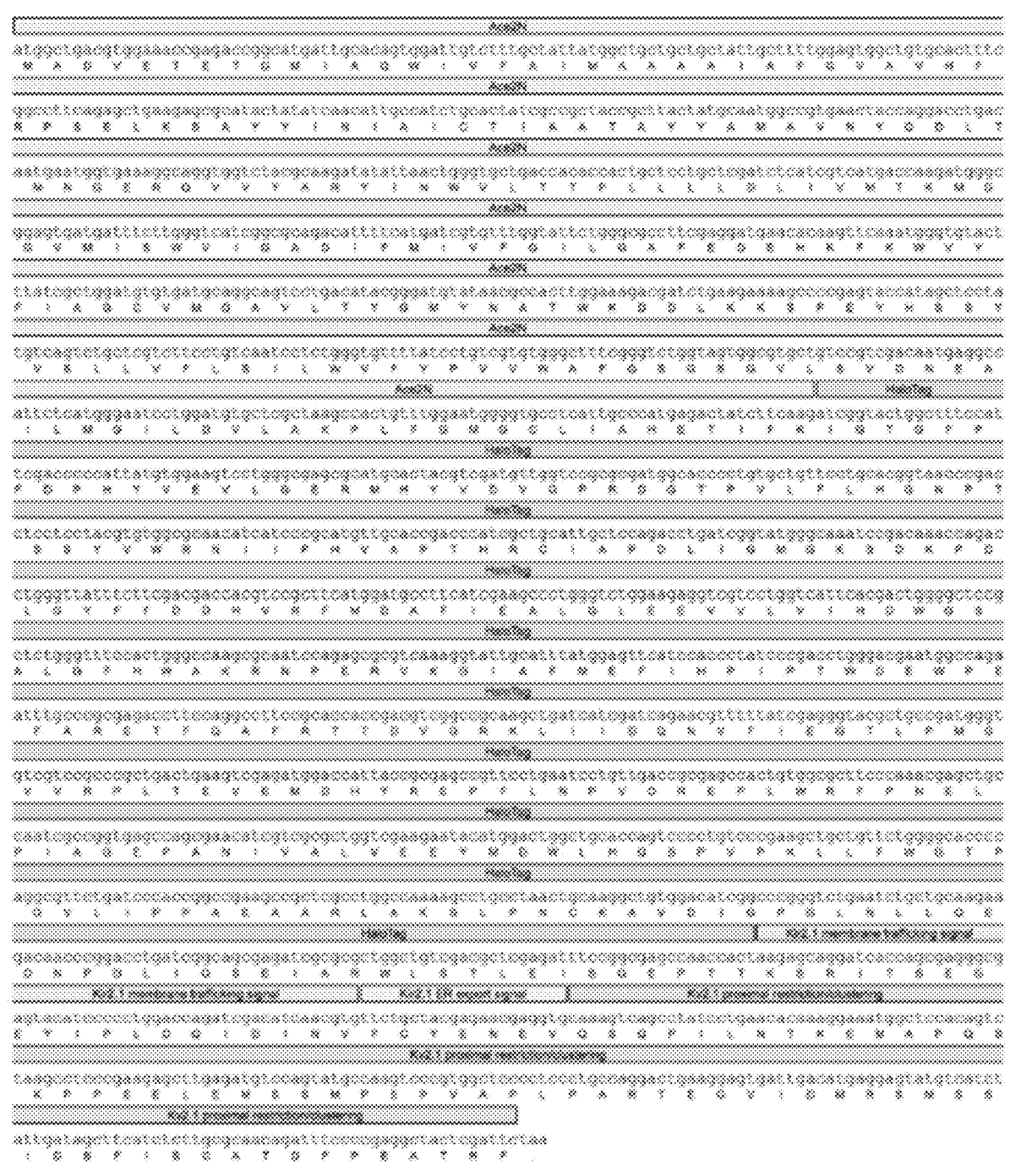

By way of comparison, FIG. 1A illustrates fluorescence change of an exemplary eFRET GEVI having the sequence as set forth in FIG. 4, where there is a decrease in fluorescence with increasing membrane potential, and voltage signals such as action potentials in neurons take on a downward-going shape. Meanwhile, FIGS. 1B-D illustrate fluorescent change in exemplary eFRET GEVIs having one or more amino acid substitutions relative to the sequence of FIG. 4, in which the fluorescence change is inverted.

In one embodiment, D92N (SEQ ID NO: 2), a single amino acid substitution inverted the florescence change (FIG. 1B), but it was desired to see if the indicator could be further modified such that fluorescence changes occur more-rapidly to follow fast voltage changes such as action potentials in neurons.

Figure 1C:
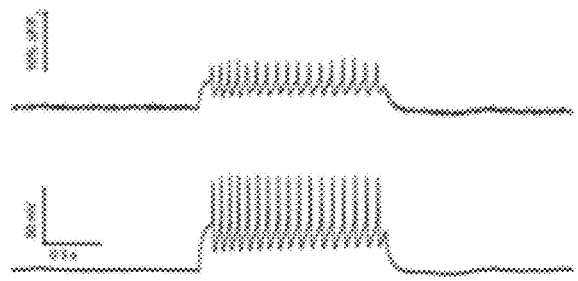

An additional amino acid substitution, N81D, increased the speed of fluorescence change such that the fluorescence could follow action potentials in neurons (FIG. 1C). The magnitude of N81D D92N (SEQ ID NO: 4) remained small relative to the indicator of FIG. 4.

Figure 1D:
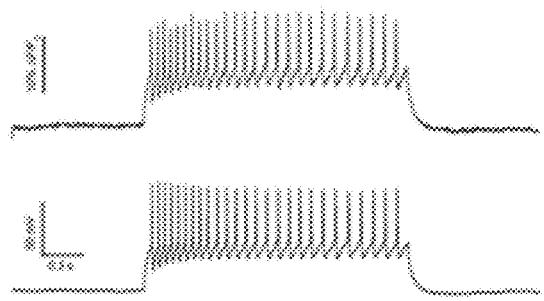
Figure 2:
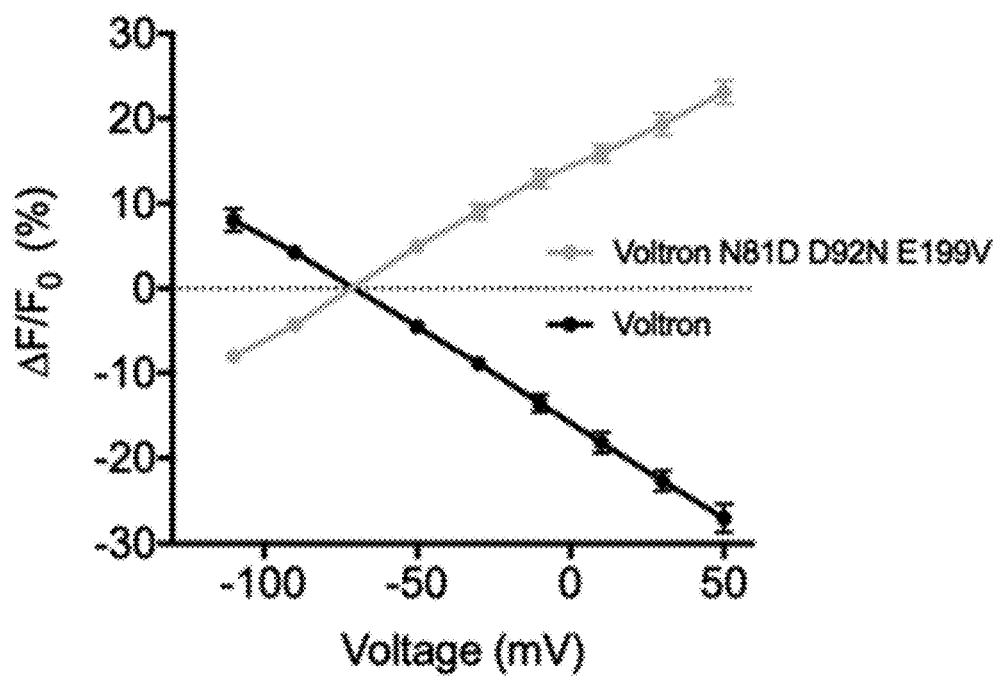
FIG. 2 includes fluorescence versus voltage in neurons for Voltron and Voltron N81D D92N E199V.
Figure 3:
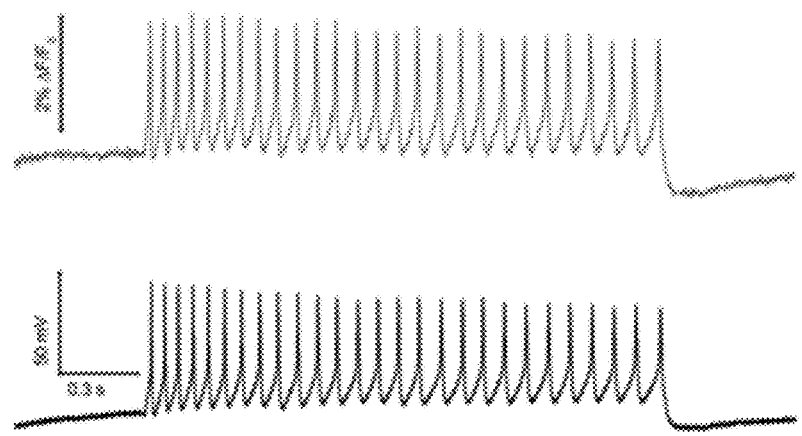
FIG. 3 includes fluorescence response (top) and membrane potential changes in neutrons (bottom) for Ace2-mNeonGreen N81D D92N.

An additional amino acid substitution (E199V) increased the sensitivity such that the fluorescence change of N81D D92N E199V (SEQ ID NO: 6) was equal in amplitude to the indicator of FIG. 4, but with an inverted response direction (FIG. 1D and FIG. 2). The present inventors additionally showed that these amino acid changes invert the signal when a fluorescent protein (Ace2-mNeonGreen N81D D92N (SEQ ID NO: 8)) is used in place of a rhodamine dye (FIG. 3).

Example 2

Voltron was used for in vivo voltage imaging in mice, zebrafish, and fruit flies. In mouse cortex, Voltron allowed single-trial recording of spikes and subthreshold voltage signals from dozens of neurons simultaneously, over 15 minutes of continuous imaging. In larval zebrafish, Voltron enabled the precise correlation of spike timing with behavior.

Figure 5A:
FIGS. 5A-5K are related to development of the chemigenetic voltage indicator Voltron.
Figure 5B:
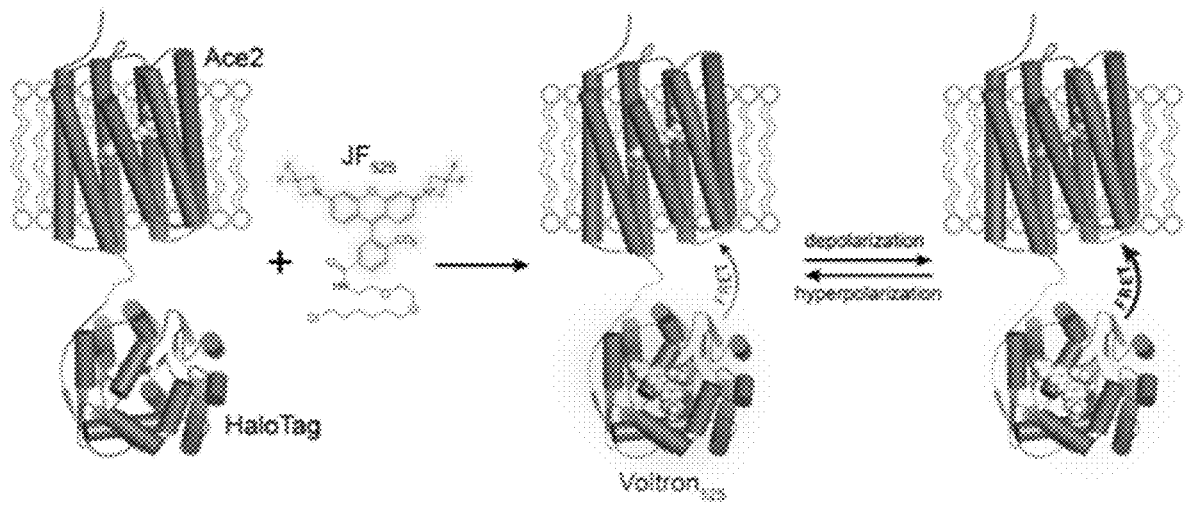
Figure 5C:
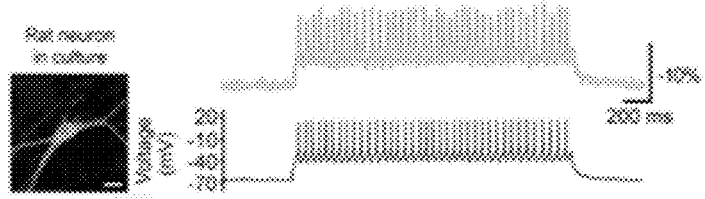
Figure 5D:
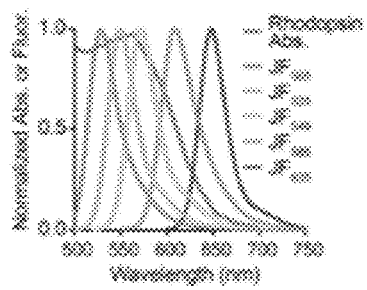

An exemplary design for a chemigenetic voltage indicator combined a voltage-sensitive microbial rhodopsin domain (6, 7, 11) with a self-labeling protein tag domain (FIG. 5A) that covalently binds a synthetic fluorophore dye ligand (14, 15) (FIG. 5B), analogous to previously reported voltage indicators using fluorescent proteins (10, 11, 18). Transmembrane-voltage-dependent changes in the absorption spectrum of the rhodopsin (6, 19) reversibly modulate the degree of fluorescence quenching of the nearby bound dye through Förster resonance energy transfer (FRET).

The modularity of this approach was investigated, and three different exemplary rhodopsin domains, QuasAr1 (7), QuasAr2 (7), and Ace2N (11, 20), were all able to modulate the fluorescence of either HaloTag (15) or SNAP-tag (21) self-labeling tag domains (FIGS. 9 to 15). Removing a modest number of amino acid residues at the junction of the rhodopsin and self-labeling tag domains increased the amplitude of fluorescent voltage signals (FIG. 9), presumably by decreasing average distance and thus increasing FRET efficiency between the dye and rhodopsin retinal cofactor. The configuration providing the best signal-to-noise ratio for spikes was Ace2N fused to HaloTag with five amino acids removed at their junction (FIGS. 5A, 5B and 4), hereafter referred to as Voltron.

Figure 5E:
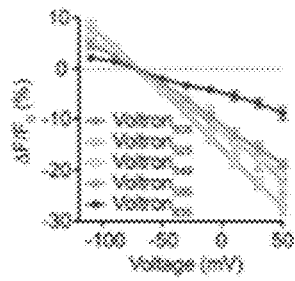
Figure 16:
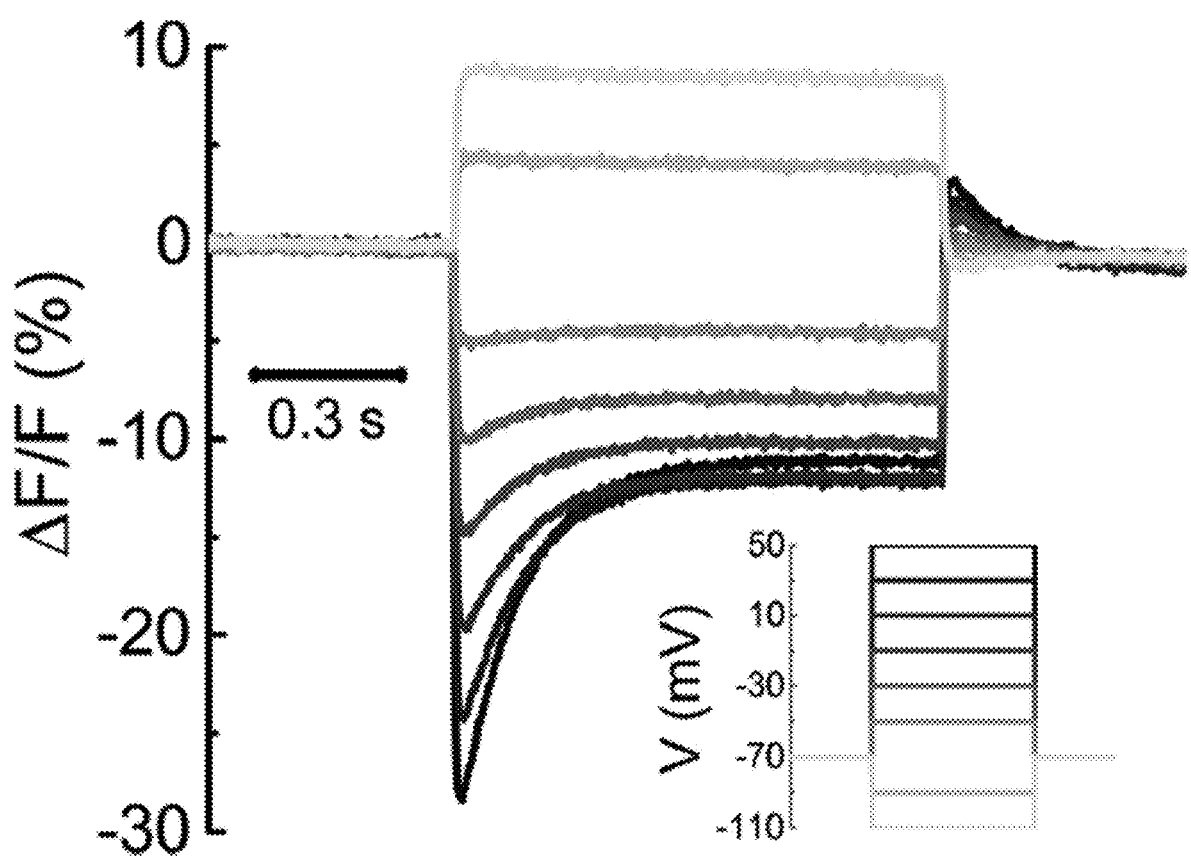
Figure 17:
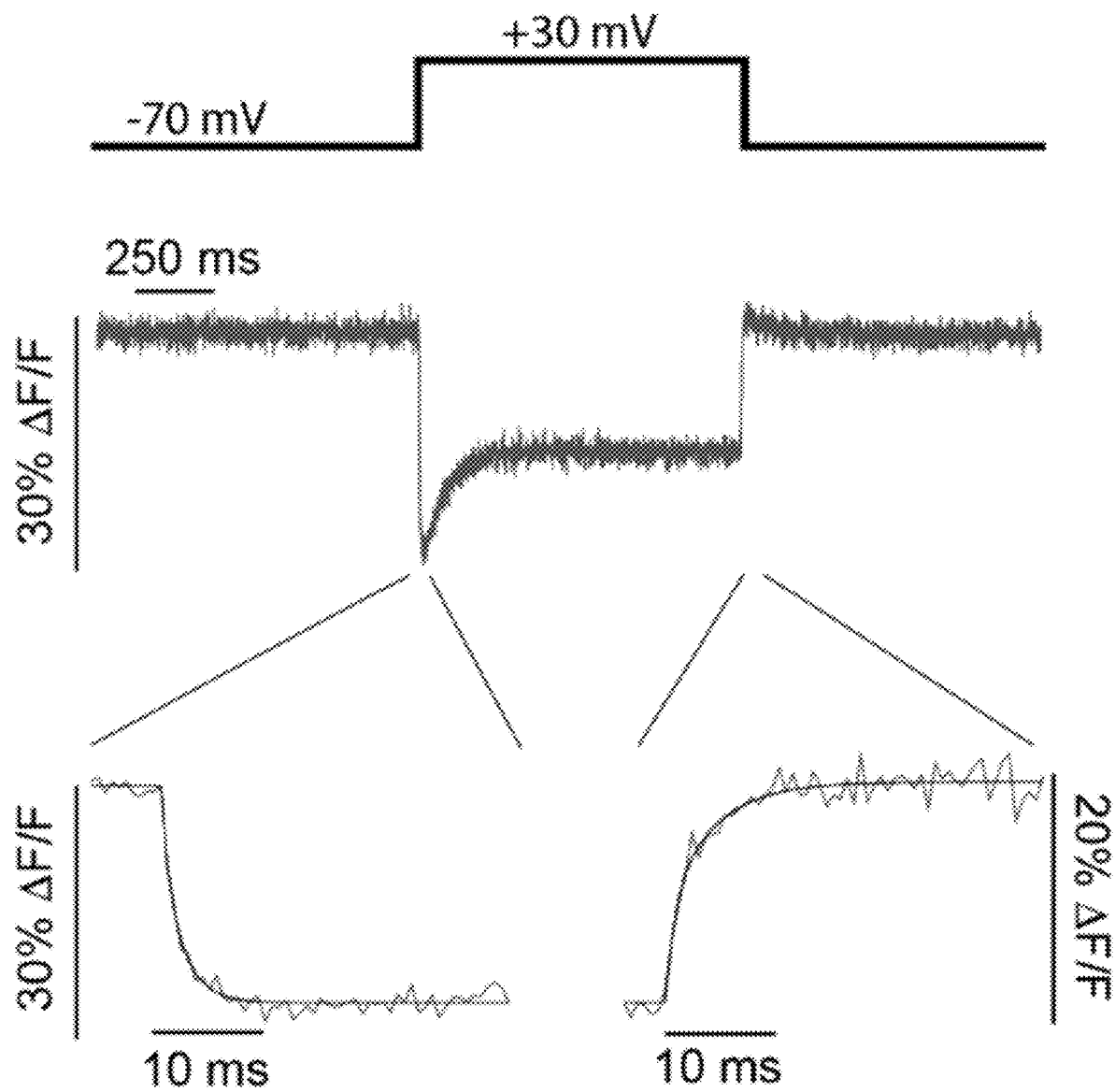
FIG. 17 illustrates a representative fluorescence response of Voltron$_{525}$ in a cultured neuron to a 100 mV potential step delivered in voltage clamp. Insets: Zoom in on change of Voltron fluorescence to depolarization and hyperpolarization. Solid black line is double exponential fit according to $\Delta F/F(t)=Ae^{t/\tau fast}+Be^{t/\tau s\ low}$. Image acquisition rate 3.2 kHz. For full kinetics data, see Table 1.

Voltron was tested in neuron cultures using high-speed imaging with simultaneous whole-cell patch clamp electrophysiology (FIG. 5C), first investigating different dye-Voltron combinations. Voltron could detect neuronal action potentials and sub-threshold potential changes using a range of JF dye ligands with emission maxima between 520 nm and 660 nm (FIGS. 5C-5E and 13). Voltron bound to $_{JF525}$ (i.e., Voltron525) exhibited the highest sensitivity, giving a fluorescence change of −23±1% for a voltage step from −70 mV to +30 mV (FIG. 5E and FIG. 16); Voltron549 showed similar sensitivity. Voltron$_{525}$ responded to voltage steps with sub-millisecond on and off time constants (Table 1 and FIG. 17).

TABLE 1

Voltron525 and Ace2N-mNeon kinetics in primary neuron culture cells

| | Activation (−70 mV to 30 mV) | | | Deactivation (30 mV to −70 mV) | | |
|---|---|---|---|---|---|---|
| | $\tau_{fast}$ (ms) | $\tau_{slow}$ (ms) | % fast | $\tau_{fast}$ (ms) | $\tau_{slow}$ (ms) | % fast |
| Ace2N-mNeon | 0.59 ± 0.10 | 6.9 ± 0.5 | 62 ± 3 | 0.63 ± 0.09 | 6.0 ± 1.1 | 55 ± 4 |
| Voltron-JF525 | 0.64 ± 0.09 | 4.1 ± 0.6 | 61 ± 4 | 0.78 ± 0.12 | 3.9 ± 0.2 | 55 ± 7 |

Figure 11:
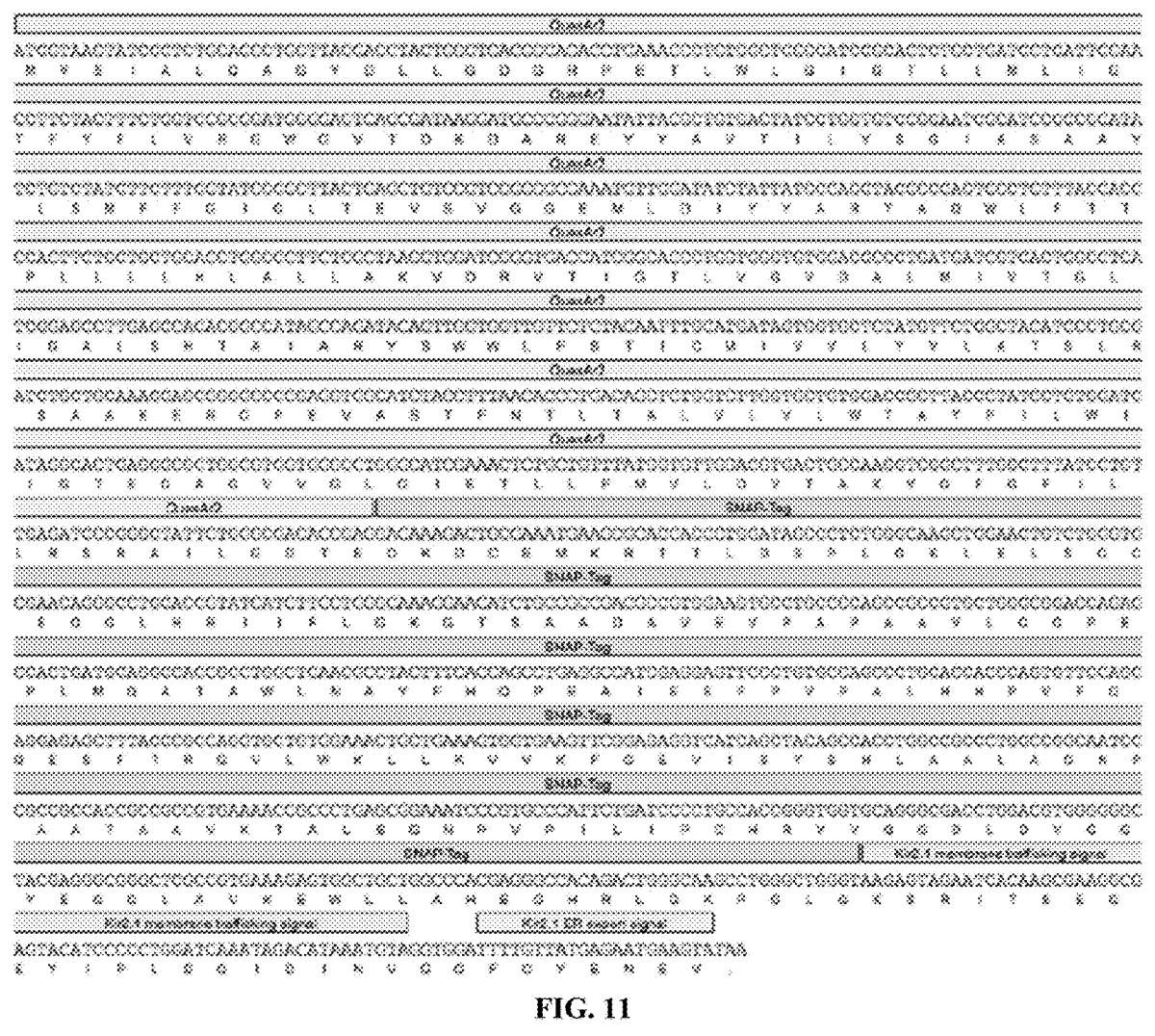

Neurons expressing Ace2N-mNeon and Voltron525 were imaged at 3.2 kHz during whole cell voltage clamp as detailed in the methods section. Fluorescence traces were then fit using a double exponential model (FIG. 11). Errors are s.e.m. n = 7 cells for Ace-mNeon and n = 8 cells for Voltron525.

Figure 5F:
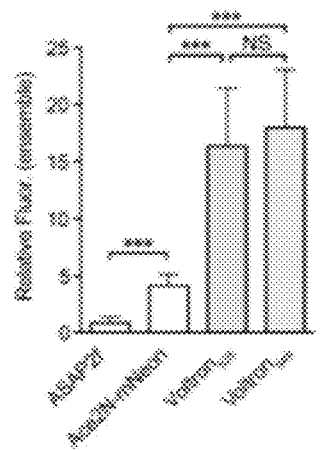
Figure 5G:
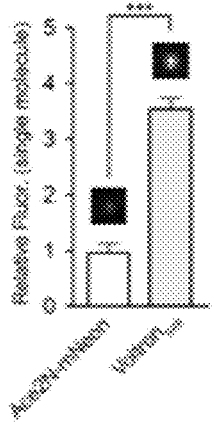
Figure 5H:
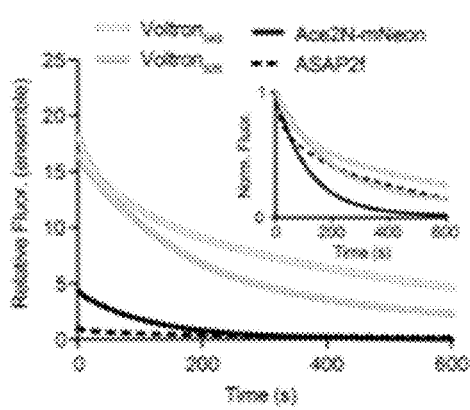
Figure 5I:
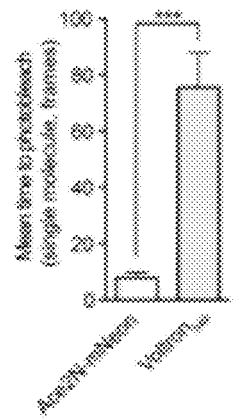
Figure 5J:
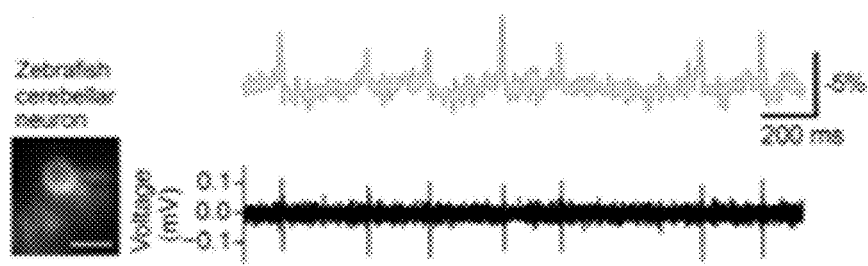
Figure 5K:
Figure 6A:
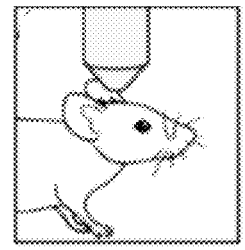
FIGS. 6A-6L are related to membrane voltage dynamics in hippocampal parvalbumin (PV) neurons (FIGS. 6A-6G)
Figure 6B:
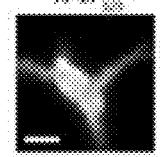
Figure 6C:
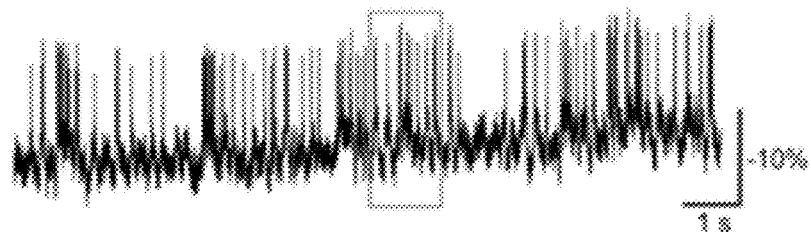
Figure 6D:
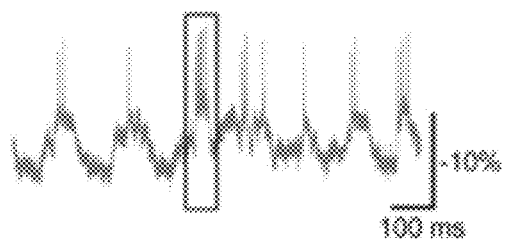
Figure 6E:
Figure 6F:
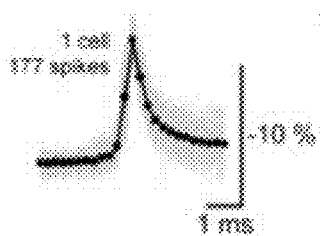
Figure 6G:
Figure 6H:
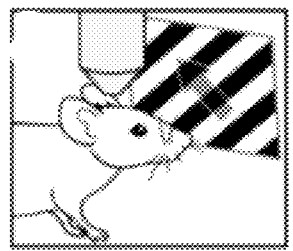
Figure 6I:
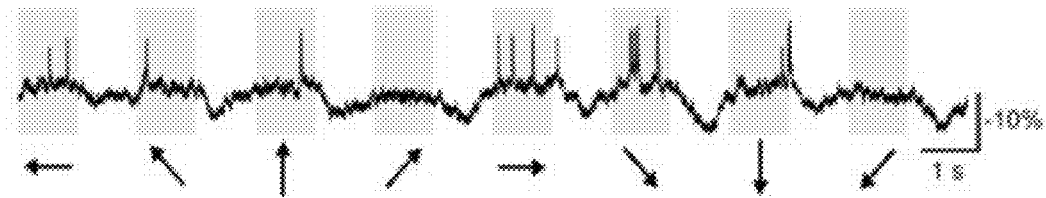
Figures 6J, 6K, 6L:
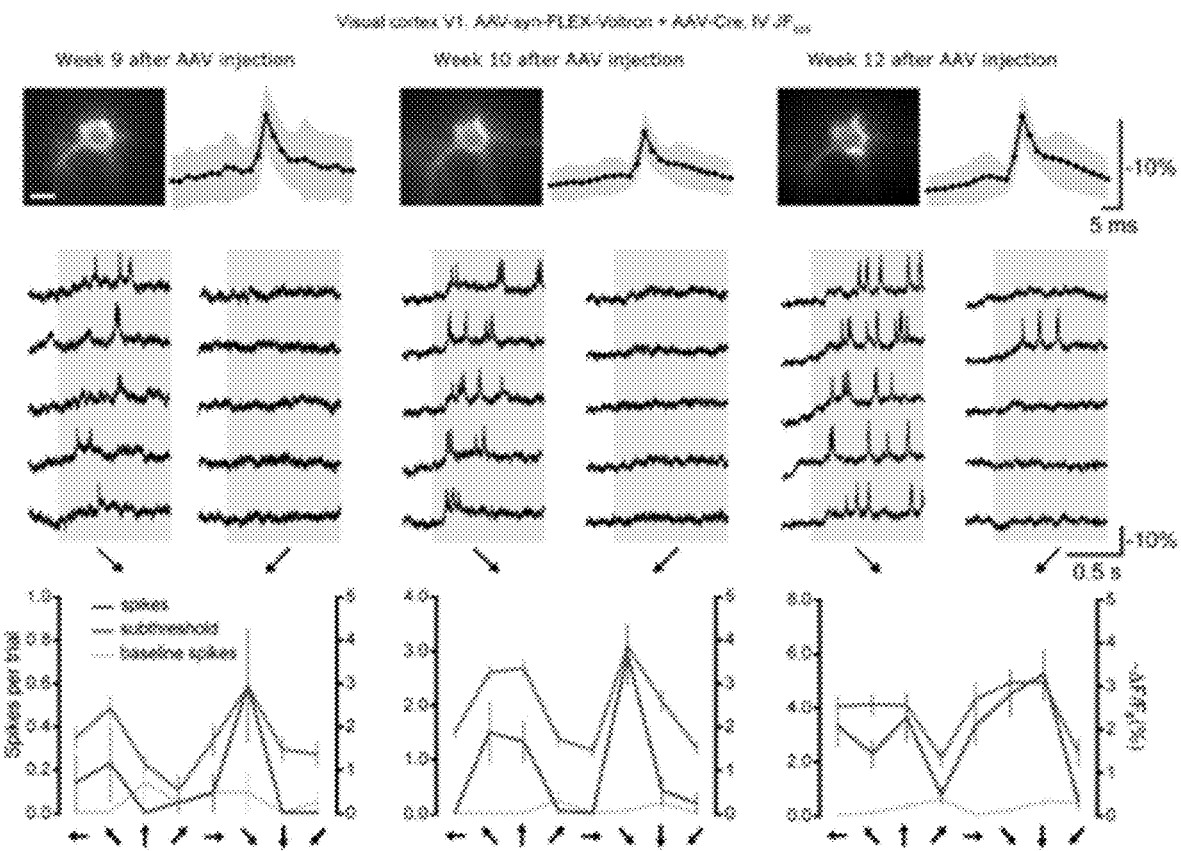
Figure 7A:
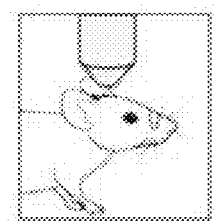
FIGS. 7A-7G include long duration and large FOV imaging of voltage activity in GABA-ergic neurons in mouse neocortex.
Figure 7B:
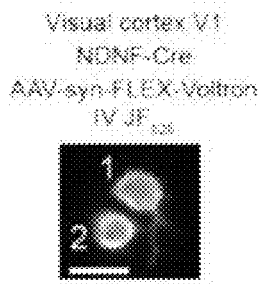
Figure 7C:
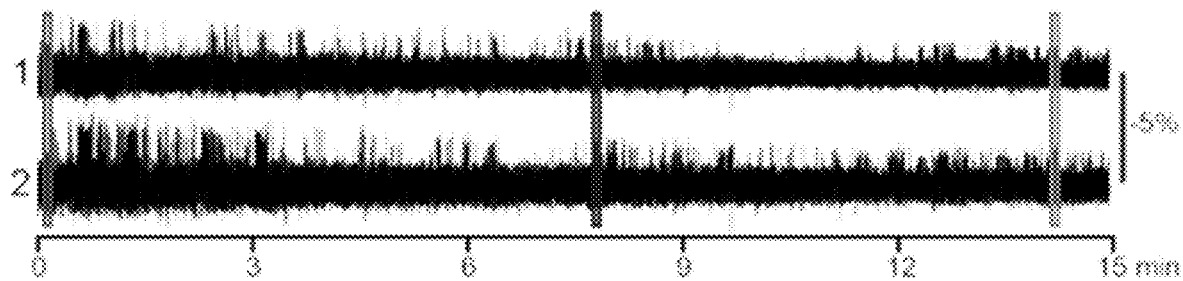
Figure 7D:
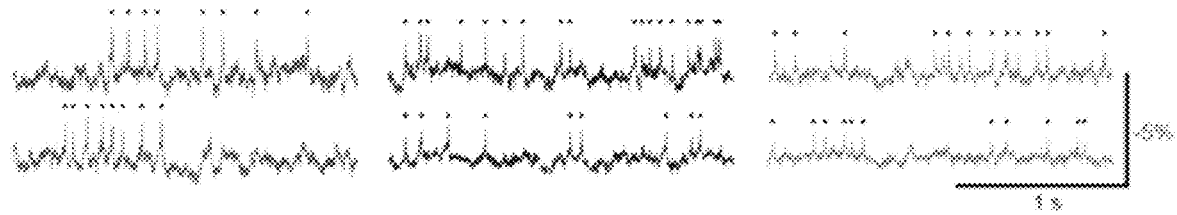
Figure 7E:
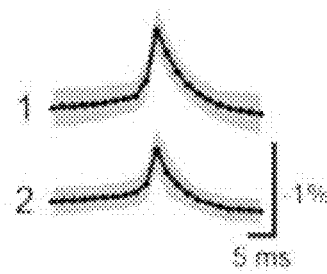
Figure 7F:
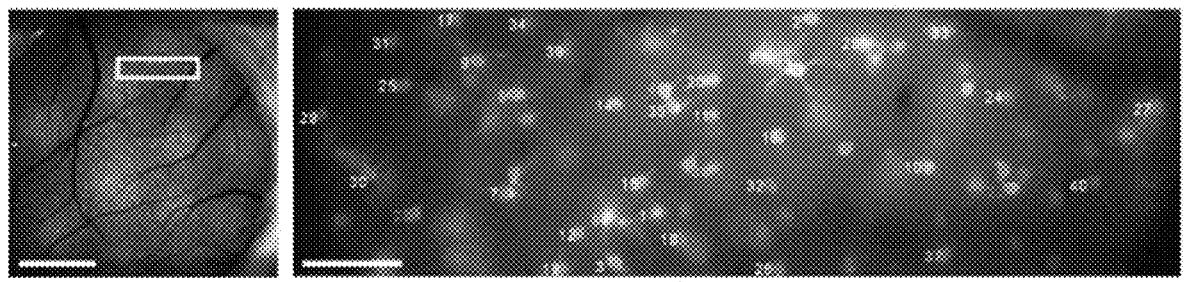
Figure 7G:
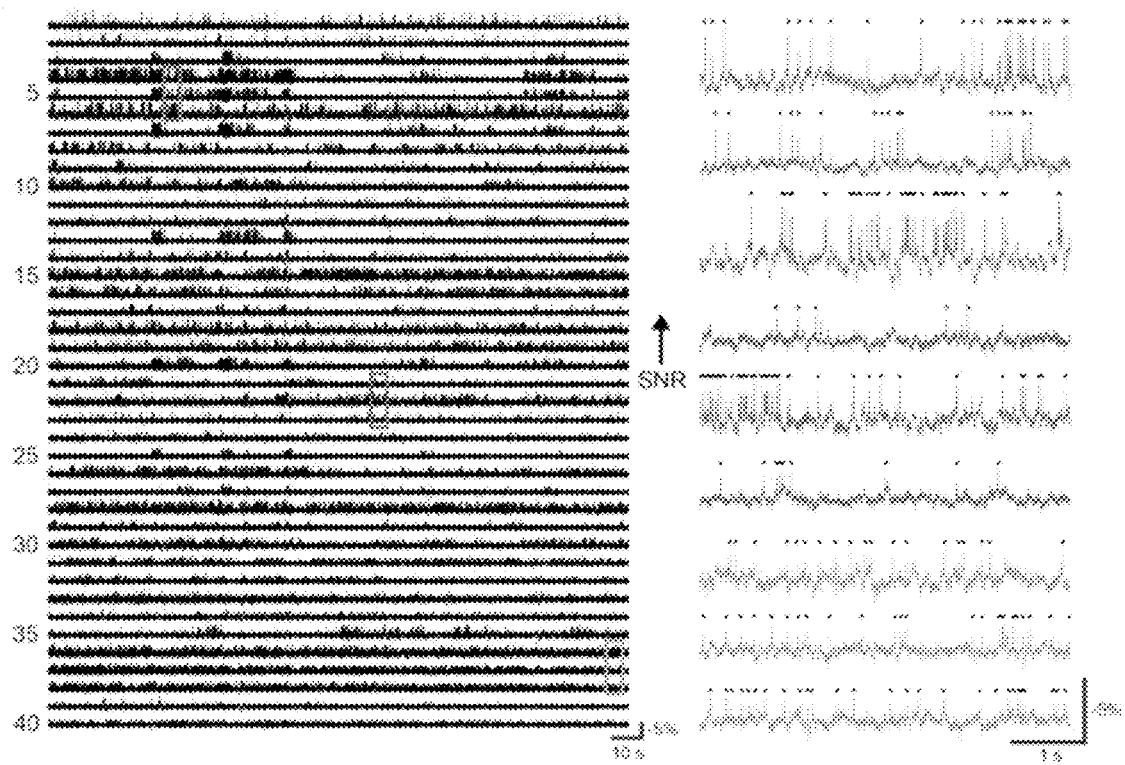
Figure 18:
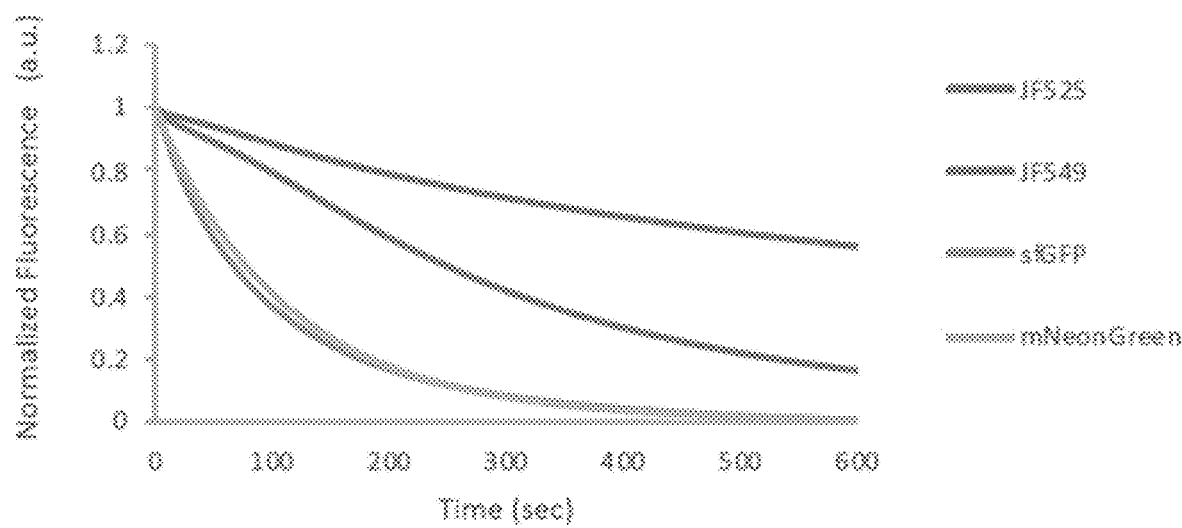
FIG. 18 includes a photobleaching profile of HaloTag-bound JF525, JF549, and fluorescent proteins sfGFP and mNeonGreen, measured in aqueous droplets with widefield microscopy. Data taken at excitation rates W for JF525 (W=1549 s$^{-1}$), JF549 (1540 s$^{-1}$), sfGFP (1597 s$^{-1}$) and mNeonGreen (1772 s-1).
Figure 19:
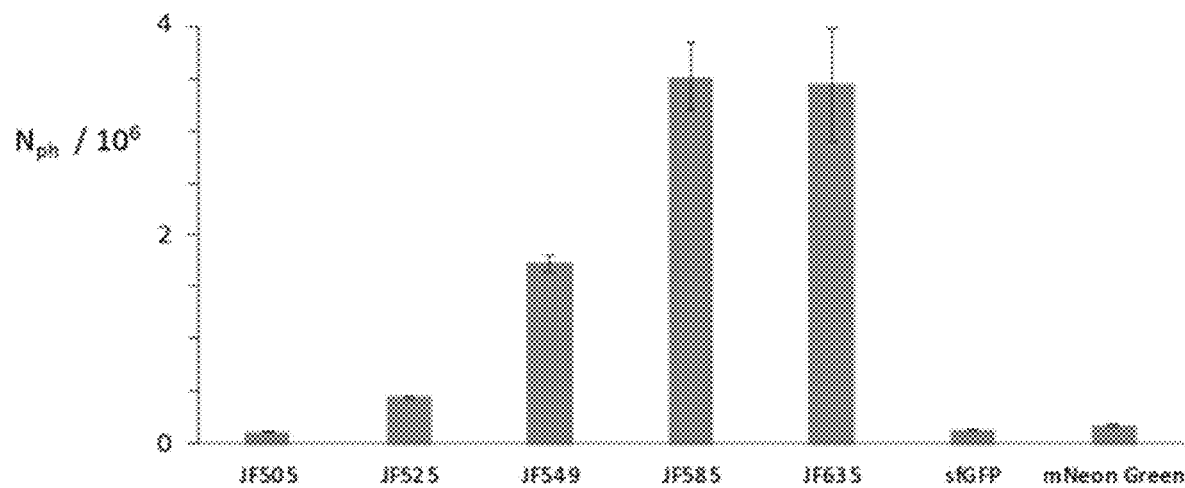
FIG. 19 is a bar graph including mean number of photons per molecule emitted before photobleaching $_{Nph}$ for JFdyes-HT conjugates and fluorescent proteins obtained in aqueous droplets using widefield microscopy. Error bars are standard deviation (n=9).
Figure 20:
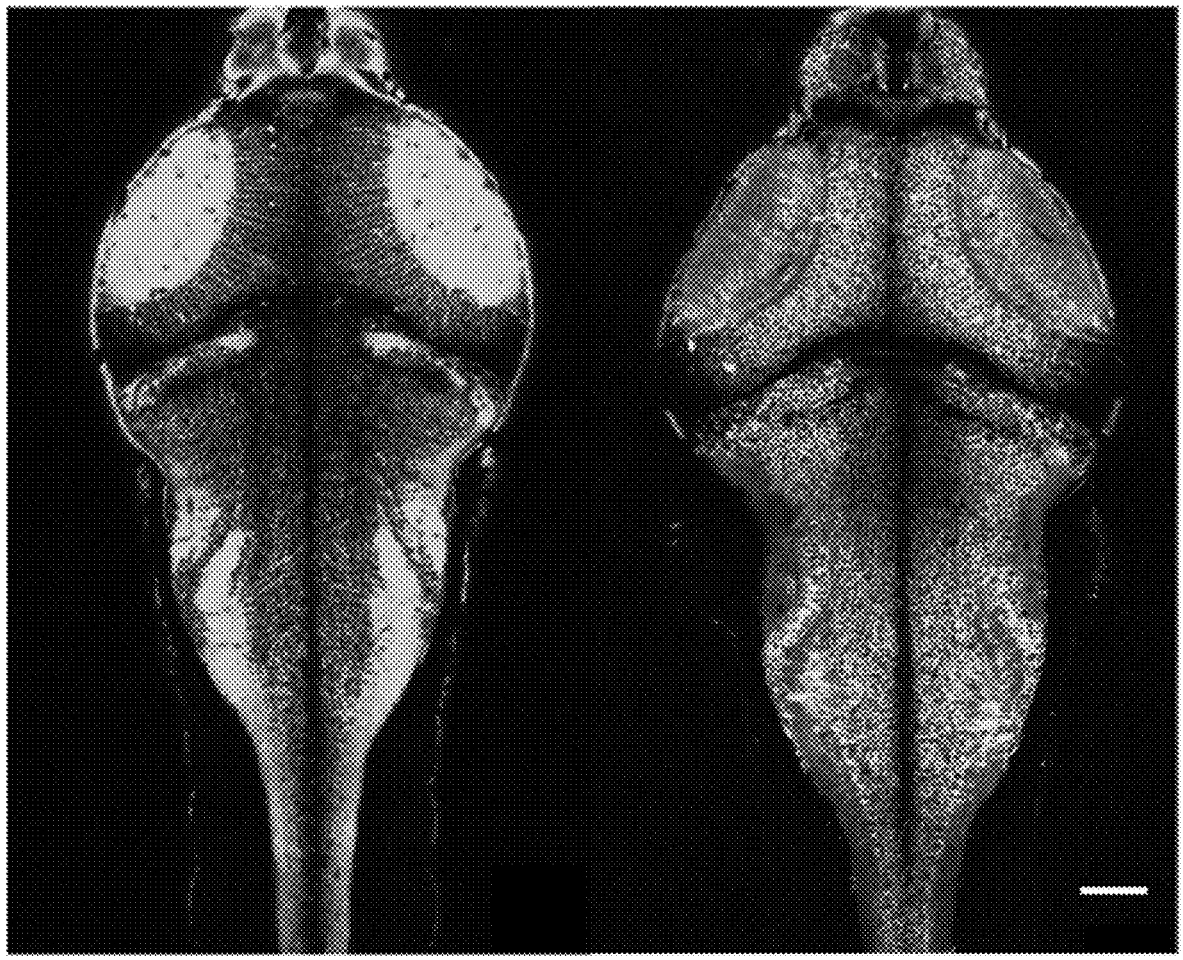
FIG. 20 includes images showing Voltron expression in zebrafish. The left panel includes a confocal image of Tg[elavl3:Voltron], and the right panel includes a confocal image of Tg[elavl3:Voltron-ST] (right) zebrafish (4 dpf) labeled with JF525 dye. Scale bar: 50 μm.
Figure 21A:
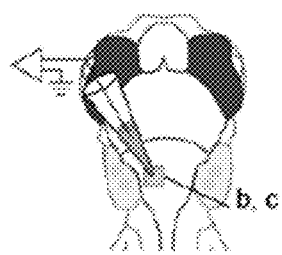
FIG. 21A-21E relate to simultaneous whole-cell recording and Voltron imaging in zebrafish.
Figure 21B:
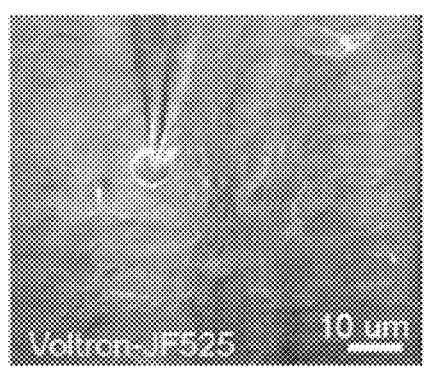
Figure 21C:
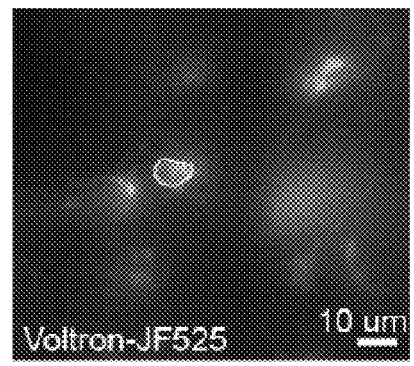
Figure 21D:
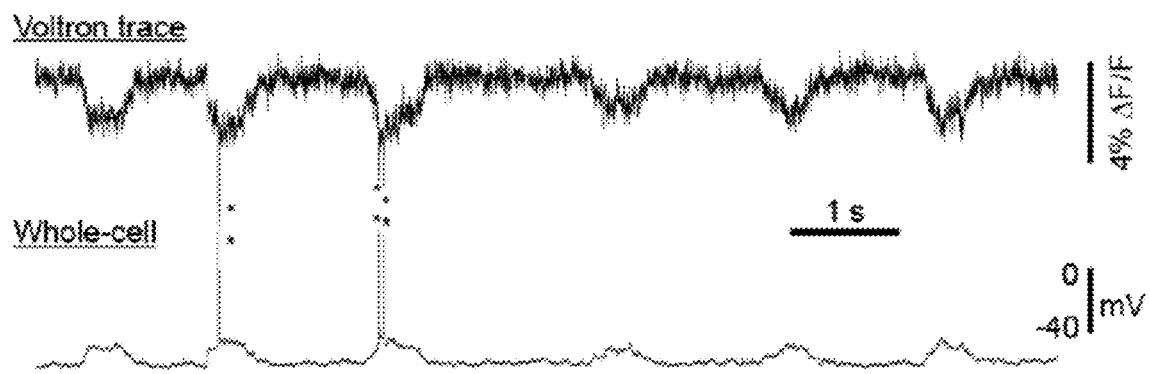
Figure 21E:
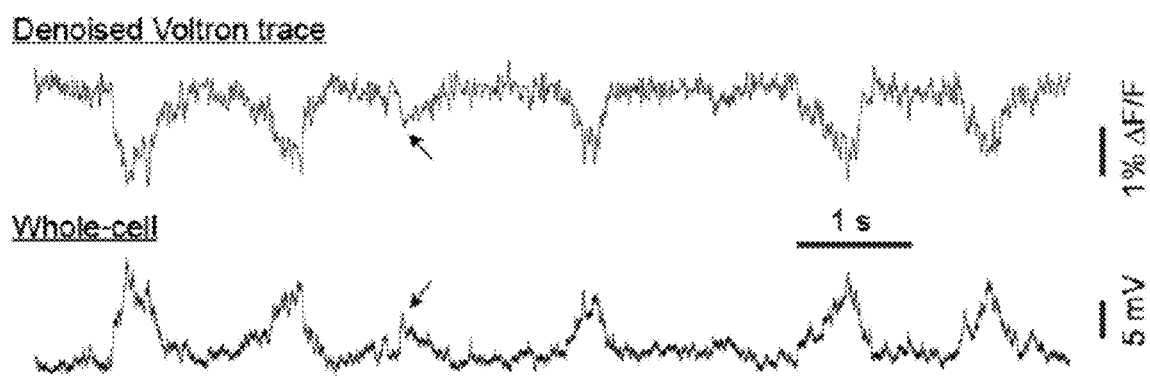

The brightness and photostability of Voltron in neuronal cultures was compared with two other recently described fluorescent protein-based GEVIs: Ace2N-mNeon (11) and ASAP-2f (13). Both Voltron525 and Voltron549 were brighter than Ace2N-mNeon (3-4×) and ASAP-2f (16-18×) (FIG. 5F) in cell culture. This difference was not due to differences in expression levels; the brightness of Voltron549 and Ace2N-mNeon were compared at the single-molecule level, and a similar 3-4× brightness difference was observed (FIG. 5G). Voltron525 and Voltron549 were also more photostable in ensemble measurements (FIG. 5H, Tables 2 and 3 and FIGS. 18,19) as well as in single-molecule assays, where photobleaching times were 8-fold longer for Voltron549 than Ace2N-mNeon (FIG. 5I). Overall, the improved brightness and photostability of Voltron increase the photon yield by at least 10-fold relative to existing GEVIs in neurons.

extended over several consecutive weeks by injection of additional JF525 HaloTag ligand prior to each imaging session (FIGS. 6J-6L).

To further assess the advantages garnered from Voltron's improved photostability and brightness, the illumination intensity, imaging duration, and field of view used for in vivo imaging were investigated (FIG. 7). Using widefield microscopy and illumination intensities between 3 and 20 mW/mm$^2$, action potentials from nearby neurons could be clearly identified and distinguished throughout 15 minutes

TABLE 2

Photophysical properties of parent fluorophore HaloTag-bound JFdyes and green fluorescent proteins (mean values, n = 9)

| Fluorophore | $\lambda abs$ (nm) | $\lambda em$ (nm) | $\varepsilon_{max}$ (mM$^{-1}$cm$^{-1}$) | $\Phi_{fl}$ | W$^{(a)}$ (sec$^{-1}$) | $\tau_1$ (A1)$^{(b)}$ (sec) | $\tau_2$ (A2) (sec) | $<\tau_b>^{(c)}$ (sec) | Pb/10$^{-6}$ $^{(d)}$ | N$_{ph}$/10$^5$ $^{(e)}$ | $\tau_{1/2}$ $^{(f)}$ (sec) |
|---|---|---|---|---|---|---|---|---|---|---|---|
| JF505 | 509 | 531 | 56.8 | 0.83 | 941 | 59 (0.59) | 264 (0.41) | 144 | 7.36 | 1.13 | 51 |
| JF525 | 532 | 553 | 83.6 | 0.87 | 1,549 | 329 (1.0) | | 330 | 1.96 | 4.43 | 336 |
| JF549 | 555 | 578 | 91.3 | 0.86 | 3,158 | 907 (0.65) | 124 (0.35) | 633 | 0.50 | 17.2 | 804 |
| JF585 | 593 | 611 | 109 | 0.83 | 4,443 | 931 (1.0) | | 950 | 0.24 | 35.1 | 3,320 |
| JF635 | 641 | 656.5 | 64.0 | 0.7 | 2,486 | 1976 (1.0) | | 1,980 | 0.20 | 34.4 | 3,130 |
| sfGFP | 488 | 511 | 51.5 | 0.66 | 1,597 | 90 (0.66) | 167 (0.34) | 117 | 5.32 | 1.24 | 71 |
| mNeon | 506 | 517.5 | 120 | 0.85 | 1,773 | 102 (0.72) | 144 (0.28) | 114 | 4.83 | 1.80 | 118 |

$^{(a)}$ Excitation rate (absorbed photons/sec) equal to the integral over wavelength of the product of extinction coefficient and spectral irradiance.
$^{(b)}$ Decay constant (normalized amplitude) of multi-exponential fit to the photobleaching decay curve.
$^{(c)}$ Amplitude-weighted lifetime equal to $A_1 \tau_1 + A_2 \tau_2$.
$^{(d)}$ Calculated probability of photobleaching per absorbed photon.
$^{(e)}$ Calculated number of photons emitted per molecule before photobleaching.
$^{(f)}$ Calculated time to bleach from a rate of 1000 to 500 photons per sec per molecule.

TABLE 3

Photobleaching properties of GEVI sensors in neuronal cell culture (mean values, n = 5)

| sensor | W$^{(a)}$ (sec$^{-1}$) | T$_1$ (A$_1$)$^{(b)}$ (sec) | T$_2$ (A$_2$) (sec) | $<\tau_b>^{(c)}$ (sec) | Pb/10$^{-6}$ $^{(d)}$ | N$_{ph}$/10$^5$ $^{(e)}$ | T$_{1/2}$ $^{(f)}$ (sec) |
|---|---|---|---|---|---|---|---|
| Voltron525 | 1,549 | 171 (0.84) | 1497 (0.15) | 373 | 1.74 | 5.03 | 206 |
| Voltron549 | 3,158 | 675 (0.67) | 61.5 (0.31) | 471 | 0.672 | 12.8 | 538 |
| ASAP-2f | 1,597 | 400 (0.68) | 24.9 (0.30) | 281 | 2.23 | 2.96 | 132 |
| Ace2N-mNeon | 1,773 | 118 (0.88) | 147 (0.11) | 120 | 4.70 | 1.81 | 119 |

$^{(a)}$ Excitation rate (absorbed photons/sec) equal to the integral over wavelength of the product of extinction coefficient and spectral irradiance.
$^{(b)}$ Decay constant (normalized amplitude) of multi-exponential fit to the photobleaching decay curve.
$^{(c)}$ Amplitude-weighted lifetime equal to $A_1 \tau_1 + A_2 \tau_2$.
$^{(d)}$ Calculated probability of photobleaching per absorbed photon.
$^{(e)}$ Calculated number of photons emitted per molecule before photobleaching.
$^{(f)}$ Calculated time to bleach from a rate of 1000 to 500 photons per sec per molecule.

The chemigenetic Voltron indicator was next deployed in vivo, observing that the protein could be reliably expressed and labeled with dye in mice, larval zebrafish, and adult fruit flies (FIGS. 5-8, FIG. 20-41). Simultaneous in vivo electrophysiology and imaging in both zebrafish and flies confirmed the detection of individual action potentials in single-trial imaging (FIGS. 5J, 5K and FIGS. 21-22). For imaging in the mouse brain, a variant of Voltron was used with a soma-targeting sequence from Kv2.1 (22, 23) (Voltron-ST, FIG. 23). The rapid kinetics of Voltron525-ST allowed clear observation of action potentials in fast-spiking parvalbumin positive interneurons in the CA1 region of mouse hippocampus (FIGS. 6A-6G and FIG. 24). Orientation tuning was measured based on both spiking and subthreshold voltage signals in layer 2/3 pyramidal neurons in mouse primary visual cortex in response to drifting grating stimuli in the contralateral visual field, a benchmark for new indicators (1, 11) (FIGS. 6H-6L and FIGS. 25-26), and confirmed that spiking activity shows sharper orientation selectivity than subthreshold voltage signals (24). The imaging period was of continuous imaging (SNR=4.4 during final minute); (FIGS. 7B-7E). The field-of-view was expanded to include dozens of cortical interneurons labeled with Voltron525-ST via an NDNF-Cre mouse line (25), while imaging at 400 Hz (FIGS. 7F, 7G, FIGS. 27-40). Even with this large field of view, clear signals for spikes and subthreshold voltage signals were observed in ~90% of neurons in focus within the imaging field. Overall, a total of 449 neurons were imaged (12 fields of view in 3 mice), demonstrating routine voltage imaging of populations of neurons in superficial mouse cortex (FIG. 7G, FIG. 27-40). This unprecedented scale of in vivo voltage imaging enabled analysis of membrane potential correlations between many neuron pairs (FIG. 28).

Voltron was then used to image behaving zebrafish larvae, which reliably respond to visual input with fast, directed swim bouts that are tailored to the details of the stimulus (26). Studies were conducted to determine how this sensory-to-motor transformation unfolds in neuronal populations at fine timescales that are inaccessible with calcium imaging.

Figure 8A:
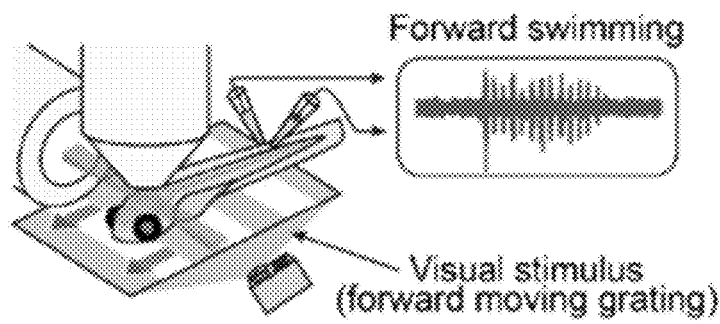
Figure 8B:
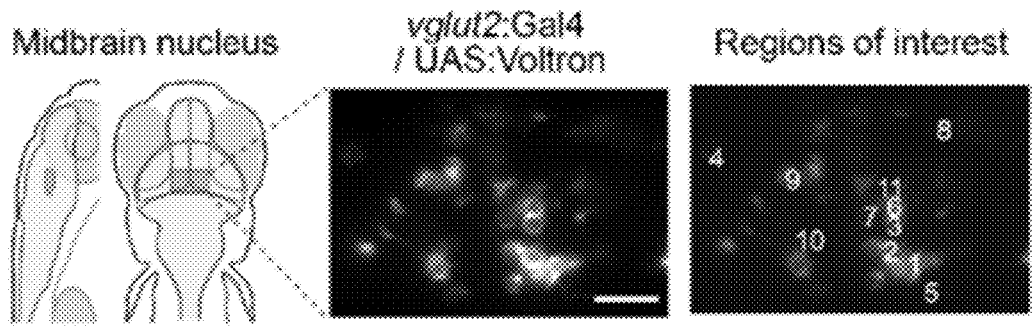
Figure 8C:
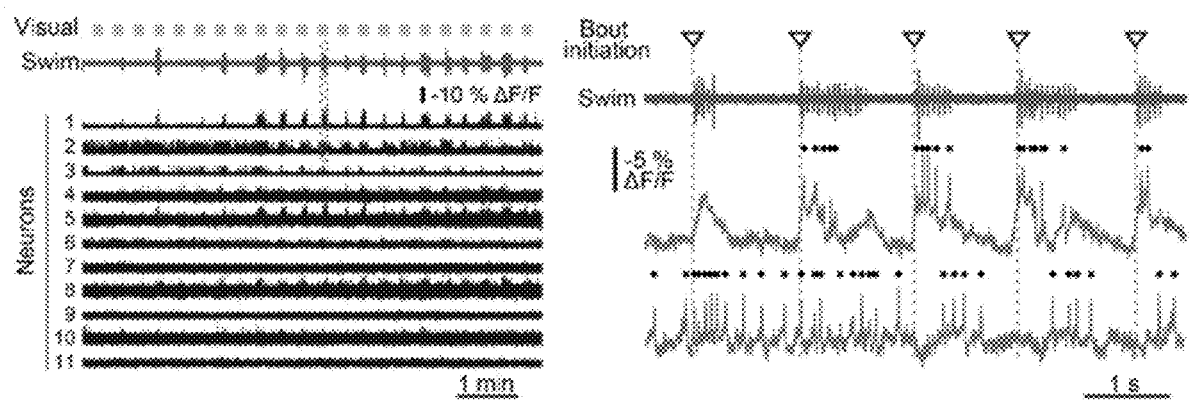
Figure 9A:
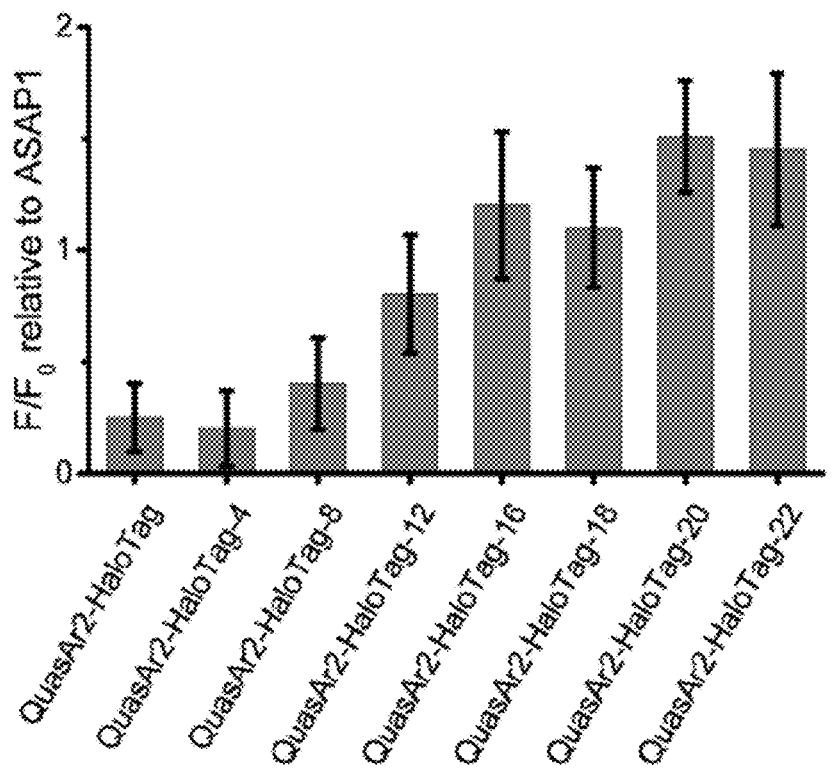
FIGS. 9A-9D includes a series of figures related to screening for a beneficial linker length between the rhodopsin and self-labeling tag domains. QuasAr2-HaloTag fusions (labeled with JF$_{549}$) and ASAP1 (32) were co-transfected into neurons and stimulated using a field stimulation electrode (see methods section). Truncating residues from the C-terminus of QuasAr2 and the N-terminus of HaloTag led to indicators with improved voltage sensitivity.
Figure 9B:
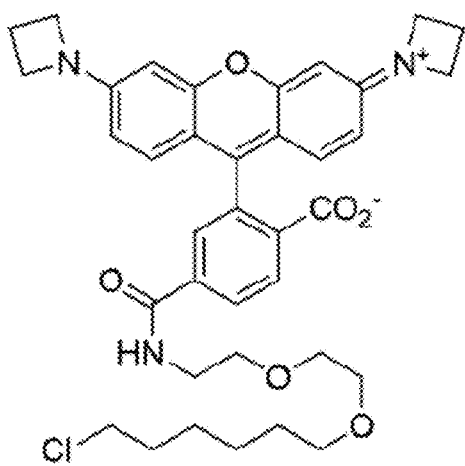
Figure 9C:
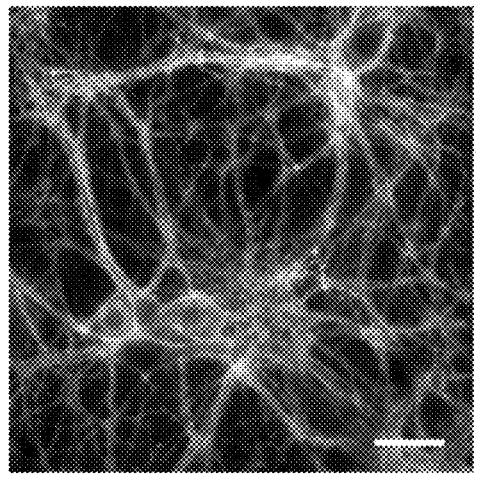
Figure 9D:
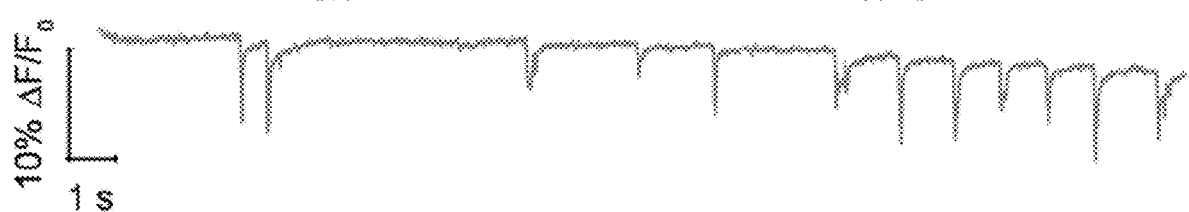
Figure 12:
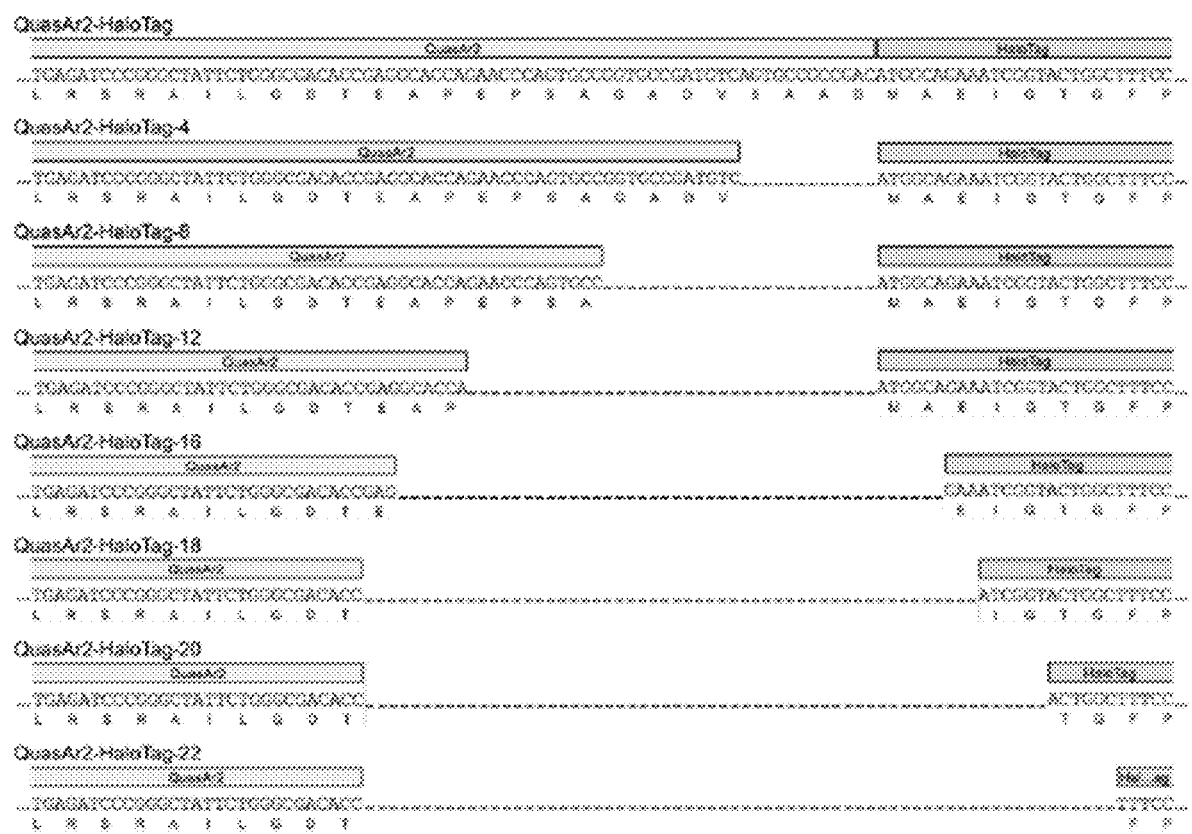
FIG. 12 includes the nucleotide sequence ((SEQ ID NOS: 25, 27, 29, 31, 33, 35, 37, 39) and amino acid sequence (SEQ ID NOS: 26, 28, 30, 32, 34, 36, 38, 40) of QuasAr2-HaloTag linker length truncations, with sequence features annotated.
Figure 14A:
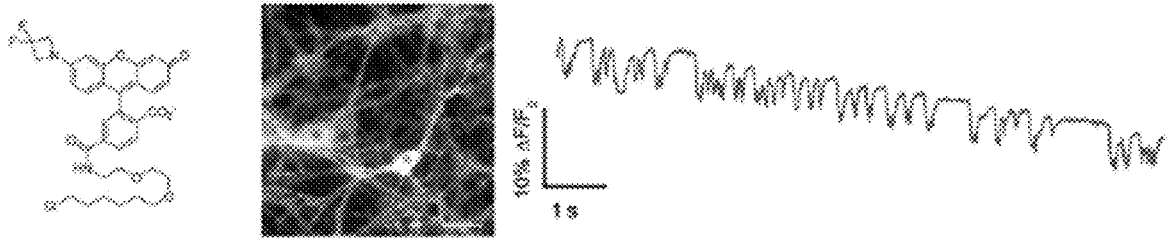
FIG. 14A includes Left: Chemical structure of JF505-HaloTag ligand, Middle: fluorescence image of hippocampal neurons in culture expressing QuasAr2-HaloTag-16 labeled with JF503. Right: Fluorescence trace over time showing voltage-dependent fluorescence changes resulting from spontaneous action potentials of the neurons.
Figure 14B:
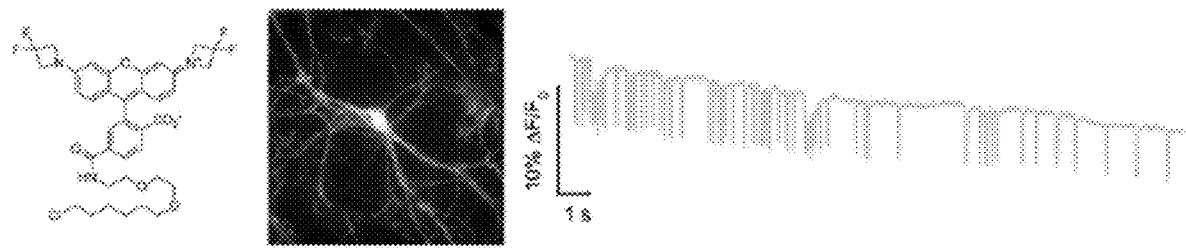
FIG. 14B includes (B) Left: Chemical structure of JF525-HaloTag ligand, Middle: fluorescence image of hippocampal neurons in culture expressing QuasAr2-HaloTag-16 labeled with JF525. Right: Fluorescence trace over time showing voltage-dependent fluorescence changes resulting from spontaneous action potentials of the neurons.
Figure 14C:
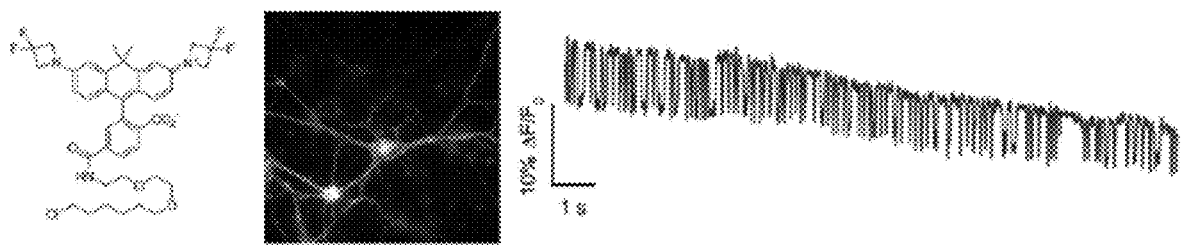
FIG. 14C includes, Left: Chemical structure of JF585-HaloTag ligand, Middle: fluorescence image of hippocampal neurons in culture expressing QuasAr2-HaloTag-16 labeled with JF585. Right: Fluorescence trace over time showing voltage-dependent fluorescence changes resulting from spontaneous action potentials of the neurons.
Figure 14D:
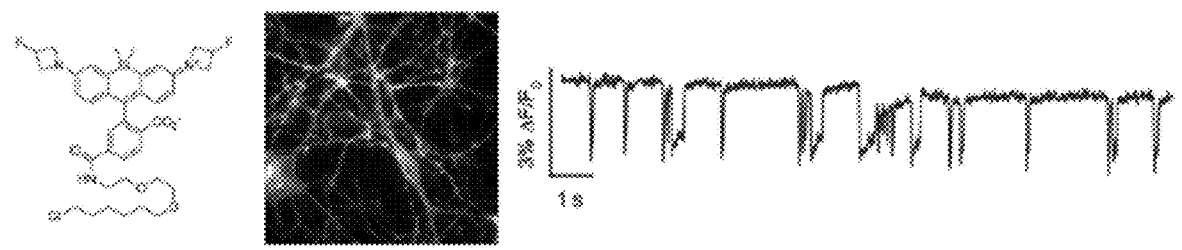
FIG. 14D includes, Left: Chemical structure of JF635-HaloTag ligand, Middle: fluorescence image of hippocampal neurons in culture expressing QuasAr2-HaloTag-16 labeled with JF635. Right: Fluorescence trace over time showing voltage-dependent fluorescence changes resulting from spontaneous action potentials of the neurons. Scale bar: 20 μm.
Figure 42A:
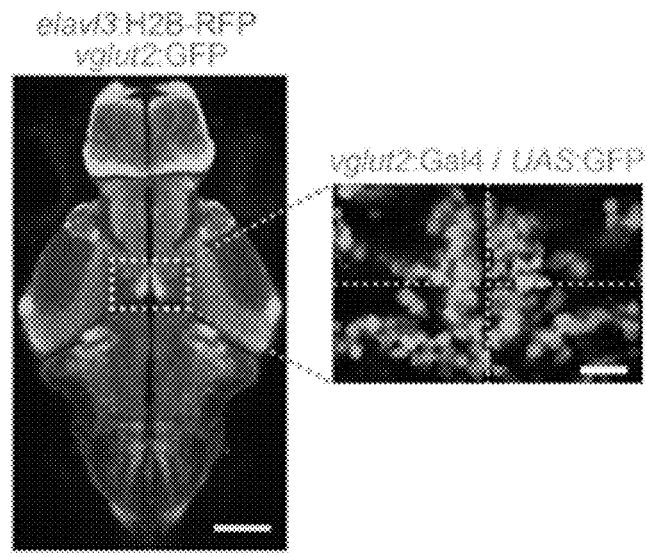
FIGS. 42A-42E relates to recording and analyzing Voltron data in behaving zebrafish.
Figure 42B:
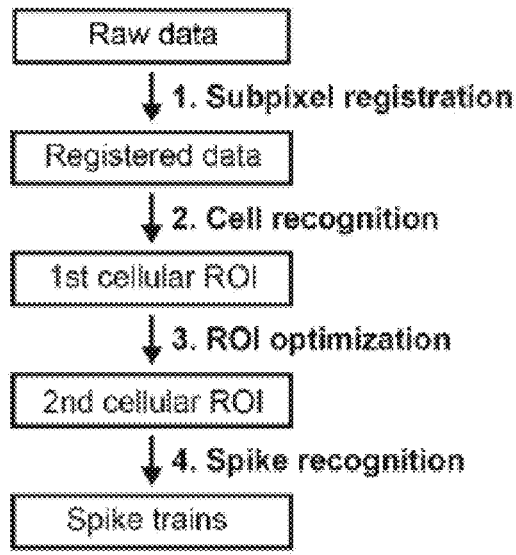
Figure 42C:
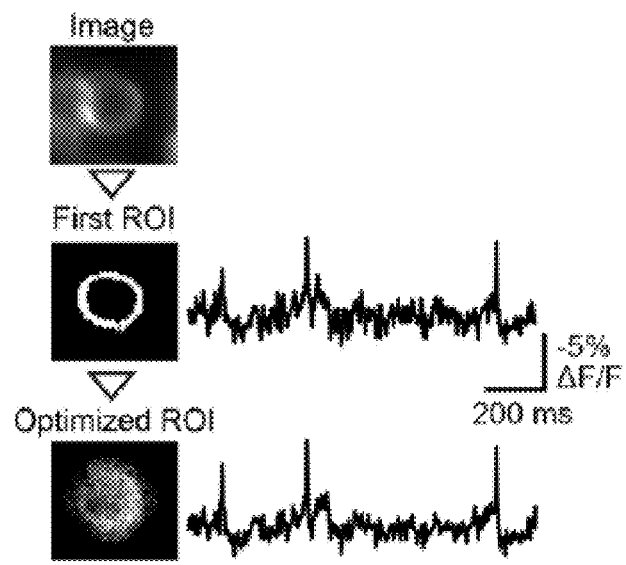
Figure 42D:
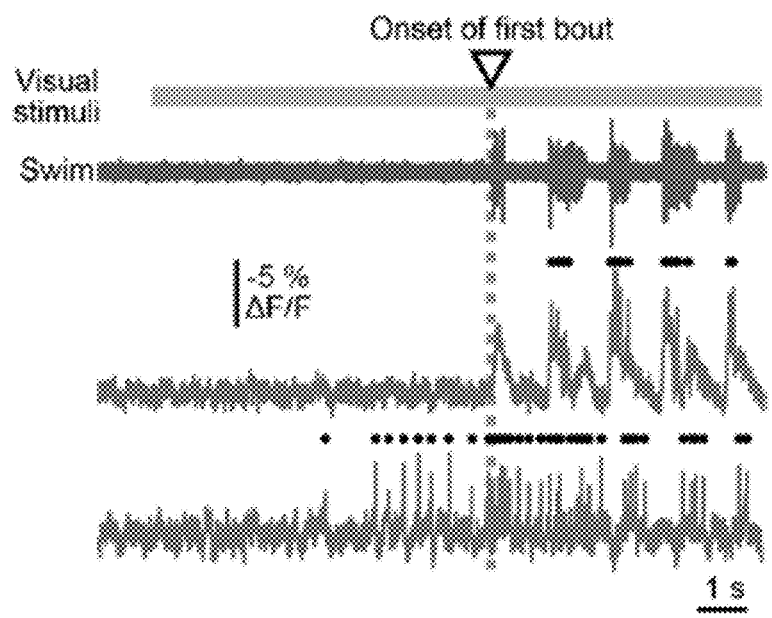

It was first verified that Voltron could detect action potentials and subthreshold voltage signals in live zebrafish using several different colors of dye ligands (FIGS. 21 and 41). Voltron$_{525}$ as then used to monitor neural spiking patterns during visual-motion-induced swims (FIG. 8A). Activity patterns from 179 neurons were recorded across 43 fish in a motor-sensory nucleus in the tegmental area of the midbrain (FIGS. 8B, 42A), yielding data on subthreshold membrane voltage modulation as well as automatically-detected spike times (FIGS. 8C, 42B-C). Neuron populations were found with different temporal activity patterns, including neurons whose firing rate increased ~1 second before the fish started swimming (FIG. 42D-E, 'Ramp'), neurons whose firing rate was suppressed each time the fish swam (FIG. 8D, 'Off'), and neurons that fired each time the fish swam (FIG. 8D, 'Onset' and 'Late'). Of the latter types, some fired just before swimming (~20 ms before swim onset, 'Onset') and others fired just after swimming (~10 ms after swim onset, 'Late'). There was a change in subthreshold voltage that preceded these firing-rate changes by tens of milliseconds (FIG. 8D). The neuron types were spatially intermingled within this midbrain nucleus (FIG. 8E-F). The existence of neurons that fired before swimming and neurons that fired after swimming suggests that this nucleus both partakes in the generation of swim bouts and receives an efference copy of motor output (FIG. 8G). Thus, Voltron allows for the dissection of population motor coding and sensorimotor integration circuits in ways that neither single-cell electrophysiology nor population calcium imaging can.

Figure 22A:
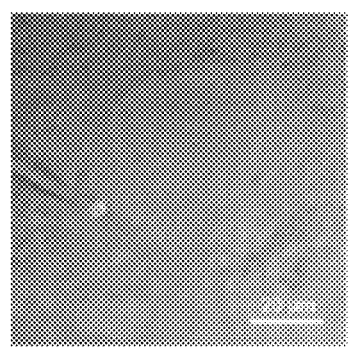
FIGS. 22A-22F relate to recording spontaneous dopamine neuron activity in living adult flies using Voltron imaging and whole-cell patch clamp.
Figure 22B:
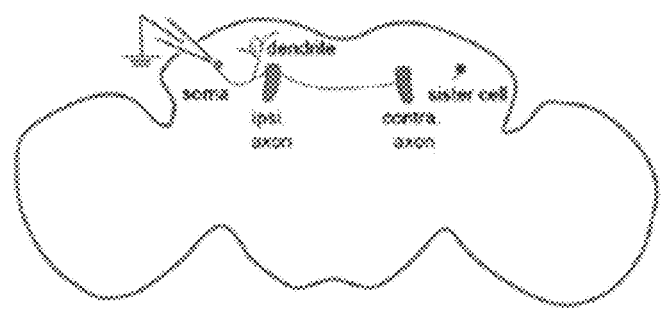
Figure 22C:
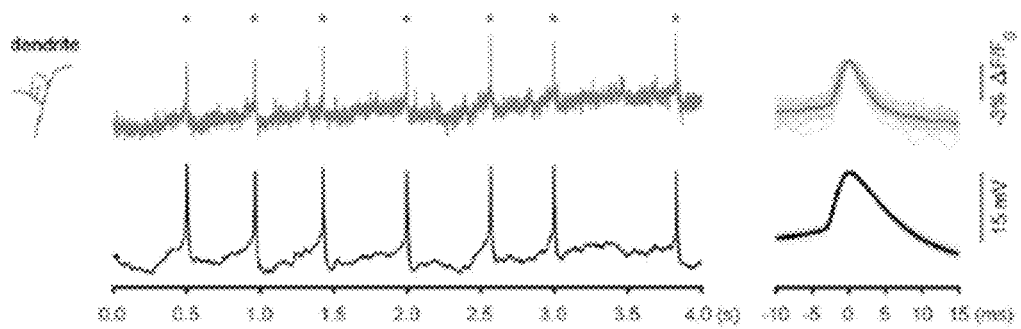
Figure 22D:
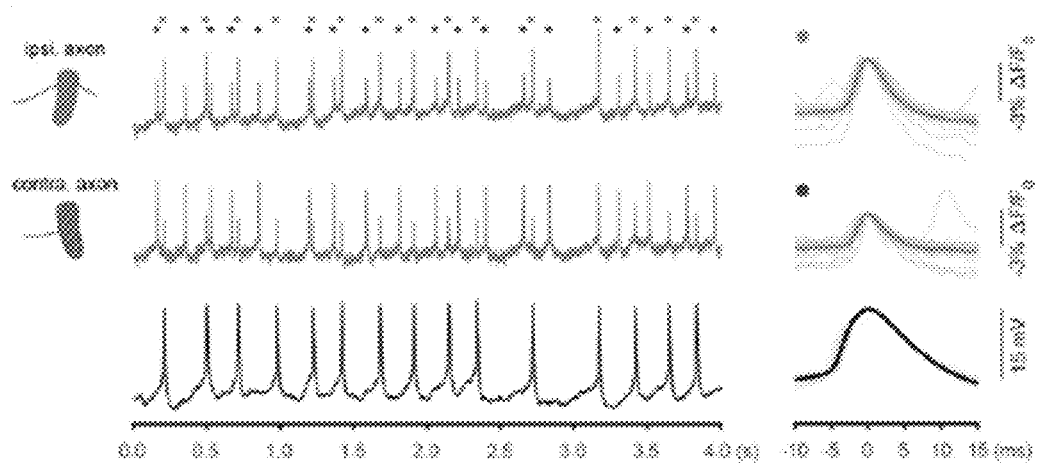
Figure 22E:
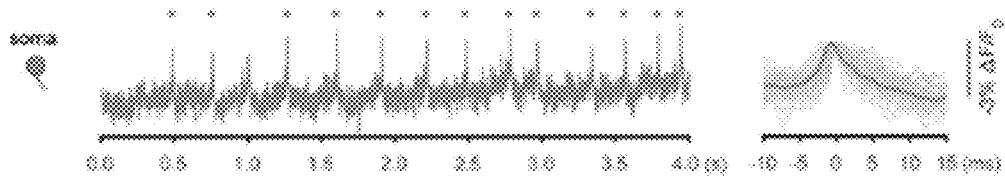
Figure 22F:
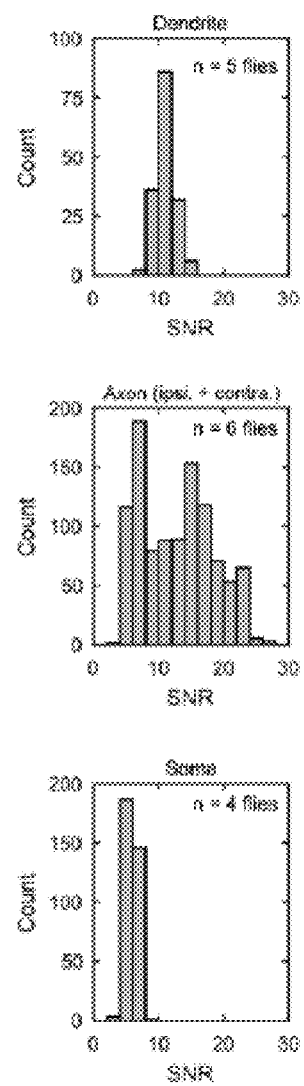
Figure 23:
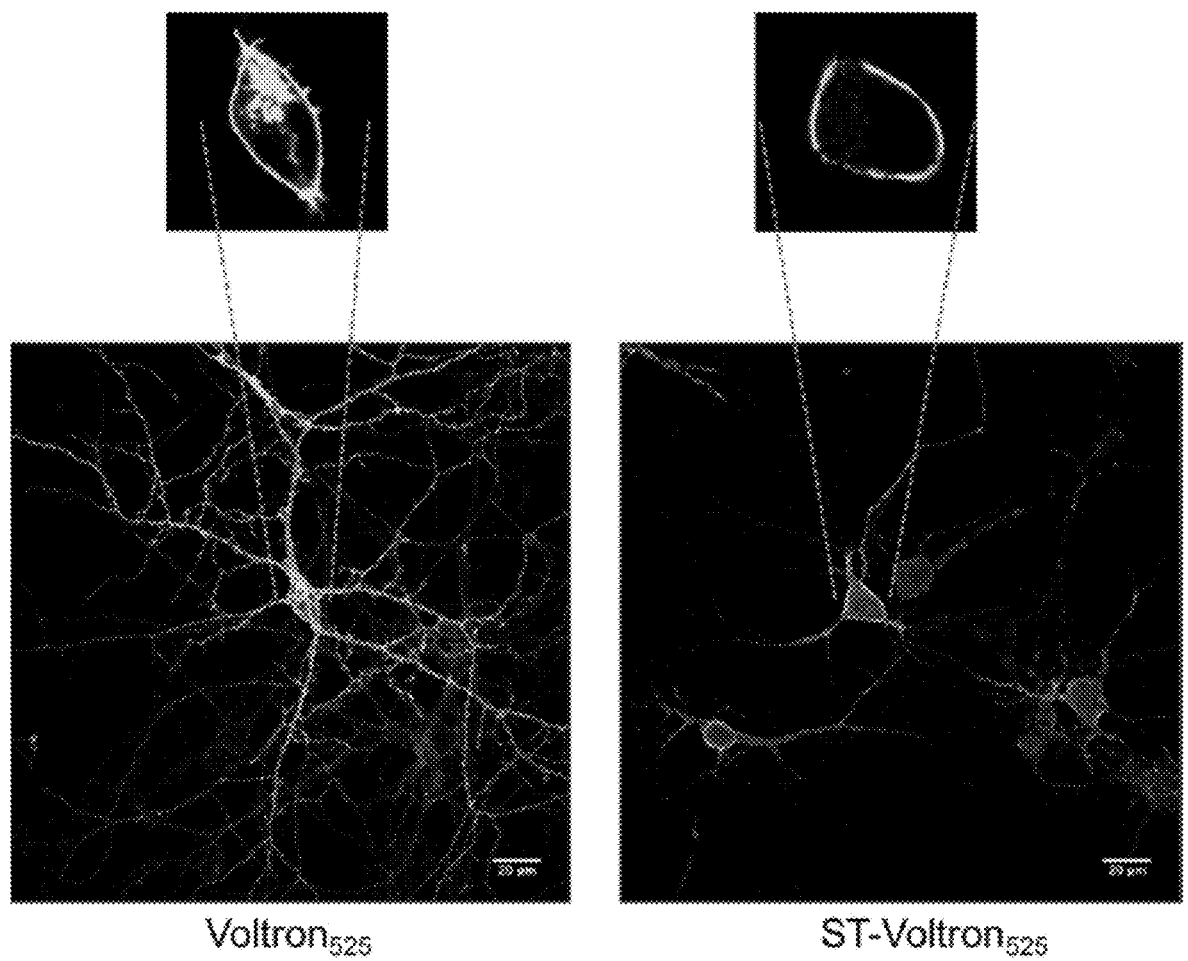
FIG. 23 includes maximum intensity projections of confocal stacks of neurons in culture (bottom panels) expressing Voltron (left) or soma-targeted Voltron (right) and labeled with $_{JF525}$. Zoom in on neuron soma showing cell membrane labeling and intracellular labelling, presumably endoplasmic reticulum (top panels). The soma localization tag limits labeling of processes and improves trafficking of Voltron to the cell membrane.

Finally, Voltron was tested in adult *Drosophila* in vivo by expressing the protein in a pair of dopaminergic neurons, one in each brain hemisphere, which innervate a single compartment in the mushroom body. Strong spiking signals were detected from axons and dendrites of these neurons using Voltron549 (FIGS. 5K, 22), which matched spikes detected using electrophysiology. In some neuronal cell types in *Drosophila*, calcium indicators located in the cell body have failed to exhibit fluorescence changes even under conditions where high spike rates are expected (27). However, spikes were clearly detectable when imaging from the soma of dopamine neurons with Voltron (FIG. 22E). Remarkably, spikes could be clearly distinguish from the two neurons based on the amplitude of the spiking signals even when imaging from neuropil where their axons overlap extensively, likely because each bilaterally-projecting cell contributes a denser innervation of the mushroom body in the ipsilateral hemisphere (FIG. 22D).

Combining the molecular specificity of genetically encoded reagents with the superior photophysics of chemical dyes is an established path to improved imaging reagents (14). However, previous attempts to create hybrid small-molecule:protein indicators using a variety of approaches have not been successful for in vivo imaging (28). Here, a modular sensor scaffold was engineered where the targeting and sensor domains are genetically encoded and only the fluorophore and its protein-binding anchor are synthetic. The resulting chemigenetic indicator, Voltron, exhibits substantially increased photon output, enabling in vivo voltage imaging of many more neurons over longer times—approximately $10^2$ more neuron-minutes than other sensors. This improvement enables imaging experiments that reveal how the precise electrical dynamics of neuronal populations orchestrate behavior over different time scales.

Example 3

Reagent availability: Voltron plasmids pCAG-Voltron (plasmid #), pCAG-Voltron-ST (plasmid #), pAAV-hsyn-Voltron (plasmid #), pAAV-hsyn-flex-Voltron (plasmid #), pAAV-hsyn-flex-Voltron-ST (plasmid #), pTo12-Huc-Voltron (plasmid #), pTo12-Huc-Voltron-ST (plasmid #), p10XUAS—IVS-Syn21-Voltron-p10 (plasmid #), and p13XLexAOP2-IVS-Syn21-Voltron-p10 (plasmid #) have been deposited at Addgene. AAV-hsyn-flex-Voltron-ST virus is available from Addgene (addgene.org).

Transgenic *Drosophila* stocks for UAS-Voltron and LexAop-Voltron in multiple landing sites are available from the Bloomington *Drosophila* Stock Center (flystocks.bio.indiana.edu).

UAS:Voltron transgenic zebrafish are available from the Ahrens Lab at Janelia Research Campus, and from ZIRC (zebrafish.org).

Cloning: Generally, cloning was done by restriction enzyme digest or PCR amplification of plasmid backbones, PCR amplification of inserted genes, and isothermal assembly to combine them, followed by Sanger sequencing to verify DNA sequences. The genes for QuasAr1 and QuasAr2 (7) were amplified from Addgene plasmids 51629 and 51692. The gene for Ace2N was synthesized (Integrated DNA Technologies) with mammalian codon optimization (11). The soma localization tag was synthesized (Integrated DNA technologies) through adding a 66 amino acid domain from the Kv2.1 potassium channel (residues 536 to 600) (22). This domain directs localization to clusters at the soma and proximal dendrites (23). Linker length variants were generated by Quikchange site-directed mutagenesis (Agilent). For expression in primary neuron cultures, sensors were cloned into a pcDNA3.1-CAG plasmid (Invitrogen) at the NheI and HindIII sites. For expression in zebrafish, Voltron and Voltron-ST were cloned into the pTol2-HuC vector (for pan-neuronal expression) at the AgeI restriction sites and into the pT2-Tbait-UAS vector (for Gal4-dependent expression) at the EcoRI and PspXI restriction sites. For expression in *Drosophila melanogaster*, Voltron was cloned into p10XUAS-IVS-Syn21-p10 at the XhoI and XbaI sites. For Cre-dependent expression in mouse brain, Voltron and Voltron-ST were cloned into a pAAV-hsyn-flex plasmid at the BamHI restriction sites. The DNA and amino acid sequences of Voltron and Voltron-ST are given in FIG. 8. Plasmids and maps are available from Addgene.

In Vitro Spectroscopy of Fluorophores:

To create JFdye-HaloTag conjugates, 5 µM JFdye HaloTag ligand and 10 µM HaloTag protein were incubated in 10 mM HEPES with 0.1 mg/ml CHAPS at pH 7.3 at 4° C. overnight. Completeness of dye-binding was determined by titrating HaloTag protein (2.5 µM to 12.5 µM) with fluorogenic $_{JF635}$ HaloTag ligand (5 µM) in overnight reactions and then measuring absorbance at 640 nm. Additionally, thin-layer chromatography was performed on a reaction of 5 µM $_{JF549}$ with 7.5 µM HaloTag, which showed >95% of the dye was bound to HaloTag. Fluorescent proteins sfGFP (parent fluorophore of ASAP2f) and mNeonGreen (parent fluorophore of Ace2N-mNeon) were purified from *E. coli*. All photophysical measurements used either 1 µM solutions of JFdye-HaloTag conjugate in 10 mM HEPES buffer at pH 7.3, or 1-3 µM purified fluorescent proteins in 100 mM MOPS buffer at pH 7.2. Absorbance measurements were performed on a UV-VIS spectrometer (Lambda 35, Perkin Elmer). Fluorescence excitation and emission spectra were measured using a fluorimeter (LS55, Perkin Elmer). Quantum yield measurements were performed using an integrating-sphere spectrometer (Quantaurus, Hamamatsu). Extinction coefficients for the JFdye-HaloTag conjugates were determined from peak absorbance at known concentration of JF dye. Extinction coefficients for fluorescent proteins were determined by the alkali denaturation method, using the extinction coefficient of denatured FP equal to that of denatured GFP (ε=44000 at 447 nm) (29).

Fluorescence Microscopy for Photobleaching:

To investigate photobleaching of fluorophores in solution, aqueous droplets of JFdye-HaloTag conjugates or fluorescent proteins were made by aliquoting 5 µl of a fluorophore solution into 45 µl of 1-Octanol and agitating by tapping or brief vortexing. 5 µl of the emulsion mixture was sandwiched between a pre-silanized glass slide and a glass coverslip to disperse isolated microdroplets of dye-conjugates or proteins for fluorescence microscopy. To perform fluorescence microscopy, microdroplets were continuously illuminated using an inverted microscope (Eclipse Ti2, Nikon) with a 40× (N.A.=1.3, Nikon) oil immersion objective (PLAN Flour, Nikon). Fluorescence excitation was achieved using an LED (SpectraX Light engine, Lumencor) with the following filter sets for the respective fluorophores: For sfGFP, mNeonGreen and $_{JF505}$ (FITC5050A cube (semrock): FF02-475/50, FF506-Dio3, FF01-540/50); for $_{JF525}$ (510/25 excitation filter, T525lprx dichroic(Chroma), 545/40 emission filter); for $_{JF549}$ (Cy34040C cube (semrock): FF01-531/40, FF562-Dio3, FF01-593/40); for $_{JF585}$ (49912 cube (Chroma): ZET594/10×, ZT594rdc, ET610lp) and for $_{JF635}$ (89000 cube (Chroma), ET645/30×, 89100bs, ET705/72m). Power at the imaging plane for each filter set was set to 12 mW determined with a microscope slide power sensor (S170C, Thorlabs). From measurement of the sample area illuminated, the irradiance was determined to be 40 mW/mm². In order to calculate the excitation rate ! (photons absorbed/sec), the LED excitation spectrum was measured after the objective for each filter set using a fiber spectrometer (QE65000, Ocean Optics). Fluorescence images were collected using a scientific CMOS camera (ORCA-Flash 4.0, Hamamatsu) and image acquisition was performed using HCImage Live (Hamamtsu). Each sample was bleached continuously for 10 min. and images were acquired at 1 Hz. Fluorescence intensity from each droplet was obtained after background subtraction using ImageJ software.

To investigate photobleaching of GEVIs in cells, Voltron, Ace2N-mNeon, and ASAP2f were transfected in hippocampal neurons extracted from P0 to P1 Sprague-Dawley rat pups. After transfection, hippocampal neurons were plated onto 35 mm glass-bottom dish (MatTek) coated with poly-D-lysine (Sigma) and cultured for 8-10 days in NbActiv4 medium (BrainBits). For labeling Voltron-expressing neurons, cells were incubated with a 100 nM JFdye-HaloTag ligand for 30 minutes. The same setup and procedure used with droplets above was used to measure photobleaching of GEVIs in cells.

Photobleaching Analysis:

The bleaching profile of individual cells or droplets was fit to either a single or double exponential function of the form $F(t)=F_0(A_1 e^{-t/\tau_1}+A_2 e^{-t/\tau_2})$ to obtain time constants $\tau_1$, $\tau_2$ and weighting $A_1$, $A_2$. Data fitting was performed in MATLAB (MathWorks) and Origin (OriginLab), and goodness of fit assessed by minimal residual sum of errors or minimal $x^2$. To quantify photobleaching across fluorophores requires knowledge of the excitation rate W and the fluorescence quantum yield $\phi_f$. The excitation rate W was computed (30) from integration over the wavelength dependence of the product of measured extinction coefficient and irradiance spectral profile. The fluorescence quantum yield for the GEVIs is not directly measured, and assumed to be the same as that measured for the parent fluorophores. Three quantities characterizing bleaching were calculated for each fluorophore or GEVI. These are (i) the calculated time $t_{1/2}$ for the fluorescence rate to drop to ½ its initial value, scaled by the excitation rate to achieve an initial fluorescence rate of $10^3$ photons/sec (30), (ii) the total number of photons emitted before photobleaching $N_p$ (the photon budget), and (iii) the photobleaching probability $P_b$. These are per-molecule quantities averaged over the ensemble of molecules in each droplet or cell. The characteristic time $t_{1/2}$ was found by determining from the raw data, the time tin, for 50% reduction in fluorescence $F(t_{raw})/F_0=0.5$, from which $$t_{1/2} \equiv t_{raw} \frac{\phi_f W}{10^3 s^{-1}}$$

where $\phi_f$ is the fluorescence quantum yield and W is the excitation rate. To determine $N_p$, the fit function F(t) was integrated over time, where initially $F_0 \equiv \phi_f W$, $$N_p = \phi_f W(A_1 \tau_1 + A_2 \tau_2) = \phi_f W \langle \tau_b \rangle$$

where $\langle \tau_b \rangle$ is the amplitude-weighted lifetime (31, 32) $\langle \tau_b \rangle = A_1 \tau_1 + A_2 \tau_2$. The photobleaching probability Pb, based on rate equation models where bleaching proceeds from singlet or triplet states, is inversely related to the total number of fluorescent photons emitted, $N_p = \phi_f/P_b$ (33, 34), or $$P_b = 1/W \langle \tau_b \rangle$$

Of the three photobleaching quantities above, the photobleaching probability is most rigorous as it is independent of the fluorescence quantum yield.

Single-Molecule Imaging and Analysis:

Hippocampal neurons extracted from P0 to 1 Sprague-Dawley rat pups were transfected with Ace2N-mNeon and Voltron plasmids by electroporation (Lonza, P3 Primary Cell 4D-Nucleofector X kit) according to the manufacturer's instruction. After transfection, hippocampal neurons were plated onto 25 mm ultra-clean cover glasses coated with poly-D-lysine (Sigma) and cultured for 9 days in NbActiv4 medium (BrainBits).

To label Voltron-expressing neurons, cultures were incubated with 2 nM JF549 HaloTag ligand for 15 mins, then transferred to the Attofluor cell chamber (Thermo Fisher Scientific) and supplemented with Tyrode's solution (140 mM NaCl, 5 mM KCl, 3 mM $CaCl_2$, 1 mM $MgCl_2$, 10 mM HEPES, 10 mM glucose, pH 7.35). Single-molecule imaging was performed on a Nikon Eclipse TiE Motorized Inverted microscope equipped with a 100× oil-immersion objective lens (N.A.=1.49, Nikon), 488/561 nm laser lines, an automatic TIRF illuminator, a perfect focusing system and a Tokai Hit environmental control (humidity, 37° C., 5% $CO_2$). Excitation light was passed through a 405/488/561/647 nm laser quad band filter set filter that allows 488 nm or 561 nm light through to the sample (Chroma set number 89902). Emission from sample was collected through the same filter set then passed through a splitter (dichroic mirror: T560Ipxr (Chroma), with perpendicular emission filters: ET525/50m (Chroma) and ET605/52m (Chroma)) to split green and red fluorescence. The light was then collected onto two EMCCD cameras (iXon Ultra 897, Andor).

Samples were first pre-bleached to achieve sparse single molecule detections. The laser power output was calibrated for 488 nm (to image Ace2N-mNeon) and 561 nm (to image Voltron549) to 17.5 mW with a Si Sensor power meter (Thorlabs, PM202). Images were acquired under TIRF imaging mode with 10 Hz frame rate. 1000 frames were recorded for each imaging area and 10 imaging areas were collected for each indicator. For image analysis, single molecules lasting for at least 3 frames were manually selected. The brightness and mean time to photobleach of these molecules were determined with ImageJ (1.51n) quantification tools to assess the single-molecule photo-stability of Ace2N-mNeon and Voltron549.

Fluorescence Imaging in Primary Neuron Culture:

All culture imaging was performed in imaging buffer containing the following (in mM): 145 NaCl, 2.5 KCl, 10 glucose, 10 HEPES, pH 7.4, 2 CaCl2, 1 MgCl2. Wide-field imaging was performed on an inverted Nikon Eclipse Ti2 microscope equipped with a SPECTRA X light engine (Lumencore), 40× oil objective (NA=1.3, Nikon), and imaged onto a scientific CMOS camera (Hamamatsu ORCA-Flash 4.0). A FITC filter set (475/50 nm (excitation), 540/50 nm (emission), and a 506LP dichroic mirror (FITC-5050A-000; Semrock)) was used to image mNeonGreen, ASAP1, and ASAP2f. A Cy3 filter set (531/40 nm (excitation), 593/40 nm (emission), and a 562LP dichroic mirror (Cy3-4040C-000; Semrock)) was used to image Volton549. A custom filter set (510/25 nm (excitation), 545/40 nm (emission), and a 525LP dichroic mirror (Semrock)) was used to image Voltron525. A quad bandpass filter (set number: 89000, Chroma) was used along with the appropriate color band from the SPECTRA X light source to image Voltron505, Voltron585 and Voltron635. For time-lapse imaging during field stimulation or simultaneous electrophysiology measurements, neurons were imaged at 200-3200 Hz depending on the experiment. The LED light power output at the imaging plane was measured with a Si Sensor power meter (Thorlabs, PM202) for each imaging experiment.

For quantifying brightness of voltage indicators expressed in neurons, the excitation spectrum was measured after the objective for each excitation filter used using a spectrometer (QE65000, Ocean Optics). The spectrum was then integrated to get the excitation rate ! as described above (see section: Photobleaching analysis). As with the photobleaching experiments, when the data sets for the light spectrum and extinction coefficient are taken at incommensurate wavelengths, interpolation was used to re-cast the wavelengths of one of the data sets using MATLAB (MathWorks). The fraction of collected fluorescence using the emission filter compared to the total emission spectrum of the fluorophore was calculated. Illumination intensity of 20 mW/mm$^2$ at imaging plane was used for all indicators. Fluorescence images were acquired from five independent transfections for each construct for brightness measurements. Using MATLAB (MathWorks), fluorescence intensity was then corrected using the calculated excitation rates (!), fraction of emission collected, and quantum efficiency of the Hamamatsu ORCA-Flash 4.0 camera over the emitted wavelengths for ASAP2f, Ace2N-mNeon, Voltron525 and Voltron549. Values were calculated relative to ASAP2f.

Simultaneous Field Stimulation and Fluorescence Imaging in Primary Neuron Cultures:

A stimulus isolator (A385, World Precision Instruments) with platinum wires was used to deliver field stimuli (50V, 83 Hz, 1 ms) to elicit action potentials in cultured neurons as described previously (35). The stimulation was controlled using an Arduino board and timing was synchronized with fluorescence acquisition using the Nikon Elements software and a national instruments PXI-6723 board.

Simultaneous Electrophysiology and Fluorescence Imaging in Primary Neuron Culture:

All imaging and electrophysiology measurements were performed in imaging buffer (see "Fluorescence imaging in primary neuron culture" section) adjusted to 310 mOsm with sucrose. For voltage clamp measurements, 500 nM TTX was added to the imaging buffer to block sodium channels. Synaptic blockers (10 µM CNQX, 10 µM CPP, 10 µM GABAZINE, and 1 mM MCPG) were added to block ionotropic glutamate, GABA, and metabotropic glutamate receptors (35).

Filamented glass micropipettes (Sutter Instruments) were pulled to a tip resistance of 4-6 MΩ. Internal solution for current clamp recordings contained the following (in mM): 130 potassium methanesulfonate, 10 HEPES, 5 NaCl, 1 MgCl2, 1 Mg-ATP, 0.4 Na-GTP, 14 Tris-phosphocreatine, adjusted to pH 7.3 with KOH, and adjusted to 300 mOsm with sucrose. Internal solution for voltage clamp recordings contained the following (in mM): 115 cesium methanesulfonate, 10 HEPES, 5 NaF, 10 EGTA, 15 CsCl, 3.5 Mg-ATP, 3 QX-314, adjusted to pH 7.3 with CsOH, and adjusted to 300 mOsm with sucrose.

Pipettes were positioned with a MPC200 manipulator (Sutter Instruments). Whole cell voltage clamp and current clamp recordings were acquired using an EPC800 amplifier (HEKA), filtered at 10 kHz with the internal Bessel filter, and digitized using a National Instruments PCIe-6353 acquisition board at 20 kHz. Data were acquired from cells with access resistance <25 MΩ. WaveSurfer software was used to generate the various analog and digital waveforms to control the amplifier, camera, light source, and record voltage and current traces. For fluorescence voltage curves, cells were held at a potential of −70 mV at the start of each step and then 1 second voltage steps were applied to step the potential from −110 mV to +50 mV in 20 mV increments. For current-clamp recordings to generate action potentials, current was injected (20-200 pA for 1-2 s) and voltage was monitored.

Imaging Parvalbumin (PV) Neurons in Mouse Hippocampus:

Hippocampal PV neuron imaging was performed using adult PV-Cre mice (JAX 008069). Imaging window was implanted using procedures similar to those described in Dombeck et. al. (36). In short, a circular craniotomy (3 mm diameter) was made centered at 2.0 mm caudal and 2.0 mm lateral to bregma. The surface of CA1 was exposed by gently removing the overlying cortex with aspiration. AAV2/1-syn-Flex-Voltron-ST virus was diluted to $1.9 \times 10^{12}$ GC/ml and injected at three locations (separated by 800 µm, 30 nl per location) 200 µm from CA1 surface. The imaging window (constructed by gluing a 3 mm diameter cover glass to a stainless steel cannula of 3 mm diameter and 1.5 mm height) was placed onto the hippocampus and glued to the skull using super-bond C&B (Sun Medical). A titanium head bar was glued to the skull for head fixation during imaging.

Imaging experiments started 4-5 weeks after surgery. JF525-HaloTag ligand (100 µl, 1 mM) was delivered using retro-orbital injection (37) 1 day before imaging. Labeled PV neurons (25-195 µm deep) were illuminated using a green LED (M530L3, Thorlabs) through an excitation filter (FF02-520-28, Semrock). A field aperture (diameter ~1 mm) was used to limit illumination to a circular area (~160 µm diameter at sample) around the cell of interest. The excitation intensity was ~25 mW/mm$^2$ at the sample plane. JF525 fluorescence was collected using a 16×0.8 NA objective (Nikon), separated from excitation light using a dichroic mirror (540lpxr, Chroma) and an emission filter (FF01-575-59, Semrock), and imaged onto a sCMOS camera (Zyla 4.2 plus, Andor). Images were collected at 3858 Hz.

Figure 24:
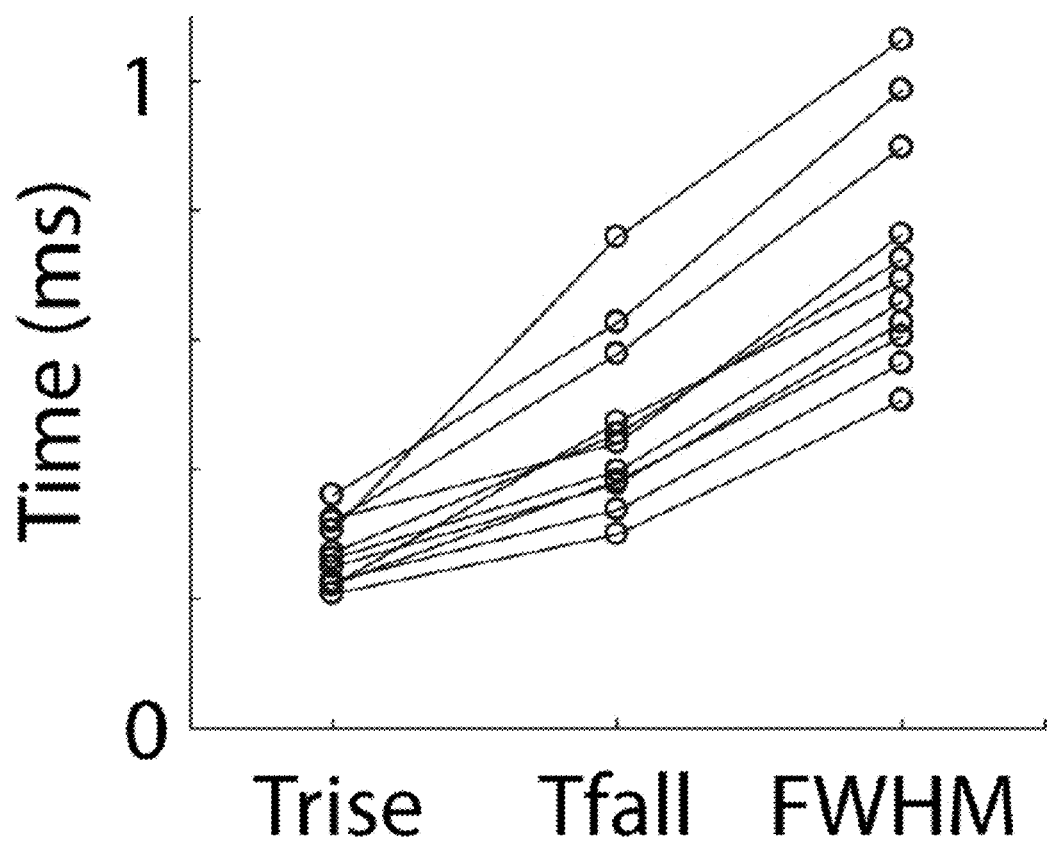
FIG. 24 include an analysis of membrane voltage dynamics in hippocampal parvalbumin (PV) neurons of awake mouse. The half rise time, half decay time, and full width half maximum of the spike waveforms shown in FIG. 6G.
Figure 25:
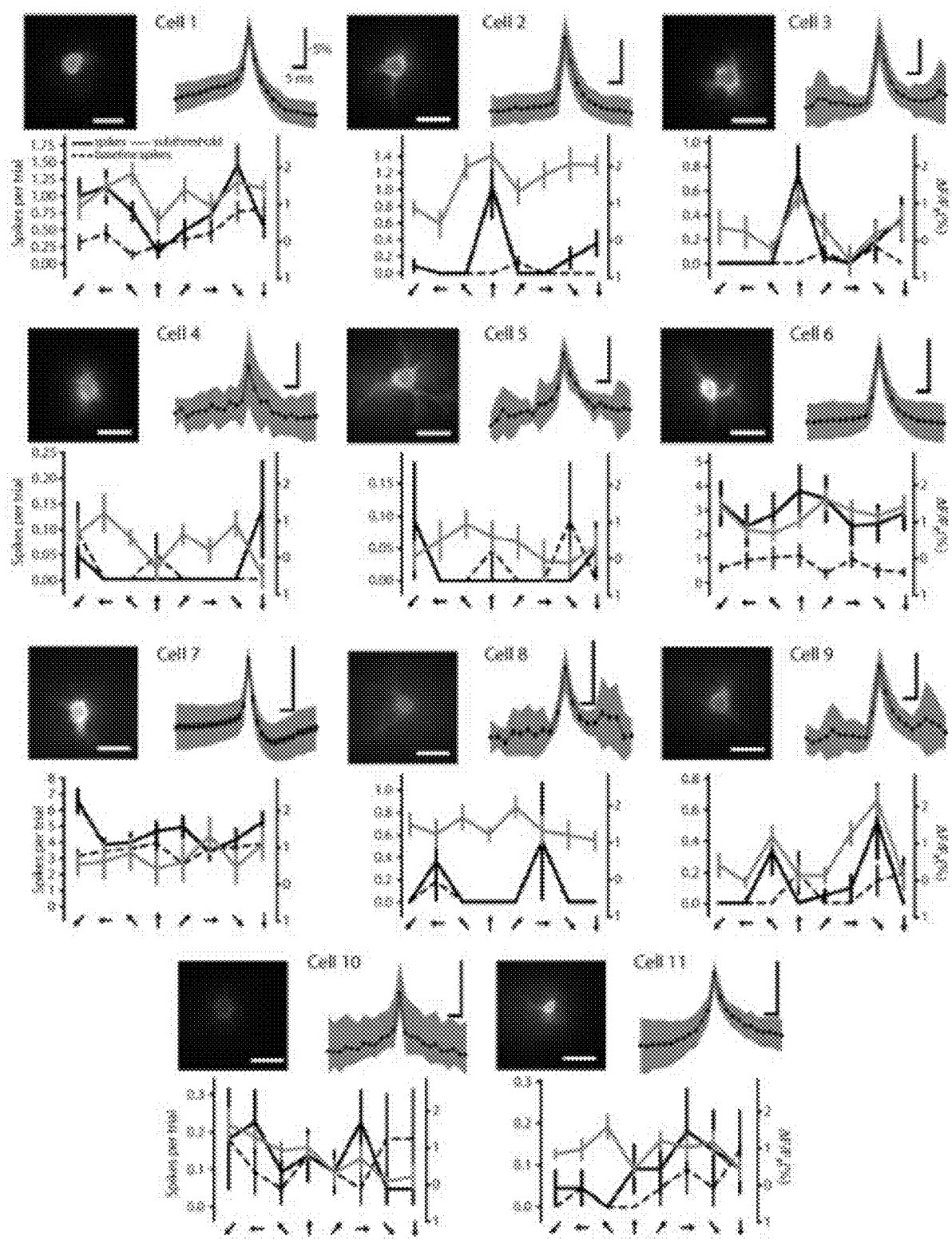
FIG. 25 includes results of orientation tuning of 11 pyramidal cells at depths of 100-250 μm in visual cortex of two C57B6 mice expressing Voltron525 under the control of CamKII-Cre. Each of the 11 cell panels includes fluorescence image of cell (top left, scalebar: 20 μm), average of all spikes in session (top right, scalebars: −5% ΔF/F, 5 ms) and orientation tuning to full-frame drifting gratings of neurons (bottom), displayed from number of spikes during trials (solid black line), number of spikes during preceding intertrial intervals (dashed black line), and subthreshold ΔF/F0 (right y-axis, solid gray line) after low-pass filtering traces using a 10-point median filter.
Figure 26A:
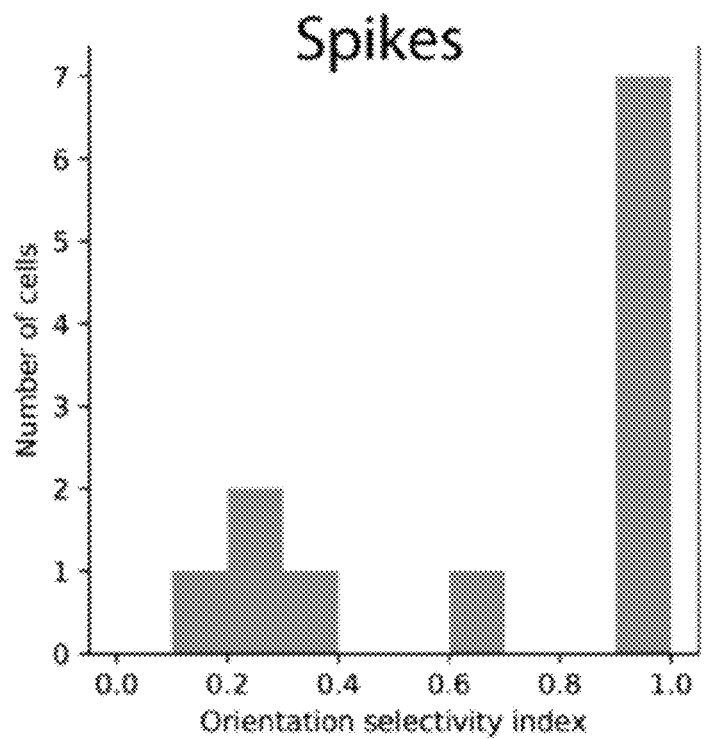
FIG. 26A includes a histogram of orientation selectivity index calculated from number of spikes in trial.
Figure 26B:
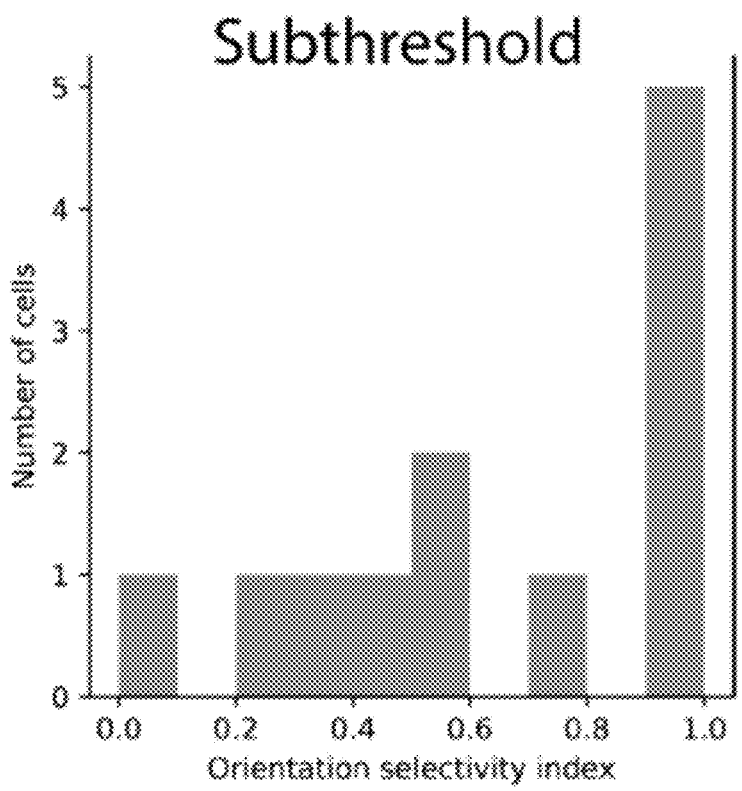
FIG. 26B includes a histogram of orientation selectivity index calculated from subthreshold membrane potential.

Image analysis was performed in MATLAB. Brain movement was corrected using ImageJ plugin TurboReg (38). A constant camera offset (measured by taking images without illumination) was subtracted from each frame. The fluorescence of each cell was measured by averaging pixels within a region of interest covering the cell body. To detect action potentials (AP), slow baseline fluctuation (measured by moving average with 20 ms window) was first subtracted from the raw fluorescence trace. The timings of AP events were detected as local minima of the baseline subtracted trace with amplitudes larger than four times the standard deviation and peaks separated by at least 5 ms from each other. To quantify AP waveform, 5 ms segments of fluorescence signal around the detected peaks were taken from the raw fluorescence trace, peak aligned and then averaged. The AP amplitude was measured as percent change (F-F0)/F0 with F0 being the fluorescence baseline averaged over a time window 2.5 ms to 1.5 ms before the peak of an individual AP. The rise time, decay time, and the width of the AP waveform was measured using the averaged trace for each cell. The rise time was the time from half the amplitude to the peak. The decay time was the time from the peak to half the amplitude in the decay phase. The width (full width at half maxima, FWHM) was the sum of rise and decay time. This is shown in FIG. 24.

Imaging Mouse Cortex:

NDNF-Cre mice (JAX 28536) were used for imaging Layer 1 neurons (2 females, 1 male; 100-120 days old at the time of the window surgery). C57BI/6NCrl (Charles River Laboratories) mice were used for imaging Layer 2/3 neurons (2 females; 100-120 days old). NDNF-Cre mice were injected with 30 nl of AAV2/1-syn-FLEX-Voltron-ST (titer, $2*10^{12}$ GC/ml) at 8-12 injection sites 200 µm deep (injection rate, 1 nl/s). C57BI/6NCrl mice were injected with 30 nl mixture of AAV2/1-syn-FLEX-Voltron-ST (titer, $2*10^{12}$ GC/ml) and AAV9-CamKIIa-Cre (titer, $10^8$ GC/ml) 250 µm deep. AAV2/1-syn-FLEX-Voltron without soma targeting signal was injected in additional NDNF-Cre mice (titer, 2*1012 GC/ml)) and C57BI/6NCrl mice (AAV2/1-syn-FLEX-Voltron (titer, $2*10^{12}$ gc/ml)+AAV9-CamKIIa-Cre (titer, $10^8$ gc/ml)). This resulted in diffuse fluorescence and was not used for imaging experiments shown in this manuscript.

Cranial windows (4 mm diameter) were implanted over the injection sites in visual cortex (centered on −2.5 mm lateral, +0.5 mm anterior from lambda). Four to nine weeks later JF525 dye was injected into the retro-orbital sinus. Imaging was done 2 to 6 days after dye injection, with subsequent dye injections and imaging 1 to 6 weeks after the first imaging session. To prepare the JF dye for injection, 100 nanomoles of lyophilized JF525 were dissolved in 20 µl of DMSO, 20 µl Pluronic F-127 (20% w/v in DMSO), and 60-80 µl of PBS (final dye concentration 1 µM). Mice were anesthetized with 2-3% isoflurane and 100 µl of the dye solution was injected into the retro-orbital sinus of the right eye using a 27-30 gauge needle (37).

For imaging experiments of Layer 1 neurons, a wide-field fluorescence microscope equipped with a water immersion objective (20×, NA 1.0, Olympus XLUMPLFLN) was used for imaging. Illumination was delivered using a 525 nm LED (Mightex, LCS-0525-60-22); intensity at the sample, <20 mW/mm². An mKO/mOrange filter set (530/30 nm (excitation), 575/40 nm (emission), and a 550LP dichroic mirror (Chroma, 49014)) was used for fluorescence imaging of Voltron525. Images were collected using a sCMOS camera (Hamamatsu Orca Flash 4.0 v3) at frame rates of 400-1000 Hz. A 0.55× magnification camera tube was placed between the objective and the camera for imaging large fields of view of 1064 µm×266 µm (FIGS. 7F-7G and FIGS. 27-40). The pixel resolution was 2.08 µm/pixel. For smaller fields of view (FIGS. 7B-7E and FIG. 25) a 1× camera tube was used. The pixel size was 1.04 µm. Mice were awake and imaged in darkness.

To image Layer 2/3 pyramidal cells, the following changes were made from the imaging protocol for Layer 1 interneurons: Images were recorded at frame rate of 500-700 Hz. Illumination intensity at the sample was <50 mW/mm². 1× camera tube was used and the field of view imaged was typically 50 µm×50 µm. The pixel size was 1.04 µm. A digital mirror device (Texas Instruments, LightCrafter) restricted the illumination to the cell being imaged. Mice were imaged while lightly anesthetized and passively viewing drifting gratings (described below).

Visual Stimulation for Pyramidal Cell Recordings:

Mice were presented with drifting grating visual stimuli during imaging sessions (spatial frequency: 0.03 cycles/degree, temporal frequency: 1 Hz, trial period: 1 s, and inter-trial interval: 1 s). Gratings were shown in blue with a black background. During the inter-trial interval, the screen was black. Eight orientations separated by 45° were presented. Mice were anesthetized during all sessions. To induce anesthesia, chlorprothixene (0.2 mg/ml, 5 ul/g weight mouse) was injected into the hind paw followed by keeping the mouse in a chamber with 2-3% isoflurane for 1-2 minutes. Anesthesia was maintained at 0.4-0.8% isoflurane for the duration of the imaging session. Mice were kept on a heating blanket at a temperature of 37°.

Analysis of Layer 2/3 Pyramidal Cell Imaging:

Motion was removed using a rigid registration algorithm. A constant camera offset was subtracted from each frame. A region of interest (ROI) was manually drawn around the neuron. The initial trace (X0) is the mean intensity over the ROI in time. X0 was fit with a piecewise linear curve using a Savitzky-Golay filter with a window size of 10 s to estimate the slow baseline fluctuations, F0. ΔF/F was calculated as $$\frac{X0 - F0}{F0}.$$

Spike times were manually selected as large amplitude local minima in the ΔF/F trace occurring in periods of depolarization and separated from other local minima by at least 2 ms.

Visual responses (FIGS. 6H-6L and FIG. 25) were calculated as the average number of spikes during the trial for each orientation, averaged over repetitions. To estimate the subthreshold fluctuations, the ΔF/F trace was low-pass filtered at 50 Hz using a median filter. The response for each orientation was calculated as the average of the low-pass filtered trace from 100 ms to 400 ms after the trial start. The baseline was calculated as the average of the low-pass filtered trace from 80 ms before trial start to 20 ms after the trial start. The baseline was subtracted from the response for each trial and averaged over 20 repetitions.

The orientation selectivity index (FIG. 26) was calculated as:

$$(R_{pref} - R_{orth})/(|R_{pref}| + |R_{orth}|)$$

where $R_{pref}$ is the response (mean spikes in trial or mean subthreshold membrane potential) to the preferred orientation, and $R_{orth}$ is the response to the orientation 90° away from the preferred orientation.

Analysis of Layer 1 Interneuron Imaging:

To identify neuronal activity and spatial structure from Voltron recordings, an iterative spatial and temporal filtering approach was designed and called: Spike Pursuit. In essence, Spike Pursuit begins with a poorly estimated voltage trace for a neuron, and uses detected spikes to iteratively estimate improved temporal and spatial filters that increase the signal to noise ratio of the spikes while controlling for overfitting. Spike pursuit relies on linear methods (the whitened matched filter for temporal filtering, and regularized linear regression for spatial filtering) (39).

Figure 29:
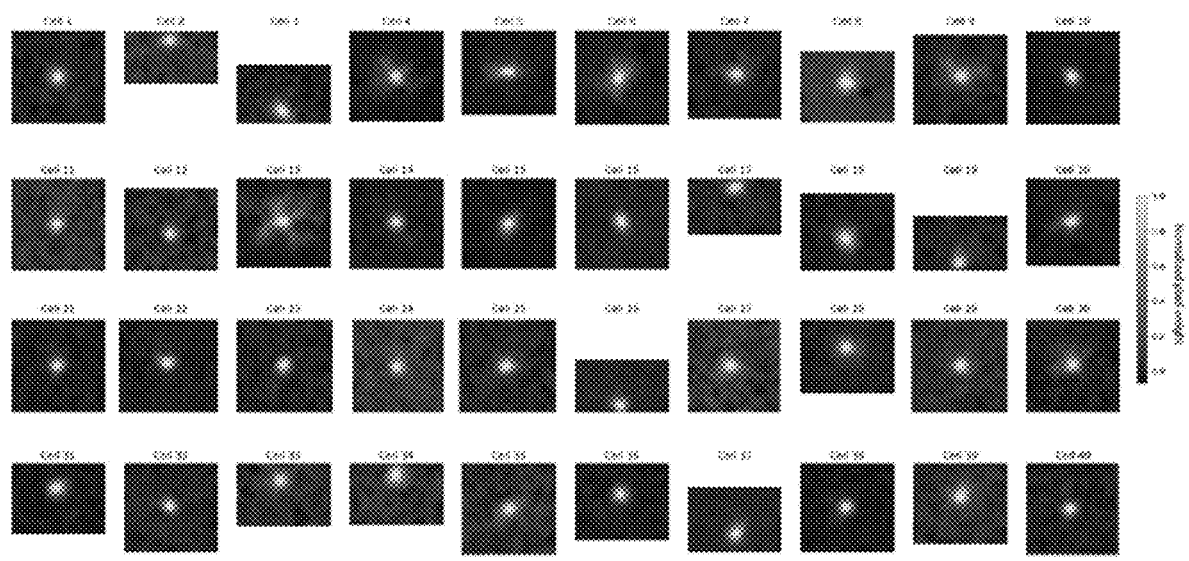
FIG. 29 includes a series of spatial filters for context regions of 50×50 pixels centered on the ROI of each cell shown in FIGS. 7F-7G and FIGS. 27A-27C. Spatial filters were estimated by Spike Pursuit. Cells near the boundary of the field of view have different sizes of context region.
Figure 30A:
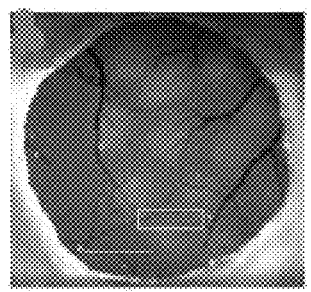
FIG. 30A includes a fluorescence image of a cranial window over primary visual cortex (V1) in an NDNF-Cre mouse showing Cre-dependent expression of soma targeted Voltron525. Scalebar, 1 mm.
Figure 30B:
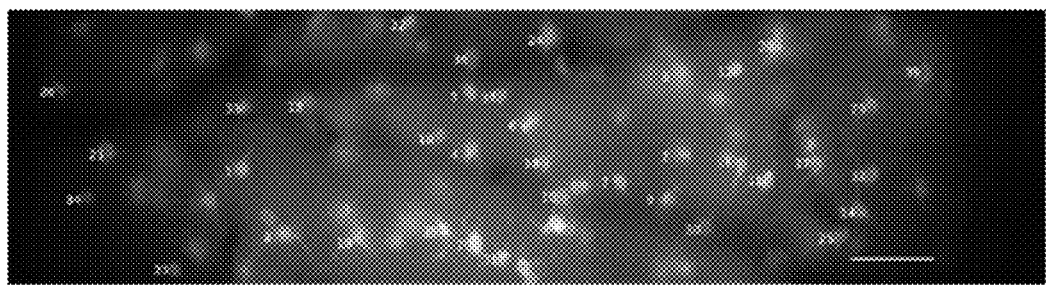
FIG. 30B includes a fluorescence image of area indicated by the white rectangle in FIG. 30A, with neuron labels corresponding to fluorescence traces in FIG. 30C. Scalebar, 100 μm.
Figure 30C:
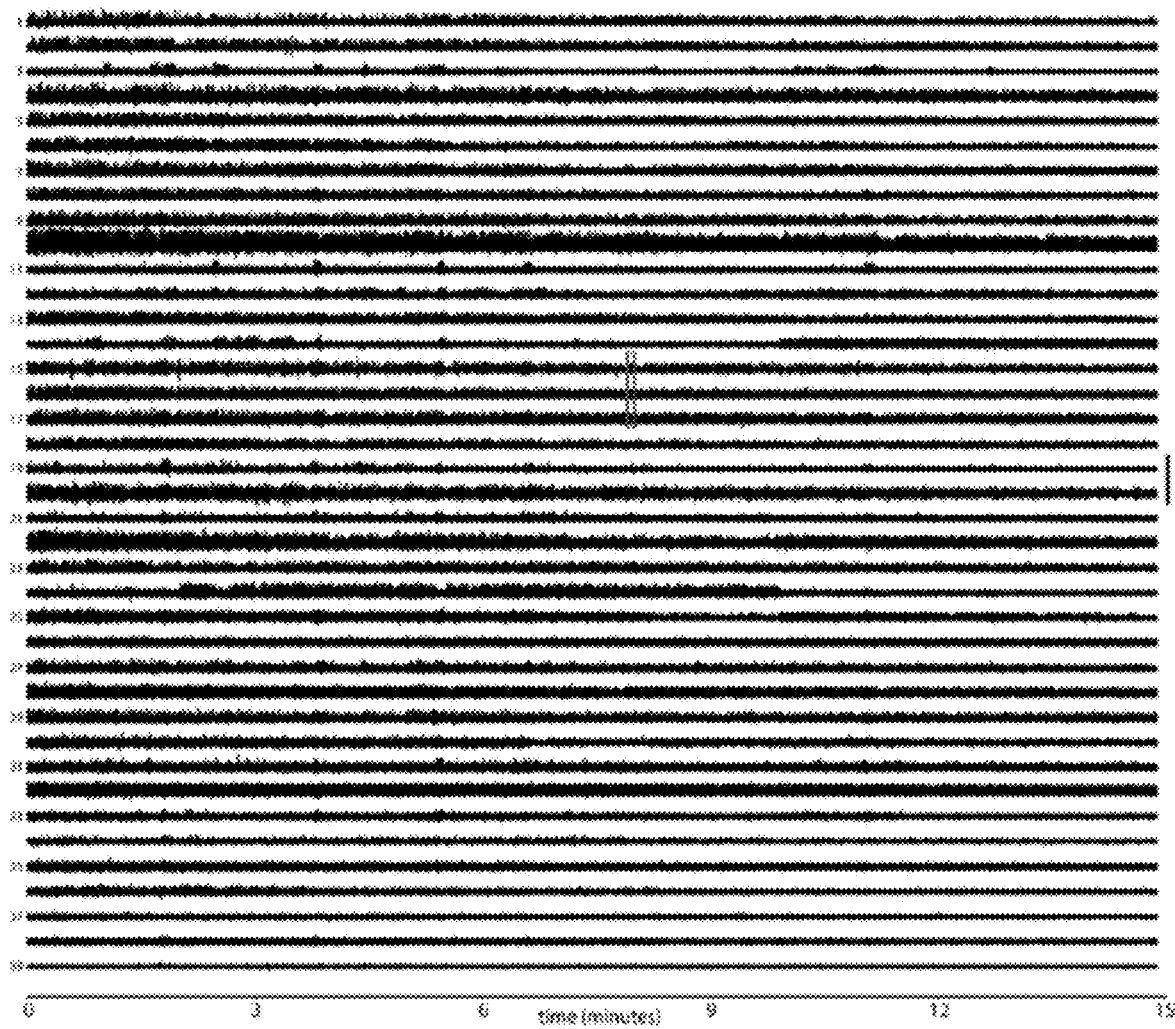
FIG. 30C: Fluorescence traces during 10-15 minutes recordings from neurons indicated in FIG. 30B, in decreasing order of signal to noise ratio.
Figure 30D:
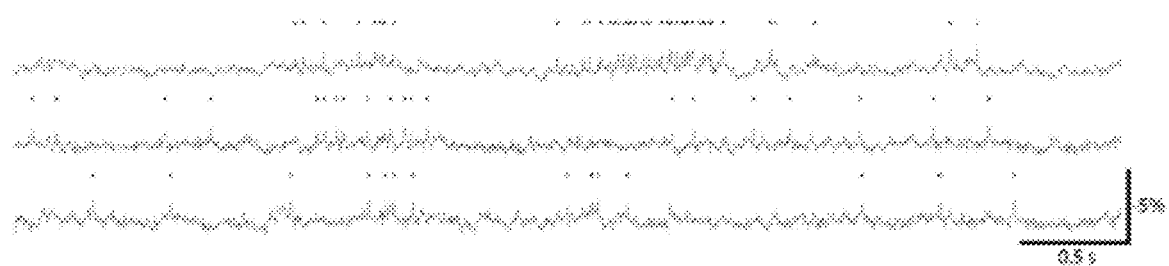
FIG. 30D includes zoom-in of fluorescence traces from area indicated by red rectangle in FIG. 30C.
Figure 31A:
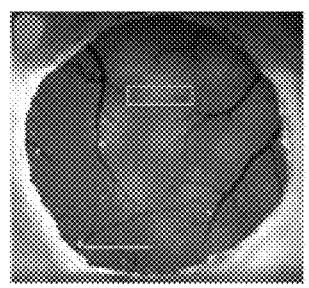
FIG. 31A includes a fluorescence image of a cranial window over primary visual cortex (V1) in an NDNF-Cre mouse showing Cre-dependent expression of soma targeted Voltron525. Scalebar, 1 mm.
Figure 31B:
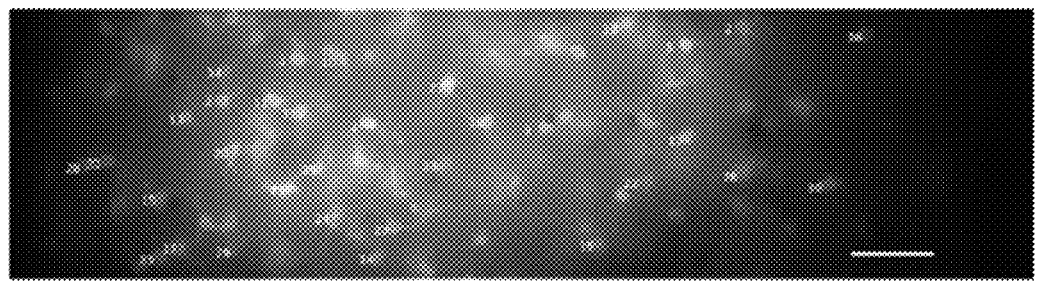
FIG. 31B includes a fluorescence image of area indicated by the white rectangle in FIG. 31A, with neuron labels corresponding to fluorescence traces in FIG. 31C. Scalebar, 100 μm.
Figure 31C:
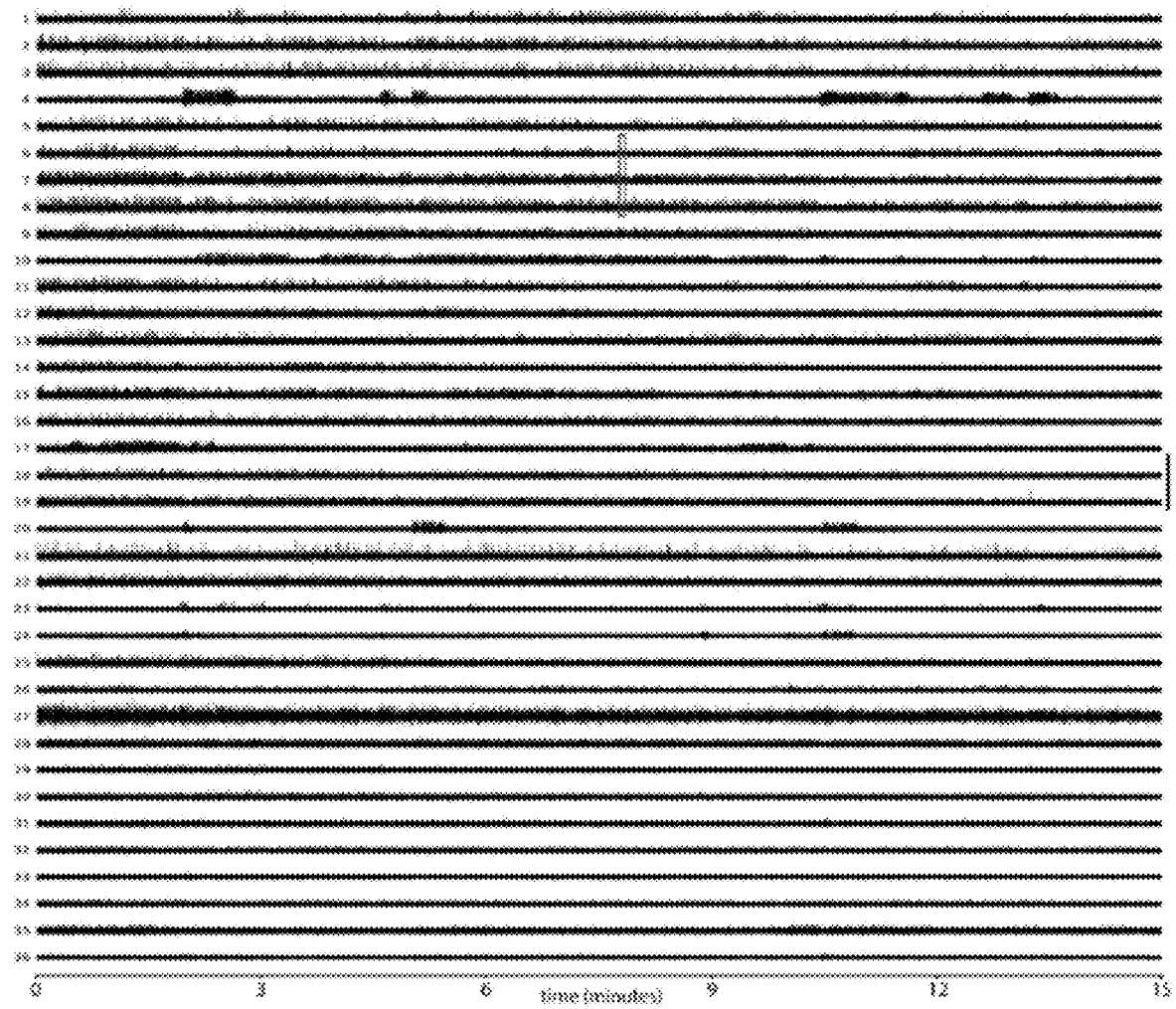
FIG. 31C includes fluorescence traces during 10-15 minutes recordings from neurons indicated in FIG. 31B, in decreasing order of signal to noise ratio.
Figure 31D:
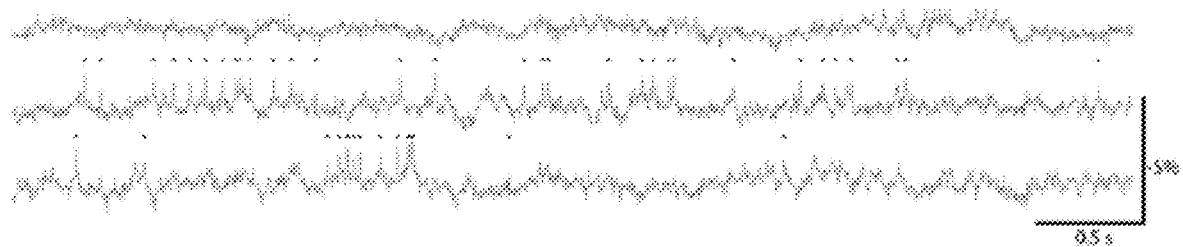
FIG. 31D includes zoom-in of fluorescence traces from area indicated by red rectangle in FIG. 31C.
Figure 32A:
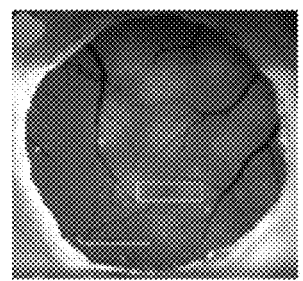
FIG. 32A includes fluorescence image of a cranial window over primary visual cortex (V1) in an NDNF-Cre mouse showing Cre-dependent expression of soma targeted Voltron525. Scalebar, 1 mm.
Figure 32B:
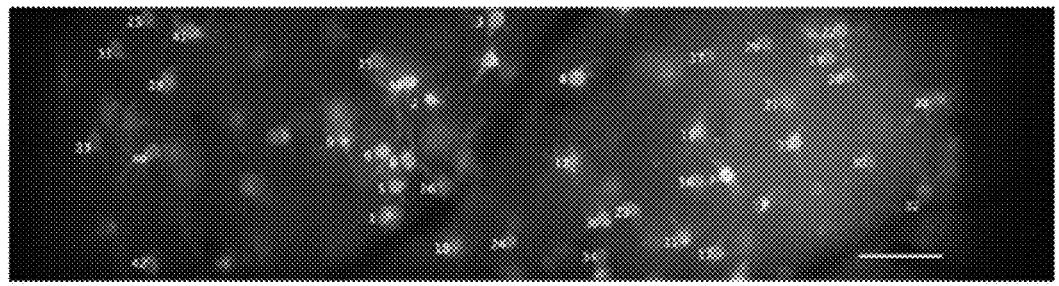
FIG. 32B includes fluorescence image of area indicated by the white rectangle in FIG. 32A, with neuron labels corresponding to fluorescence traces in FIG. 32C. Scalebar, 100 μm.
Figure 32C:
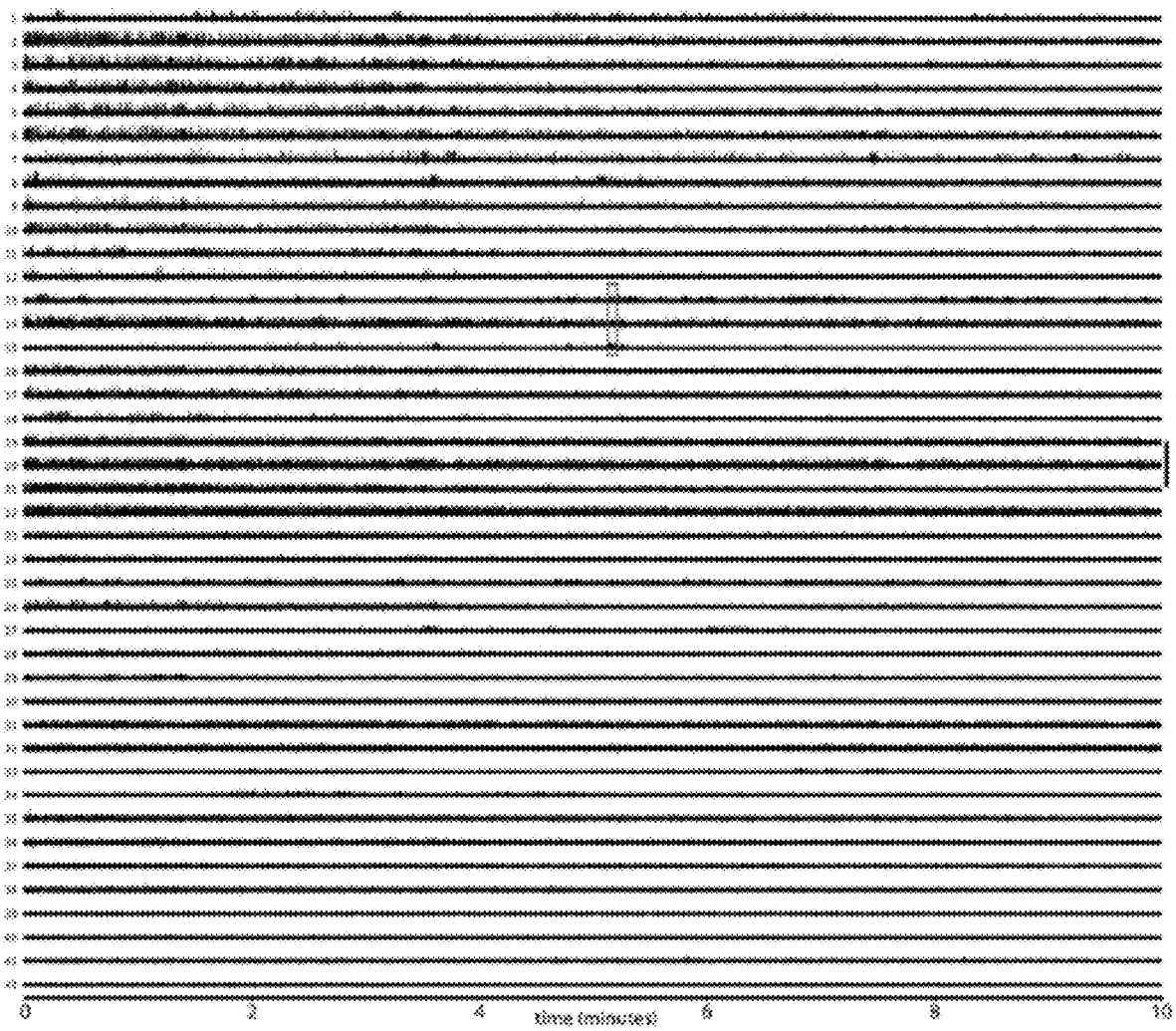
FIG. 32C Fluorescence traces during 10-15 minutes recordings from neurons indicated in FIG. 32B, in decreasing order of signal to noise ratio.
Figure 32D:
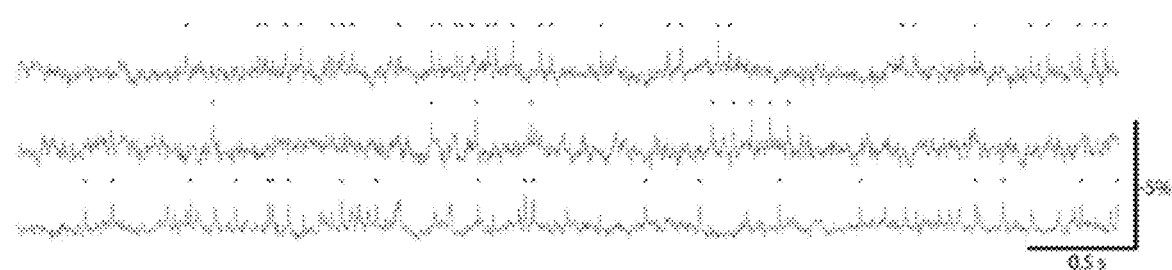
FIG. 32D includes zoom-in of fluorescence traces from area indicated by red rectangle in FIG. 32C.
Figure 33A:
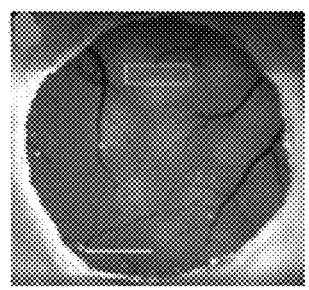
FIG. 33A includes fluorescence image of a cranial window over primary visual cortex (V1) in an NDNF-Cre mouse showing Cre-dependent expression of soma targeted Voltron525. Scalebar, 1 mm.
Figure 33B:
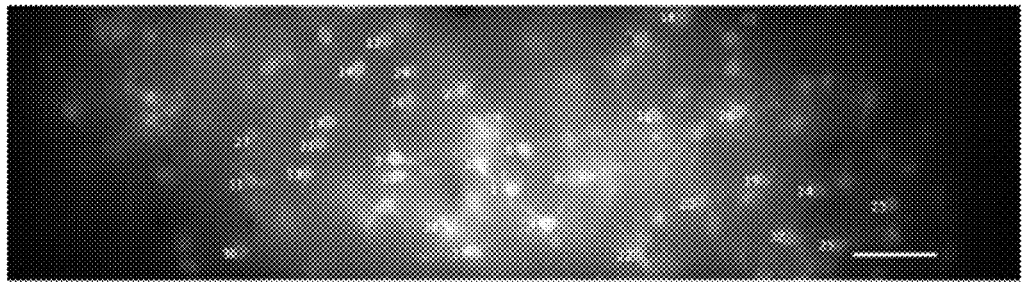
FIG. 33B includes fluorescence image of area indicated by the white rectangle in FIG. 33A, with neuron labels corresponding to fluorescence traces in FIG. 33C. Scalebar, 100 μm.
Figure 33C:
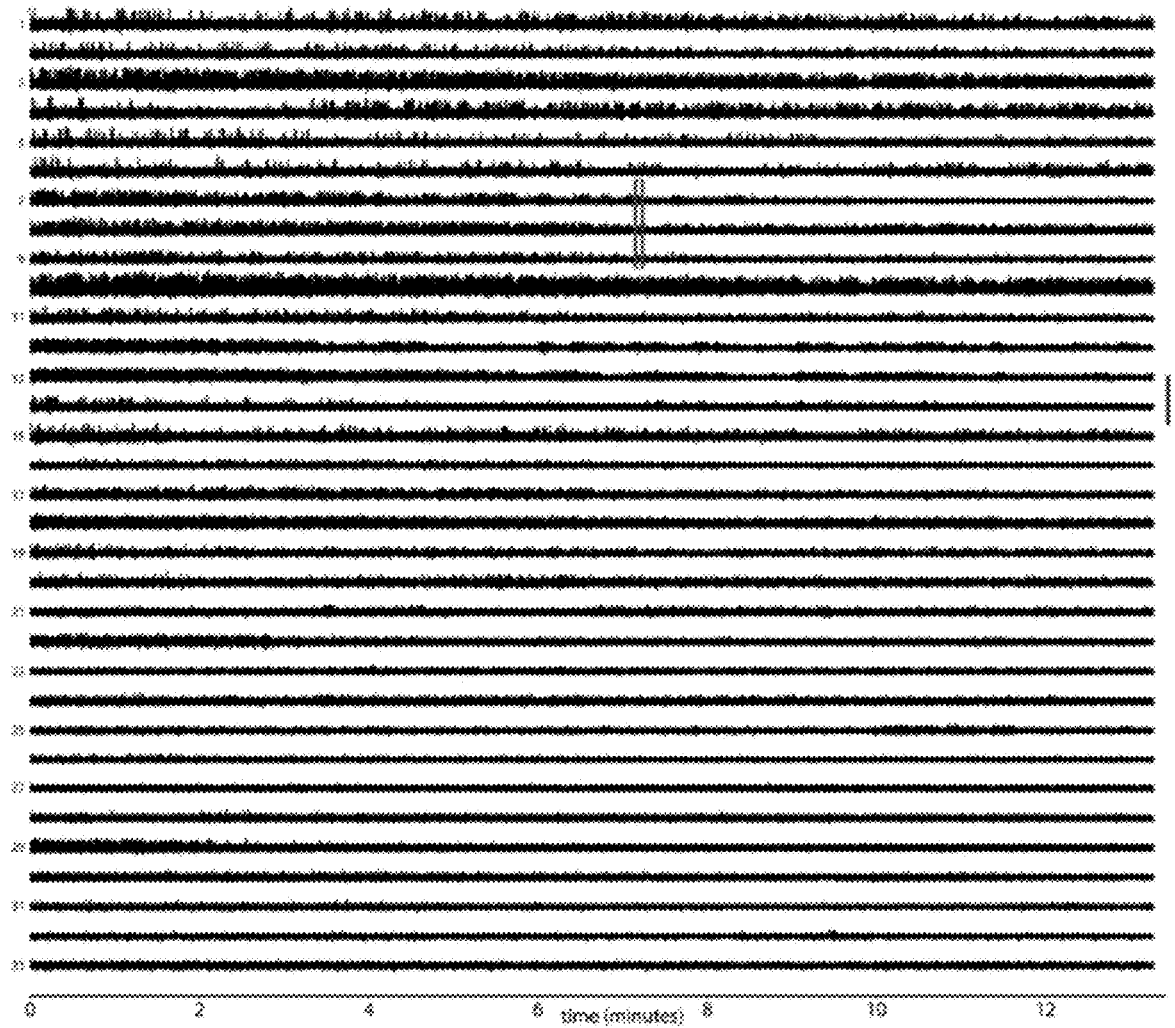
FIG. 33C includes fluorescence traces during 10-15 minutes recordings from neurons indicated in FIG. 33B, in decreasing order of signal to noise ratio.
Figure 33D:
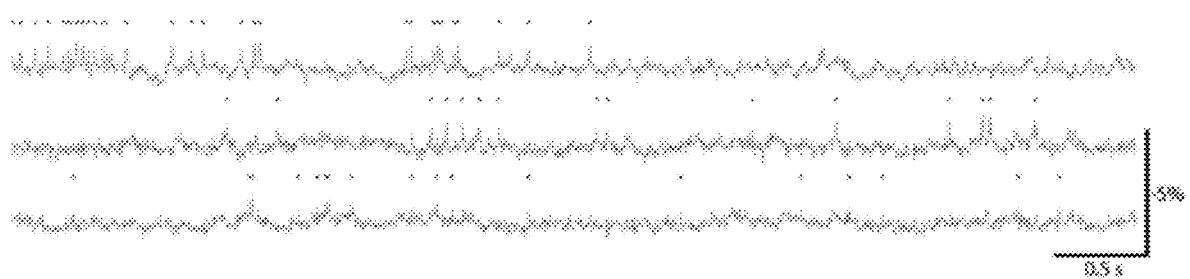
FIG. 33D includes zoom-in of fluorescence traces from area indicated by red rectangle in FIG. 33C.
Figure 34A:
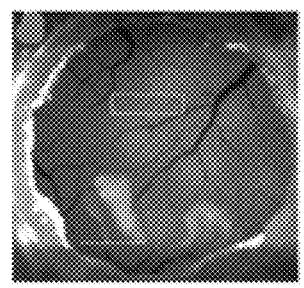
FIG. 34A includes fluorescence image of a cranial window over primary visual cortex (V1) in an NDNF-Cre mouse showing Cre-dependent expression of soma targeted Voltron525. Scalebar, 1 mm.
Figure 34B:
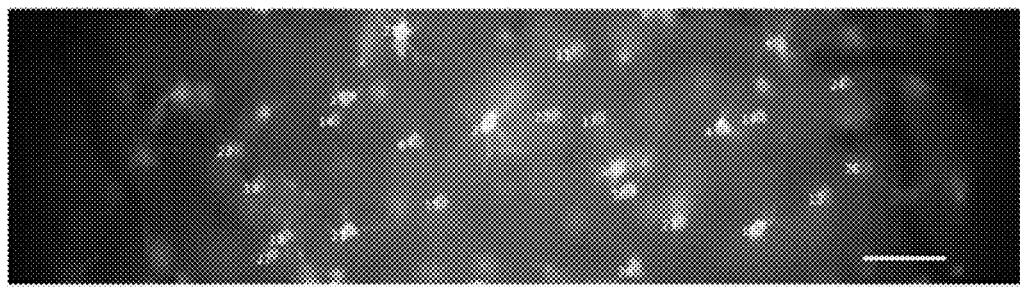
FIG. 34B includes fluorescence image of area indicated by the white rectangle in FIG. 34A, with neuron labels corresponding to fluorescence traces in FIG. 34C. Scalebar, 100 μm.
Figure 34C:
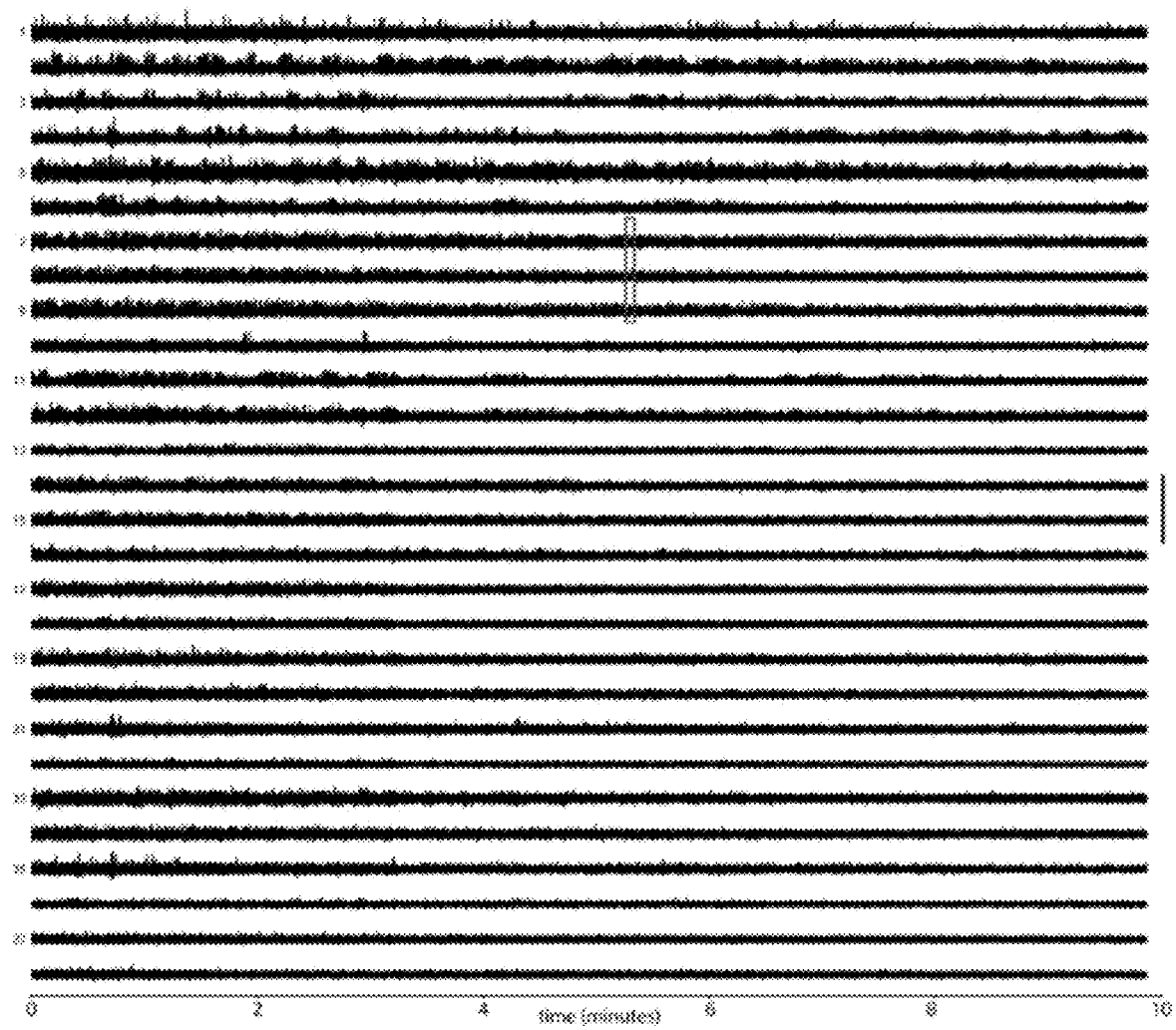
FIG. 34C includes fluorescence traces during 10-15 minutes recordings from neurons indicated in FIG. 34B, in decreasing order of signal to noise ratio.
Figure 34D:
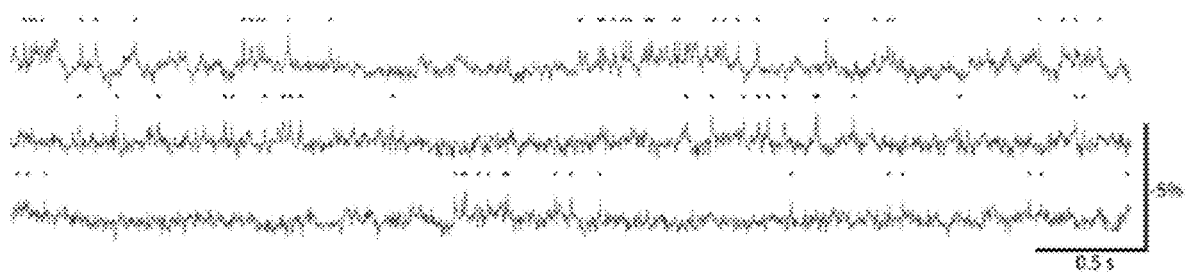
FIG. 34D includes zoom-in of fluorescence traces from area indicated by red rectangle in FIG. 34C.
Figure 35A:
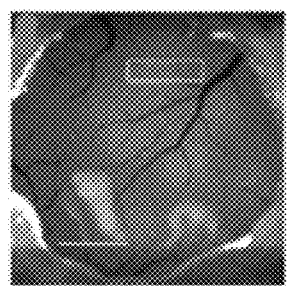
FIG. 35A includes fluorescence image of a cranial window over primary visual cortex (V1) in an NDNF-Cre mouse showing Cre-dependent expression of soma targeted Voltron525. Scalebar, 1 mm.
Figure 35B:
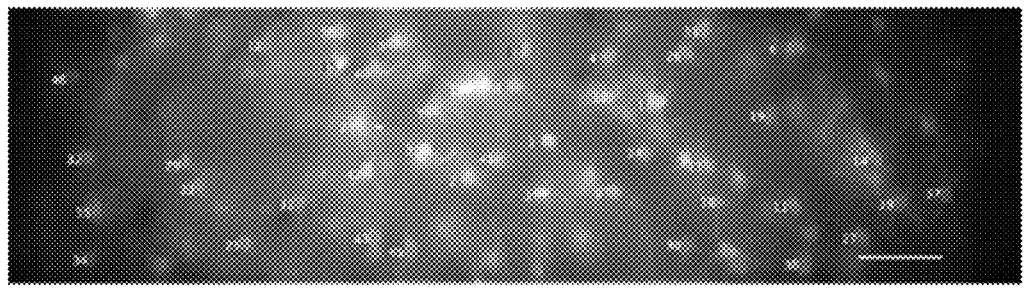
FIG. 35B includes fluorescence image of area indicated by the white rectangle in FIG. 35A, with neuron labels corresponding to fluorescence traces in FIG. 35C. Scalebar, 100 μm.
Figure 35C:
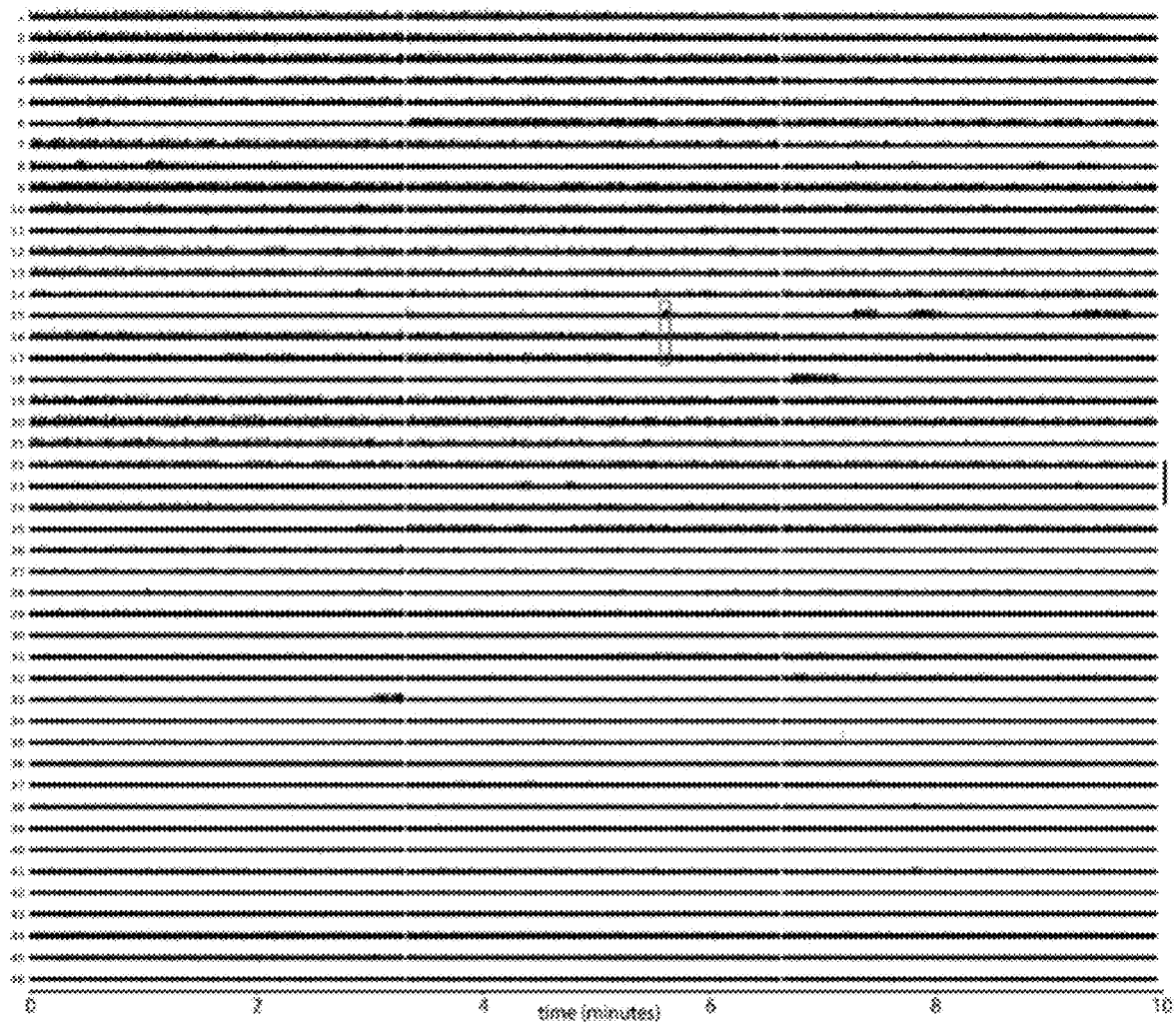
FIG. 35C includes fluorescence traces during 10-15 minutes recordings from neurons indicated in FIG. 35B, in decreasing order of signal to noise ratio.
Figure 35D:
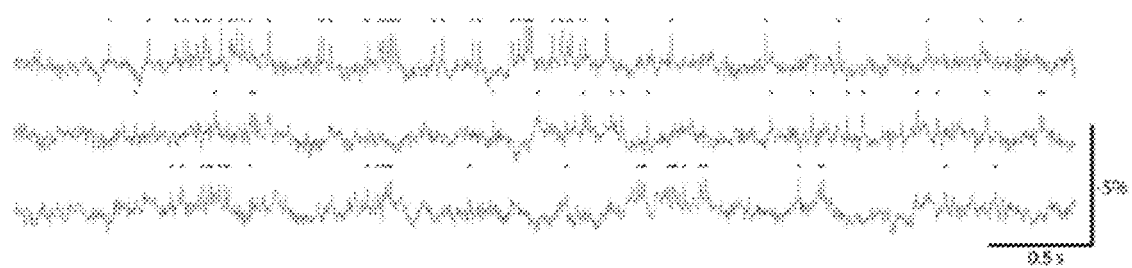
FIG. 35D includes zoom-in of fluorescence traces from area indicated by red rectangle in FIG. 35C.
Figure 36A:
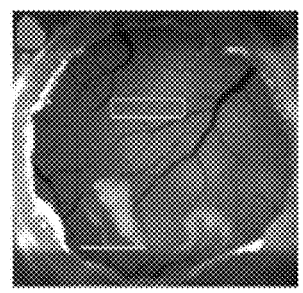
FIG. 36A includes a fluorescence image of a cranial window over primary visual cortex (V1) in an NDNF-Cre mouse showing Cre-dependent expression of soma targeted Voltron525. Scalebar, 1 mm.
Figure 36B:
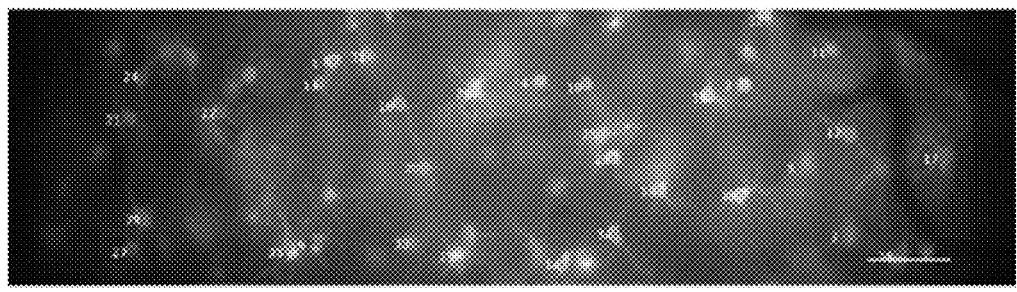
FIG. 36B includes fluorescence image of area indicated by the white rectangle in FIG. 36A, with neuron labels corresponding to fluorescence traces in FIG. 36C. Scalebar, 100 µm.
Figure 36C:
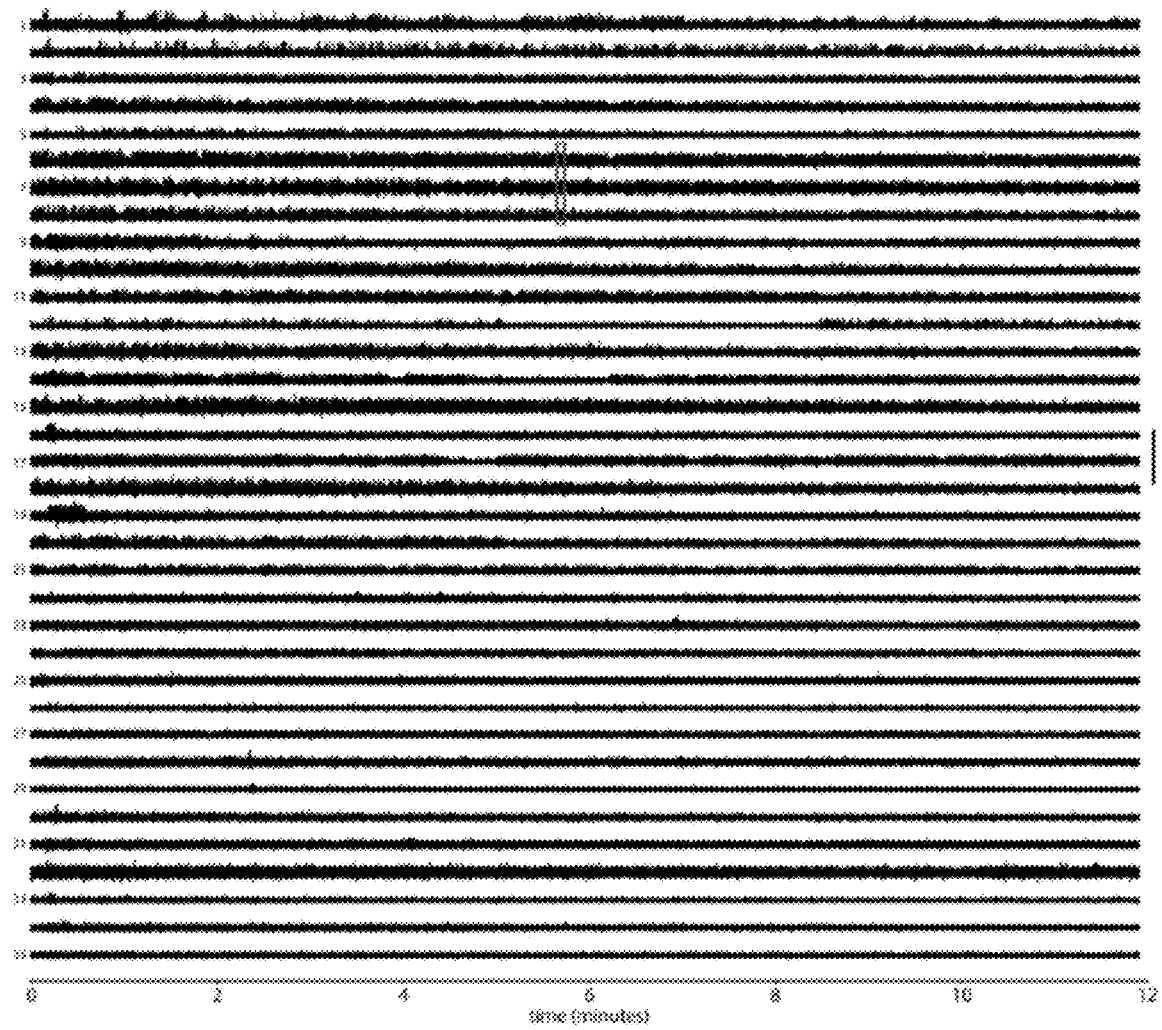
FIG. 36C includes fluorescence traces during 10-15 minutes recordings from neurons indicated in FIG. 36B, in decreasing order of signal to noise ratio.
Figure 36D:
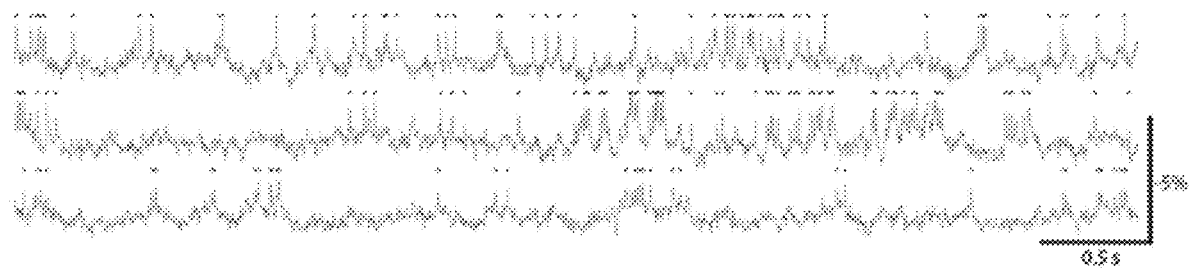
FIG. 36D Zoom-in of fluorescence traces from area indicated by red rectangle in FIG. 36C.
Figure 37A:
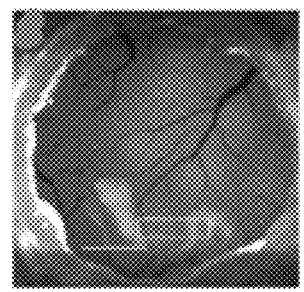
FIG. 37A includes a fluorescence image of a cranial window over primary visual cortex (V1) in an NDNF-Cre mouse showing Cre-dependent expression of soma targeted Voltron525. Scalebar, 1 mm.
Figure 37B:
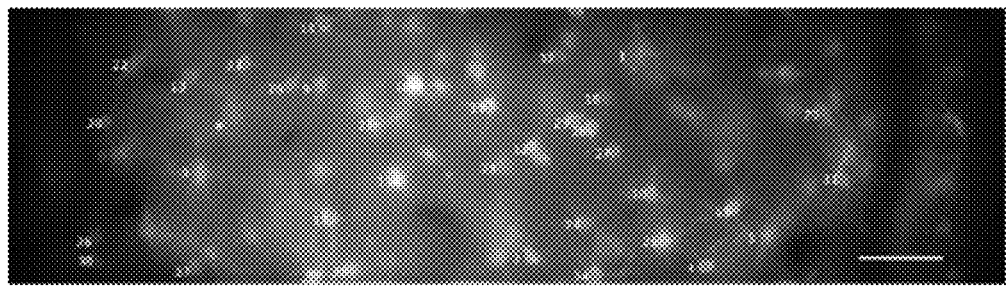
FIG. 37B includes fluorescence image of area indicated by the white rectangle in FIG. 37A, with neuron labels corresponding to fluorescence traces in FIG. 37C. Scalebar, 100 µm.
Figure 37C:
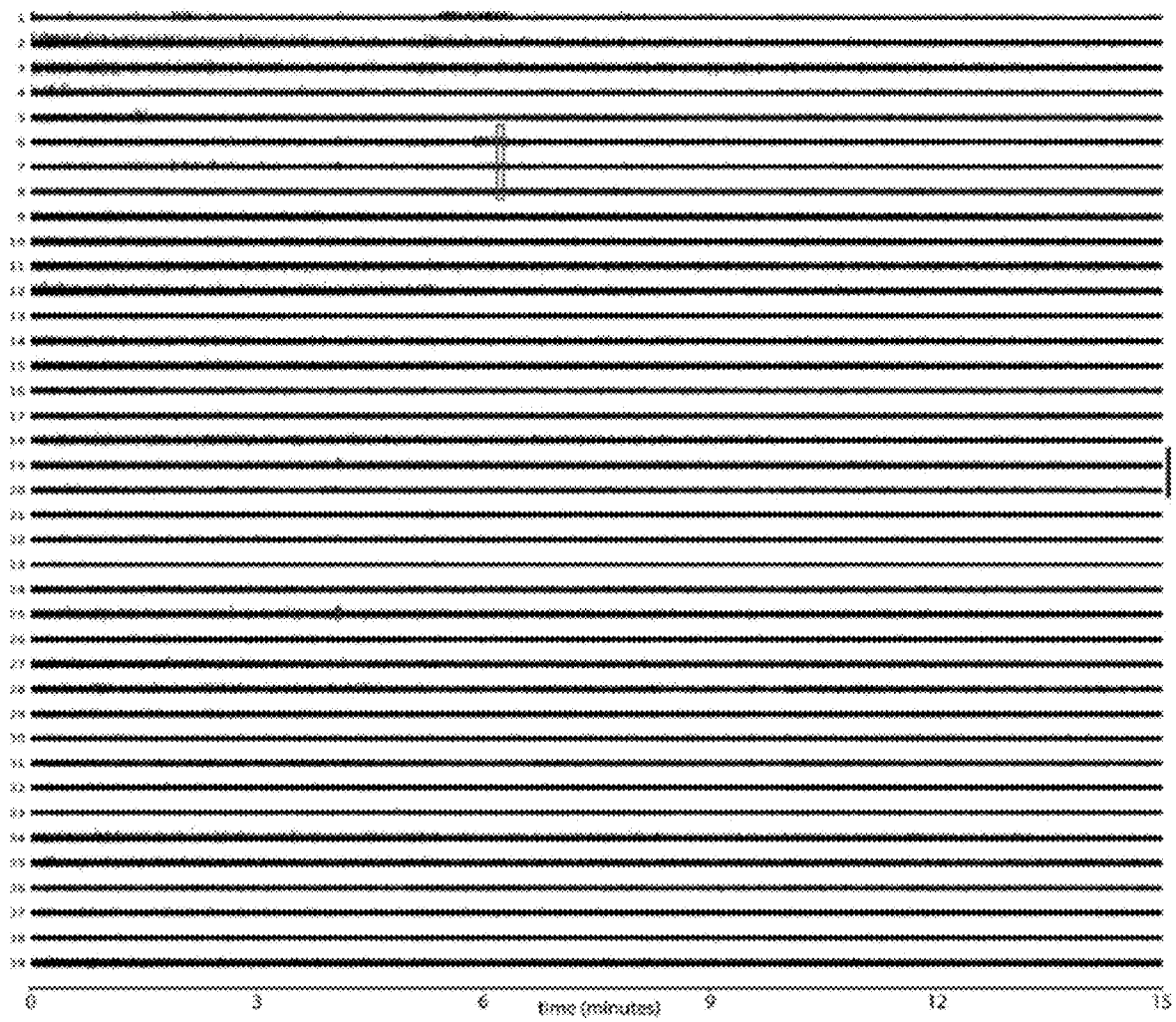
FIG. 37C includes fluorescence traces during 10-15 minutes recordings from neurons indicated in FIG. 37B, in decreasing order of signal to noise ratio.
Figure 37D:
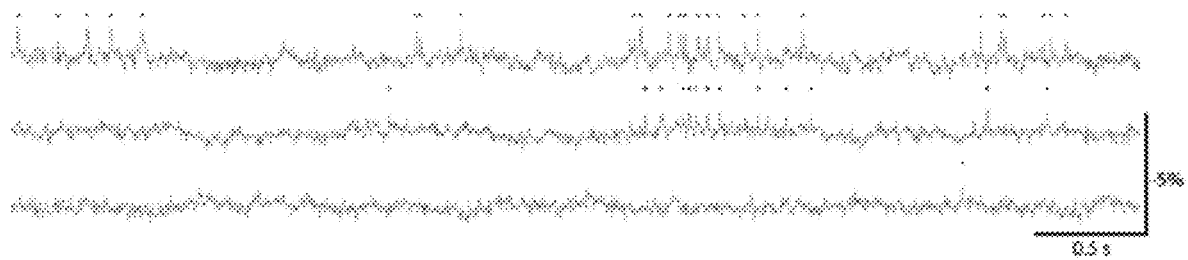
FIG. 37D includes zoom-in of fluorescence traces from area indicated by red rectangle in FIG. 37C.
Figure 38A:
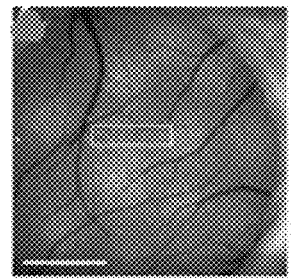
FIG. 38A includes a fluorescence image of a cranial window over primary visual cortex (V1) in an NDNF-Cre mouse showing Cre-dependent expression of soma targeted Voltron525. Scalebar, 1 mm.
Figure 38B:
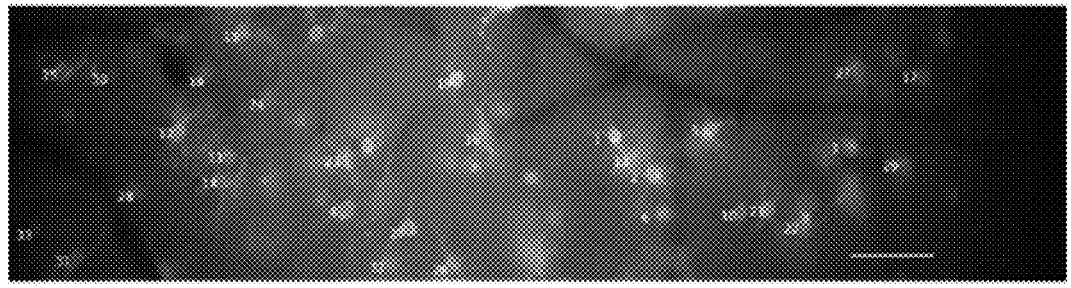
FIG. 38B includes a fluorescence image of area indicated by the white rectangle in FIG. 38A, with neuron labels corresponding to fluorescence traces in FIG. 38C. Scalebar, 100 µm.
Figure 38C:
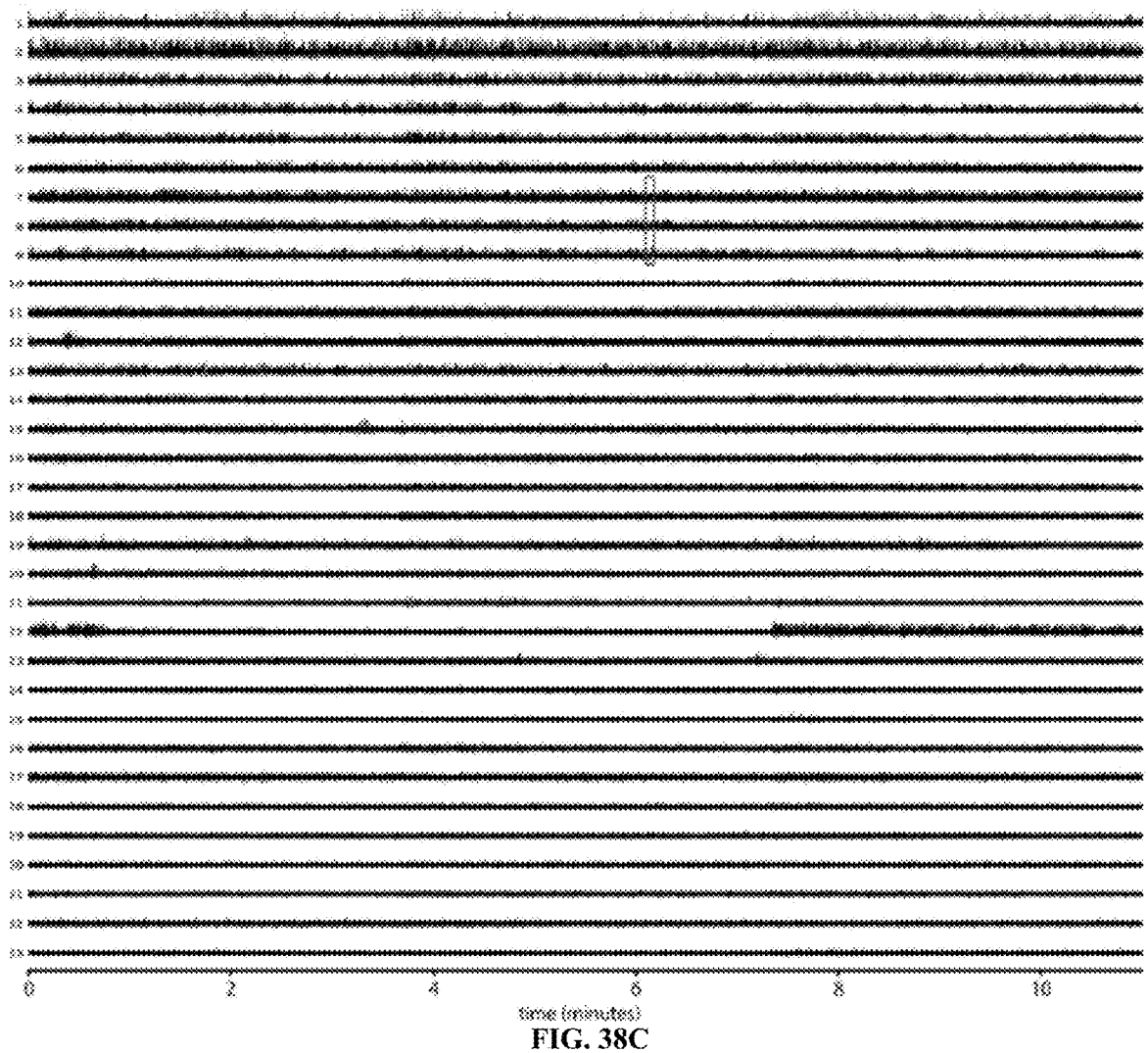
FIG. 38C includes fluorescence traces during 10-15 minutes recordings from neurons indicated in FIG. 38B, in decreasing order of signal to noise ratio.
Figure 38D:
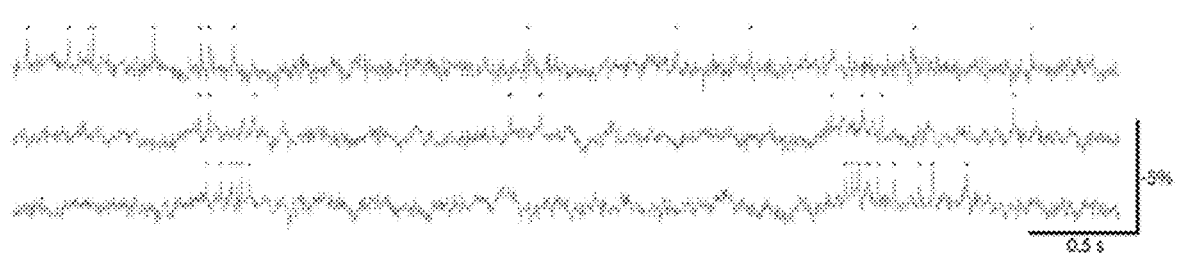
FIG. 38D includes zoom-in of fluorescence traces from area indicated by red rectangle in FIG. 38C.
Figure 39A:
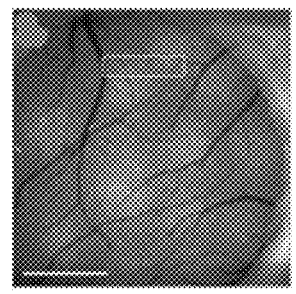
FIG. 39A includes a fluorescence image of a cranial window over primary visual cortex (V1) in an NDNF-Cre mouse showing Cre-dependent expression of soma targeted Voltron525. Scalebar, 1 mm.
Figure 39B:
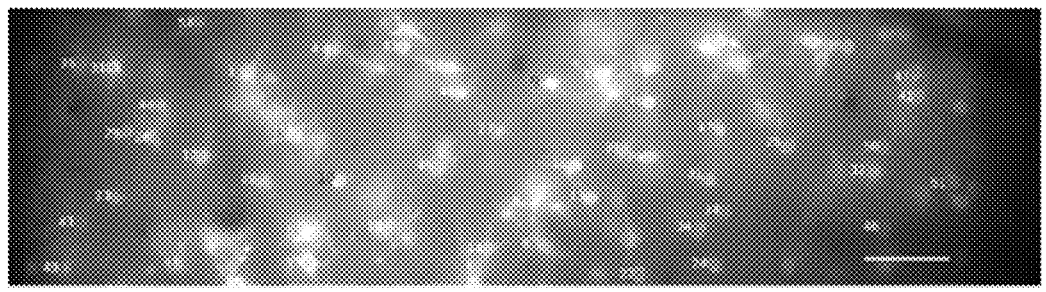
FIG. 39B includes a fluorescence image of area indicated by the white rectangle in FIG. 39A, with neuron labels corresponding to fluorescence traces in FIG. 39C. Scalebar, 100 µm.
Figure 39C:
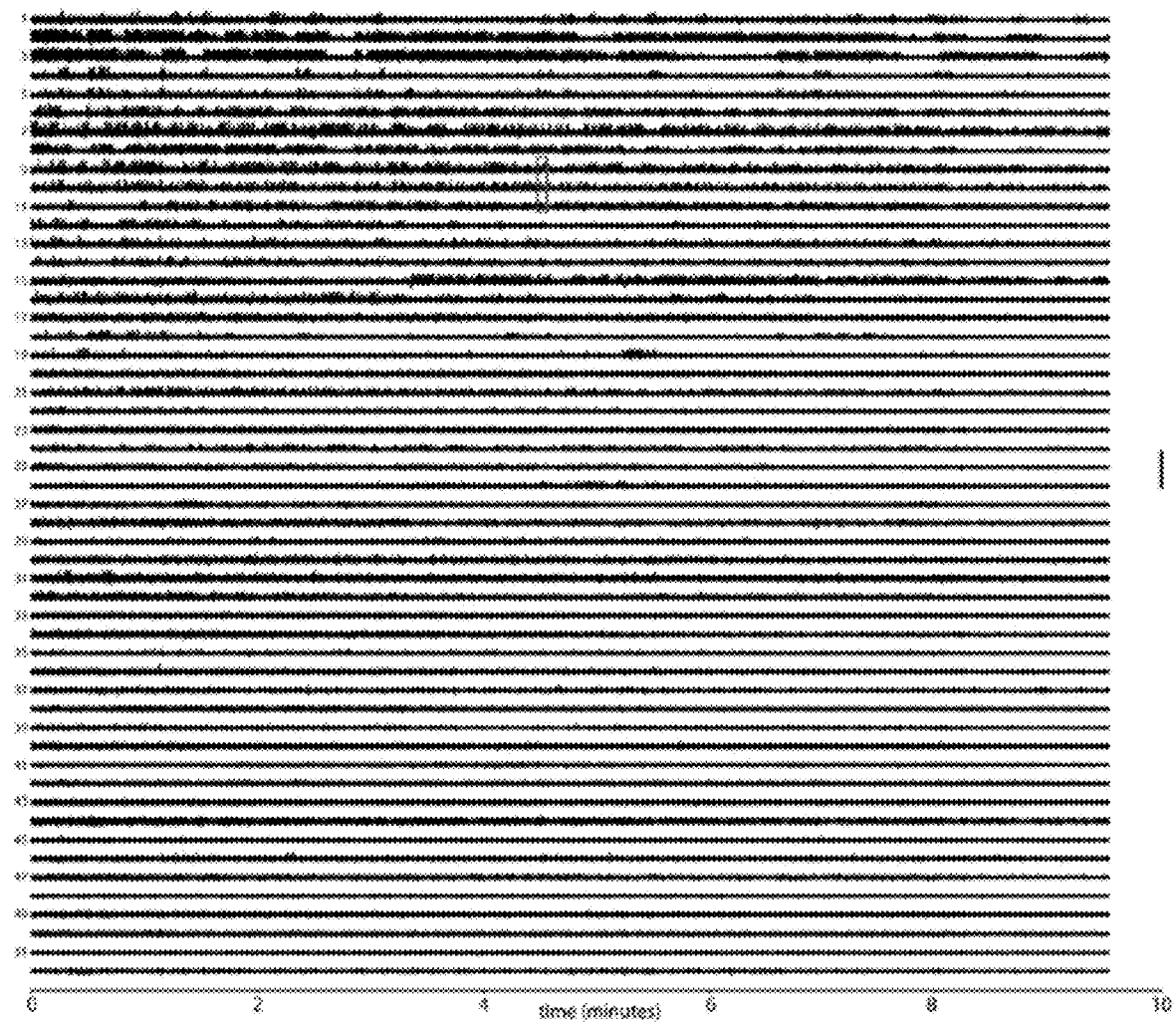
FIG. 39C includes fluorescence traces during 10-15 minutes recordings from neurons indicated in FIG. 39B, in decreasing order of signal to noise ratio.
Figure 39D:
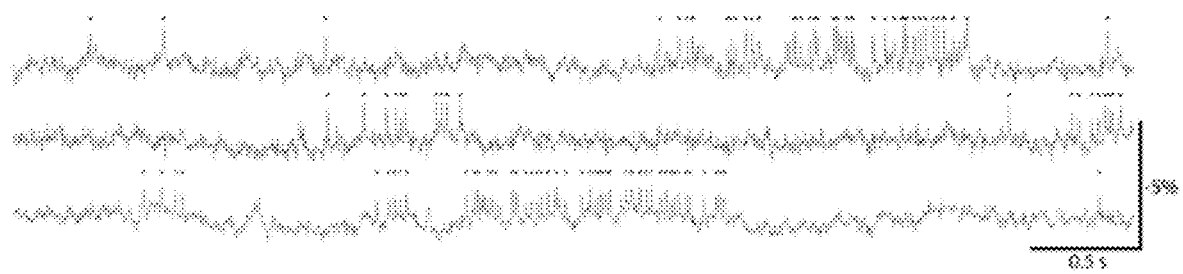
FIG. 39D includes zoom-in of fluorescence traces from area indicated by red rectangle in FIG. 39C.
Figure 40A:
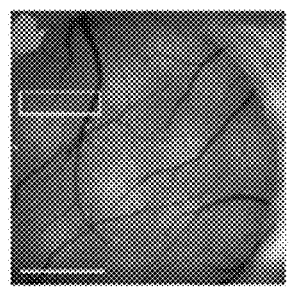
FIG. 40A includes a fluorescence image of a cranial window over primary visual cortex (V1) in an NDNF-Cre mouse showing Cre-dependent expression of soma targeted Voltron525. Scalebar, 1 mm.
Figure 40B:
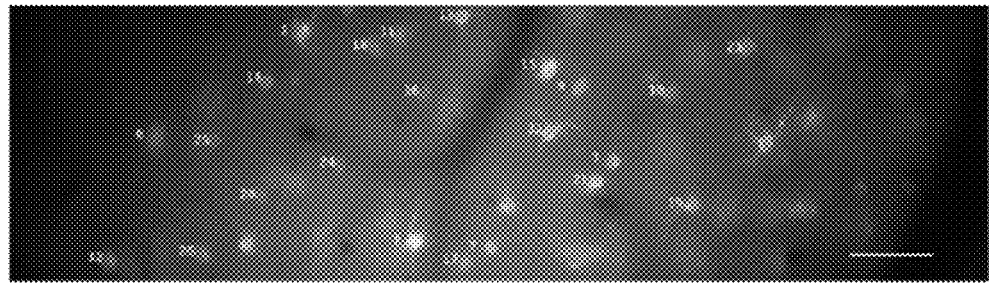
FIG. 40B includes a fluorescence image of area indicated by the white rectangle in FIG. 40A, with neuron labels corresponding to fluorescence traces in FIG. 40C. Scalebar, 100 µm.
Figure 40C:
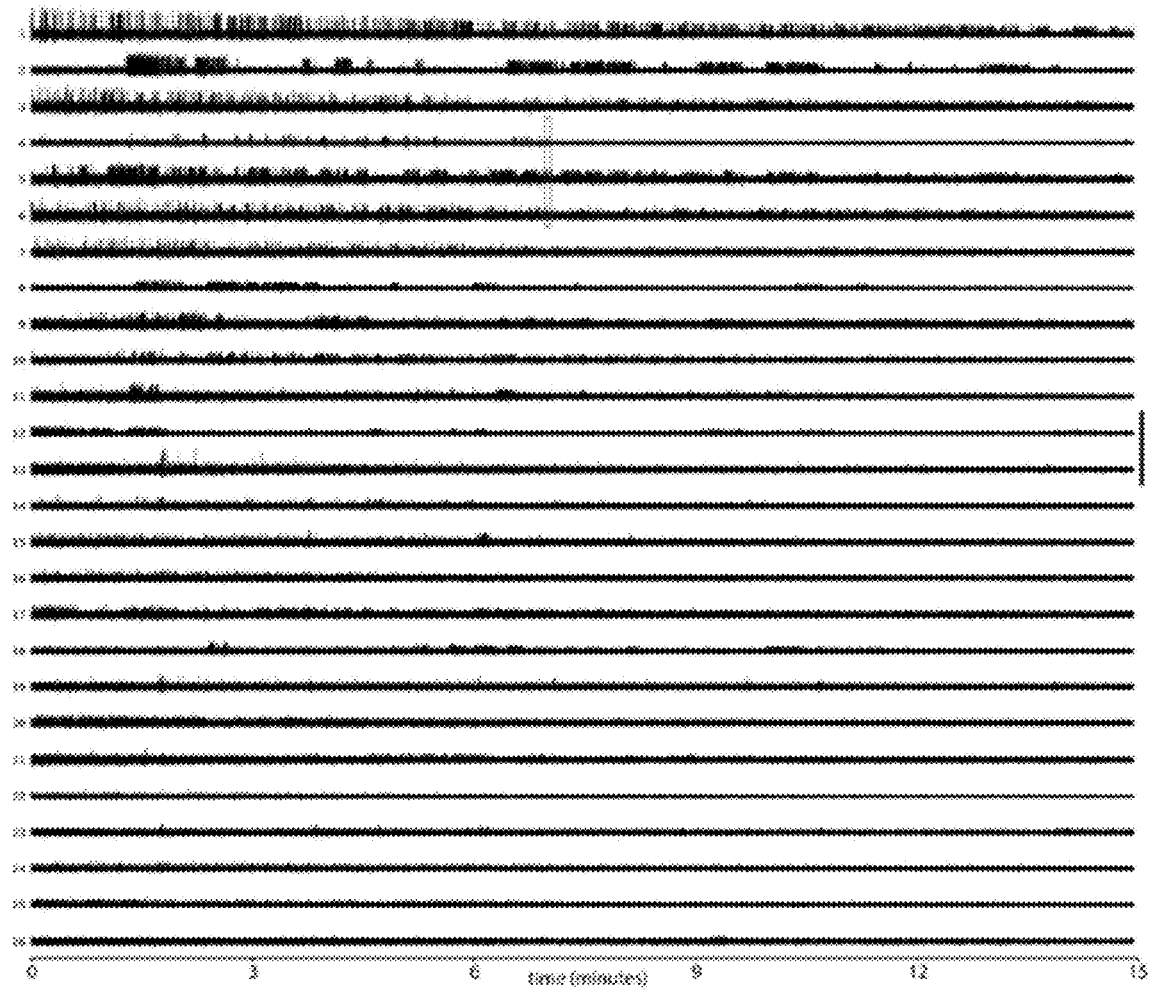
FIG. 40C includes fluorescence traces during 10-15 minutes recordings from neurons indicated in FIG. 40B, in decreasing order of signal to noise ratio.
Figure 40D:
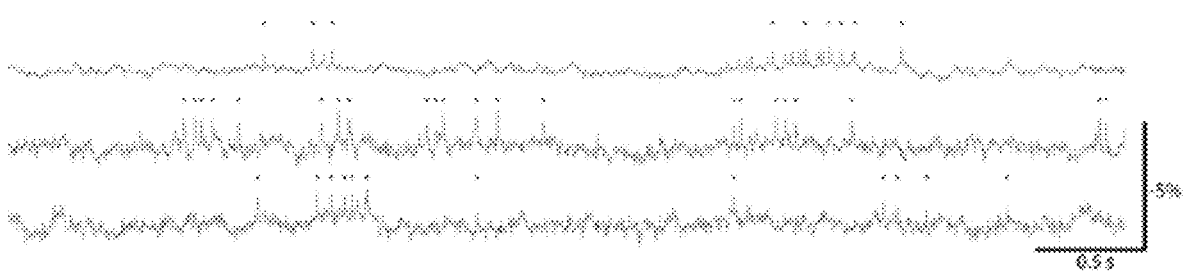
FIG. 40D includes zoom-in of fluorescence traces from area indicated by red rectangle in FIG. 40C.
Figure 41A:
FIG. 41A includes pictures of forebrain neurons expressing Voltron-ST labeled with Janelia Fluor 525 (JF525) with an inset schematic drawing showing the location of the image (Panel A1), and fluorescence signal from a neuron labeled with Voltron-ST+JF525 showing spontaneous spiking activity (Panel A2).
Figure 41A:
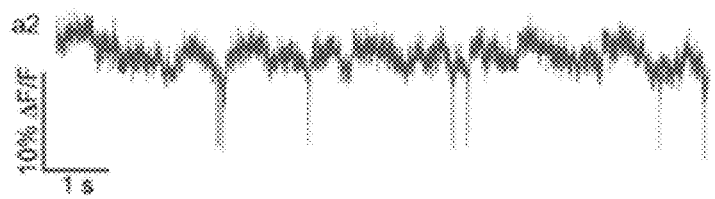
Figure 41B:
FIG. 41B includes pictures of forebrain neurons expressing Voltron-ST labeled with Janelia Fluor 549 (JF549) with an inset schematic drawing showing the location of the image (Panel B1), and fluorescence signal from a neuron labeled with Voltron-ST+JF549 showing spontaneous spiking activity (Panel B2).
Figure 41B:
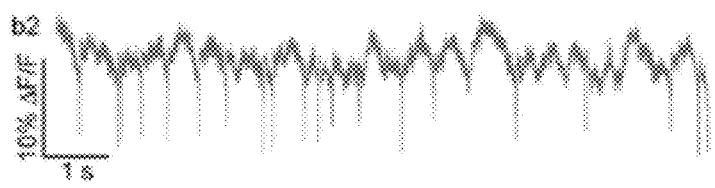
Figure 41C:
FIG. 41C includes pictures of forebrain neurons expressing Voltron-ST labeled with Janelia Fluor 585 (JF585) with an inset schematic drawing showing the location of the image (Panel C1), and fluorescence signal from a neuron labeled with Voltron-ST+JF584 showing spontaneous spiking activity (Panel C2).
Figure 41C:
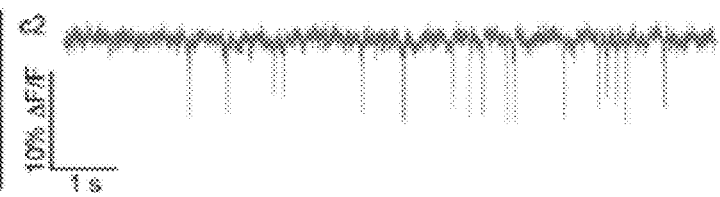
Figure 41D:
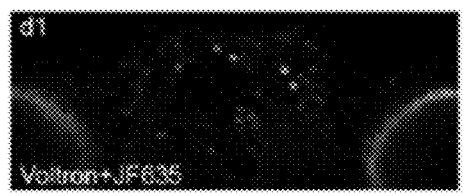
FIG. 41D includes pictures of forebrain neurons expressing Voltron-ST labeled with Janelia Fluor 635 (JF635) with an inset schematic drawing showing the location of the image (Panel D1), and fluorescence signal from a neuron labeled with Voltron-ST+JF635 showing spontaneous spiking activity (Panel D2).
Figure 41D:
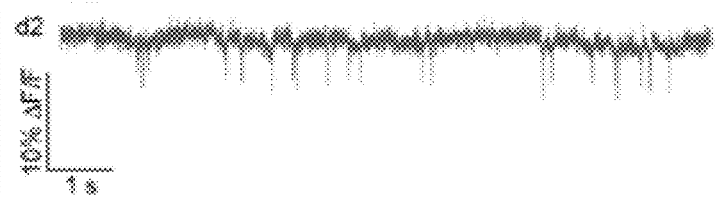

Motion was removed using Fast Fourier transform-based rigid registration in MATLAB. Initial ROIs were manually drawn around each neuron in the field of view. Data was processed in chunks of N=40,000 frames. The same initial ROIs were used for each chunk. For each neuron in each chunk, a region of 50×50 pixels centered on the neuron (the 'context region', C) was selected for further processing (FIG. 29). The data was high-pass filtered (MATLAB filtfilt) in the context region at 0.33 Hz using a $3^{rd}$ order Butterworth filter to correct for photobleaching. The high-pass filtered movie was denoted as $D_{N \times T}$ where N=n(C) is the number of pixels in the context region. The raw data was also high-pass filtered at 60 Hz using a $3^{rd}$ order Butterworth filter; this high-pass filtered movie as was denoted as $D_{N \times T}^h$.

The initial temporal trace $X_0(t)$ was the mean of the 0.33 Hz high-pass filtered video over the pixels in the ROI (R):

$$X_0(t) = \frac{1}{n(R)} \sum_{p \in R} D_{p,t}; t \in \{1, 2, \ldots T\}$$

where H denotes the set of pixels in the ROI, n(R) is the number of pixels in the ROI. $X_0$ and the high-pass filtered videos $D_{N \times T}$ and $D_{N \times T}^h$ were provided as input to the Spike Pursuit algorithm, which consisted of a two-step loop for each iteration (i):

Step 1: Spike Time Estimation

To detect spikes in the initial trace, contributions were subtracted from local background. This is intended to reduce the chance of optical crosstalk producing a false spike detection due to an adjacent neuron overlapping the initial ROI, and was not performed when computing the final trace with the optimized spatial filter. The 'local background' (B) was defined as the all pixels in the context region more than 12 pixels away from any pixel in the ROI, with M=n(B) pixels. The SVD (singular value decomposition) of the background movie was computed $D_{M \times T}^b$:

$$D_{M \times T}^b = U_{M \times M} \Sigma_{M \times T} V_{T \times T}^*$$

Multiple linear regression of the trace $X_{i-1}$ was performed against the top eight background principal components:

$$b_i = (V_8^* V_8)^{-1} V_8^* X_{i-1}$$

where $V_8$ is the first eight columns of V; $b_i$ are the regression coefficients. The trace $X_{i-1}(t)$ was denoised by subtracting the contribution of background pixels:

$$X_i^1 = X_{i-1} - V_8 b_i$$

$X_i^1(t)$ was high-pass filtered at 60 Hz using a third order Butterworth filter. Local minima in the filtered trace below a threshold $s_i$ were selected as an initial estimate of spike times. The threshold was chosen as follows: the distribution of local minima $P_{min,i}(x)$ was calculated by kernel density estimation and its median μ was computed. The distribution of the noise $P_{noise,i}(x)$ was estimated by symmetrizing about the median; i.e. setting.

$$\widetilde{P_{noise,i}}(\mu + x) := \begin{cases} P_{min,i}(\mu + x); & x > 0 \\ P_{min,i}(\mu - x); & x < 0 \end{cases}$$

The distribution of spikes $P_{spike}$ was estimated as:

$$\widetilde{P_{spike,i}}(x) := \max(0, P_{min,i}(x) - \widetilde{P_{noise,i}}(x))$$

The threshold was selected as:

$$s_i = \operatorname*{argmax}_{s \in \mathbb{R}} \left( \sqrt{\int_{-\infty}^s \widetilde{P_{spike,i}}(x)dx} - \sqrt{\int_{-\infty}^s \widetilde{P_{noise,i}}(x)dx} \right)$$

Thus, the initial estimate of spike times was $$S_i = \{t | X_i^1(t) < s_i, X_i^1(t) > X_i^1(t+1),$$

$$X_i^1(t) < X_i^1(t-1)\}.$$

This approach assumes that spikes only occur in a small proportion of time points, that $P_{noise}(x)$ is symmetric about p in the absence of spikes, that local minima are uncorrelated to the voltage trace in the absence of spikes, and that no spikes produce local minima larger than ρ. These assumptions are only approximately satisfied, but results of this method agree well with manual threshold selection.

Following the first round of spike detection, an action potential template $Z_i(r)$ was generated as:

$$Z_i(\tau) = \frac{1}{n(S_i)} \sum_{t \in S_i} X_i^1(t + \tau); \tau \in [-20 \text{ ms}, 20 \text{ ms}]$$

The template $Z_i(\tau)$ was used to perform a whitened matched filter (39) on $X_i^1(t)$, producing the temporally filtered trace $X_i^f(t)$. $X_i^f(t)$ was again adaptively thresholded to obtain the estimated spike times $S_i^f$ for iteration i, and regenerate the action potential template, $Z_i^f(\tau)$.

Step 2: Spatial Filter Estimation

A target trace $\hat{X}_t(t)$ was produced by convolving the action potential template with the spike time indicator function:

$$\hat{X}_t(t) = Z_i^f * Y_i \text{ where } Y_i(t) = \begin{cases} 1, t \in S_i^f \\ 0, \text{otherwise} \end{cases}$$

A spatial filter wiN×(was estimated by ridge regression of the target trace $\hat{X}_t$ against $D_{N \times T}^h$ (FIG. 29).

$$w_i = (D^{h*} D^h + \lambda (\|D^h\|_F^2) I)^{-1} D^{h*} \hat{X}_t$$

Where $\|D^h\|_F$ is the Frobenius norm of the high pass filtered data. The regularization parameter λ was selected by cross-validation on one dataset, and fixed for the remaining datasets. The activity trace corresponding to the spatial filter was calculated:

$$X_i = D w_i$$

The Spike Pursuit loop was performed for five iterations. As a final step, the contribution of pixels was removed from a 'global background' (G), defined as the entire field of view excluding all pixels less than 12 pixels away from any ROI, with L=n(G) pixels. The SVD of the global background movie was high pass filtered at 0.3 Hz, $D_{L \times T}^g$:

$$D_{L \times T}^g = U_{L \times L}^g \Sigma_{L \times T}^g V_{T \times T}^{g*}$$

Multiple linear regression of the trace $X_5$ was performed against the top 8 principal components of the global background movie:

$$b_g = (V_8^{g*} V_8^g)^{-1} V_8^{g*} X_5$$

$$X_{final} = X_5 - V_8^g b_g$$

Figure 27A:
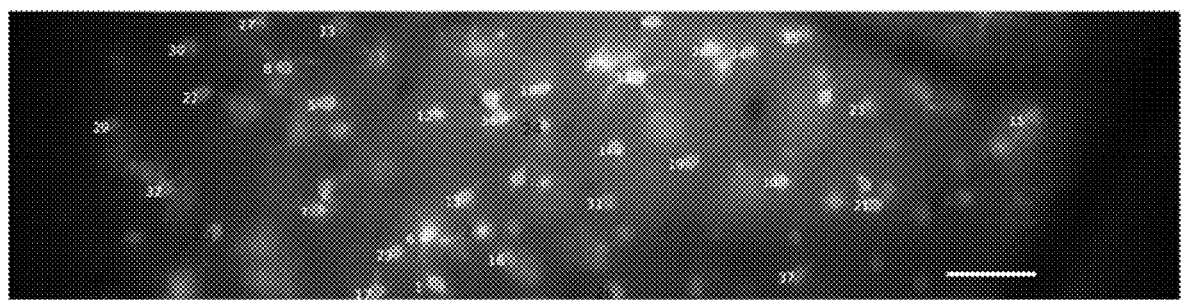
FIG. 27A includes an image showing Layer 1 interneurons expressing Voltron525 (same field of view as in FIG. 3F). Scalebar: 100 μm.
Figure 27B:
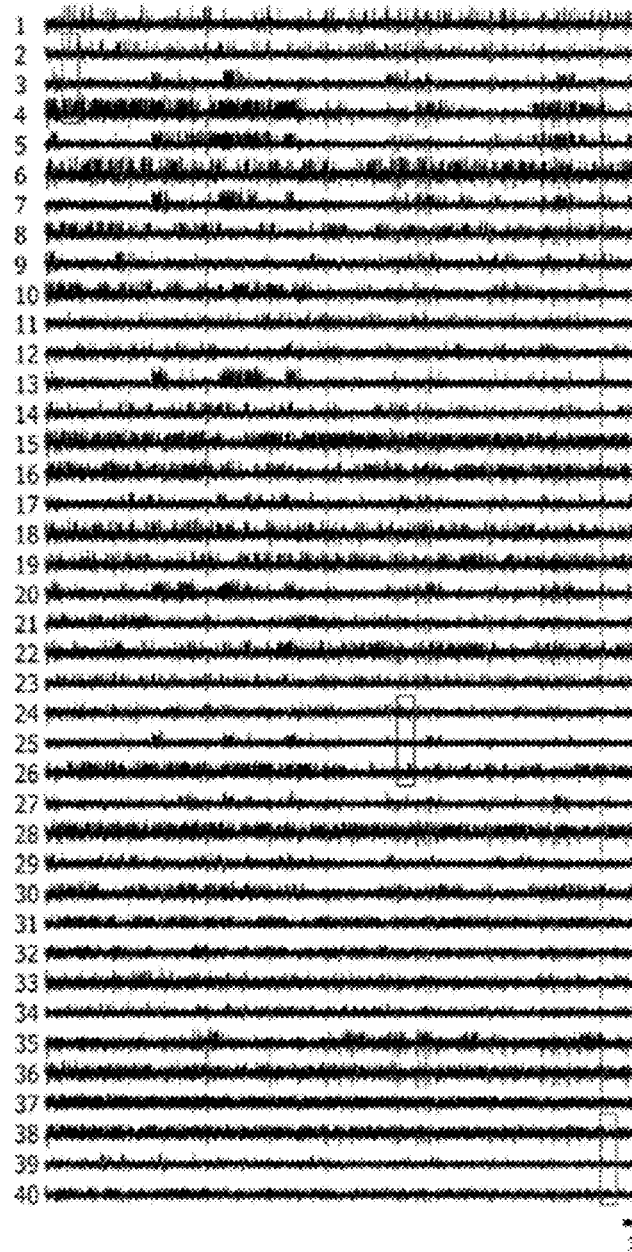
FIG. 27B includes fluorescence traces from neurons labeled in FIG. 27A, in decreasing order of signal to noise ratio. Signals processed as in FIG. 7G but without the last step of global background subtraction.
Figure 27C:
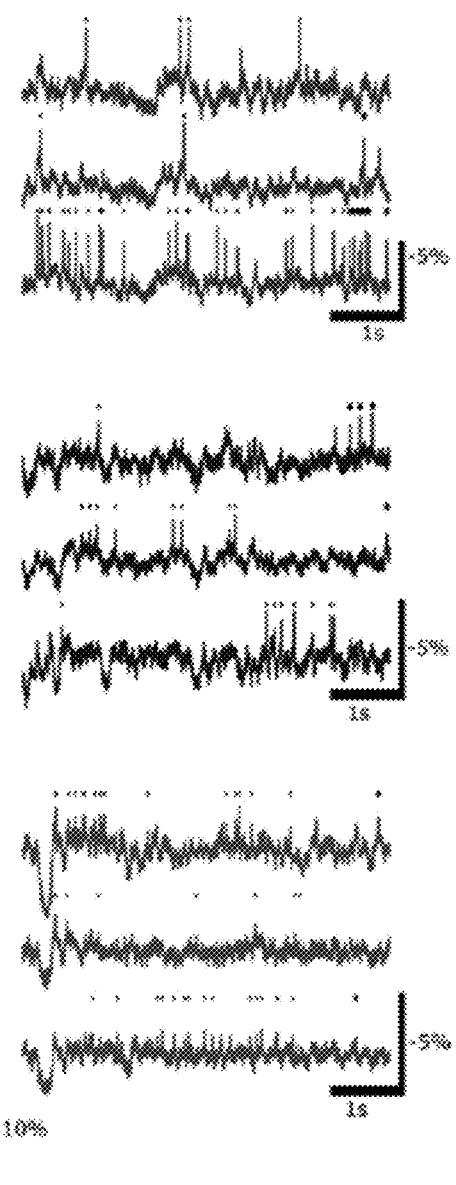
FIG. 27C includes image zooms of fluorescence traces from color coded regions of FIG. 27A with detected action potentials represented as black dots above, illustrating representative traces with high (top), medium (middle), and low (bottom) SNR.

Global background subtraction removes fluorescence fluctuations that are shared across most pixels of the movie. It remains unclear to what degree these fluctuations reflect shared membrane potential transients versus other sources of shared variability. Traces without global background subtraction ($X_5$) are shown in FIG. 27.

Calculating Spike Triggered Averages for Layer 1 Interneurons:

For each pair of neurons (p, q) the spike triggered average from neuron p to neuron q was calculated as:

$$STA_{p \to q}(\tau) = \frac{1}{n(S_s^p)} \sum_{t \in S_s^p} X_5^q(t + \tau); \tau \in [-200 \text{ ms}, 200 \text{ ms}]$$

Figure 28A:
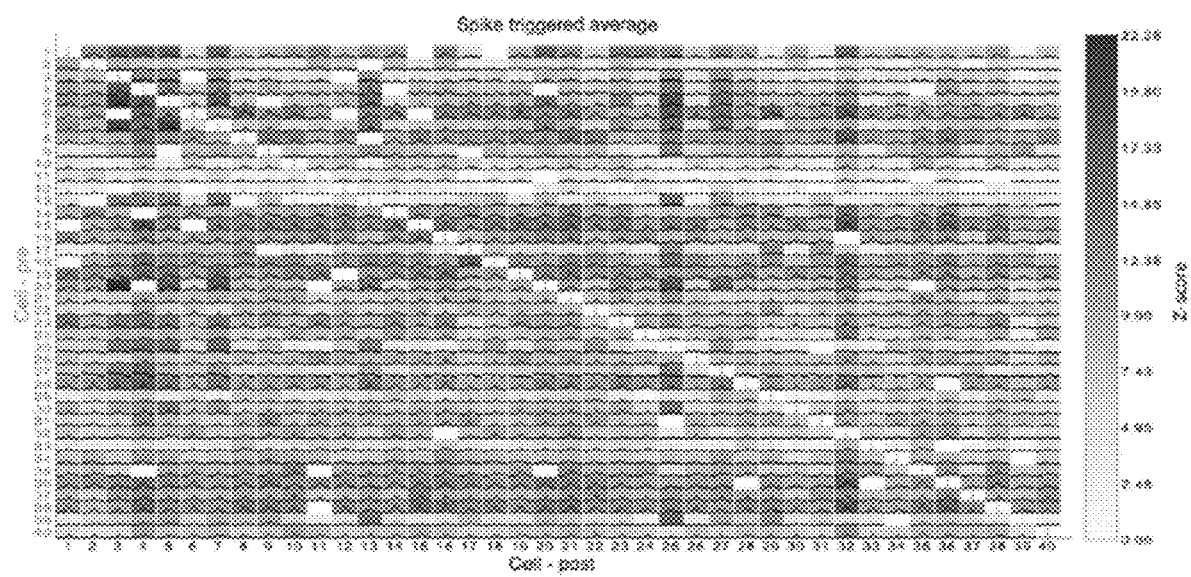
FIG. 28A-28D include spike triggered averages of neuron ensemble.
Figure 28B:
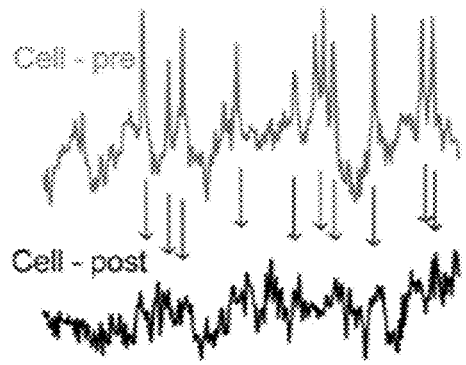
Figure 28C:
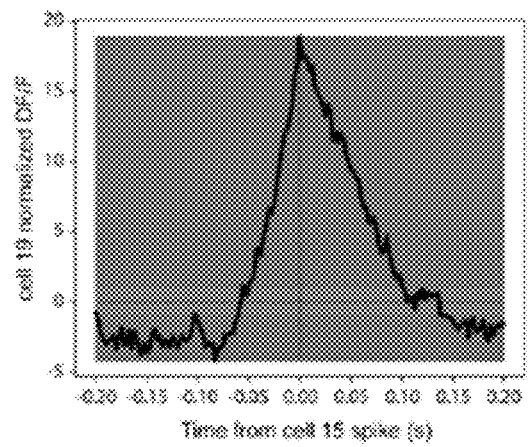
Figure 28D:
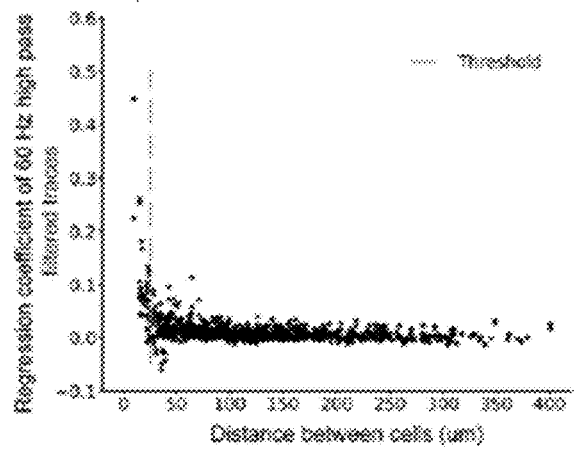

To calculate the shuffled distribution of spike triggered averages, each spike time was shifted by a random amount ranging from 2 s to 4 s (minimum of 2 s chosen based on the typical autocorrelation function of the fluorescence traces). The spike triggered average of each pair was normalized by the standard deviation of the distribution of shuffled spike triggered averages (gray bar in FIG. 28C). The 'modulation' of one neuron was estimated by another as the L2 norm of the spike triggered average. To z-score this norm, a log-normal distribution was fit to its shuffle distribution. The background color in FIG. 28A and FIG. 28C represents this z-score.

Similar results (not shown) were obtained for the spike triggered averages using raw fluorescence traces, calculated as:

$$STA_{p \to q}(\tau) = \frac{1}{n(S_s^p)} \sum_{t \in S_s^p} X_0^q(t + \tau); \tau \in [-200 \text{ ms}, 200 \text{ ms}]$$

Transgenic Zebrafish:

Transgenic zebrafish which expresses Voltron under UAS promoter were generated as follows. A sequence of Voltron (Ace2-HaloTag) was cloned downstream of a 10×UAS sequence and the E1B minimal promoter (40). This plasmid was injected into 2-cell stage embryos of Casper mutant zebrafish (41) with mRNA of Tol2 transposase (42) to generate founder (F0) transgenic zebrafish.

Figure 15A:
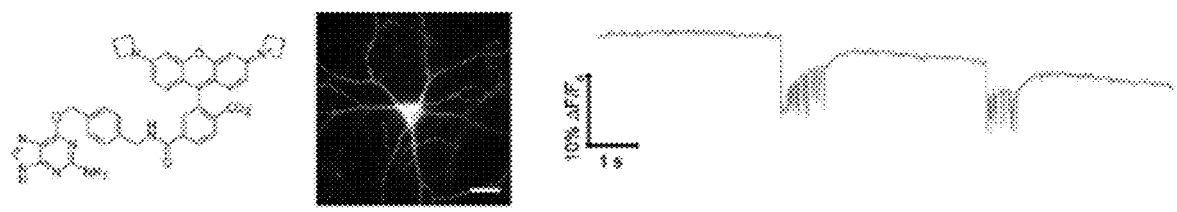
FIG. 15A includes, Left: Chemical structure of JF549-SNAP-tag ligand, Middle: fluorescence image of hippocampal neurons in culture expressing QuasAr2-SNAP-tag labeled with $_{JF549}$. Right: Fluorescence trace over time showing voltage-dependent fluorescence changes resulting from spontaneous action potentials of the neurons.
Figure 15B:
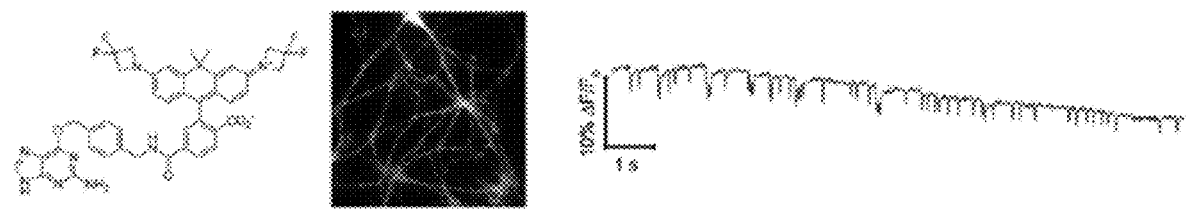
FIG. 15B includes, Left: Chemical structure of JF585-SNAP-tag ligand, Middle: fluorescence image of hippocampal neurons in culture expressing QuasAr2-SNAP-tag labeled with JF585. Right: Fluorescence trace over time showing voltage-dependent fluorescence changes resulting from spontaneous action potentials of the neurons. Scale bar: 20 μm FIG. 16 includes representative fluorescence traces of Voltron525 in response to a series of voltage steps (from −110 mV to +50 mV in 20 mV increments). Image acquisition rate=400 Hz.

Transgenic zebrafish which expresses Voltron under elavl3 promoter for FIG. 15 were generated as follows. A sequence of Voltron (Ace2-HaloTag) and its soma-localized variant (Ace2-HaloTag-SOM2) was cloned downstream of an elavl3 promoter sequence. This plasmid was injected into 2-cell stage embryos of Casper mutant zebrafish (41) with mRNA of Tol2 transposase (42) to generate founder (F0) transgenic zebrafish. Images of the brains of their embryos (F1) were used for FIG. 20.

Experiments described in FIGS. 8 and 42 were performed using embryos generated by crossing the UAS: Voltron F0 founder and vglut2a:Gal4 transgenic zebrafish (43) (a gift from Dr. Shin-ichi Higashijima). To label Voltron-expressing neurons with the accompanying fluorescent dye, 4-day old embryos were incubated in dye solution [3.3 μM JF$_{525}$-HaloTag ligand (17) and 0.3% DMSO] in fish rearing water at room temperature for two hours. After screening for the fluorescence of the JF dye in the brain, the fish were returned to fish rearing water with food until the time of the experiment.

Preparation for Zebrafish Imaging Experiments:

Imaging experiments were performed using 5- or 6-day larval zebrafish. The zebrafish was immobilized and mounted to an imaging chamber as described previously (44) with minor modifications. Briefly, the zebrafish were habituated in an artificial cerebrospinal fluid (ACSF) [in mM: 120 NaCl, 2.9 KCl, 2.1 CaCl2, 1.2 MgCl2, 20 NaHCO$_3$, 1.25 NaHPO4, 10 Glucose] bubbled with carbogen gas (95% oxygen, 5% carbon dioxide) for 30 minutes. The muscle of the zebrafish was paralyzed by a short (up to 30 seconds) bath incubation with alpha-bungarotoxin (1 mg/ml, Thermo Fischer Scientific, B1601) dissolved in external solution. After the fish became immobile, heart movement of the zebrafish was stopped by microforceps to prevent the shadowing effect of blood cells in the brain during imaging experiments. The zebrafish showed robust optomotor behavior in ACSF (bubbled with carbogen gas for 30 minutes before the experiment) for several hours after this treatment. The zebrafish was further mounted to a custom-made chamber using 2% agarose (Sigma-Aldrich, A9414) and placed under a light-sheet microscope (45) with a 20× objective lens (Olympus, XLUMPLFLN).

Light-sheet imaging of zebrafish Voltron signals: Imaging was performed in a light-sheet microscope according to a published design (46) with modifications targeted at optimizing Voltron imaging. To increase the fraction of time the imaged cells were exposed to the excitation laser beam, the beam was expanded in the horizontal dimension using a pair of cylindrical lens (LJ1878L1-A (f=10 mm) and LJ1402L1-A (f=40 mm), Thorlabs). Imaging was performed using a 488 nm excitation laser (80 μW) and a 562/40 emission filter (Semrock, FF01-562/40) and with a frame rate of 300 frames/second recorded by a sCMOS camera (Hamamatsu, ORCA Flash4.0 v2). In this setup, the pixel dimension on the camera was 0.293 μm/pixel and the imaged neurons occupied an area of 150-200 pixels on the image.

Simultaneous Cell-Attached Extracellular Recordings and Voltage Imaging in Zebrafish:

Electrophysiology and imaging of neurons expressing Voltron in Tg(vglut2:Gal4); Tg(UAS: Voltron) transgenic zebrafish were simultaneously performed as described previously (44) with a minor modification. Fire-polished borosilicate glass pipettes (Sutter, BF150-75-7.5) were pulled using a heat puller (Sutter, P1000). The tip of the pipette was further coated by quantum dots (Ocean Nanotech, QSR-600) using a previously reported method (47). The pipette resistance after the quantum dot coating was 10-12 MΩ.

The fish was bathed in an external solution and a small incision on the top of the head was made using a sharp glass needle. The pipette was filled with an external solution and inserted into the cerebellum of the brain using a micromanipulator (Sutter, MPC-200), and extracellular spiking signals were recorded from vGlut2-positive neurons in the dorsal part of the cerebellum using cell-attached extracellular recordings. These neurons are assumed to be eurydendroid neurons in the cerebellum, homologues of neurons in the deep cerebellar nuclei in mammalian brains (48), based on their previously described anatomical locations (49) and their expression of the vglut2 gene (49). Signals from the pipette were amplified by an amplifier (Molecular Devices, AxoClamp 700B) and recorded by custom software written in C # (Microsoft) at 6 KHz. Optical signals from the same neurons were simultaneously imaged as described above.

Behavioral experiments in zebrafish: Recording of fictive swim signals and presentation of visual stimuli were performed as described previously (44, 45). To record swim signals from the axonal bundles of spinal motoneurons in the tail, a pair of large barrel electrodes was attached to the dorsal left and right side of the tail. Signals were amplified by an amplifier (Molecular Devices, AxoClamp 700B) and recorded at 6 KHz using custom software written in C # (Microsoft). For synchronization between the swimming signals and neural activity imaging, camera trigger signals that initiate the acquisition of individual frames in the light-sheet microscope were recorded simultaneously with the swim signals. During the experiments, red visual stimuli (red/black gratings with bars 2 mm thick) was projected to the bottom of the fish chamber. The speed of the moving the visual stimulus alternated between 0 mm/s (stopped) and 2 mm/s (moving forward) every 10 seconds. Every trial (20 seconds) contained a stop period and a forward-motion period. In a subset of tested fish, the forward moving speed was changed from 2 mm/s to 0.5 mm/s every other trial. Swimming behavior was continuously recorded for a duration ranging from 6 minutes to 12 minutes (18 to 36 trials).

Signals from the electrodes were processed and individual swim events were detected according to a method described previously (44). Briefly, the raw signals were high-pass filtered, squared and smoothed by applying a Gaussian filter ($\sigma$=3.3 milliseconds). The resulting traces were defined to be the swim signal, as shown in FIG. 8. Individual swim bouts were detected by finding the time points at which the swim signal crossed a threshold. This threshold was automatically set to lie just above a noise level based on a histogram of the swim signals (45, 50).

Analysis of Imaging Dataset:

The flow of the data processing is described below and in FIGS. 42B and 42C. Custom Python scripts are provided for this analysis on Github (git.io/vA2Ee).

Step 1. Image Registration

Sequences of recorded images were corrected for horizontal drift during the imaging session at the subpixel level with a phase correlation algorithm (51) using a custom Python script and a GPU computing board.

Step 2. Segmentation of Neurons

Individual neurons in the imaging field were segmented in a semi-automatic way. This was done using a combination of cell recognition by a pre-trained convolutional neural network build with the Python Keras library (keras.io/) and manual correction. This convolutional network discriminates whether a locally darkest point in a circular patch (radius=2.67 µm) is a center of a Voltron-expressing neuron or not. Once the cells are segmented, ring-shaped masks are drawn automatically over the cells ($1^{st}$ pixel weights in FIGS. 42B and 42C). This is achieved by (1) selecting the brightest points on a line (at 0 degrees) from the center of a cell, (2) selecting such points for different angles around the cell (0 to 342 degrees in 18-degree steps), (3) smoothing the line connecting these brightest points by median filtering the distance from the center of the cell to the brightest points, and (4) dilating the resulting line by 1 pixel. Pixels on this dilated line are given an initial weight of 1, and all other pixels an initial weight of 0, to create the mask.

Step 3. Optimization of Pixel Weights for Individual Neurons

Weights on the pixels of the above masks were optimized to maximize the signal-to-noise ratio of the voltage signals in individual neurons (FIG. 42C). This is necessary because the light scattering through the tissue during the imaging experiment mixes to a small extent the optical signals across pixels surrounding the cell. This process optimizes the weights on the pixels over the cell to maximize the objective function J:

$$J = \frac{(E(F_S))^2}{\text{Var}(F)} - \|W\|^2$$

where W is a matrix of weights over pixels, Var(F) is a variance of a weighted mean fluorescence time-series of candidate pixels using W, E(Fs) is the average of the weighted mean fluorescent values at the time of detected spikes, and $\|W\|\|^2$ is the $L^2$ norm of the pixel weights for regularization. This objective function measures the ratio between the mean heights of the spikes and the noise level of the estimated fluorescence time-series of a cell. Pixel weights W are optimized so that they maximize the objective function J using a gradient ascent method. Spiking events used for this optimization are detected using the fluorescence time series of the $1^{st}$ pixel weights using the same algorithm as described below. The final fluorescence time series is obtained by (1) calculating the weighted average of fluorescence values across pixels using the optimized W, (2) subtracting the camera background (i.e., the pixel value when the camera records dark images), and (3) normalizing the resulting time-series by dividing by its baseline time-series, which is a rolling percentile (80% [since Voltron becomes dimmer with increasing voltage, an upper percentile was used instead of a lower percentile used for calcium imaging data], 500-ms time window) of the time-series.

Step 4. Spike Detection

Lastly, spiking events were detected for individual neurons using an iterative method that first estimates the subthreshold potential and subtracts it from the raw voltage trace, and secondly estimates spiking events on the resulting trace. These three steps were iterated three times:

1. The subthreshold potential was obtained by subtracting the current estimate of the voltage trace attributable to spikes (i.e. the convolution of the estimated spike train s with spike shape k, s*k) from the raw trace followed by low pass filtering to remove the noise. Using a simple Butterworth filter of order 5 with a cutoff at 10 Hz was effective. Subtracting the subthreshold potential yielded the high-frequency component y that consists of voltage transients due to spikes corrupted by noise.

2. Spiking events were detected using a method based on adaptive template matching. First, large spiking events were detected using a high threshold (3.5*rolling standard deviation+rolling median, window size of 3 seconds) to avoid false positives. The neuron's spike shape was constrained to have non-zero values only in a small window around the time of a spike and was calculated using linear regression of y on s.

3. The less clear spike events were detected using this mean spike shape k as a template instead of merely relying on a threshold. Potential spike candidates were detected using a low threshold (2.5*rolling standard deviation+rolling median) to avoid false negatives. Template matching by regressing y on k yielded the sizes of these candidate events. The candidates that were not actual spikes but were merely due to noise had a small size and were iteratively removed with the regression being repeated. After the three outer iterations a reasonable estimate of the spike shape k and the spike times were obtained at frame-rate resolution.

Step 5. Validation of the Authenticity of the Detected Spikes

To minimize the false-positive detection rate of spiking events, the authenticity of the spike shapes were measured throughout the time-series by measuring the gradient of the voltage trace just before the estimated spiking events. This is based on an assumption that spiking events are always preceded with an increase of subthreshold membrane voltage and that non-spike high-frequency noise does not have this preceding component. The gradient of voltage signals from 10 milliseconds to 3.3 milliseconds (3 time points) before the spiking events were quantified for individual spikes. Detected spiking events were binned into contiguous blocks of 50 spiking events. The gradient values for each block of spiking events were tested for its deviation from zero using a Wilcoxon signed rank test. Spiking events in blocks that had significantly positive gradients ($p<0.05$) are used for subsequent analysis.

Analysis of the Relationships Between Neural Activity and Behavior:

Neurons that were used for analysis in FIG. 8 and FIG. 42 were statistically selected based on their modulation of spiking activity by visual stimuli and behavior. Two criteria were used for this. First, the difference of numbers of spikes in the two task periods (stop, forward visual motion) across multiple trials was tested using Wilcoxon's ranked sum test. Second, the modulation of subthreshold signals at the initiation of swim bouts (−100 ms to 100 ms) was tested across all swim bouts using two-way analysis of variance. Neurons which showed significant differences ($p<0.05$) for both criteria were used for subsequent analyses. A total of 468 neurons from 81 fish were tested, and 179 neurons from 43 fish were used for subsequent analyses.

Figure 42E:
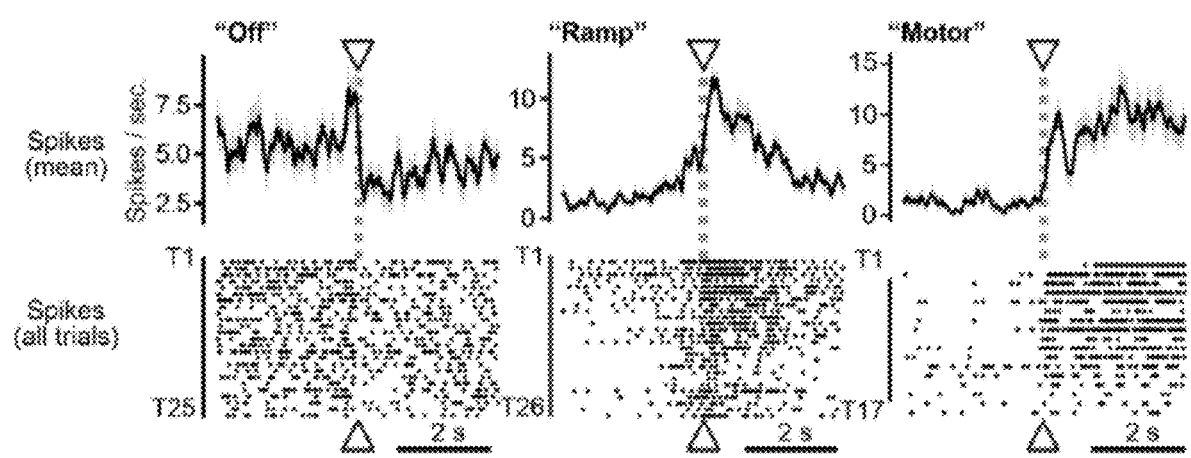

Mean subthreshold signals and firing rates on FIGS. 8E and 42E were smoothed by gamma density causal filters ($t^*\exp(-t/\theta)$ for $t>0$) with a hyperparameter $\theta$ set differently for each panel (3.3 ms for FIG. 8E and 200 ms for FIG. 42E).

For classifying neurons in FIG. 8E, subthreshold voltage signals were first smoothed by a gamma density causal filter ($\theta=3.3$ ms) and then averaged centered at the onset of all swim bouts (−100 to +100 milliseconds, 60 time points). The resulting averaged subthreshold signals were normalized to between 0 and 1 using their minimum and maximum values. Non-negative matrix factorization (NMF) was applied to the pool of these normalized subthreshold signals with a prior number of components set to 3. It was confirmed that three components similar to the ones shown in FIG. 8D ('Off', 'Onset' and 'Late') always appear as NMF components regardless of the initial conditions. Component weights for each of the neurons are further adjusted so that the sum of weights for three components becomes 1, and these adjusted weights are allocated to red, green and blue channels to color neurons.

Widefield Imaging of Voltron Expressing Neurons in Zebrafish:

Mitfa$^{w2/w2}$ roy$^{a9/a9}$ (Casper) zebrafish were maintained under standard conditions at 28° C. and a 14:10 hr light:dark cycle. Embryos (1-2 cell stage) of Tg(elavl3:Gal4-VP16) were injected with 25 ng/µl DNA plasmid encoding the Voltron-ST indicator under the control of the 10×UAS promoter, and 25 ng/µl Tol2 transposase mRNA diluted in E3 medium.

Subsequently, the injected embryos at three day post-fertilization (dpf) were incubated in system water containing JF dye-HaloTag ligands ($JF_{525}$, $JF_{549}$, $JF_{585}$ or $JF_{635}$) at 3 µM for 2 hours and then washed in dye-free system water. Larvae at 5 or 6 dpf were screened for the expression of the Voltron-ST based on the fluorescence from JF dye-HaloTag ligands. They were paralyzed by 5-min bath application of 1 mg/ml a-bungarotoxin (Sigma, 203980) and mounted dorsal-side up with 1.5% low-melting point agarose. Spontaneously active forebrain and olfactory neurons were imaged using a custom widefield microscope. The objective was a 60× 1.0 NA water immersion lens (Nikon, MRD07620). Fluorophores were excited with a LED light source (Luminus, CBT-90-W for $JF_{525}$, $JF_{549}$ and $JF_{585}$, Luminus, CBT-90-RX for $JF_{635}$) with a proper filter set (Semrock, FITC-A-Basic-000 for $JF_{525}$; Semrock, Cy3-4040C-000 for $_{JF549}$; Semrock, LED-mCherry-A-000 for $JF_{585}$; Semrock, LF635-C-000 for $JF_{635}$). The images were acquired with sCMOS camera (PCO, pco.edge 4.2) at 400 Hz (2.5 ms exposure time) for 1-2 min. Data were analyzed using MATLAB (Mathworks). Regions of interest (ROIs) corresponding to identifiable cell bodies were selected manually and the mean signal from each ROI was extracted. The baseline was estimated by fitting the raw fluorescence time course with an exponential curve to account for bleaching. The estimated baseline was used to calculate the $\Delta F/F_0$.

Simultaneous Whole-Cell Recording and Voltron Imaging in Zebrafish:

Experiments were performed on 6-day old progeny of a cross between Tg(10×UAS:Voltron) and TgBAC(slc17ab:LOXP-mCherry-LOXP-GAL4FF;vsx2:Cre). Fish were loaded with JF525 and then paralyzed as described above. After anesthetizing fish with MS-222, they were head-fixed and prepared for whole-cell recording and imaging of V2a hindbrain neurons. They were secured to a Sylgard-coated glass-bottom dish containing extracellular solution (134 mM NaCl, 2.9 mM KCl, 1.2 mM MgCl2, 2.1 mM CaCl$_2$), 10 mM HEPES, and 10 mM glucose, adjusted to pH 7.8 with NaOH) with etched tungsten wires through the notochord. Then the head was rotated and secured ventral side up with etched tungsten pins placed through the ears and the rostral part of the jaw. The ventral surface of the hindbrain was carefully exposed by removing the notochord using an etched tungsten pin and fine forceps. Whole-cell recordings were guided based on fluorescence image and scanned Dodt gradient contrast image acquired with a custom two-photon microscope equipped with 40× 0.8 NA objective lens (Nikon, MRD07420). Borosilicate glass pipettes (Sutter, BF150-86-15) were pulled by a micropipette puller (Sutter, P-1000) and filled with intracellular solution (125 mM potassium gluconate, 2.5 mM MgCl2, 10 mM EGTA, 10 mM HEPES and 4 mM ATP-Na$_2$ adjusted to pH 7.3 with KOH). The resistance of the pipette was 5 to 7 MOhm. Recordings were made using the EPC 10 Quadro amplifier and PatchMaster (HEKA instruments). Voltron signal was acquired as described above but with 40× objective lens. After extracting Voltron signal from the patched cell using the procedure described above, the signal was further denoised using wden function in Wavelet Toolbox in MATLAB (Mathworks) to reveal Voltron signal corresponding to small subthreshold voltage changes.

Simultaneous Voltron Imaging and Whole-Cell Patch Clamp in Live Adult Flies:

Experiments were performed on 2- to 10-day-old heterozygous progeny of a cross between UAS-IVS-syn21-Voltron-p10 and MB058B-Gal4 (52). The cross was kept on standard cornmeal food supplemented with all-trans-retinal (0.2 mM before eclosion and then 0.4 mM). Flies were head-fixed and prepared for imaging and electrophysiology as described previously (53). A small window was opened on the head cuticle, and fat cells and trachea that overlaid the target region were removed. The exposed brain was bathed in a drop (~200 µL) of dye-containing saline (1 µM for JF$_{549}$ and 5 µM for JF$_{525}$) for 1 hr. Saline contains (in mM): NaCl, 103; KCl, 3; CaCl$_2$, 1.5; MgCl$_2$, 4; NaHCO$_3$, 26; N-tris (hydroxymethyl) methyl-2-aminoethane-sulfonic acid, 5; NaH$_2$PO$_4$, 1; trehalose, 10; glucose, 10 (pH 7.3 when bubbled with 95% O2 and 5% CO$_2$, 275 mOsm. The brain was then washed with fresh saline several times, and maintained in the saline for 1 hr.

During the dye application and washout, animals were placed in a moist chamber to avoid dehydration. After that, they were moved to the imaging rig, where superfusion continued at 1-2 mL/min with oxygenated saline. To minimize movement during imaging, the proboscis was fixed with a UV-curable glue (NOA 68T, Norland products) and the frontal pulsatile organ muscle 16 was removed. Imaging was performed on a wide-field fluorescence microscope (SOM, Sutter Instruments) equipped with a 60×, NA 1.0, water-immersion objective (LUMPlanFl/IR; Olympus) and a sCMOS camera (Orca Flash 4.0 V2+, Hamamatsu). Images were acquired at 800 Hz with 4×4 binning through the Hamamatsu imaging software (HCImage Live). Data presented used $_{JF549}$. Illumination was provided by a 530 nm LED (SA-530, Sutter) with an excitation filter (FF01-543/22-25, Semrock); intensity at the sample plane was ~5 mW/mm$^2$ for axons and dendrites, and 8-16 mW/mm$^2$ for soma; emission was separated from excitation light using a dichroic mirror (FF562-Di03-25×36, Semrock) and an emission filter (LP02-568RU-25, Semrock).

Experiments with JF$_{525}$ tended to yield shorter duration imaging sessions (~2 min versus >5 min for JF$_{549}$ in dopamine neurons), likely because of greater phototoxicity with the shorter wavelength light. For JF$_{525}$, illumination was provided by a 506 nm LED (SA-506-1PLUS, Sutter) with an excitation filter (FF01-503/40-25, Semrock); intensity at the sample plane was typically 10-25 mW/mm$^2$; emission was separated from excitation light using a dichroic mirror (Di02-R532-25×36, Semrock) and an emission filter (FF01-562/40-25, Semrock).

Whole-cell recordings (54) were guided by Voltron fluorescence from target cells. The patch pipettes were pulled for a resistance of 5-7 MΩ and filled with pipette solution containing (in mM): L-potassium aspartate, 125; HEPES, 10; EGTA, 1.1; CaCl$_2$), 0.1; Mg-ATP, 4; Na-GTP, 0.5; biocytin hydrazide, 13; with pH adjusted to 7.3 with KOH (265 mOsm). Recordings were made using the Axon MultiClamp 700B amplifier (Molecular Devices). Cells were held at around −60 mV by injecting hyperpolarizing current (<50 pA). Signals were low-pass filtered at 5 kHz and digitized at 10 kHz.

Voltron data were analyzed in MATLAB. Regions of interest (ROIs) corresponding to different neuron compartments were manually selected, and the mean intensity of the ROI was extracted. Median filtering with a 50-ms time window was performed on the raw fluorescence traces to get a filtered trace, and F0 was calculated as the mean over the first 1 s of imaging session. For detecting action potential spikes and quantifying SNR, the filtered trace was subtracted from the raw trace. Spikes were detected by finding local minima with peak amplitude over 3.5 times the standard deviation of the entire subtracted trace, and SNR was quantified as peak amplitude over the standard deviation of the trace excluding the time zone (50 ms) containing spikes. To analyze the axon signals, the ROIs of ipsilateral and contralateral axons were first pooled together to detect spikes. The spikes were then assigned to either the patched cell or its sister cell depending on the relative peak amplitude, i.e. if ipsilateral/contralateral >1, spike is assigned to the patched cell, otherwise it is assigned to the sister cell.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. T. W. Chen et al., Ultrasensitive fluorescent proteins for imaging neuronal activity. Nature. 499, 295-300 (2013).
2. K. Svoboda, W. Denk, D. Kleinfeld, D. W. Tank, In vivo dendritic calcium dynamics in neocortical pyramidal neurons. Nature. 385, 161-165 (1997).
3. V. Emiliani, A. E. Cohen, K. Deisseroth, M. Hausser, All-optical interrogation of neural circuits. J. Neurosci. 35, 13917-13926 (2015).
4. Y. Xu, P. Zou, A. E. Cohen, Voltage imaging with genetically encoded indicators. Curr. Opin. Chem. Biol. 39, 1-10 (2017).
5. M. Z. Lin, M. J. Schnitzer, Genetically encoded indicators of neuronal activity. Nat. Neurosci. 19 (2016), pp. 1142-1153.
6. J. M. Kralj, A. D. Douglass, D. R. Hochbaum, D. Maclaurin, A. E. Cohen, Optical recording of action potentials in mammalian neurons using a microbial rhodopsin. Nat. Methods. 9, 90-95 (2011).
7. D. R. Hochbaum et al., All-optical electrophysiology in mammalian neurons using engineered microbial rhodopsins. Nat. Methods. 11, 825-833 (2014).
8. Y. Adam et al., All-optical electrophysiology reveals brain-state dependent changes in hippocampal subthreshold dynamics and excitability. bioRxiv (2018), doi: 10.1101/281618.
9. L. Jin et al., Single action potentials and subthreshold electrical events imaged in neurons with a fluorescent protein voltage probe. Neuron. 75, 779-785 (2012).
10. P. Zou et al., Bright and fast multicoloured voltage reporters via electrochromic FRET. Nat. Commun. 5, 4625 (2014).
11. 4. Y. Gong et al., High-speed recording of neural spikes in awake mice and flies with a fluorescent voltage sensor. Science. 350, 1361-1366 (2015).
12. A. S. Abdelfattah et al., A bright and fast red fluorescent protein voltage indicator that reports neuronal activity in organotypic brain slices. J. Neurosci. 36, 2458-2472 (2016).
13. H. H. H. Yang et al., Subcellular Imaging of Voltage and Calcium Signals Reveals Neural Processing In Vivo. Cell. 166, 245-257 (2016).
14. J. B. Grimm et al., A general method to improve fluorophores for live-cell and single-molecule microscopy. Nat. Methods. 12, 244-250 (2015).
15. G. V. Los et al., HaloTag: A novel protein labeling technology for cell imaging and protein analysis. ACS Chem. Biol. 3, 373-382 (2008).
16. L. P. Encell et al., Development of a dehalogenase-based protein fusion tag capable of rapid, selective and covalent attachment to customizable ligands. Curr. Chem. Genomics. 6, 55-71 (2012).
17. J. B. Grimm et al., A general method to fine-tune fluorophores for live-cell and in vivo imaging. Nat. Methods. 14, 987 (2017).

18. Y. Gong, M. J. Wagner, J. Zhong Li, M. J. Schnitzer, Imaging neural spiking in brain tissue using FRET-opsin protein voltage sensors. *Nat. Commun.* 5, 3674 (2014).

19. J. M. Kralj, D. R. Hochbaum, A. D. Douglass, A. E. Cohen, Electrical spiking in *Escherichia coli* probed with a fluorescent voltage-indicating protein. Science (80,). 333, 345-348 (2011).

20. T. Wada et al., Crystal structure of the eukaryotic light-driven proton-pumping rhodopsin, *Acetabularia* rhodopsin II, from marine alga. *J. Mol. Biol.* 411, 986-998 (2011).

21. A. Keppler et al., A general method for the covalent labeling of fusion proteins with small molecules in vivo. *Nat. Biotechnol.* 21, 86-89 (2003).

22. C. A. Baker, Y. M. Elyada, A. Parra, M. M. L. Bolton, Cellular resolution circuit mapping with temporal-focused excitation of soma-targeted channel rhodopsin. *Elife.* 5, 1-15 (2016).

23. S. T. Lim, D. E. Antonucci, R. H. Scannevin, J. S. Trimmer, A novel targeting signal for proximal clustering of the Kv2.1 K+channel in hippocampal neurons. *Neuron.* 25, 385-397 (2000).

24. S. L. Smith, I. T. Smith, T. Branco, M. Häusser, Dendritic spikes enhance stimulus selectivity in cortical neurons in vivo. *Nature.* 503, 115-120 (2013).

25. B. Tasic et al., Adult mouse cortical cell taxonomy revealed by single cell transcriptomics. *Nat. Neurosci.* 19, 335-346 (2016).

26. M. B. Ahrens et al., Brain-wide neuronal dynamics during motor adaptation in zebrafish. *Nature.* 485, 471-7 (2012).

27. T. Hige, Y. Aso, G. M. Rubin, G. C. Turner, Plasticity-driven individualization of olfactory coding in mushroom body output neurons. *Nature.* 526, 258-262 (2015).

28. A. Wang, J. Feng, Y. Li, P. Zou, Beyond fluorescent proteins: hybrid and bioluminescent indicators for imaging neural activities. *ACS Chem. Neurosci.* 9, 639-650 (2018).

29. L. A. Gross, G. S. Baird, R. C. Hoffman, K. K. Baldridge, R. Y. Tsien, The structure of the chromophore within DsRed, a red fluorescent protein from coral. *Proc. Natl. Acad. Sci.* 97, 11990-11995 (2000).

30. N. C. Shaner, P. A. Steinbach, R. Y. Tsien, A guide to choosing fluorescent proteins. *Nat. Methods.* 2, 905-909 (2005).

31. D. Wüstner, T. Christensen, L. M. Solanko, D. Sage, Photobleaching kinetics and time-integrated emission of fluorescent probes in cellular membranes. *Molecules.* 19, 11096-11130 (2014).

32. J. R. Lakowicz, *Principles of Fluorescence Spectroscopy* (Springer New York, N.Y., 2006).

33. S. J. Lord et al., DCDHF fluorophores for single-molecule imaging in cells. *ChemPhysChem.* 10, 55-65 (2009).

34. C. Eggeling, A. Volkmer, C. A. M. Seidel, Molecular photobleaching kinetics of Rhodamine 6G by one- and two-photon induced confocal fluorescence microscopy. *ChemPhysChem.* 6, 791-804 (2005).

35. T. J. Wardill et al., A Neuron-Based Screening Platform for Optimizing Genetically-Encoded Calcium Indicators. *PLoS One.* 8, 1-12 (2013).

36. D. A. Dombeck, C. D. Harvey, L. Tian, L. L. Looger, D. W. Tank, Functional imaging of hippocampal place cells at cellular resolution during virtual navigation. *Nat. Neurosci.* 13, 1433-1440 (2010).

37. T. Yardeni, M. Eckhaus, H. D. Morris, M. Huizing, S. Hoogstraten-Miller, Retro-orbital injections in mice. *Lab Anim.* (NY). 40, 155-160 (2011).

38. P. Thévenaz, U. E. Ruttimann, M. Unser, A pyramid approach to subpixel registration based on intensity. *IEEE Trans. Image Process.* 7, 27-41 (1998).

39. F. Franke, R. Quian Quiroga, A. Hierlemann, K. Obermayer, Bayes optimal template matching for spike sorting-combining fisher discriminant analysis with optimal filtering. *J. Comput. Neurosci.* 38, 439-459 (2015).

40. R. W. Koster, S. E. Fraser, Tracing Transgene Expression in Living Zebrafish Embryos. *Dev. Biol.* 233, 329-346 (2001).

41. R. M. White et al., Transparent Adult Zebrafish as a Tool for In Vivo Transplantation Analysis. *Cell Stem Cell.* 2, 183-189 (2008).

42. K. Kawakami et al., A transposon-mediated gene trap approach identifies developmentally regulated genes in zebrafish. *Dev. Cell.* 7, 133-44 (2004).

43. C. Satou et al., Transgenic tools to characterize neuronal properties of discrete populations of zebrafish neurons. *Development.* 140, 3927-31 (2013).

44. T. Kawashima et al., The Serotonergic System Tracks the Outcomes of Actions to Mediate Short-Term Motor Learning. *Cell.* 167, 933-946.e20 (2016).

45. N. Vladimirov et al., Light-sheet functional imaging in fictively behaving zebrafish. *Nat. Methods.* 11, 883-884 (2014).

46. N. Vladimirov et al., Light-sheet functional imaging in fictively behaving zebrafish. *Nat. Methods* 11, 883-884 (2014).

47. B. K. Andrásfalvy et al., Quantum dot-based multiphoton fluorescent pipettes for targeted neuronal electrophysiology. *Nat. Methods.* 11, 1237-1241 (2014).

48. Y.-K. Bae et al., Anatomy of zebrafish cerebellum and screen for mutations affecting its development. *Dev. Biol.* 330, 406-26 (2009).

49. M. Takeuchi et al., Establishment of Gal4 transgenic zebrafish lines for analysis of development of cerebellar neural circuitry. *Dev. Biol.* 397, 1-17 (2015).

50. M. B. Ahrens et al., Brain-wide neuronal dynamics during motor adaptation in zebrafish. *Nature.* 485, 471-7 (2012).

51. M. Guizar-Sicairos, S. T. Thurman, J. R. Fienup, Efficient subpixel image registration algorithms. *Opt. Lett.* 33, 156 (2008).

52. Y. Aso et al., The neuronal architecture of the mushroom body provides a logic for associative learning. *Elife.* 3, e04577 (2014).

53. M. Murthy, G. Turner, Dissection of the head cuticle and sheath of living flies for whole-cell patch-clamp recordings in the brain. *Cold Spring Harb. Protoc.* 8, 134-139 (2013).

54. R. I. Wilson, G. C. Turner, G. Laurent, Transformation of Olfactory *Drosophila* Antennal Lobe. *Science* (80-.). 303, 366-370 (2004).

55. F. St-Pierre et al., High-fidelity optical reporting of neuronal electrical activity with an ultrafast fluorescent voltage sensor. *Nat. Neurosci.* 17, 884-889 (2014).

56. O. Randlett et al., Whole-brain activity mapping onto a zebrafish brain atlas. *Nat. Methods.* 12, 1039-1046 (2015).

57. S. Chamberland et al., Fast two-photon imaging of subcellular voltage dynamics in neuronal tissue with genetically encoded indicators. *Elife.* 6, e25690 (2017).

58. Govorunova, E. G., et al., Microbial Rhodopsins: Diversity, Mechanisms, and Optogenetic Applications. *Annu Rev Biochm.* 86, 845-872 (2017).
59. Beja, O., et al. Proteorhodopsin phototrophy in the ocean. *Nature* 411, 786-789 (2001)
60. U.S. Patent Application Publication NO. 2020/0123218 for "OPTOGENETIC PROBES FOR MEASURING MEMBRANE POTENTIAL."
61. U.S. Pat. Nos. 9,933,417, 10,018,624, 10,161,932, and 10,495,632.

It will be understood that various details of the presently disclosed subject matter can be changed without departing from the scope of the subject matter disclosed herein. Furthermore, the foregoing description is for the purpose of illustration only, and not for the purpose of limitation.

```
SEQUENCE LISTING
SEQ ID NO: 1 - DNA sequence of Voltron D92N
ATGGCTGACGTGGAAACCGAGACCGGCATGATTGCACAGTGGATTGTCTTTGCTATT

ATGGCTGCTGCTGCTATTGCTTTTGGAGTGGCTGTGCACTTTCGGCCTTCAGAGCTG

AAGAGCGCATACTATATCAACATTGCCATCTGCACTATCGCCGCTACCGCTTACTAT

GCAATGGCCGTGAACTACCAGGACCTGACAATGAATGGTGAAAGGCAGGTGGTCTAC

GCAAGATATATTAACTGGGTGCTGACCACACCACTGCTCCTGCTCAACCTCATCGTC

ATGACCAAGATGGGCGGAGTGATGATTTCTTGGGTCATCGGCGCAGACATTTTCATG

ATCGTGTTTGGTATTCTGGGCGCCTTCGAGGATGAACACAAGTTCAAATGGGTGTAC

TTTATCGCTGGATGTGTGATGCAGGCAGTCCTGACATACGGGATGTATAACGCCACT

TGGAAAGACGATCTGAAGAAAAGCCCCGAGTACCATAGCTCCTATGTCAGTCTGCTC

GTCTTCCTGTCAATCCTCTGGGTGTTTATCCTGTCGTGTGGGCTTTCGGGTCTGGT

AGTGGCGTGCTGTCCGTCGACAATGAGGCCATTCTCATGGGAATCCTGGATGTGCTC

GCTAAGCCACTGTTTGGAATGGGGTGCCTCATTGCCCATGAGACTATCTTCAAGATC

GGTACTGGCTTTCCATTCGACCCCCATTATGTGGAAGTCCTGGGCGAGCGCATGCAC

TACGTCGATGTTGGTCCGCGCGATGGCACCCCTGTGCTGTTCCTGCACGGTAACCCG

ACCTCCTCCTACGTGTGGCGCAACATCATCCCGCATGTTGCACCGACCCATCGCTGC

ATTGCTCCAGACCTGATCGGTATGGGCAAATCCGACAAACCAGACCTGGGTTATTTC

TTCGACGACCACGTCCGCTTCATGGATGCCTTCATCGAAGCCCTGGGTCTGGAAGAG

GTCGTCCTGGTCATTCACGACTGGGGCTCCGCTCTGGGTTTCCACTGGGCCAAGCGC

AATCCAGAGCGCGTCAAAGGTATTGCATTTATGGAGTTCATCCGCCCTATCCCGACC

TGGGACGAATGGCCAGAATTTGCCCGCGAGACCTTCCAGGCCTTCCGCACCACCGAC

GTCGGCCGCAAGCTGATCATCGATCAGAACGTTTTTATCGAGGGTACGCTGCCGATG

GGTGTCGTCCGCCCGCTGACTGAAGTCGAGATGGACCATTACCGCGAGCCGTTCCTG

AATCCTGTTGACCGCGAGCCACTGTGGCGCTTCCCAAACGAGCTGCCAATCGCCGGT

GAGCCAGCGAACATCGTCGCGCTGGTCGAAGAATACATGGACTGGCTGCACCAGTCC

CCTGTCCCGAAGCTGCTGTTCTGGGGCACCCCAGGCGTTCTGATCCCACCGGCCGAA

GCCGCTCGCCTGGCCAAAAGCCTGCCTAACTGCAAGGCTGTGGACATCGGCCCGGGT

CTGAATCTGCTGCAAGAAGACAACCCGGACCTGATCGGCAGCGAGATCGCGCGCTGG

CTGTCGACGCTCGAGATTTCCGGCGAGCCAACCACTAAGAGCAGGATCACCAGCGAG

GGCGAGTACATCCCCCTGGACCAGATCGACATCAACGTGTTCTGCTACGAGAACGAG

GTGTAA

SEQ ID NO: 2 - Protein sequence of Voltron D92N
MADVETETGMIAQWIVFAIMAAAAIAFGVAVHFRPSELKSAYYINIAICTIAATAYY

AMAVNYQDLTMNGERQVVYARYINWVLTTPLLLLNLIVMTKMGGVMISWVIGADIFM

IVFGILGAFEDEHKFKWVYFIAGCVMQAVLTYGMYNATWKDDLKKSPEYHSSYVSLL

VFLSILWVEYPVVWAFGSGSGVLSVDNEAILMGILDVLAKPLEGMGCLIAHETIFKI
```

-continued

GTGFPFDPHYVEVLGERMHYVDVGPRDGTPVLFLHGNPTSSYVWRNIIPHVAPTHRC

IAPDLIGMGKSDKPDLGYFFDDHVREMDAFIEALGLEEVVLVIHDWGSALGFHWAKR

NPERVKGIAFMEFIRPIPTWDEWPEFARETFQAFRTTDVGRKLIIDQNVFIEGTLPM

GVVRPLTEVEMDHYREPFLNPVDREPLWRFPNELPIAGEPANIVALVEEYMDWLHQS

PVPKLLFWGTPGVLIPPAEAARLAKSLPNCKAVDIGPGLNLLQEDNPDLIGSEIARW

LSTLEISGEPTTKSRITSEGEYIPLDQIDINVFCYENEV*

SEQ ID NO: 3 - DNA sequence of Voltron N81D D92N
ATGGCTGACGTGGAAACCGAGACCGGCATGATTGCACAGTGGATTGTCTTTGCTATT

ATGGCTGCTGCTGCTATTGCTTTTGGAGTGGCTGTGCACTTTCGGCCTTCAGAGCTG

AAGAGCGCATACTATATCAACATTGCCATCTGCACTATCGCCGCTACCGCTTACTAT

GCAATGGCCGTGAACTACCAGGACCTGACAATGAATGGTGAAAGGCAGGTGGTCTAC

GCAAGATATATTGACTGGGTGCTGACCACACCACTGCTCCTGCTCAACCTCATCGTC

ATGACCAAGATGGGCGGAGTGATGATTTCTTGGGTCATCGGCGCAGACATTTTCATG

ATCGTGTTTGGTATTCTGGGCGCCTTCGAGGATGAACACAAGTTCAAATGGGTGTAC

TTTATCGCTGGATGTGTGATGCAGGCAGTCCTGACATACGGGATGTATAACGCCACT

TGGAAAGACGATCTGAAGAAAAGCCCCGAGTACCATAGCTCCTATGTCAGTCTGCTC

GTCTTCCTGTCAATCCTCTGGGTGTTTTATCCTGTCGTGTGGGCTTTCGGGTCTGGT

AGTGGCGTGCTGTCCGTCGACAATGAGGCCATTCTCATGGGAATCCTGGATGTGCTC

GCTAAGCCACTGTTTGGAATGGGGTGCCTCATTGCCCATGAGACTATCTTCAAGATC

GGTACTGGCTTTCCATTCGACCCCCATTATGTGGAAGTCCTGGGCGAGCGCATGCAC

TACGTCGATGTTGGTCCGCGCGATGGCACCCCTGTGCTGTTCCTGCACGGTAACCCG

ACCTCCTCCTACGTGTGGCGCAACATCATCCCGCATGTTGCACCGACCCATCGCTGC

ATTGCTCCAGACCTGATCGGTATGGGCAAATCCGACAAACCAGACCTGGGTTATTTC

TTCGACGACCACGTCCGCTTCATGGATGCCTTCATCGAAGCCCTGGGTCTGGAAGAG

GTCGTCCTGGTCATTCACGACTGGGGCTCCGCTCTGGGTTTCCACTGGGCCAAGCGC

AATCCAGAGCGCGTCAAAGGTATTGCATTTATGGAGTTCATCCGCCCTATCCCGACC

TGGGACGAATGGCCAGAATTTGCCCGCGAGACCTTCCAGGCCTTCCGCACCACCGAC

GTCGGCCGCAAGCTGATCATCGATCAGAACGTTTTTATCGAGGGTACGCTGCCGATG

GGTGTCGTCCGCCCGCTGACTGAAGTCGAGATGGACCATTACCGCGAGCCGTTCCTG

AATCCTGTTGACCGCGAGCCACTGTGGCGCTTCCCAAACGAGCTGCCAATCGCCGGT

GAGCCAGCGAACATCGTCGCGCTGGTCGAAGAATACATGGACTGGCTGCACCAGTCC

CCTGTCCCGAAGCTGCTGTTCTGGGGCACCCCAGGCGTTCTGATCCCACCGGCCGAA

GCCGCTCGCCTGGCCAAAAGCCTGCCTAACTGCAAGGCTGTGGACATCGGCCCGGGT

CTGAATCTGCTGCAAGAAGACAACCCGGACCTGATCGGCAGCGAGATCGCGCGCTGG

CTGTCGACGCTCGAGATTTCCGGCGAGCCAACCACTAAGAGCAGGATCACCAGCGAG

GGCGAGTACATCCCCCTGGACCAGATCGACATCAACGTGTTCTGCTACGAGAACGAG

GTGTAA

SEQ ID NO: 4 - Protein sequence of N81D D92N
MADVETETGMIAQWIVFAIMAAAAIAFGVAVHFRPSELKSAYYINIAICTIAATAYY

AMAVNYQDLTMNGERQVVYARYIDWVLTTPLLLLNLIVMTKMGGVMISWVIGADIFM

IVFGILGAFEDEHKFKWVYFIAGCVMQAVLTYGMYNATWKDDLKKSPEYHSSYVSLL

-continued

VFLSILWVFYPVVWAFGSGSGVLSVDNEAILMGILDVLAKPLFGMGCLIAHETIFKI

GTGFPFDPHYVEVLGERMHYVDVGPRDGTPVLFLHGNPTSSYVWRNIIPHVAPTHRC

IAPDLIGMGKSDKPDLGYFFDDHVRFMDAFIEALGLEEVVLVIHDWGSALGFHWAKR

NPERVKGIAFMEFIRPIPTWDEWPEFARETFQAFRTTDVGRKLIIDQNVFIEGTLPM

GVVRPLTEVEMDHYREPFLNPVDREPLWRFPNELPIAGEPANIVALVEEYMDWLHQS

PVPKLLFWGTPGVLIPPAEAARLAKSLPNCKAVDIGPGLNLLQEDNPDLIGSEIARW

LSTLEISGEPTTKSRITSEGEYIPLDQIDINVFCYENEV*

SEQ ID NO: 5 - DNA sequence of Voltron N81D D92N E199V
ATGGCTGACGTGGAAACCGAGACCGGCATGATTGCACAGTGGATTGTCTTTGCTATT

ATGGCTGCTGCTGCTATTGCTTTTGGAGTGGCTGTGCACTTTCGGCCTTCAGAGCTG

AAGAGCGCATACTATATCAACATTGCCATCTGCACTATCGCCGCTACCGCTTACTAT

GCAATGGCCGTGAACTACCAGGACCTGACAATGAATGGTGAAAGGCAGGTGGTCTAC

GCAAGATATATTGACTGGGTGCTGACCACACCACTGCTCCTGCTCAACCTCATCGTC

ATGACCAAGATGGGCGGAGTGATGATTTCTTGGGTCATCGGCGCAGACATTTTCATG

ATCGTGTTTGGTATTCTGGGCGCCTTCGAGGATGAACACAAGTTCAAATGGGTGTAC

TTTATCGCTGGATGTGTGATGCAGGCAGTCCTGACATACGGGATGTATAACGCCACT

TGGAAAGACGATCTGAAGAAAAGCCCCGAGTACCATAGCTCCTATGTCAGTCTGCTC

GTCTTCCTGTCAATCCTCTGGGTGTTTTATCCTGTCGTGTGGGCTTTCGGGTCTGGT

AGTGGCGTGCTGTCCGTCGACAATGTGGCCATTCTCATGGGAATCCTGGATGTGCTC

GCTAAGCCACTGTTTGGAATGGGGTGCCTCATTGCCCATGAGACTATCTTCAAGATC

GGTACTGGCTTTCCATTCGACCCCCATTATGTGGAAGTCCTGGGCGAGCGCATGCAC

TACGTCGATGTTGGTCCGCGCGATGGCACCCCTGTGCTGTTCCTGCACGGTAACCCG

ACCTCCTCCTACGTGTGGCGCAACATCATCCCGCATGTTGCACCGACCCATCGCTGC

ATTGCTCCAGACCTGATCGGTATGGGCAAATCCGACAAACCAGACCTGGGTTATTTC

TTCGACGACCACGTCCGCTTCATGGATGCCTTCATCGAAGCCCTGGGTCTGGAAGAG

GTCGTCCTGGTCATTCACGACTGGGGCTCCGCTCTGGGTTTCCACTGGGCCAAGCGC

AATCCAGAGCGCGTCAAAGGTATTGCATTTATGGAGTTCATCCGCCCTATCCCGACC

TGGGACGAATGGCCAGAATTTGCCCGCGAGACCTTCCAGGCCTTCCGCACCACCGAC

GTCGGCCGCAAGCTGATCATCGATCAGAACGTTTTTATCGAGGGTACGCTGCCGATG

GGTGTCGTCCGCCCGCTGACTGAAGTCGAGATGGACCATTACCGCGAGCCGTTCCTG

AATCCTGTTGACCGCGAGCCACTGTGGCGCTTCCCAAACGAGCTGCCAATCGCCGGT

GAGCCAGCGAACATCGTCGCGCTGGTCGAAGAATACATGGACTGGCTGCACCAGTCC

CCTGTCCCGAAGCTGCTGTTCTGGGGCACCCCAGGCGTTCTGATCCCACCGGCCGAA

GCCGCTCGCCTGGCCAAAAGCCTGCCTAACTGCAAGGCTGTGGACATCGGCCCGGGT

CTGAATCTGCTGCAAGAAGACAACCCGGACCTGATCGGCAGCGAGATCGCGCGCTGG

CTGTCGACGCTCGAGATTTCCGGCGAGCCAACCACTAAGAGCAGGATCACCAGCGAG

GGCGAGTACATCCCCCTGGACCAGATCGACATCAACGTGTTCTGCTACGAGAACGAG

GTGTAA

SEQ ID NO: 6 -Protein sequence of Voltron N81D D92N E199V
MADVETETGMIAQWIVFAIMAAAAIAFGVAVHFRPSELKSAYYINIAICTIAATAYY

AMAVNYQDLTMNGERQVVYARYIDWVLTTPLLLLNLIVMTKMGGVMISWVIGADIFM

-continued

IVFGILGAFEDEHKFKWVYFIAGCVMQAVLTYGMYNATWKDDLKKSPEYHSSYVSLL

VFLSILWVFYPVVWAFGSGSGVLSVDNVAILMGILDVLAKPLFGMGCLIAHETIFKI

GTGFPFDPHYVEVLGERMHYVDVGPRDGTPVLFLHGNPTSSYVWRNIIPHVAPTHRC

IAPDLIGMGKSDKPDLGYFFDDHVRFMDAFIEALGLEEVVLVIHDWGSALGFHWAKR

NPERVKGIAFMEFIRPIPTWDEWPEFARETFQAFRTTDVGRKLIIDQNVFIEGTLPM

GVVRPLTEVEMDHYREPFLNPVDREPLWRFPNELPIAGEPANIVALVEEYMDWLHQS

PVPKLLFWGTPGVLIPPAEAARLAKSLPNCKAVDIGPGLNLLQEDNPDLIGSEIARW

LSTLEISGEPTTKSRITSEGEYIPLDQIDINVFCYENEV*

SEQ ID NO: 7 - DNA sequence of Ace2-mNeonGreen N81D D92N
ATGGCTGACGTGGAAACCGAGACCGGCATGATTGCACAGTGGATTGTCTTTGCTATT

ATGGCTGCTGCTGCTATTGCTTTTGGAGTGGCTGTGCACTTTCGGCCTTCAGAGCTG

AAGAGCGCATACTATATCAACATTGCCATCTGCACTATCGCCGCTACCGCTTACTAT

GCAATGGCCGTGAACTACCAGGACCTGACAATGAATGGTGAAAGGCAGGTGGTCTAC

GCAAGATATATTGACTGGGTGCTGACCACACCACTGCTCCTGCTCAACCTCATCGTC

ATGACCAAGATGGGCGGAGTGATGATTTCTTGGGTCATCGGCGCAGACATTTTCATG

ATCGTGTTTGGTATTCTGGGCGCCTTCGAGGATGAACACAAGTTCAAATGGGTGTAC

TTTATCGCTGGATGTGTGATGCAGGCAGTCCTGACATACGGGATGTATAACGCCACT

TGGAAAGACGATCTGAAGAAAAGCCCCGAGTACCATAGCTCCTATGTCAGTCTGCTC

GTCTTCCTGTCAATCCTCTGGGTGTTTTATCCTGTCGTGTGGGCTTTCGGGTCTGGT

AGTGGCGTGCTGTCCGTCGACAATGAGGCCATTCTCATGGGAATCCTGGATGTGCTC

GCTAAGCCACTGTTTGGAATGGGGTGCCTCATTGCCCATGAGACTATCTTCAAGAAG

ATGCTGAGGTCTCTCCCAGCGACACATGAGTTACACATCTTTGGCTCCATCAACGGT

GTGGACTTTGACATGGTGGGTCAGGGCACCGGCAATCCAAATGATGGTTATGAGGAG

TTAAACCTGAAGTCCACCAAGGGTGACCTCCAGTTCTCCCCCTGGATTCTGGTCCCT

CATATCGGGTATGGCTTCCATCAGTACCTGCCCTACCCTGACGGGATGTCGCCTTTC

CAGGCCGCCATGGTAGATGGCTCCGGATACCAAGTCCATCGCACAATGCAGTTTGAA

GATGGTGCCTCCCTTACTGTTAACTACCGCTACACCTACGAGGGAAGCCACATCAAA

GGAGAGGCCCAGGTGAAGGGGACTGGTTTCCCTGCTGACGGTCCTGTGATGACCAAC

TCGCTGACCGCTGCGGACTGGTGCAGGTCGAAGAAGACTTACCCCAACGACAAACC

ATCATCAGTACCTTTAAGTGGAGTTACACCACTGGAAATGGCAAGCGCTACAGGAGC

ACTGCGCGGACCACCTACACCTTTGCCAAGCCAATGGCGGCTAACTATCTGAAGAAC

CAGCCGATGTACGTGTTCCGTAAGACGGAGCTCAAGCACTCCAAGACCGAGCTCAAC

TTCAAGGAGTGGCAAAAGGCCTTTACCGATGTGATGGGCATGGACGAGCTGTACAAG

AAGAGCAGGATCACCAGCGAGGGCGAGTACATCCCCCTGGACCAGATCGACATCAAC

GTGTTCTGCTACGAGAACGAGGTGTAA

SEQ ID NO: 8 - Protein sequence of Ace2-mNeonGreen N81D D92N
MADVETETGMIAQWIVFAIMAAAAIAFGVAVHFRPSELKSAYYINIAICTIAATAYY

AMAVNYQDLTMNGERQVVYARYIDWVLTTPLLLLNLIVMTKMGGVMISWVIGADIFM

IVFGILGAFEDEHKFKWVYFIAGCVMQAVLTYGMYNATWKDDLKKSPEYHSSYVSLL

VFLSILWVFYPVVWAFGSGSGVLSVDNEAILMGILDVLAKPLFGMGCLIAHETIFKK

MLRSLPATHELHIFGSINGVDFDMVGQGTGNPNDGYEELNLKSTKGDLQFSPWILVP

HIGYGFHQYLPYPDGMSPFQAAMVDGSGYQVHRTMQFEDGASLTVNYRYTYEGSHIK

GEAQVKGTGFPADGPVMTNSLTAADWCRSKKTYPNDKTIISTFKWSYTTGNGKRYRS

TARTTYTFAKPMAANYLKNQPMYVFRKTELKHSKTELNFKEWQKAFTDVMGMDELYK

KSRITSEGEYIPLDQIDINVFCYENEV*

SEQ ID NO: 9 - Protein sequence of Ace2N
MADVETETGMIAQWIVFAIMAAAAIAFGVAVHFRPSELKSAYYINIAICTIAATAYY

AMAVNYQDLTMNGERQVVYARYINWVLTTPLLLLDLIVMTKMGGVMISWVIGADIFM

IVFGILGAFEDEHKFKWVYFIAGCVMQAVLTYGMYNATWKDDLKKSPEYHSSYVSLL

VFLSILWVFYPVVWAFGSGSGVLSVDNEAILMGILDVLAKPLFGMGCLIAHETIFK

SEQ ID NO: 10 - Protein sequence of HaloTag
IGTGFPFDPHYVEVLGERMHYVDVGPRDGTPVLFLHGNPTSSYVWRNIIPHVAPTHR

CIAPDLIGMGKSDKPDLGYFFDDHVRFMDAFIEALGLEEVVLVIHDWGSALGFHWAK

RNPERVKGIAFMEFIRPIPTWDEWPEFARETFQAFRTTDVGRKLIIDQNVFIEGTLP

MGVVRPLTEVEMDHYREPFLNPVDREPLWRFPNELPIAGEPANIVALVEEYMDWLHQ

SPVPKLLFWGTPGVLIPPAEAARLAKSLPNCKAVDIGPGLNLLQEDNPDLIGSEIAR

WLSTLEISGEPTT

SEQ ID NO: 11 - Protein sequence of exemplary a capture protein domain
KMLRSLPATHELHIFGSINGVDFDMVGQGTGNPNDGYEELNLKSTKGDLQFSPWILV

PHIGYGFHQYLPYPDGMSPFQAAMVDGSGYQVHRTMQFEDGASLTVNYRYTYEGSHI

KGEAQVKGTGFPADGPVMTNSLTAADWCRSKKTYPNDKTIISTFKWSYTTGNGKRYR

STARTTYTFAKPMAANYLKNQPMYVFRKTELKHSKTELNFKEWQKAFTDVMGMDELY

K

SEQ ID NO: 12 - Protein sequence of Kv2.1 membrane trafficking signal
KSRITSEGEYIPLDQIDINV SEQ ID NO: 13 - Protein sequence of Kv2.1 ER export signal
FCYENEV SEQ ID NO: 14: Protein sequence of Kv2.1 Proximal restriction/clustering
QSQPILNTKEMAPQSKPPEELEMSSMPSPVAPLPARTEGVIDMRSMSSIDSFISCAT

DFPEATRF

SEQ ID NO: 15: - Protein sequence of QuarAr1.
IALQAGYDLLGDGRPETLWLGIGTLLMLIGTFYFLVRGWGVTDKDAREYYAVTILVS

GIASAAYLSMFFGIGLTEVSVGGEMLDIYYARYAHWLFTTLLLLHLALLAKVDRVTI

GTLVGVDALMIVTGLIGALSHTAIARYSWWLFSTICMIVVLYVLATSLRSAAKERGP

EVASTFNTLTALVLVLWTAYPILWIIGTEGAGVVGLGIETLLFMVLDVTAKVGFGFI

LLRSRAILGDTEAPEPSAGADVSAAD

Figure 10:
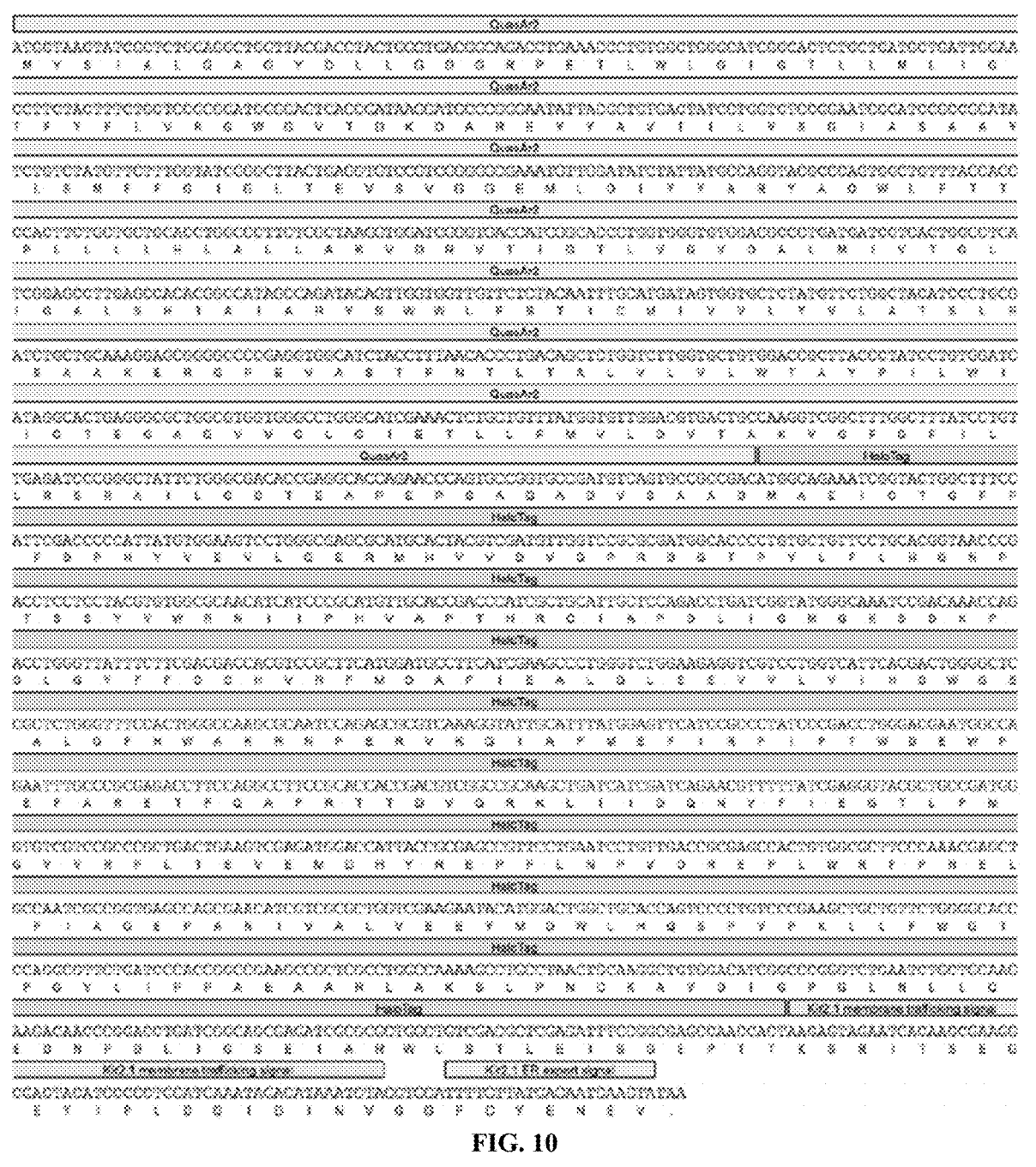

SEQ ID NO: 16 - Protein sequence of QuasAr2, as in FIG. 10.
IALQAGYDLLGDGRPETLWLGIGTLLMLIGTFYFLVRGWGVTDKDAREYYAVTILVS

GIASAAYLSMFFGIGLTEVSVGGEMLDIYYARYAQWLFTTPLLLLHLALLAKVDRVT

IGTLVGVDALMIVTGLIGALSHTAIARYSWWLFSTICMIVVLYVLATSLRSAAKERG

PEVASTFNTLTALVLVLWTAYPILWIIGTEGAGVVGLGIETLLFMVLDVTAKVGFGF

ILLRSRAILGDTEAPEPSAGADVSAAD

SEQ ID NO: 17 - Protein Sequences of QuasAr2, as in

FIG. 11.
IALQAGYDLLGDGRPETLWLGIGTLLMLIGTFYFLVRGWGVTDKDAREYYAVTILVS

GIASAAYLSNIFFGIGLTEVSVGGEMLDIYYARYAQWLFTTPLLLLHLALLAKVDRV

TIGTLVGVDALMIVTGLIGALSHTAIARYSWWLFSTICMIVVLYVLATSLRSAAKER

GPEVASTFNTLTALVLVLWTAYPILWIIGTEGAGVVGLGIETLLFMVLDVTAKVGFG

FILLRSRAILGDTE

---

What is claimed is:

1. A voltage indicator, comprising: a voltage-sensitive microbial rhodopsin domain comprising the amino acid sequence of SEQ ID NO: 9 with an amino acid mutation at one or more of residue 81, 92, and 199; and a capture protein that covalently or noncovalently binds a fluorescent dye ligand that is (i) a fluorescent protein; or (ii) a fluorescent dye, wherein the capture protein is provided together with the voltage-sensitive microbial rhodopsin domain in a fusion protein.

2. A voltage indicator, comprising an amino acid sequence selected from the group of amino acid sequences of SEQ ID NOS: 2, 4, 6, and 8.

3. The voltage indicator of claim 1, wherein the capture protein is selected from the group consisting of biotin-avidin, a self-labeling protein tag, or a combination thereof.

4. The voltage indicator of claim 1, wherein the capture protein domain is a self-labeling protein tag.

5. The voltage indicator of claim 1, wherein 1, 2, 3, 4, 5, 6, 7, 8, 9, or 10 amino acids are removed from the junction between the rhodopsin domain and the capture protein.

6. The voltage indicator of claim 1, and further comprising a targeting sequence.

7. The voltage indicator of claim 6, wherein the targeting sequence is a soma targeting sequence.

8. The voltage indicator of claim 6, wherein the capture protein is positioned at the c-terminal end of the voltage-sensitive microbial rhodopsin domain.

9. The voltage indicator of claim 1, wherein the fluorescent dye ligand is an azetidine-containing fluorescent dye.

10. The voltage indicator of claim 1, wherein the fluorescent dye ligand is a fluorescent protein.

11. A method of measuring voltage, the method comprising contacting the voltage indicator of claim 1 and a fluorescent dye ligand with a cell, and determining changes in fluorescence of the fluorescent dye ligand when the fluorescent dye ligand is captured by the voltage indicator.

12. The method of claim 11, wherein the cell is a neuron.

13. The method of claim 11, and further comprising observing changes in fluorescence with a microscope.

14. The method of claim 11, wherein the voltage indicator further comprises a linker between the voltage-sensitive domain and the capture protein.

15. The method of claim 11, further comprising modifying a length of the linker.

16. The method of claim 11, wherein an increase in membrane potential lead to an increase in fluorescence.

17. A voltage indicator, comprising the amino acid sequence of SEQ ID NO: 20.

18. A method of measuring voltage, the method comprising contacting the voltage indicator of claim 17 and a fluorescent dye ligand with a cell, and determining changes in fluorescence when the fluorescent dye ligand is captured by the voltage indicator.

\* \* \* \* \*

SEQUENCE LISTING

<160> NUMBER OF SEQ ID NOS: 40

<210> SEQ ID NO 1
<211> LENGTH: 1659
<212> TYPE: DNA
<213> ORGANISM: Artificial Sequence
<220> FEATURE:
<223> OTHER INFORMATION: Synthetic

<400> SEQUENCE: 1

| | | | | | | |
|---|---|---|---|---|---|---|
| atggctgacg | tggaaaccga | gaccggcatg | attgcacagt | ggattgtctt | tgctattatg | 60 |
| gctgctgctg | ctattgcttt | tggagtggct | gtgcactttc | ggccttcaga | gctgaagagc | 120 |
| gcatactata | tcaacattgc | catctgcact | atcgccgcta | ccgcttacta | tgcaatggcc | 180 |
| gtgaactacc | aggacctgac | aatgaatggt | gaaaggcagg | tggtctacgc | aagatatatt | 240 |
| aactgggtgc | tgaccacacc | actgctcctg | ctcaacctca | tcgtcatgac | caagatgggc | 300 |
| ggagtgatga | tttcttgggt | catcggcgca | gacattttca | tgatcgtgtt | tggtattctg | 360 |
| ggcgccttcg | aggatgaaca | caagttcaaa | tgggtgtact | ttatcgctgg | atgtgtgatg | 420 |
| caggcagtcc | tgacatacgg | gatgtataac | gccacttgga | agacgatct | gaagaaaagc | 480 |
| cccgagtacc | atagctccta | tgtcagtctg | ctcgtcttcc | tgtcaatcct | ctgggtgttt | 540 |
| tatcctgtcg | tgtgggcttt | cgggtctggt | agtggcgtgc | tgtccgtcga | caatgaggcc | 600 |
| attctcatgg | gaatcctgga | tgtgctcgct | aagccactgt | ttggaatggg | gtgcctcatt | 660 |
| gcccatgaga | ctatcttcaa | gatcggtact | ggctttccat | cgacccca | ttatgtggaa | 720 |
| gtcctgggcg | agcgcatgca | ctacgtcgat | gttggtccgc | gcgatggcac | ccctgtgctg | 780 |
| ttcctgcacg | gtaacccgac | ctcctcctac | gtgtggcgca | acatcatccc | gcatgttgca | 840 |
| ccgacccatc | gctgcattgc | tccagacctg | atcggtatgg | gcaaatccga | caaaccagac | 900 |
| ctgggttatt | tcttcgacga | ccacgtccgc | ttcatggatg | ccttcatcga | agccctgggt | 960 |
| ctggaagagg | tcgtcctggt | cattcacgac | tggggctccg | ctctgggttt | ccactgggcc | 1020 |
| aagcgcaatc | cagagcgcgt | caaaggtatt | gcatttatgg | agttcatccg | ccctatcccg | 1080 |
| acctgggacg | aatggccaga | atttgcccgc | gagaccttcc | aggccttccg | caccaccgac | 1140 |
| gtcggccgca | agctgatcat | cgatcagaac | gtttttatcg | agggtacgct | gccgatgggt | 1200 |
| gtcgtccgcc | cgctgactga | agtcgagatg | gaccattacc | gcgagccgtt | cctgaatcct | 1260 |
| gttgaccgcg | agccactgtg | gcgcttccca | aacgagctgc | caatcgccgg | tgagccagcg | 1320 |
| aacatcgtcg | cgctggtcga | gaatacatg | gactggctgc | accagtcccc | tgtcccgaag | 1380 |
| ctgctgttct | ggggcacccc | aggcgttctg | atcccaccgg | ccgaagccgc | tcgcctggcc | 1440 |
| aaaagcctgc | ctaactgcaa | ggctgtggac | atcggcccgg | gtctgaatct | gctgcaagaa | 1500 |
| gacaacccgg | aactgatcgg | cagcgagatc | gcgcgctggc | tgtcgacgct | cgagatttcc | 1560 |
| ggcgagccaa | ccactaagag | caggatcacc | agcgagggcg | agtacatccc | cctggaccag | 1620 |

```
atcgacatca acgtgttctg ctacgagaac gaggtgtaa                              1659
```

<210> SEQ ID NO 2
<211> LENGTH: 552
<212> TYPE: PRT
<213> ORGANISM: Artificial Sequence
<220> FEATURE:
<223> OTHER INFORMATION: Synthetic

<400> SEQUENCE: 2

```
Met Ala Asp Val Glu Thr Glu Thr Gly Met Ile Ala Gln Trp Ile Val
1               5                   10                  15

Phe Ala Ile Met Ala Ala Ala Ile Ala Phe Gly Val Ala Val His
                20                  25                  30

Phe Arg Pro Ser Glu Leu Lys Ser Ala Tyr Tyr Ile Asn Ile Ala Ile
                35                  40                  45

Cys Thr Ile Ala Ala Thr Ala Tyr Tyr Ala Met Ala Val Asn Tyr Gln
            50                  55                  60

Asp Leu Thr Met Asn Gly Glu Arg Gln Val Val Tyr Ala Arg Tyr Ile
65                  70                  75                  80

Asn Trp Val Leu Thr Thr Pro Leu Leu Leu Asn Leu Ile Val Met
                    85                  90                  95

Thr Lys Met Gly Gly Val Met Ile Ser Trp Val Ile Gly Ala Asp Ile
                100                 105                 110

Phe Met Ile Val Phe Gly Ile Leu Gly Ala Phe Glu Asp Glu His Lys
            115                 120                 125

Phe Lys Trp Val Tyr Phe Ile Ala Gly Cys Val Met Gln Ala Val Leu
    130                 135                 140

Thr Tyr Gly Met Tyr Asn Ala Thr Trp Lys Asp Asp Leu Lys Lys Ser
145                 150                 155                 160

Pro Glu Tyr His Ser Ser Tyr Val Ser Leu Leu Val Phe Leu Ser Ile
                165                 170                 175

Leu Trp Val Phe Tyr Pro Val Val Trp Ala Phe Gly Ser Gly Ser Gly
                180                 185                 190

Val Leu Ser Val Asp Asn Glu Ala Ile Leu Met Gly Ile Leu Asp Val
            195                 200                 205

Leu Ala Lys Pro Leu Phe Gly Met Gly Cys Leu Ile Ala His Glu Thr
    210                 215                 220

Ile Phe Lys Ile Gly Thr Gly Phe Pro Phe Asp Pro His Tyr Val Glu
225                 230                 235                 240

Val Leu Gly Glu Arg Met His Tyr Val Asp Val Gly Pro Arg Asp Gly
                245                 250                 255

Thr Pro Val Leu Phe Leu His Gly Asn Pro Thr Ser Ser Tyr Val Trp
                260                 265                 270

Arg Asn Ile Ile Pro His Val Ala Pro Thr His Arg Cys Ile Ala Pro
            275                 280                 285

Asp Leu Ile Gly Met Gly Lys Ser Asp Lys Pro Asp Leu Gly Tyr Phe
    290                 295                 300

Phe Asp Asp His Val Arg Phe Met Asp Ala Phe Ile Glu Ala Leu Gly
305                 310                 315                 320

Leu Glu Glu Val Val Leu Val Ile His Asp Trp Gly Ser Ala Leu Gly
                325                 330                 335

Phe His Trp Ala Lys Arg Asn Pro Glu Arg Val Lys Gly Ile Ala Phe
                340                 345                 350
```

```
Met Glu Phe Ile Arg Pro Ile Pro Thr Trp Asp Glu Trp Pro Glu Phe
            355                 360                 365

Ala Arg Glu Thr Phe Gln Ala Phe Arg Thr Thr Asp Val Gly Arg Lys
        370                 375                 380

Leu Ile Ile Asp Gln Asn Val Phe Ile Glu Gly Thr Leu Pro Met Gly
385                 390                 395                 400

Val Val Arg Pro Leu Thr Glu Val Glu Met Asp His Tyr Arg Glu Pro
                405                 410                 415

Phe Leu Asn Pro Val Asp Arg Glu Pro Leu Trp Arg Phe Pro Asn Glu
            420                 425                 430

Leu Pro Ile Ala Gly Glu Pro Ala Asn Ile Val Ala Leu Val Glu Glu
        435                 440                 445

Tyr Met Asp Trp Leu His Gln Ser Pro Val Pro Lys Leu Leu Phe Trp
    450                 455                 460

Gly Thr Pro Gly Val Leu Ile Pro Pro Ala Glu Ala Ala Arg Leu Ala
465                 470                 475                 480

Lys Ser Leu Pro Asn Cys Lys Ala Val Asp Ile Gly Pro Gly Leu Asn
                485                 490                 495

Leu Leu Gln Glu Asp Asn Pro Asp Leu Ile Gly Ser Glu Ile Ala Arg
            500                 505                 510

Trp Leu Ser Thr Leu Glu Ile Ser Gly Glu Pro Thr Thr Lys Ser Arg
        515                 520                 525

Ile Thr Ser Glu Gly Glu Tyr Ile Pro Leu Asp Gln Ile Asp Ile Asn
    530                 535                 540

Val Phe Cys Tyr Glu Asn Glu Val
545                 550

<210> SEQ ID NO 3
<211> LENGTH: 1659
<212> TYPE: DNA
<213> ORGANISM: Artificial Sequence
<220> FEATURE:
<223> OTHER INFORMATION: Synthetic

<400> SEQUENCE: 3
atggctgacg tggaaaccga gaccggcatg attgcacagt ggattgtctt tgctattatg      60
gctgctgctg ctattgcttt tggagtggct gtgcactttc ggccttcaga gctgaagagc     120
gcatactata tcaacattgc catctgcact atcgccgcta ccgcttacta tgcaatggcc     180
gtgaactacc aggacctgac aatgaatggt gaaaggcagg tggtctacgc aagatatatt     240
gactgggtgc tgaccacacc actgctcctg ctcaacctca tcgtcatgac caagatgggc     300
ggagtgatga tttcttgggt catcggcgca gacattttca tgatcgtgtt tggtattctg     360
ggcgccttcg aggatgaaca caagttcaaa tgggtgtact ttatcgctgg atgtgtgatg     420
caggcagtcc tgcatacgg gatgtataac gccacttgga agacgatct gaagaaaagc       480 cccgagtacc atagctccta tgtcagtctg ctcgtcttcc tgtcaatcct ctgggtgttt     540
tatcctgtcg tgtgggcttt cgggtctggt agtggcgtgc tgtccgtcga caatgaggcc     600
attctcatgg gaatcctgga tgtgctcgct aagccactgt ttggaatggg gtgcctcatt     660
gcccatgaga ctatcttcaa gatcggtact ggctttccat cgaccccca ttatgtggaa      720 gtcctgggcg agcgcatgca ctacgtcgat gttggtccgc gcgatggcac ccctgtgctg     780
ttcctgcacg gtaacccgac ctcctcctac gtgtggcgca acatcatccc gcatgttgca     840
ccgacccatc gctgcattgc tccagacctg atcggtatgg caaatccgac caaaccagac     900
```

```
ctgggttatt tcttcgacga ccacgtccgc ttcatggatg ccttcatcga agccctgggt    960
ctggaagagg tcgtcctggt cattcacgac tggggctccg ctctgggttt ccactgggcc   1020
aagcgcaatc cagagcgcgt caaaggtatt gcatttatgg agttcatccg ccctatcccg   1080
acctgggacg aatggccaga atttgcccgc gagaccttcc aggccttccg caccaccgac   1140
gtcggccgca agctgatcat cgatcagaac gttttatcg agggtacgct gccgatgggt   1200
gtcgtccgcc cgctgactga agtcgagatg gaccattacc gcgagccgtt cctgaatcct   1260
gttgaccgcg agccactgtg gcgcttccca acgagctgc caatcgccgg tgagccagcg   1320
aacatcgtcg cgctggtcga agaatacatg gactggctgc accagtcccc tgtcccgaag   1380
ctgctgttct ggggcacccc aggcgttctg atcccaccgg ccgaagccgc tcgcctggcc   1440
aaaagcctgc taactgcaa ggctgtggac atcggcccgg tctgaatct gctgcaagaa    1500
gacaacccgg acctgatcgg cagcgagatc gcgcgctggc tgtcgacgct cgagatttcc   1560
ggcgagccaa ccactaagag caggatcacc agcgagggcg agtacatccc cctggaccag   1620
atcgacatca acgtgttctg ctacgagaac gaggtgtaa                           1659
```

<210> SEQ ID NO 4
<211> LENGTH: 552
<212> TYPE: PRT
<213> ORGANISM: Artificial Sequence
<220> FEATURE:
<223> OTHER INFORMATION: Synthetic

<400> SEQUENCE: 4

```
Met Ala Asp Val Glu Thr Glu Thr Gly Met Ile Ala Gln Trp Ile Val
1               5                   10                  15

Phe Ala Ile Met Ala Ala Ala Ile Ala Phe Gly Val Ala Val His
            20                  25                  30

Phe Arg Pro Ser Glu Leu Lys Ser Ala Tyr Tyr Ile Asn Ile Ala Ile
        35                  40                  45

Cys Thr Ile Ala Ala Thr Ala Tyr Tyr Ala Met Ala Val Asn Tyr Gln
    50                  55                  60

Asp Leu Thr Met Asn Gly Glu Arg Gln Val Val Tyr Ala Arg Tyr Ile
65                  70                  75                  80

Asp Trp Val Leu Thr Thr Pro Leu Leu Leu Leu Asn Leu Ile Val Met
                85                  90                  95

Thr Lys Met Gly Gly Val Met Ile Ser Trp Val Ile Gly Ala Asp Ile
            100                 105                 110

Phe Met Ile Val Phe Gly Ile Leu Gly Ala Phe Glu Asp Glu His Lys
        115                 120                 125

Phe Lys Trp Val Tyr Phe Ile Ala Gly Cys Val Met Gln Ala Val Leu
    130                 135                 140

Thr Tyr Gly Met Tyr Asn Ala Thr Trp Lys Asp Asp Leu Lys Lys Ser
145                 150                 155                 160

Pro Glu Tyr His Ser Ser Tyr Val Ser Leu Leu Val Phe Leu Ser Ile
                165                 170                 175

Leu Trp Val Phe Tyr Pro Val Val Trp Ala Phe Gly Ser Gly Ser Gly
            180                 185                 190

Val Leu Ser Val Asp Asn Glu Ala Ile Leu Met Gly Ile Leu Asp Val
        195                 200                 205

Leu Ala Lys Pro Leu Phe Gly Met Gly Cys Leu Ile Ala His Glu Thr
    210                 215                 220

Ile Phe Lys Ile Gly Thr Gly Phe Pro Phe Asp Pro His Tyr Val Glu
```

```
                    225                 230                 235                 240
Val Leu Gly Glu Arg Met His Tyr Val Asp Val Gly Pro Arg Asp Gly
                    245                 250                 255

Thr Pro Val Leu Phe Leu His Gly Asn Pro Thr Ser Ser Tyr Val Trp
                    260                 265                 270

Arg Asn Ile Ile Pro His Val Ala Pro Thr His Arg Cys Ile Ala Pro
                    275                 280                 285

Asp Leu Ile Gly Met Gly Lys Ser Asp Lys Pro Asp Leu Gly Tyr Phe
                    290                 295                 300

Phe Asp Asp His Val Arg Phe Met Asp Ala Phe Ile Glu Ala Leu Gly
305                 310                 315                 320

Leu Glu Glu Val Val Leu Val Ile His Asp Trp Gly Ser Ala Leu Gly
                    325                 330                 335

Phe His Trp Ala Lys Arg Asn Pro Glu Arg Val Lys Gly Ile Ala Phe
                    340                 345                 350

Met Glu Phe Ile Arg Pro Ile Pro Thr Trp Asp Glu Trp Pro Glu Phe
                    355                 360                 365

Ala Arg Glu Thr Phe Gln Ala Phe Arg Thr Thr Asp Val Gly Arg Lys
                    370                 375                 380

Leu Ile Ile Asp Gln Asn Val Phe Ile Glu Gly Thr Leu Pro Met Gly
385                 390                 395                 400

Val Val Arg Pro Leu Thr Glu Val Glu Met Asp His Tyr Arg Glu Pro
                    405                 410                 415

Phe Leu Asn Pro Val Asp Arg Glu Pro Leu Trp Arg Phe Pro Asn Glu
                    420                 425                 430

Leu Pro Ile Ala Gly Glu Pro Ala Asn Ile Val Ala Leu Val Glu Glu
                    435                 440                 445

Tyr Met Asp Trp Leu His Gln Ser Pro Val Pro Lys Leu Leu Phe Trp
                    450                 455                 460

Gly Thr Pro Gly Val Leu Ile Pro Pro Ala Glu Ala Ala Arg Leu Ala
465                 470                 475                 480

Lys Ser Leu Pro Asn Cys Lys Ala Val Asp Ile Gly Pro Gly Leu Asn
                    485                 490                 495

Leu Leu Gln Glu Asp Asn Pro Asp Leu Ile Gly Ser Glu Ile Ala Arg
                    500                 505                 510

Trp Leu Ser Thr Leu Glu Ile Ser Gly Glu Pro Thr Thr Lys Ser Arg
                    515                 520                 525

Ile Thr Ser Glu Gly Tyr Ile Pro Leu Asp Gln Ile Asp Ile Asn
                    530                 535                 540

Val Phe Cys Tyr Glu Asn Glu Val
545                 550
```

<210> SEQ ID NO 5
<211> LENGTH: 1659
<212> TYPE: DNA
<213> ORGANISM: Artificial Sequence
<220> FEATURE:
<223> OTHER INFORMATION: Synthetic

<400> SEQUENCE: 5

```
atggctgacg tggaaaccga daccggcatg attgcacagt ggattgtctt tgctattatg    60
gctgctgctg ctattgcttt tggagtggct gtgcactttc ggccttcaga gctgaagagc   120
gcatactata tcaacattgc catctgcact atcgccgcta ccgcttacta tgcaatggcc   180
gtgaactacc aggacctgac aatgaatggt gaaaggcagg tggtctacgc aagatatatt   240
```

```
gactgggtgc tgaccacacc actgctcctg ctcaacctca tcgtcatgac caagatgggc    300
ggagtgatga tttcttgggt catcggcgca gacattttca tgatcgtgtt tggtattctg    360
ggcgccttcg aggatgaaca caagttcaaa tgggtgtact ttatcgctgg atgtgtgatg    420
caggcagtcc tgcatacgg gatgtataac gccacttgga agacgatct gaagaaaagc     480 cccgagtacc atagctccta tgtcagtctg ctcgtcttcc tgtcaatcct ctgggtgttt    540
tatcctgtcg tgtgggcttt cgggtctggt agtggcgtgc tgtccgtcga caatgtggcc    600
attctcatgg gaatcctgga tgtgctcgct aagccactgt ttggaatggg gtgcctcatt    660
gcccatgaga ctatcttcaa gatcggtact ggctttccat tcgaccccca ttatgtggaa    720
gtcctgggcg agcgcatgca ctacgtcgat gttggtccgc gcgatggcac ccctgtgctg    780
ttcctgcacg gtaacccgac ctcctcctac gtgtggcgca acatcatccc gcatgttgca    840
ccgacccatc gctgcattgc tccagacctg atcggtatgg gcaaatccga caaaccagac    900
ctgggttatt tcttcgacga ccacgtccgc ttcatggatg ccttcatcga agccctgggt    960
ctggaagagg tcgtcctggt cattcacgac tggggctccg ctctgggttt ccactgggcc   1020
aagcgcaatc cagagcgcgt caaaggtatt gcatttatgg agttcatccg ccctatcccg   1080
acctgggacg aatggccaga atttgcccgc gagaccttcc aggccttccg caccaccgac   1140
gtcggccgca agctgatcat cgatcagaac gtttttatcg agggtacgct gccgatgggt   1200
gtcgtccgcc cgctgactga agtcgagatg gaccattacc gcgagccgtt cctgaatcct   1260
gttgaccgcg agccactgtg gcgcttccca aacgagctgc caatcgccgg tgagccagcg   1320
aacatcgtcg cgctggtcga agaatacatg gactggctgc accagtcccc tgtcccgaag   1380
ctgctgttct ggggcaccccc aggcgttctg atcccaccgg ccgaagccgc tcgcctggcc   1440
aaaagcctgc taactgcaa ggctgtggac atcggcccgg tctgaatct gctgcaagaa    1500 gacaacccgg acctgatcgg cagcgagatc gcgcgctggc tgtcgacgct cgagatttcc   1560
ggcgagccaa ccactaagag caggatcacc agcgagggcg agtacatccc cctggaccag   1620
atcgacatca acgtgttctg ctacgagaac gaggtgtaa                           1659
```

<210> SEQ ID NO 6
<211> LENGTH: 552
<212> TYPE: PRT
<213> ORGANISM: Artificial Sequence
<220> FEATURE:
<223> OTHER INFORMATION: Synthetic

<400> SEQUENCE: 6

```
Met Ala Asp Val Glu Thr Glu Thr Gly Met Ile Ala Gln Trp Ile Val
1               5                   10                  15

Phe Ala Ile Met Ala Ala Ala Ile Ala Phe Gly Val Ala Val His
                20                  25                  30

Phe Arg Pro Ser Glu Leu Lys Ser Ala Tyr Tyr Ile Asn Ile Ala Ile
            35                  40                  45

Cys Thr Ile Ala Ala Thr Ala Tyr Tyr Ala Met Ala Val Asn Tyr Gln
        50                  55                  60

Asp Leu Thr Met Asn Gly Glu Arg Gln Val Val Tyr Ala Arg Tyr Ile
65                  70                  75                  80

Asp Trp Val Leu Thr Thr Pro Leu Leu Leu Asn Leu Ile Val Met
                85                  90                  95

Thr Lys Met Gly Gly Val Met Ile Ser Trp Val Ile Gly Ala Asp Ile
                100                 105                 110
```

```
Phe Met Ile Val Phe Gly Ile Leu Gly Ala Phe Glu Asp Glu His Lys
            115                 120                 125

Phe Lys Trp Val Tyr Phe Ile Ala Gly Cys Val Met Gln Ala Val Leu
    130                 135                 140

Thr Tyr Gly Met Tyr Asn Ala Thr Trp Lys Asp Asp Leu Lys Lys Ser
145                 150                 155                 160

Pro Glu Tyr His Ser Ser Tyr Val Ser Leu Leu Val Phe Leu Ser Ile
                165                 170                 175

Leu Trp Val Phe Tyr Pro Val Val Trp Ala Phe Gly Ser Gly Ser Gly
                180                 185                 190

Val Leu Ser Val Asp Asn Val Ala Ile Leu Met Gly Ile Leu Asp Val
            195                 200                 205

Leu Ala Lys Pro Leu Phe Gly Met Gly Cys Leu Ile Ala His Glu Thr
    210                 215                 220

Ile Phe Lys Ile Gly Thr Gly Phe Pro Phe Asp Pro His Tyr Val Glu
225                 230                 235                 240

Val Leu Gly Glu Arg Met His Tyr Val Asp Val Gly Pro Arg Asp Gly
                245                 250                 255

Thr Pro Val Leu Phe Leu His Gly Asn Pro Thr Ser Ser Tyr Val Trp
                260                 265                 270

Arg Asn Ile Ile Pro His Val Ala Pro Thr His Arg Cys Ile Ala Pro
    275                 280                 285

Asp Leu Ile Gly Met Gly Lys Ser Asp Lys Pro Asp Leu Gly Tyr Phe
    290                 295                 300

Phe Asp Asp His Val Arg Phe Met Asp Ala Phe Ile Glu Ala Leu Gly
305                 310                 315                 320

Leu Glu Glu Val Val Leu Val Ile His Asp Trp Gly Ser Ala Leu Gly
                325                 330                 335

Phe His Trp Ala Lys Arg Asn Pro Glu Arg Val Lys Gly Ile Ala Phe
            340                 345                 350

Met Glu Phe Ile Arg Pro Ile Pro Thr Trp Asp Glu Trp Pro Glu Phe
    355                 360                 365

Ala Arg Glu Thr Phe Gln Ala Phe Arg Thr Thr Asp Val Gly Arg Lys
    370                 375                 380

Leu Ile Ile Asp Gln Asn Val Phe Ile Glu Gly Thr Leu Pro Met Gly
385                 390                 395                 400

Val Val Arg Pro Leu Thr Glu Val Glu Met Asp His Tyr Arg Glu Pro
            405                 410                 415

Phe Leu Asn Pro Val Asp Arg Glu Pro Leu Trp Arg Phe Pro Asn Glu
            420                 425                 430

Leu Pro Ile Ala Gly Glu Pro Ala Asn Ile Val Ala Leu Val Glu Glu
            435                 440                 445

Tyr Met Asp Trp Leu His Gln Ser Pro Val Pro Lys Leu Leu Phe Trp
450                 455                 460

Gly Thr Pro Gly Val Leu Ile Pro Pro Ala Glu Ala Ala Arg Leu Ala
465                 470                 475                 480

Lys Ser Leu Pro Asn Cys Lys Ala Val Asp Ile Gly Pro Gly Leu Asn
                485                 490                 495

Leu Leu Gln Glu Asp Asn Pro Asp Leu Ile Gly Ser Glu Ile Ala Arg
            500                 505                 510

Trp Leu Ser Thr Leu Glu Ile Ser Gly Glu Pro Thr Thr Lys Ser Arg
            515                 520                 525
```

Ile Thr Ser Glu Gly Glu Tyr Ile Pro Leu Asp Gln Ile Asp Ile Asn
   530                 535                 540

Val Phe Cys Tyr Glu Asn Glu Val
545                 550

<210> SEQ ID NO 7
<211> LENGTH: 1452
<212> TYPE: DNA
<213> ORGANISM: Artificial Sequence
<220> FEATURE:
<223> OTHER INFORMATION: Synthetic

<400> SEQUENCE: 7

| | |
|---|---|
| atggctgacg tggaaaccga gaccggcatg attgcacagt ggattgtctt tgctattatg | 60 |
| gctgctgctg ctattgcttt tggagtggct gtgcactttc ggccttcaga gctgaagagc | 120 |
| gcatactata tcaacattgc catctgcact atcgccgcta ccgcttacta tgcaatggcc | 180 |
| gtgaactacc aggacctgac aatgaatggt gaaaggcagg tggtctacgc aagatatatt | 240 |
| gactgggtgc tgaccacacc actgctcctg ctcaacctca tcgtcatgac caagatgggc | 300 |
| ggagtgatga tttcttgggt catcggcgca gacattttca tgatcgtgtt tggtattctg | 360 |
| ggcgccttcg aggatgaaca caagttcaaa tgggtgtact ttatcgctgg atgtgtgatg | 420 |
| caggcagtcc tgacatacgg gatgtataac gccacttgga agacgatct gaagaaaagc | 480 |
| cccgagtacc atagctccta tgtcagtctg ctcgtcttcc tgtcaatcct ctgggtgttt | 540 |
| tatcctgtcg tgtgggcttt cgggtctggt agtggcgtgc tgtccgtcga caatgaggcc | 600 |
| attctcatgg gaatcctgga tgtgctcgct aagccactgt ttggaatggg gtgcctcatt | 660 |
| gcccatgaga ctatcttcaa gaagatgctg aggtctctcc cagcgacaca tgagttacac | 720 |
| atctttggct ccatcaacgg tgtggacttt gacatggtgg tcagggcac cggcaatcca | 780 |
| aatgatggtt atgaggagtt aaacctgaag tccaccaagg gtgacctcca gttctccccc | 840 |
| tggattctgg tccctcatat cgggtatggc ttccatcagt acctgcccta ccctgacggg | 900 |
| atgtcgcctt ccaggccgc catggtagat ggctccggat accaagtcca tcgcacaatg | 960 |
| cagtttgaag atggtgcctc ccttactgtt aactaccgct acacctacga gggaagccac | 1020 |
| atcaaaggag aggcccaggt gaaggggact ggtttccctg ctgacggtcc tgtgatgacc | 1080 |
| aactcgctga ccgctgcgga ctggtgcagg tcgaagaaga cttaccccaa cgacaaaacc | 1140 |
| atcatcagta cctttaagtg gagttacacc actggaaatg gcaagcgcta caggagcact | 1200 |
| gcgcggacca cctacacctt tgccaagcca atggcggcta actatctgaa gaaccagccg | 1260 |
| atgtacgtgt tccgtaagac ggagctcaag cactccaaga ccgagctcaa cttcaaggag | 1320 |
| tggcaaaagg cctttaccga tgtgatgggc atggacgagc tgtacaagaa gagcaggatc | 1380 |
| accagcgagg gcgagtacat cccccctggac cagatcgaca tcaacgtgtt ctgctacgag | 1440 |
| aacgaggtgt aa | 1452 |

<210> SEQ ID NO 8
<211> LENGTH: 483
<212> TYPE: PRT
<213> ORGANISM: Artificial Sequence
<220> FEATURE:
<223> OTHER INFORMATION: Synthetic

<400> SEQUENCE: 8

Met Ala Asp Val Glu Thr Glu Thr Gly Met Ile Ala Gln Trp Ile Val
1               5                   10                  15

```
Phe Ala Ile Met Ala Ala Ala Ile Ala Phe Gly Val Ala Val His
             20                  25                  30
Phe Arg Pro Ser Glu Leu Lys Ser Ala Tyr Tyr Ile Asn Ile Ala Ile
         35                  40                  45
Cys Thr Ile Ala Ala Thr Ala Tyr Tyr Ala Met Ala Val Asn Tyr Gln
     50                  55                  60
Asp Leu Thr Met Asn Gly Glu Arg Gln Val Val Tyr Ala Arg Tyr Ile
 65                  70                  75                  80
Asp Trp Val Leu Thr Thr Pro Leu Leu Leu Asn Leu Ile Val Met
             85                  90                  95
Thr Lys Met Gly Gly Val Met Ile Ser Trp Val Ile Gly Ala Asp Ile
                100                 105                 110
Phe Met Ile Val Phe Gly Ile Leu Gly Ala Phe Glu Asp Glu His Lys
            115                 120                 125
Phe Lys Trp Val Tyr Phe Ile Ala Gly Cys Val Met Gln Ala Val Leu
         130                 135                 140
Thr Tyr Gly Met Tyr Asn Ala Thr Trp Lys Asp Asp Leu Lys Lys Ser
145                 150                 155                 160
Pro Glu Tyr His Ser Ser Tyr Val Ser Leu Leu Val Phe Leu Ser Ile
                165                 170                 175
Leu Trp Val Phe Tyr Pro Val Val Trp Ala Phe Gly Ser Gly Ser Gly
            180                 185                 190
Val Leu Ser Val Asp Asn Glu Ala Ile Leu Met Gly Ile Leu Asp Val
        195                 200                 205
Leu Ala Lys Pro Leu Phe Gly Met Gly Cys Leu Ile Ala His Glu Thr
    210                 215                 220
Ile Phe Lys Lys Met Leu Arg Ser Leu Pro Ala Thr His Glu Leu His
225                 230                 235                 240
Ile Phe Gly Ser Ile Asn Gly Val Asp Phe Asp Met Val Gly Gln Gly
                245                 250                 255
Thr Gly Asn Pro Asn Asp Gly Tyr Glu Glu Leu Asn Leu Lys Ser Thr
            260                 265                 270
Lys Gly Asp Leu Gln Phe Ser Pro Trp Ile Leu Val Pro His Ile Gly
        275                 280                 285
Tyr Gly Phe His Gln Tyr Leu Pro Tyr Pro Asp Gly Met Ser Pro Phe
    290                 295                 300
Gln Ala Ala Met Val Asp Gly Ser Gly Tyr Gln Val His Arg Thr Met
305                 310                 315                 320
Gln Phe Glu Asp Gly Ala Ser Leu Thr Val Asn Tyr Arg Tyr Thr Tyr
                325                 330                 335
Glu Gly Ser His Ile Lys Gly Glu Ala Gln Val Lys Gly Thr Gly Phe
            340                 345                 350
Pro Ala Asp Gly Pro Val Met Thr Asn Ser Leu Thr Ala Ala Asp Trp
        355                 360                 365
Cys Arg Ser Lys Lys Thr Tyr Pro Asn Asp Lys Thr Ile Ile Ser Thr
    370                 375                 380
Phe Lys Trp Ser Tyr Thr Thr Gly Asn Gly Lys Arg Tyr Arg Ser Thr
385                 390                 395                 400
Ala Arg Thr Thr Tyr Thr Phe Ala Lys Pro Met Ala Ala Asn Tyr Leu
                405                 410                 415
Lys Asn Gln Pro Met Tyr Val Phe Arg Lys Thr Glu Leu Lys His Ser
            420                 425                 430
Lys Thr Glu Leu Asn Phe Lys Glu Trp Gln Lys Ala Phe Thr Asp Val
```

435                 440                 445
Met Gly Met Asp Glu Leu Tyr Lys Lys Ser Arg Ile Thr Ser Glu Gly
            450                 455                 460

Glu Tyr Ile Pro Leu Asp Gln Ile Asp Ile Asn Val Phe Cys Tyr Glu
465                 470                 475                 480

Asn Glu Val

<210> SEQ ID NO 9
<211> LENGTH: 227
<212> TYPE: PRT
<213> ORGANISM: Artificial Sequence
<220> FEATURE:
<223> OTHER INFORMATION: Synthetic

<400> SEQUENCE: 9

Met Ala Asp Val Glu Thr Glu Thr Gly Met Ile Ala Gln Trp Ile Val
1               5                   10                  15

Phe Ala Ile Met Ala Ala Ala Ile Ala Phe Gly Val Ala Val His
                20                  25                  30

Phe Arg Pro Ser Glu Leu Lys Ser Ala Tyr Tyr Ile Asn Ile Ala Ile
            35                  40                  45

Cys Thr Ile Ala Ala Thr Ala Tyr Tyr Ala Met Ala Val Asn Tyr Gln
        50                  55                  60

Asp Leu Thr Met Asn Gly Glu Arg Gln Val Val Tyr Ala Arg Tyr Ile
65                  70                  75                  80

Asn Trp Val Leu Thr Thr Pro Leu Leu Leu Leu Asp Leu Ile Val Met
                85                  90                  95

Thr Lys Met Gly Gly Val Met Ile Ser Trp Val Ile Gly Ala Asp Ile
            100                 105                 110

Phe Met Ile Val Phe Gly Ile Leu Gly Ala Phe Glu Asp Glu His Lys
        115                 120                 125

Phe Lys Trp Val Tyr Phe Ile Ala Gly Cys Val Met Gln Ala Val Leu
130                 135                 140

Thr Tyr Gly Met Tyr Asn Ala Thr Trp Lys Asp Asp Leu Lys Lys Ser
145                 150                 155                 160

Pro Glu Tyr His Ser Ser Tyr Val Ser Leu Leu Val Phe Leu Ser Ile
                165                 170                 175

Leu Trp Val Phe Tyr Pro Val Val Trp Ala Phe Gly Ser Gly Ser Gly
            180                 185                 190

Val Leu Ser Val Asp Asn Glu Ala Ile Leu Met Gly Ile Leu Asp Val
        195                 200                 205

Leu Ala Lys Pro Leu Phe Gly Met Gly Cys Leu Ile Ala His Glu Thr
    210                 215                 220

Ile Phe Lys
225

<210> SEQ ID NO 10
<211> LENGTH: 298
<212> TYPE: PRT
<213> ORGANISM: Artificial Sequence
<220> FEATURE:
<223> OTHER INFORMATION: Synthetic

<400> SEQUENCE: 10

Ile Gly Thr Gly Phe Pro Phe Asp Pro His Tyr Val Glu Val Leu Gly
1               5                   10                  15

Glu Arg Met His Tyr Val Asp Val Gly Pro Arg Asp Gly Thr Pro Val

```
            20                  25                  30
Leu Phe Leu His Gly Asn Pro Thr Ser Ser Tyr Val Trp Arg Asn Ile
         35                  40                  45
Ile Pro His Val Ala Pro Thr His Arg Cys Ile Ala Pro Asp Leu Ile
 50                  55                  60
Gly Met Gly Lys Ser Asp Lys Pro Asp Leu Gly Tyr Phe Phe Asp Asp
 65                  70                  75                  80
His Val Arg Phe Met Asp Ala Phe Ile Glu Ala Leu Gly Leu Glu Glu
                 85                  90                  95
Val Val Leu Val Ile His Asp Trp Gly Ser Ala Leu Gly Phe His Trp
                100                 105                 110
Ala Lys Arg Asn Pro Glu Arg Val Lys Gly Ile Ala Phe Met Glu Phe
                115                 120                 125
Ile Arg Pro Ile Pro Thr Trp Asp Glu Trp Pro Glu Phe Ala Arg Glu
            130                 135                 140
Thr Phe Gln Ala Phe Arg Thr Thr Asp Val Gly Arg Lys Leu Ile Ile
145                 150                 155                 160
Asp Gln Asn Val Phe Ile Glu Gly Thr Leu Pro Met Gly Val Val Arg
                165                 170                 175
Pro Leu Thr Glu Val Glu Met Asp His Tyr Arg Glu Pro Phe Leu Asn
                180                 185                 190
Pro Val Asp Arg Glu Pro Leu Trp Arg Phe Pro Asn Glu Leu Pro Ile
                195                 200                 205
Ala Gly Glu Pro Ala Asn Ile Val Ala Leu Val Glu Glu Tyr Met Asp
            210                 215                 220
Trp Leu His Gln Ser Pro Val Pro Lys Leu Leu Phe Trp Gly Thr Pro
225                 230                 235                 240
Gly Val Leu Ile Pro Pro Ala Glu Ala Ala Arg Leu Ala Lys Ser Leu
                245                 250                 255
Pro Asn Cys Lys Ala Val Asp Ile Gly Pro Gly Leu Asn Leu Leu Gln
                260                 265                 270
Glu Asp Asn Pro Asp Leu Ile Gly Ser Glu Ile Ala Arg Trp Leu Ser
            275                 280                 285
Thr Leu Glu Ile Ser Gly Glu Pro Thr Thr
        290                 295

<210> SEQ ID NO 11
<211> LENGTH: 229
<212> TYPE: PRT
<213> ORGANISM: Artificial Sequence
<220> FEATURE:
<223> OTHER INFORMATION: Synthetic

<400> SEQUENCE: 11

Lys Met Leu Arg Ser Leu Pro Ala Thr His Glu Leu His Ile Phe Gly
 1               5                  10                  15
Ser Ile Asn Gly Val Asp Phe Asp Met Val Gly Gln Gly Thr Gly Asn
                 20                  25                  30
Pro Asn Asp Gly Tyr Glu Glu Leu Asn Leu Lys Ser Thr Lys Gly Asp
             35                  40                  45
Leu Gln Phe Ser Pro Trp Ile Leu Val Pro His Ile Gly Tyr Gly Phe
         50                  55                  60
His Gln Tyr Leu Pro Tyr Pro Asp Gly Met Ser Pro Phe Gln Ala Ala
 65                  70                  75                  80
Met Val Asp Gly Ser Gly Tyr Gln Val His Arg Thr Met Gln Phe Glu
```

```
            85                  90                  95
Asp Gly Ala Ser Leu Thr Val Asn Tyr Arg Tyr Thr Tyr Glu Gly Ser
            100                 105                 110

His Ile Lys Gly Glu Ala Gln Val Lys Gly Thr Gly Phe Pro Ala Asp
            115                 120                 125

Gly Pro Val Met Thr Asn Ser Leu Thr Ala Ala Asp Trp Cys Arg Ser
    130                 135                 140

Lys Lys Thr Tyr Pro Asn Asp Lys Thr Ile Ile Ser Thr Phe Lys Trp
145                 150                 155                 160

Ser Tyr Thr Thr Gly Asn Gly Lys Arg Tyr Arg Ser Thr Ala Arg Thr
                165                 170                 175

Thr Tyr Thr Phe Ala Lys Pro Met Ala Ala Asn Tyr Leu Lys Asn Gln
            180                 185                 190

Pro Met Tyr Val Phe Arg Lys Thr Glu Leu Lys His Ser Lys Thr Glu
            195                 200                 205

Leu Asn Phe Lys Glu Trp Gln Lys Ala Phe Thr Asp Val Met Gly Met
    210                 215                 220

Asp Glu Leu Tyr Lys
225

<210> SEQ ID NO 12
<211> LENGTH: 27
<212> TYPE: PRT
<213> ORGANISM: Artificial Sequence
<220> FEATURE:
<223> OTHER INFORMATION: Synthetic

<400> SEQUENCE: 12

Lys Ser Arg Ile Thr Ser Glu Gly Glu Tyr Ile Pro Leu Asp Gln Ile
1               5                   10                  15

Asp Ile Asn Val Phe Cys Tyr Glu Asn Glu Val
            20                  25

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Phe Cys Tyr Glu Asn Glu Val
1               5

<210> SEQ ID NO 14
<211> LENGTH: 65
<212> TYPE: PRT
<213> ORGANISM: Artificial Sequence
<220> FEATURE:
<223> OTHER INFORMATION: Synthetic

<400> SEQUENCE: 14

Gln Ser Gln Pro Ile Leu Asn Thr Lys Glu Met Ala Pro Gln Ser Lys
1               5                   10                  15

Pro Pro Glu Glu Leu Glu Met Ser Ser Met Pro Ser Pro Val Ala Pro
            20                  25                  30

Leu Pro Ala Arg Thr Glu Gly Val Ile Asp Met Arg Ser Met Ser Ser
        35                  40                  45

Ile Asp Ser Phe Ile Ser Cys Ala Thr Asp Phe Pro Glu Ala Thr Arg
    50                  55                  60
```

Phe
65

<210> SEQ ID NO 15
<211> LENGTH: 254
<212> TYPE: PRT
<213> ORGANISM: Artificial Sequence
<220> FEATURE:
<223> OTHER INFORMATION: Synthetic

<400> SEQUENCE: 15

Ile Ala Leu Gln Ala Gly Tyr Asp Leu Leu Gly Asp Gly Arg Pro Glu
1               5                   10                  15

Thr Leu Trp Leu Gly Ile Gly Thr Leu Met Leu Ile Gly Thr Phe
            20                  25                  30

Tyr Phe Leu Val Arg Gly Trp Gly Val Thr Asp Lys Asp Ala Arg Glu
            35                  40                  45

Tyr Tyr Ala Val Thr Ile Leu Val Ser Gly Ile Ala Ser Ala Ala Tyr
    50                  55                  60

Leu Ser Met Phe Phe Gly Ile Gly Leu Thr Glu Val Ser Val Gly Gly
65                  70                  75                  80

Glu Met Leu Asp Ile Tyr Tyr Ala Arg Tyr Ala His Trp Leu Phe Thr
                85                  90                  95

Thr Leu Leu Leu Leu His Leu Ala Leu Leu Ala Lys Val Asp Arg Val
            100                 105                 110

Thr Ile Gly Thr Leu Val Gly Val Asp Ala Leu Met Ile Val Thr Gly
        115                 120                 125

Leu Ile Gly Ala Leu Ser His Thr Ala Ile Ala Arg Tyr Ser Trp Trp
130                 135                 140

Leu Phe Ser Thr Ile Cys Met Ile Val Val Leu Tyr Val Leu Ala Thr
145                 150                 155                 160

Ser Leu Arg Ser Ala Ala Lys Glu Arg Gly Pro Glu Val Ala Ser Thr
                165                 170                 175

Phe Asn Thr Leu Thr Ala Leu Val Leu Val Leu Trp Thr Ala Tyr Pro
            180                 185                 190

Ile Leu Trp Ile Ile Gly Thr Glu Gly Ala Gly Val Val Gly Leu Gly
        195                 200                 205

Ile Glu Thr Leu Leu Phe Met Val Leu Asp Val Thr Ala Lys Val Gly
    210                 215                 220

Phe Gly Phe Ile Leu Leu Arg Ser Arg Ala Ile Leu Gly Asp Thr Glu
225                 230                 235                 240

Ala Pro Glu Pro Ser Ala Gly Ala Asp Val Ser Ala Ala Asp
                245                 250

<210> SEQ ID NO 16
<211> LENGTH: 255
<212> TYPE: PRT
<213> ORGANISM: Artificial Sequence
<220> FEATURE:
<223> OTHER INFORMATION: Synthetic

<400> SEQUENCE: 16

Ile Ala Leu Gln Ala Gly Tyr Asp Leu Leu Gly Asp Gly Arg Pro Glu
1               5                   10                  15

Thr Leu Trp Leu Gly Ile Gly Thr Leu Met Leu Ile Gly Thr Phe
            20                  25                  30

Tyr Phe Leu Val Arg Gly Trp Gly Val Thr Asp Lys Asp Ala Arg Glu

```
            35                  40                  45
Tyr Tyr Ala Val Thr Ile Leu Val Ser Gly Ile Ala Ser Ala Ala Tyr
 50                  55                  60

Leu Ser Met Phe Phe Gly Ile Gly Leu Thr Glu Val Ser Val Gly Gly
 65                  70                  75                  80

Glu Met Leu Asp Ile Tyr Tyr Ala Arg Tyr Ala Gln Trp Leu Phe Thr
                 85                  90                  95

Thr Pro Leu Leu Leu Leu His Leu Ala Leu Leu Ala Lys Val Asp Arg
                100                 105                 110

Val Thr Ile Gly Thr Leu Val Gly Val Asp Ala Leu Met Ile Val Thr
            115                 120                 125

Gly Leu Ile Gly Ala Leu Ser His Thr Ala Ile Ala Arg Tyr Ser Trp
        130                 135                 140

Trp Leu Phe Ser Thr Ile Cys Met Ile Val Val Leu Tyr Val Leu Ala
145                 150                 155                 160

Thr Ser Leu Arg Ser Ala Ala Lys Glu Arg Gly Pro Glu Val Ala Ser
                165                 170                 175

Thr Phe Asn Thr Leu Thr Ala Leu Val Leu Val Leu Trp Thr Ala Tyr
            180                 185                 190

Pro Ile Leu Trp Ile Ile Gly Thr Glu Gly Ala Gly Val Val Gly Leu
        195                 200                 205

Gly Ile Glu Thr Leu Leu Phe Met Val Leu Asp Val Thr Ala Lys Val
210                 215                 220

Gly Phe Gly Phe Ile Leu Leu Arg Ser Arg Ala Ile Leu Gly Asp Thr
225                 230                 235                 240

Glu Ala Pro Glu Pro Ser Ala Gly Ala Asp Val Ser Ala Ala Asp
                245                 250                 255

<210> SEQ ID NO 17
<211> LENGTH: 241
<212> TYPE: PRT
<213> ORGANISM: Artificial Sequence
<220> FEATURE:
<223> OTHER INFORMATION: Synthetic

<400> SEQUENCE: 17

Ile Ala Leu Gln Ala Gly Tyr Asp Leu Leu Gly Asp Gly Arg Pro Glu
1               5                  10                  15

Thr Leu Trp Leu Gly Ile Gly Thr Leu Leu Met Leu Ile Gly Thr Phe
            20                  25                  30

Tyr Phe Leu Val Arg Gly Trp Gly Val Thr Asp Lys Asp Ala Arg Glu
        35                  40                  45

Tyr Tyr Ala Val Thr Ile Leu Val Ser Gly Ile Ala Ser Ala Ala Tyr
 50                  55                  60

Leu Ser Met Phe Phe Gly Ile Gly Leu Thr Glu Val Ser Val Gly Gly
 65                  70                  75                  80

Glu Met Leu Asp Ile Tyr Tyr Ala Arg Tyr Ala Gln Trp Leu Phe Thr
                 85                  90                  95

Thr Pro Leu Leu Leu Leu His Leu Ala Leu Leu Ala Lys Val Asp Arg
                100                 105                 110

Val Thr Ile Gly Thr Leu Val Gly Val Asp Ala Leu Met Ile Val Thr
            115                 120                 125

Gly Leu Ile Gly Ala Leu Ser His Thr Ala Ile Ala Arg Tyr Ser Trp
        130                 135                 140

Trp Leu Phe Ser Thr Ile Cys Met Ile Val Val Leu Tyr Val Leu Ala
```

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |

Thr Ser Leu Arg Ser Ala Ala Lys Glu Arg Gly Pro Glu Val Ala Ser
                165                 170                 175

Thr Phe Asn Thr Leu Thr Ala Leu Val Leu Val Leu Trp Thr Ala Tyr
                180                 185                 190

Pro Ile Leu Trp Ile Ile Gly Thr Glu Gly Ala Gly Val Val Gly Leu
                195                 200                 205

Gly Ile Glu Thr Leu Leu Phe Met Val Leu Asp Val Thr Ala Lys Val
210                 215                 220

Gly Phe Gly Phe Ile Leu Leu Arg Ser Arg Ala Ile Leu Gly Asp Thr
225                 230                 235                 240

Glu

<210> SEQ ID NO 18
<211> LENGTH: 181
<212> TYPE: PRT
<213> ORGANISM: Artificial Sequence
<220> FEATURE:
<223> OTHER INFORMATION: Synthetic

<400> SEQUENCE: 18

Asp Lys Asp Cys Glu Met Lys Arg Thr Thr Leu Asp Ser Pro Leu Gly
1               5                   10                  15

Lys Leu Glu Leu Ser Gly Cys Glu Gln Gly Leu His Arg Ile Ile Phe
                20                  25                  30

Leu Gly Lys Gly Thr Ser Ala Ala Asp Ala Val Glu Val Pro Ala Pro
            35                  40                  45

Ala Ala Val Leu Gly Gly Pro Glu Pro Leu Met Gln Ala Thr Ala Trp
        50                  55                  60

Leu Asn Ala Tyr Phe His Gln Pro Glu Ala Ile Glu Glu Phe Pro Val
65                  70                  75                  80

Pro Ala Leu His His Pro Val Phe Gln Gln Glu Ser Phe Thr Arg Gln
                85                  90                  95

Val Leu Trp Lys Leu Leu Lys Val Val Lys Phe Gly Glu Val Ile Ser
                100                 105                 110

Tyr Ser His Leu Ala Ala Leu Ala Gly Asn Pro Ala Ala Thr Ala Ala
            115                 120                 125

Val Lys Thr Ala Leu Ser Gly Asn Pro Val Pro Ile Leu Ile Pro Cys
        130                 135                 140

His Arg Val Val Gln Gly Asp Leu Asp Val Gly Gly Tyr Glu Gly Gly
145                 150                 155                 160

Leu Ala Val Lys Glu Trp Leu Leu Ala His Glu Gly His Arg Leu Gly
                165                 170                 175

Lys Pro Gly Leu Gly
            180

<210> SEQ ID NO 19
<211> LENGTH: 1854
<212> TYPE: DNA
<213> ORGANISM: Artificial Sequence
<220> FEATURE:
<223> OTHER INFORMATION: Synthetic

<400> SEQUENCE: 19
atggctgacg tggaaaccga gaccggcatg attgcacagt ggattgtctt tgctattatg    60
gctgctgctg ctattgcttt tggagtggct gtgcactttc ggccttcaga gctgaagagc   120

```
gcatactata tcaacattgc catctgcact atcgccgcta ccgcttacta tgcaatggcc    180
gtgaactacc aggacctgac aatgaatggt gaaaggcagg tggtctacgc aagatatatt    240
aactgggtgc tgaccacacc actgctcctg ctcgatctca tcgtcatgac caagatgggc    300
ggagtgatga tttcttgggt catcggcgca gacattttca tgatcgtgtt tggtattctg    360
ggcgccttcg aggatgaaca aagttcaaa tgggtgtact ttatcgctgg atgtgtgatg    420
caggcagtcc tgcatacgg gatgtataac gccacttgga agacgatct gaagaaaagc    480 cccgagtacc atagctccta tgtcagtctg ctcgtcttcc tgtcaatcct ctgggtgttt    540
tatcctgtcg tgtgggcttt cgggtctggt agtggcgtgc tgtccgtcga caatgaggcc    600
attctcatgg gaatcctgga tgtgctcgct aagccactgt ttggaatggg gtgcctcatt    660
gcccatgaga ctatcttcaa gatcggtact ggctttccat cgacccccca ttatgtggaa    720
gtcctgggcg agcgcatgca ctacgtcgat gttggtccgc gcgatggcac ccctgtgctg    780
ttcctgcacg gtaacccgac ctcctcctac gtgtggcgca acatcatccc gcatgttgca    840
ccgacccatc gctgcattgc tccagacctg atcggtatgg gcaaatccga caaaccagac    900
ctgggttatt tcttcgacga ccacgtccgc ttcatggatg ccttcatcga agccctgggt    960
ctggaagagg tcgtcctggt cattcacgac tgggctccg ctctgggttt ccactgggcc   1020
aagcgcaatc cagagcgcgt caaaggtatt gcatttatgg agttcatccg ccctatcccg   1080
acctgggacg aatggccaga atttgcccgc gagaccttcc aggccttccg caccaccgac   1140
gtcggccgca agctgatcat cgatcagaac gttttttatcg agggtacgct gccgatgggt   1200
gtcgtccgcc cgctgactga agtcgagatg gaccattacc gcgagccgtt cctgaatcct   1260
gttgaccgcg agccactgtg gcgcttccca acgagctgc caatcgccgg tgagccagcg   1320
aacatcgtcg cgctggtcga agaatacatg gactggctgc accagtcccc tgtcccgaag   1380
ctgctgttct ggggcacccc aggcgttctg atcccaccgg ccgaagccgc tcgcctggcc   1440
aaaagcctgc taactgcaa ggctgtggac atcggcccgg tctgaatct gctgcaagaa   1500 gacaacccgg acctgatcgg cagcgagatc gcgcgctggc tgtcgacgct cgagatttcc   1560
ggcgagccaa ccactaagag caggatcacc agcgagggcg agtacatccc cctggaccag   1620
atcgacatca acgtgttctg ctacgagaac gaggtgcaaa gtcagcctat cctgaacaca   1680
aaggaaatgg ctccacagtc taagcctccc gaagagcttg agatgtccag tatgccaagt   1740
cccgtggctc ccctccctgc caggactgaa ggagtgattg acatgaggag tatgtcatct   1800
attgatagct tcatctcttg cgcaacagat ttccccgagg ctactcgatt ctaa          1854
```

<210> SEQ ID NO 20
<211> LENGTH: 617
<212> TYPE: PRT
<213> ORGANISM: Artificial Sequence
<220> FEATURE:
<223> OTHER INFORMATION: Synthetic

<400> SEQUENCE: 20

```
Met Ala Asp Val Glu Thr Glu Thr Gly Met Ile Ala Gln Trp Ile Val
1               5                   10                  15

Phe Ala Ile Met Ala Ala Ala Ile Ala Phe Gly Val Ala Val His
            20                  25                  30

Phe Arg Pro Ser Glu Leu Lys Ser Ala Tyr Tyr Ile Asn Ile Ala Ile
        35                  40                  45

Cys Thr Ile Ala Ala Thr Ala Tyr Tyr Ala Met Ala Val Asn Tyr Gln
    50                  55                  60
```

```
Asp Leu Thr Met Asn Gly Glu Arg Gln Val Val Tyr Ala Arg Tyr Ile
 65                  70                  75                  80

Asn Trp Val Leu Thr Thr Pro Leu Leu Leu Asp Leu Ile Val Met
             85                  90                  95

Thr Lys Met Gly Gly Val Met Ile Ser Trp Val Ile Gly Ala Asp Ile
            100                 105                 110

Phe Met Ile Val Phe Gly Ile Leu Gly Ala Phe Glu Asp Glu His Lys
        115                 120                 125

Phe Lys Trp Val Tyr Phe Ile Ala Gly Cys Val Met Gln Ala Val Leu
    130                 135                 140

Thr Tyr Gly Met Tyr Asn Ala Thr Trp Lys Asp Asp Leu Lys Lys Ser
145                 150                 155                 160

Pro Glu Tyr His Ser Ser Tyr Val Ser Leu Leu Val Phe Leu Ser Ile
                165                 170                 175

Leu Trp Val Phe Tyr Pro Val Val Trp Ala Phe Gly Ser Gly Ser Gly
            180                 185                 190

Val Leu Ser Val Asp Asn Glu Ala Ile Leu Met Gly Ile Leu Asp Val
        195                 200                 205

Leu Ala Lys Pro Leu Phe Gly Met Gly Cys Leu Ile Ala His Glu Thr
    210                 215                 220

Ile Phe Lys Ile Gly Thr Gly Phe Pro Phe Asp Pro His Tyr Val Glu
225                 230                 235                 240

Val Leu Gly Glu Arg Met His Tyr Val Asp Val Gly Pro Arg Asp Gly
                245                 250                 255

Thr Pro Val Leu Phe Leu His Gly Asn Pro Thr Ser Ser Tyr Val Trp
            260                 265                 270

Arg Asn Ile Ile Pro His Val Ala Pro Thr His Arg Cys Ile Ala Pro
        275                 280                 285

Asp Leu Ile Gly Met Gly Lys Ser Asp Lys Pro Asp Leu Gly Tyr Phe
    290                 295                 300

Phe Asp Asp His Val Arg Phe Met Asp Ala Phe Ile Glu Ala Leu Gly
305                 310                 315                 320

Leu Glu Glu Val Val Leu Val Ile His Asp Trp Gly Ser Ala Leu Gly
                325                 330                 335

Phe His Trp Ala Lys Arg Asn Pro Glu Arg Val Lys Gly Ile Ala Phe
            340                 345                 350

Met Glu Phe Ile Arg Pro Ile Pro Thr Trp Asp Glu Trp Pro Glu Phe
        355                 360                 365

Ala Arg Glu Thr Phe Gln Ala Phe Arg Thr Thr Asp Val Gly Arg Lys
    370                 375                 380

Leu Ile Ile Asp Gln Asn Val Phe Ile Glu Gly Thr Leu Pro Met Gly
385                 390                 395                 400

Val Val Arg Pro Leu Thr Glu Val Glu Met Asp His Tyr Arg Glu Pro
                405                 410                 415

Phe Leu Asn Pro Val Asp Arg Glu Pro Leu Trp Arg Phe Pro Asn Glu
            420                 425                 430

Leu Pro Ile Ala Gly Glu Pro Ala Asn Ile Val Ala Leu Val Glu Glu
        435                 440                 445

Tyr Met Asp Trp Leu His Gln Ser Pro Val Pro Lys Leu Leu Phe Trp
    450                 455                 460

Gly Thr Pro Gly Val Leu Ile Pro Pro Ala Glu Ala Ala Arg Leu Ala
465                 470                 475                 480
```

Lys Ser Leu Pro Asn Cys Lys Ala Val Asp Ile Gly Pro Gly Leu Asn
            485                 490                 495

Leu Leu Gln Glu Asp Asn Pro Asp Leu Ile Gly Ser Glu Ile Ala Arg
        500                 505                 510

Trp Leu Ser Thr Leu Glu Ile Ser Gly Glu Pro Thr Thr Lys Ser Arg
        515                 520                 525

Ile Thr Ser Glu Gly Glu Tyr Ile Pro Leu Asp Gln Ile Asp Ile Asn
    530                 535                 540

Val Phe Cys Tyr Glu Asn Glu Val Gln Ser Gln Pro Ile Leu Asn Thr
545                 550                 555                 560

Lys Glu Met Ala Pro Gln Ser Lys Pro Pro Glu Glu Leu Glu Met Ser
                565                 570                 575

Ser Met Pro Ser Pro Val Ala Pro Leu Pro Ala Arg Thr Glu Gly Val
                580                 585                 590

Ile Asp Met Arg Ser Met Ser Ser Ile Asp Ser Phe Ile Ser Cys Ala
            595                 600                 605

Thr Asp Phe Pro Glu Ala Thr Arg Phe
        610                 615

<210> SEQ ID NO 21
<211> LENGTH: 1767
<212> TYPE: DNA
<213> ORGANISM: Artificial Sequences
<220> FEATURE:
<223> OTHER INFORMATION: Synthetic

<400> SEQUENCE: 21

```
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcggggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aaggagcggg ccccgaggt ggcatctacc      540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggcaccaga acccagtgcc ggtgccgatg tcagtgccgc cgacatggca     780
gaaatcggta ctggctttcc attcgacccc cattatgtgg aagtcctggg cgagcgcatg     840
cactacgtcg atgttggtcc gcgcgatggc acccctgtgc tgttcctgca cggtaacccg     900
acctcctcct acgtgtggcg caacatcatc ccgcatgttg caccgaccca tcgctgcatt     960
gctccagacc tgatcggtat gggcaaatcc gacaaaccag acctgggtta tttcttcgac    1020
gaccacgtcc gcttcatgga tgccttcatc gaagccctgg gtctggaaga ggtcgtcctg    1080
gtcattcacg actggggctc cgctctgggt ttccactggg ccaagcgcaa tccagagcgc    1140
gtcaaaggta ttgcatttat ggagttcatc cgccctatcc cgacctggga cgaatggcca    1200
gaatttgccc gcgagacctt ccaggccttc cgcaccaccg acgtcggccg caagctgatc    1260
```

```
atcgatcaga acgttttat cgagggtacg ctgccgatgg gtgtcgtccg cccgctgact    1320
gaagtcgaga tggaccatta ccgcgagccg ttcctgaatc ctgttgaccg cgagccactg    1380
tggcgcttcc caaacgagct gccaatcgcc ggtgagccag cgaacatcgt cgcgctggtc    1440
gaagaataca tggactggct gcaccagtcc cctgtcccga agctgctgtt ctggggcacc    1500
ccaggcgttc tgatcccacc ggccgaagcc gctcgcctgg ccaaaagcct gcctaactgc    1560
aaggctgtgg acatcggccc gggtctgaat ctgctgcaag aagacaaccc ggacctgatc    1620
ggcagcgaga tcgcgcgctg gctgtcgacg ctcgagattt ccggcgagcc aaccactaag    1680
agtagaatca aagcgaagg cgagtacatc cccctggatc aaatagacat aaatgtaggt    1740
ggattttgtt atgagaatga agtataa                                       1767
```

<210> SEQ ID NO 22
<211> LENGTH: 588
<212> TYPE: PRT
<213> ORGANISM: Artificial Sequence
<220> FEATURE:
<223> OTHER INFORMATION: Synthetic

<400> SEQUENCE: 22

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Met Ala Glu Ile Gly Thr Gly Phe Pro Phe Pro His Tyr
            260                 265                 270
```

Val Glu Val Leu Gly Glu Arg Met His Tyr Val Asp Val Gly Pro Arg
              275                 280                 285

Asp Gly Thr Pro Val Leu Phe Leu His Gly Asn Pro Thr Ser Ser Tyr
        290                 295                 300

Val Trp Arg Asn Ile Ile Pro His Val Ala Pro Thr His Arg Cys Ile
305                 310                 315                 320

Ala Pro Asp Leu Ile Gly Met Gly Lys Ser Asp Lys Pro Asp Leu Gly
                325                 330                 335

Tyr Phe Phe Asp Asp His Val Arg Phe Met Asp Ala Phe Ile Glu Ala
                340                 345                 350

Leu Gly Leu Glu Glu Val Val Leu Val Ile His Asp Trp Gly Ser Ala
            355                 360                 365

Leu Gly Phe His Trp Ala Lys Arg Asn Pro Glu Arg Val Lys Gly Ile
        370                 375                 380

Ala Phe Met Glu Phe Ile Arg Pro Ile Pro Thr Trp Asp Glu Trp Pro
385                 390                 395                 400

Glu Phe Ala Arg Glu Thr Phe Gln Ala Phe Arg Thr Thr Asp Val Gly
                405                 410                 415

Arg Lys Leu Ile Ile Asp Gln Asn Val Phe Ile Glu Gly Thr Leu Pro
                420                 425                 430

Met Gly Val Val Arg Pro Leu Thr Glu Val Glu Met Asp His Tyr Arg
            435                 440                 445

Glu Pro Phe Leu Asn Pro Val Asp Arg Glu Pro Leu Trp Arg Phe Pro
        450                 455                 460

Asn Glu Leu Pro Ile Ala Gly Glu Pro Ala Asn Ile Val Ala Leu Val
465                 470                 475                 480

Glu Glu Tyr Met Asp Trp Leu His Gln Ser Pro Val Pro Lys Leu Leu
                485                 490                 495

Phe Trp Gly Thr Pro Gly Val Leu Ile Pro Pro Ala Glu Ala Ala Arg
            500                 505                 510

Leu Ala Lys Ser Leu Pro Asn Cys Lys Ala Val Asp Ile Gly Pro Gly
        515                 520                 525

Leu Asn Leu Leu Gln Glu Asp Asn Pro Asp Leu Ile Gly Ser Glu Ile
530                 535                 540

Ala Arg Trp Leu Ser Thr Leu Glu Ile Ser Gly Glu Pro Thr Thr Lys
545                 550                 555                 560

Ser Arg Ile Thr Ser Glu Gly Glu Tyr Ile Pro Leu Asp Gln Ile Asp
                565                 570                 575

Ile Asn Val Gly Gly Phe Cys Tyr Glu Asn Glu Val
                580                 585

<210> SEQ ID NO 23
<211> LENGTH: 1365
<212> TYPE: DNA
<213> ORGANISM: Artificial Sequence
<220> FEATURE:
<223> OTHER INFORMATION: Synthetic

<400> SEQUENCE: 23
atggtaagta tcgctctgca ggctggttac gacctactgg gtgacggcag acctgaaacc      60
ctgtggctgg gcatcggcac tctgctgatg ctgattggaa ccttctactt ctgtggtccgc     120 ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcgggggcg aaatgttgga tatctattat gccaggtacg cccagtggct gtttaccacc     300

```
ccacttctgc tgctgcacct ggcccttctc gctaaggtgg atcgggtgac catcggcacc    360
ctggtgggtg tggacgccct gatgatcgtc actggcctca tcggagcctt gagccacacg    420
gccatagcca gatacagttg gtggttgttc tctacaattt gcatgatagt ggtgctctat    480
gttctggcta catccctgcg atctgctgca aaggagcggg gccccgaggt ggcatctacc    540
tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggacaaaga ctgcgaaatg aagcgcacca ccctggatag ccctctgggc    780
aagctggaac tgtctgggtg cgaacagggc ctgcaccgta tcatcttcct gggcaaagga    840
acatctgccg ccgacgccgt ggaagtgcct gccccagccg ccgtgctggg cggaccagag    900
ccactgatgc aggccaccgc ctggctcaac gcctactttc accagcctga ggccatcgag    960
gagttccctg tgccagccct gcaccaccca gtgttccagc aggagagctt tacccgccag   1020
gtgctgtgga aactgctgaa agtggtgaag ttcggagagg tcatcagcta cagccacctg   1080
gccgccctgg ccggcaatcc cgccgccacc gccgccgtga aaaccgccct gagcggaaat   1140
cccgtgccca ttctgatccc ctgccaccgg gtggtgcagg gcgacctgga cgtgggggc    1200
tacgagggcg ggctcgccgt gaaagagtgg ctgctggccc acgagggcca cagactgggc   1260
aagcctgggc tgggtaagag tagaatcaca agcgaaggcg agtacatccc cctggatcaa   1320
atagacataa atgtaggtgg attttgttat gagaatgaag tataa                   1365
```

<210> SEQ ID NO 24
<211> LENGTH: 454
<212> TYPE: PRT
<213> ORGANISM: Artificial Sequence
<220> FEATURE:
<223> OTHER INFORMATION: Synthetic

<400> SEQUENCE: 24

```
Met Val Ser Ile Ala Leu Gln Ala Gly Tyr Asp Leu Leu Gly Asp Gly
1               5                  10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175
```

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Asp Lys Asp Cys Glu Met Lys Arg Thr Thr Leu Asp
                245                 250                 255

Ser Pro Leu Gly Lys Leu Glu Leu Ser Gly Cys Glu Gln Gly Leu His
            260                 265                 270

Arg Ile Ile Phe Leu Gly Lys Gly Thr Ser Ala Ala Asp Ala Val Glu
        275                 280                 285

Val Pro Ala Pro Ala Ala Val Leu Gly Gly Pro Glu Pro Leu Met Gln
    290                 295                 300

Ala Thr Ala Trp Leu Asn Ala Tyr Phe His Gln Pro Glu Ala Ile Glu
305                 310                 315                 320

Glu Phe Pro Val Pro Ala Leu His His Pro Val Phe Gln Gln Glu Ser
                325                 330                 335

Phe Thr Arg Gln Val Leu Trp Lys Leu Leu Lys Val Val Lys Phe Gly
            340                 345                 350

Glu Val Ile Ser Tyr Ser His Leu Ala Ala Leu Ala Gly Asn Pro Ala
        355                 360                 365

Ala Thr Ala Ala Val Lys Thr Ala Leu Ser Gly Asn Pro Val Pro Ile
    370                 375                 380

Leu Ile Pro Cys His Arg Val Val Gln Gly Asp Leu Asp Val Gly Gly
385                 390                 395                 400

Tyr Glu Gly Gly Leu Ala Val Lys Glu Trp Leu Leu Ala His Glu Gly
                405                 410                 415

His Arg Leu Gly Lys Pro Gly Leu Gly Lys Ser Arg Ile Thr Ser Glu
            420                 425                 430

Gly Glu Tyr Ile Pro Leu Asp Gln Ile Asp Ile Asn Val Gly Gly Phe
        435                 440                 445

Cys Tyr Glu Asn Glu Val
    450

<210> SEQ ID NO 25
<211> LENGTH: 1767
<212> TYPE: DNA
<213> ORGANISM: Artificial Sequence
<220> FEATURE:
<223> OTHER INFORMATION: Synthetic

<400> SEQUENCE: 25
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcgggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420

```
gccatagcca gatacagttg gtggttgttc tctacaattt gcatgatagt ggtgctctat    480
gttctggcta catccctgcg atctgctgca aggagcggg gccccgaggt ggcatctacc    540
tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggcaccaga acccagtgcc ggtgccgatg tcagtgccgc cgacatggca    780
gaaatcggta ctggctttcc attcgacccc cattatgtgg aagtcctggg cgagcgcatg    840
cactacgtcg atgttggtcc gcgcgatggc accctgtgc tgttcctgca cggtaacccg    900
acctcctcct acgtgtggcg caacatcatc ccgcatgttg caccgaccca tcgctgcatt    960
gctccagacc tgatcggtat gggcaaatcc gacaaaccag acctgggtta tttcttcgac   1020
gaccacgtcc gcttcatgga tgccttcatc gaagccctgg gtctggaaga ggtcgtcctg   1080
gtcattcacg actggggctc cgctctgggt ttccactggg ccaagcgcaa tccagagcgc   1140
gtcaaaggta ttgcatttat ggagttcatc cgccctatcc cgacctggga cgaatggcca   1200
gaatttgccc gcgagacctt ccaggccttc cgcaccaccg acgtcggccg caagctgatc   1260
atcgatcaga acgtttttat cgagggtacg ctgccgatgg tgtcgtccg cccgctgact   1320
gaagtcgaga tggaccatta ccgcgagccg ttcctgaatc ctgttgaccg cgagccactg   1380
tggcgcttcc caaacgagct gccaatcgcc ggtgagccag cgaacatcgt cgcgctggtc   1440
gaagaataca tggactggct gcaccagtcc cctgtcccga agctgctgtt ctggggcacc   1500
ccaggcgttc tgatcccacc ggccgaagcc gctcgcctgg ccaaaagcct gcctaactgc   1560
aaggctgtgg acatcggccc gggtctgaat ctgctgcaag aagacaaccc ggacctgatc   1620
ggcagcgaga tcgcgcgctg gctgtcgacg ctcgagattt ccggcgagcc aaccactaag   1680
agtagaatca aagcgaagg cgagtacatc ccctggatc aaatagacat aaatgtaggt   1740
ggattttgtt atgagaatga agtataa                                       1767
```

<210> SEQ ID NO 26
<211> LENGTH: 588
<212> TYPE: PRT
<213> ORGANISM: Artificial Sequence
<220> FEATURE:
<223> OTHER INFORMATION: Synthetic

<400> SEQUENCE: 26

Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

```
Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Leu Trp Ile Ile Gly Thr Glu Gly Ala Gly Val
                195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Met Ala Glu Ile Gly Thr Gly Phe Pro Phe Asp Pro His Tyr
                260                 265                 270

Val Glu Val Leu Gly Glu Arg Met His Tyr Val Asp Val Gly Pro Arg
                275                 280                 285

Asp Gly Thr Pro Val Leu Phe Leu His Gly Asn Pro Thr Ser Ser Tyr
    290                 295                 300

Val Trp Arg Asn Ile Ile Pro His Val Ala Pro Thr His Arg Cys Ile
305                 310                 315                 320

Ala Pro Asp Leu Ile Gly Met Gly Lys Ser Asp Lys Pro Asp Leu Gly
                325                 330                 335

Tyr Phe Phe Asp Asp His Val Arg Phe Met Asp Ala Phe Ile Glu Ala
                340                 345                 350

Leu Gly Leu Glu Glu Val Val Leu Val Ile His Asp Trp Gly Ser Ala
                355                 360                 365

Leu Gly Phe His Trp Ala Lys Arg Asn Pro Glu Arg Val Lys Gly Ile
    370                 375                 380

Ala Phe Met Glu Phe Ile Arg Pro Ile Pro Thr Trp Asp Glu Trp Pro
385                 390                 395                 400

Glu Phe Ala Arg Glu Thr Phe Gln Ala Phe Arg Thr Thr Asp Val Gly
                405                 410                 415

Arg Lys Leu Ile Ile Asp Gln Asn Val Phe Ile Glu Gly Thr Leu Pro
                420                 425                 430

Met Gly Val Val Arg Pro Leu Thr Glu Val Glu Met Asp His Tyr Arg
    435                 440                 445

Glu Pro Phe Leu Asn Pro Val Asp Arg Glu Pro Leu Trp Arg Phe Pro
    450                 455                 460

Asn Glu Leu Pro Ile Ala Gly Glu Pro Ala Asn Ile Val Ala Leu Val
465                 470                 475                 480

Glu Glu Tyr Met Asp Trp Leu His Gln Ser Pro Val Pro Lys Leu Leu
                485                 490                 495

Phe Trp Gly Thr Pro Gly Val Leu Ile Pro Pro Ala Glu Ala Ala Arg
                500                 505                 510

Leu Ala Lys Ser Leu Pro Asn Cys Lys Ala Val Asp Ile Gly Pro Gly
                515                 520                 525

Leu Asn Leu Leu Gln Glu Asp Asn Pro Asp Leu Ile Gly Ser Glu Ile
    530                 535                 540
```

```
Ala Arg Trp Leu Ser Thr Leu Glu Ile Ser Gly Glu Pro Thr Thr Lys
545                 550                 555                 560

Ser Arg Ile Thr Ser Glu Gly Glu Tyr Ile Pro Leu Asp Gln Ile Asp
                565                 570                 575

Ile Asn Val Gly Gly Phe Cys Tyr Glu Asn Glu Val
            580                 585

<210> SEQ ID NO 27
<211> LENGTH: 1755
<212> TYPE: DNA
<213> ORGANISM: Artificial Sequence
<220> FEATURE:
<223> OTHER INFORMATION: Sythentic

<400> SEQUENCE: 27
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcgggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aaggagcggg gccccgaggt ggcatctacc     540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggcaccaga acccagtgcc ggtgccgatg tcatggcaga aatcggtact     780
ggctttccat tcgaccccca ttatgtggaa gtcctgggcg agcgcatgca ctacgtcgat     840
gttggtccgc gcgatggcac ccctgtgctg ttcctgcacg gtaacccgac ctcctcctac     900
gtgtggcgca acatcatccc gcatgttgca ccgacccatc gctgcattgc tccagacctg     960
atcggtatgg gcaaatccga caaccagac ctgggttatt tcttcgacga ccacgtccgc    1020
ttcatggatg ccttcatcga agccctgggt ctggaagagg tcgtcctggt cattcacgac    1080
tggggctccg ctctgggttt ccactgggcc aagcgcaatc cagagcgcgt caaaggtatt    1140
gcatttatgg agttcatccg ccctatcccg acctgggacg aatggccaga atttgcccgc    1200
gagaccttcc aggccttccg caccaccgac gtcggccgca agctgatcat cgatcagaac    1260
gtttttatcg agggtacgct gccgatgggt gtcgtccgcc cgctgactga agtcgagatg    1320
gaccattacc gcgagccgtt cctgaatcct gttgaccgcg agccactgtg gcgcttccca    1380
aacgagctgc aatcgccgg tgagccagcg aacatcgtcg cgctggtcga gaatacatg     1440 gactggctgc accagtcccc tgtcccgaag ctgctgttct ggggcaccccc aggcgttctg    1500 atcccaccgg ccgaagccgc tcgcctggcc aaaagcctgc ctaactgcaa ggctgtggac    1560
atcggcccgg tctgaatct gctgcaagaa gacaaccccgg acctgatcgg cagcgagatc    1620
gcgcgctggc tgtcgacgct cgagatttcc ggcgagccaa ccactaagag tagaatcaca    1680
agcgaaggcg agtacatccc cctggatcaa atagacataa atgtaggtgg attttgttat    1740
gagaatgaag tataa                                                    1755
```

<210> SEQ ID NO 28
<211> LENGTH: 584
<212> TYPE: PRT
<213> ORGANISM: Artificial Sequence
<220> FEATURE:
<223> OTHER INFORMATION: Synthetic

<400> SEQUENCE: 28

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Met Ala
                245                 250                 255

Glu Ile Gly Thr Gly Phe Pro Phe Asp Pro His Tyr Val Glu Val Leu
            260                 265                 270

Gly Glu Arg Met His Tyr Val Asp Val Gly Pro Arg Asp Gly Thr Pro
        275                 280                 285

Val Leu Phe Leu His Gly Asn Pro Thr Ser Ser Tyr Val Trp Arg Asn
    290                 295                 300

Ile Ile Pro His Val Ala Pro Thr His Arg Cys Ile Ala Pro Asp Leu
305                 310                 315                 320

Ile Gly Met Gly Lys Ser Asp Lys Pro Asp Leu Gly Tyr Phe Phe Asp
                325                 330                 335

Asp His Val Arg Phe Met Asp Ala Phe Ile Glu Ala Leu Gly Leu Glu
            340                 345                 350

Glu Val Val Leu Val Ile His Asp Trp Gly Ser Ala Leu Gly Phe His
        355                 360                 365
```

```
Trp Ala Lys Arg Asn Pro Glu Arg Val Lys Gly Ile Ala Phe Met Glu
    370                 375                 380
Phe Ile Arg Pro Ile Pro Thr Trp Asp Glu Trp Pro Glu Phe Ala Arg
385                 390                 395                 400
Glu Thr Phe Gln Ala Phe Arg Thr Thr Asp Val Gly Arg Lys Leu Ile
                405                 410                 415
Ile Asp Gln Asn Val Phe Ile Glu Gly Thr Leu Pro Met Gly Val Val
                420                 425                 430
Arg Pro Leu Thr Glu Val Glu Met Asp His Tyr Arg Glu Pro Phe Leu
            435                 440                 445
Asn Pro Val Asp Arg Glu Pro Leu Trp Arg Phe Pro Asn Glu Leu Pro
450                 455                 460
Ile Ala Gly Glu Pro Ala Asn Ile Val Ala Leu Val Glu Glu Tyr Met
465                 470                 475                 480
Asp Trp Leu His Gln Ser Pro Val Pro Lys Leu Leu Phe Trp Gly Thr
                485                 490                 495
Pro Gly Val Leu Ile Pro Pro Ala Glu Ala Ala Arg Leu Ala Lys Ser
                500                 505                 510
Leu Pro Asn Cys Lys Ala Val Asp Ile Gly Pro Gly Leu Asn Leu Leu
            515                 520                 525
Gln Glu Asp Asn Pro Asp Leu Ile Gly Ser Glu Ile Ala Arg Trp Leu
530                 535                 540
Ser Thr Leu Glu Ile Ser Gly Glu Pro Thr Thr Lys Ser Arg Ile Thr
545                 550                 555                 560
Ser Glu Gly Glu Tyr Ile Pro Leu Asp Gln Ile Asp Ile Asn Val Gly
                565                 570                 575
Gly Phe Cys Tyr Glu Asn Glu Val
            580
```

<210> SEQ ID NO 29
<211> LENGTH: 1743
<212> TYPE: DNA
<213> ORGANISM: Artificial Sequence
<220> FEATURE:
<223> OTHER INFORMATION: Sythentic

<400> SEQUENCE: 29

```
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcgggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aaggagcggg ccccgaggt ggcatctacc     540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggcaccaga acccagtgcc atggcagaaa tcggtactgg ctttccattc     780
gaccccccatt atgtggaagt cctgggcgag cgcatgcact acgtcgatgt tggtccgcgc     840
```

```
gatggcaccc ctgtgctgtt cctgcacggt aacccgacct cctcctacgt gtggcgcaac    900
atcatcccgc atgttgcacc gacccatcgc tgcattgctc cagacctgat cggtatgggc    960
aaatccgaca aaccagacct gggttatttc ttcgacgacc acgtccgctt catggatgcc   1020
ttcatcgaag ccctgggtct ggaagaggtc gtcctggtca ttcacgactg gggctccgct   1080
ctgggtttcc actgggccaa gcgcaatcca gagcgcgtca aggtattgc atttatggag    1140
ttcatccgcc ctatcccgac ctgggacgaa tggccagaat tgcccgcga gaccttccag    1200
gccttccgca ccaccgacgt cggccgcaag ctgatcatcg atcagaacgt ttttatcgag   1260
ggtacgctgc cgatgggtgt cgtccgcccg ctgactgaag tcgagatgga ccattaccgc   1320
gagccgttcc tgaatcctgt tgaccgcgag ccactgtggc gcttcccaaa cgagctgcca   1380
atcgccggtg agccagcgaa catcgtcgcg ctggtcgaag aatacatgga ctggctgcac   1440
cagtcccctg tcccgaagct gctgttctgg ggcacccag gcgttctgat cccaccggcc    1500
gaagccgctc gcctggccaa aagcctgcct aactgcaagg ctgtggacat cggcccgggt   1560
ctgaatctgc tgcaagaaga caacccggac ctgatcggca gcgagatcgc gcgctggctg   1620
tcgacgctcg agatttccgg cgagccaacc actaagagta gaatcacaag cgaaggcgag   1680
tacatccccc tggatcaaat agacataaat gtaggtggat tttgttatga aatgaagta    1740
taa                                                                 1743

<210> SEQ ID NO 30
<211> LENGTH: 580
<212> TYPE: PRT
<213> ORGANISM: Artificial Sequence
<220> FEATURE:
<223> OTHER INFORMATION: Synthetic

<400> SEQUENCE: 30

Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190
```

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
        210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Met Ala Glu Ile Gly Thr
                245                 250                 255

Gly Phe Pro Phe Asp Pro His Tyr Val Glu Val Leu Gly Glu Arg Met
            260                 265                 270

His Tyr Val Asp Val Gly Pro Arg Asp Gly Thr Pro Val Leu Phe Leu
        275                 280                 285

His Gly Asn Pro Thr Ser Ser Tyr Val Trp Arg Asn Ile Ile Pro His
    290                 295                 300

Val Ala Pro Thr His Arg Cys Ile Ala Pro Asp Leu Ile Gly Met Gly
305                 310                 315                 320

Lys Ser Asp Lys Pro Asp Leu Gly Tyr Phe Phe Asp Asp His Val Arg
                325                 330                 335

Phe Met Asp Ala Phe Ile Glu Ala Leu Gly Leu Glu Glu Val Val Leu
            340                 345                 350

Val Ile His Asp Trp Gly Ser Ala Leu Gly Phe His Trp Ala Lys Arg
        355                 360                 365

Asn Pro Glu Arg Val Lys Gly Ile Ala Phe Met Glu Phe Ile Arg Pro
    370                 375                 380

Ile Pro Thr Trp Asp Glu Trp Pro Glu Phe Ala Arg Glu Thr Phe Gln
385                 390                 395                 400

Ala Phe Arg Thr Thr Asp Val Gly Arg Lys Leu Ile Ile Asp Gln Asn
                405                 410                 415

Val Phe Ile Glu Gly Thr Leu Pro Met Gly Val Val Arg Pro Leu Thr
            420                 425                 430

Glu Val Glu Met Asp His Tyr Arg Glu Pro Phe Leu Asn Pro Val Asp
        435                 440                 445

Arg Glu Pro Leu Trp Arg Phe Pro Asn Glu Leu Pro Ile Ala Gly Glu
    450                 455                 460

Pro Ala Asn Ile Val Ala Leu Val Glu Glu Tyr Met Asp Trp Leu His
465                 470                 475                 480

Gln Ser Pro Val Pro Lys Leu Leu Phe Trp Gly Thr Pro Gly Val Leu
                485                 490                 495

Ile Pro Pro Ala Glu Ala Ala Arg Leu Ala Lys Ser Leu Pro Asn Cys
            500                 505                 510

Lys Ala Val Asp Ile Gly Pro Gly Leu Asn Leu Leu Gln Glu Asp Asn
        515                 520                 525

Pro Asp Leu Ile Gly Ser Glu Ile Ala Arg Trp Leu Ser Thr Leu Glu
    530                 535                 540

Ile Ser Gly Glu Pro Thr Thr Lys Ser Arg Ile Thr Ser Glu Gly Glu
545                 550                 555                 560

Tyr Ile Pro Leu Asp Gln Ile Asp Ile Asn Val Gly Gly Phe Cys Tyr
                565                 570                 575

Glu Asn Glu Val
            580

<210> SEQ ID NO 31
<211> LENGTH: 1731
<212> TYPE: DNA

<213> ORGANISM: Artificial Sequence
<220> FEATURE:
<223> OTHER INFORMATION: Synthetic

<400> SEQUENCE: 31

```
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcgggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aaggagcggg ccccgaggt ggcatctacc      540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggcaccaat ggcagaaatc ggtactggct ttccattcga cccccattat     780
gtggaagtcc tgggcgagcg catgcactac gtcgatgttg tccgcgcga tggcacccct      840
gtgctgttcc tgcacggtaa cccgacctcc tcctacgtgt ggcgcaacat catcccgcat     900
gttgcaccga cccatcgctg cattgctcca gacctgatcg gtatgggcaa atccgacaaa     960
ccagacctgg gttatttctt cgacgaccac gtccgcttca tggatgcctt catcgaagcc    1020
ctgggtctgg aagaggtcgt cctggtcatt cacgactggg gctccgctct gggtttccac    1080
tgggccaagc gcaatccaga gcgcgtcaaa ggtattgcat ttatggagtt catccgccct    1140
atcccgacct gggacgaatg gccagaattt gcccgcgaga ccttccaggc cttccgcacc    1200
accgacgtcg gccgcaagct gatcatcgat cagaacgttt ttatcgaggg tacgctgccg    1260
atgggtgtcg tccgcccgct gactgaagtc gagatggacc attaccgcga gccgttcctg    1320
aatcctgttg accgcgagcc actgtggcgc ttcccaaacg agctgccaat cgccggtgag    1380
ccagcgaaca tcgtcgcgct ggtcgaagaa tacatggact ggctgcacca gtcccctgtc    1440
ccgaagctgc tgttctgggg caccccaggc gttctgatcc caccggccga agccgctcgc    1500
ctggccaaaa gcctgcctaa ctgcaaggct gtggacatcg gcccgggtct gaatctgctg    1560
caagaagaca acccggacct gatcggcagc gagatcgcgc gctggctgtc gacgctcgag    1620
atttccggcg agccaaccac taagagtaga atcacaagcg aaggcgagta catcccctg     1680
gatcaaatag acataaatgt aggtggattt tgttatgaga atgaagtata a             1731
```

<210> SEQ ID NO 32
<211> LENGTH: 576
<212> TYPE: PRT
<213> ORGANISM: Artificial Sequence
<220> FEATURE:
<223> OTHER INFORMATION: Synthetic

<400> SEQUENCE: 32

Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

```
Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Ser Gly Ile Ala Ser
 50                  55                  60

Ala Ala Tyr Leu Ser Met Phe Phe Gly Ile Gly Leu Thr Glu Val Ser
 65                  70                  75                  80

Val Gly Gly Glu Met Leu Asp Ile Tyr Tyr Ala Arg Tyr Ala Gln Trp
                    85                  90                  95

Leu Phe Thr Thr Pro Leu Leu Leu His Leu Ala Leu Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Met Ala Glu Ile Gly Thr Gly Phe Pro Phe
                245                 250                 255

Asp Pro His Tyr Val Glu Val Leu Gly Glu Arg Met His Tyr Val Asp
            260                 265                 270

Val Gly Pro Arg Asp Gly Thr Pro Val Leu Phe Leu His Gly Asn Pro
        275                 280                 285

Thr Ser Ser Tyr Val Trp Arg Asn Ile Ile Pro His Val Ala Pro Thr
    290                 295                 300

His Arg Cys Ile Ala Pro Asp Leu Ile Gly Met Gly Lys Ser Asp Lys
305                 310                 315                 320

Pro Asp Leu Gly Tyr Phe Phe Asp Asp His Val Arg Phe Met Asp Ala
                325                 330                 335

Phe Ile Glu Ala Leu Gly Leu Glu Glu Val Val Leu Val Ile His Asp
            340                 345                 350

Trp Gly Ser Ala Leu Gly Phe His Trp Ala Lys Arg Asn Pro Glu Arg
        355                 360                 365

Val Lys Gly Ile Ala Phe Met Glu Phe Ile Arg Pro Ile Pro Thr Trp
    370                 375                 380

Asp Glu Trp Pro Glu Phe Ala Arg Glu Thr Phe Gln Ala Phe Arg Thr
385                 390                 395                 400

Thr Asp Val Gly Arg Lys Leu Ile Ile Asp Gln Asn Val Phe Ile Glu
                405                 410                 415

Gly Thr Leu Pro Met Gly Val Val Arg Pro Leu Thr Glu Val Glu Met
            420                 425                 430

Asp His Tyr Arg Glu Pro Phe Leu Asn Pro Val Asp Arg Glu Pro Leu
        435                 440                 445
```

```
Trp Arg Phe Pro Asn Glu Leu Pro Ile Ala Gly Glu Pro Ala Asn Ile
450                 455                 460

Val Ala Leu Val Glu Glu Tyr Met Asp Trp Leu His Gln Ser Pro Val
465                 470                 475                 480

Pro Lys Leu Leu Phe Trp Gly Thr Pro Gly Val Leu Ile Pro Pro Ala
                485                 490                 495

Glu Ala Ala Arg Leu Ala Lys Ser Leu Pro Asn Cys Lys Ala Val Asp
                500                 505                 510

Ile Gly Pro Gly Leu Asn Leu Leu Gln Glu Asp Asn Pro Asp Leu Ile
            515                 520                 525

Gly Ser Glu Ile Ala Arg Trp Leu Ser Thr Leu Glu Ile Ser Gly Glu
530                 535                 540

Pro Thr Thr Lys Ser Arg Ile Thr Ser Glu Gly Glu Tyr Ile Pro Leu
545                 550                 555                 560

Asp Gln Ile Asp Ile Asn Val Gly Gly Phe Cys Tyr Glu Asn Glu Val
                565                 570                 575

<210> SEQ ID NO 33
<211> LENGTH: 1719
<212> TYPE: DNA
<213> ORGANISM: Artificial Sequence
<220> FEATURE:
<223> OTHER INFORMATION: Synthetic

<400> SEQUENCE: 33
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcgggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aaggagcggg gccccgaggt ggcatctacc     540
tttaacaccc tgcagctctc tggtcttggt ctgtggaccg cttacccat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggaaatcgg tactggcttt ccattcgacc ccattatgt ggaagtcctg     780
ggcgagcgca tgcactacgt cgatgttggt ccgcgcgatg cacccctgt gctgttcctg     840
cacggtaacc cgacctcctc ctacgtgtgg cgcaacatca tcccgcatgt tgcaccgacc     900
catcgctgca ttgctccaga cctgatcggt atgggcaaat ccgacaaacc agacctgggt     960
tatttcttcg acgaccacgt ccgcttcatg gatgccttca tcgaagccct gggtctggaa    1020
gaggtcgtcc tggtcattca cgactggggc tccgctctgg gtttccactg ggccaagcgc    1080
aatccagagc gcgtcaaagg tattgcattt atggagttca tccgccctat ccgacctgg    1140
gacgaatggc cagaatttgc ccgcgagacc ttccaggcct tccgcaccac cgacgtcggc    1200
cgcaagctga tcatcgatca gaacgttttt atcgaggta cgctgccgat gggtgtcgtc    1260
cgcccgctga ctgaagtcga gatggaccat taccgcgagc cgttcctgaa tcctgttgac    1320
cgcgagccac tgtggcgctt cccaaacgag ctgccaatcg ccggtgagcc agcgaacatc    1380
```

-continued

```
gtcgcgctgg tcgaagaata catggactgg ctgcaccagt cccctgtccc gaagctgctg   1440
ttctggggca ccccaggcgt tctgatccca ccggccgaag ccgctcgcct ggccaaaagc   1500
ctgcctaact gcaaggctgt ggacatcggc ccgggtctga atctgctgca agaagacaac   1560
ccggacctga tcggcagcga gatcgcgcgc tggctgtcga cgctcgagat ttccggcgag   1620
ccaaccacta agagtagaat cacaagcgaa ggcgagtaca tcccctgga tcaaatagac   1680 ataaatgtag gtggatttg ttatgagaat gaagtataa                           1719
```

<210> SEQ ID NO 34
<211> LENGTH: 572
<212> TYPE: PRT
<213> ORGANISM: Artificial Sequence
<220> FEATURE:
<223> OTHER INFORMATION: Synthetic

<400> SEQUENCE: 34

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Glu Ile Gly Thr Gly Phe Pro Phe Asp Pro His Tyr
                245                 250                 255

Val Glu Val Leu Gly Glu Arg Met His Tyr Val Asp Val Gly Pro Arg
            260                 265                 270

Asp Gly Thr Pro Val Leu Phe Leu His Gly Asn Pro Thr Ser Ser Tyr
        275                 280                 285

Val Trp Arg Asn Ile Ile Pro His Val Ala Pro Thr His Arg Cys Ile
    290                 295                 300
```

Ala Pro Asp Leu Ile Gly Met Gly Lys Ser Asp Lys Pro Asp Leu Gly
305                 310                 315                 320

Tyr Phe Phe Asp Asp His Val Arg Phe Met Asp Ala Phe Ile Glu Ala
            325                 330                 335

Leu Gly Leu Glu Glu Val Val Leu Val Ile His Asp Trp Gly Ser Ala
            340                 345                 350

Leu Gly Phe His Trp Ala Lys Arg Asn Pro Glu Arg Val Lys Gly Ile
            355                 360                 365

Ala Phe Met Glu Phe Ile Arg Pro Ile Pro Thr Trp Asp Glu Trp Pro
370                 375                 380

Glu Phe Ala Arg Glu Thr Phe Gln Ala Phe Arg Thr Thr Asp Val Gly
385                 390                 395                 400

Arg Lys Leu Ile Ile Asp Gln Asn Val Phe Ile Glu Gly Thr Leu Pro
            405                 410                 415

Met Gly Val Val Arg Pro Leu Thr Glu Val Glu Met Asp His Tyr Arg
            420                 425                 430

Glu Pro Phe Leu Asn Pro Val Asp Arg Glu Pro Leu Trp Arg Phe Pro
            435                 440                 445

Asn Glu Leu Pro Ile Ala Gly Glu Pro Ala Asn Ile Val Ala Leu Val
450                 455                 460

Glu Glu Tyr Met Asp Trp Leu His Gln Ser Pro Val Pro Lys Leu Leu
465                 470                 475                 480

Phe Trp Gly Thr Pro Gly Val Leu Ile Pro Pro Ala Glu Ala Ala Arg
            485                 490                 495

Leu Ala Lys Ser Leu Pro Asn Cys Lys Ala Val Asp Ile Gly Pro Gly
            500                 505                 510

Leu Asn Leu Leu Gln Glu Asp Asn Pro Asp Leu Ile Gly Ser Glu Ile
            515                 520                 525

Ala Arg Trp Leu Ser Thr Leu Glu Ile Ser Gly Glu Pro Thr Thr Lys
            530                 535                 540

Ser Arg Ile Thr Ser Glu Gly Glu Tyr Ile Pro Leu Asp Gln Ile Asp
545                 550                 555                 560

Ile Asn Val Gly Gly Phe Cys Tyr Glu Asn Glu Val
            565                 570

<210> SEQ ID NO 35
<211> LENGTH: 1713
<212> TYPE: DNA
<213> ORGANISM: Artificial Sequence
<220> FEATURE:
<223> OTHER INFORMATION: Synthetic

<400> SEQUENCE: 35
atggtaagta tcgctctgca ggctggttac gacctactgg gtgacggcag acctgaaacc    60
ctgtggctgg gcatcggcac tctgctgatg ctgattggaa ccttctactt tctggtccgc   120
ggatggggag tcaccgataa ggatgcccgg gaatattacg ctgtgactat cctggtgtcc   180
ggaatcgcat ccgccgcata tctgtctatg ttctttggta tcgggcttac tgaggtgtcc   240
gtcgggggcg aaatgttgga tatctattat gccaggtacg cccagtggct gtttaccacc   300
ccacttctgc tgctgcacct ggcccttctc gctaaggtgg atcgggtgac catcggcacc   360
ctggtgggtg tggacgccct gatgatcgtc actggcctca tcggagcctt gagccacacg   420
gccatagcca gatacagttg gtggttgttc tctacaattt gcatgatagt ggtgctctat   480
gttctggcta catccctgcg atctgctgca aaggagcggg gccccgaggt ggcatctacc   540

-continued

```
tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacacca tcggtactgg cttcccattc gaccccatt atgtggaagt cctgggcgag     780
cgcatgcact acgtcgatgt tggtccgcgc gatggcaccc ctgtgctgtt cctgcacggt    840
aacccgacct cctcctacgt gtggcgcaac atcatcccgc atgttgcacc gacccatcgc    900
tgcattgctc cagacctgat cggtatgggc aaatccgaca accagacct gggttatttc     960 ttcgacgacc acgtccgctt catggatgcc ttcatcgaag ccctgggtct ggaagaggtc   1020
gtcctggtca ttcacgactg gggctccgct ctgggtttcc actgggccaa gcgcaatcca   1080
gagcgcgtca aggtattgc atttatgag ttcatccgcc ctatcccgac ctgggacgaa     1140
tggccagaat ttgcccgcga ccttccag gccttccgca ccaccgacgt cggccgcaag     1200
ctgatcatcg atcagaacgt ttttatcgag ggtacgctgc cgatgggtgt cgtccgcccg   1260
ctgactgaag tcgagatgga ccattaccgc gagccgttcc tgaatcctgt tgaccgcgag   1320
ccactgtggc gcttcccaaa cgagctgcca atcgccggtg agccagcgaa catcgtcgcg   1380
ctggtcgaag aatacatgga ctggctgcac cagtcccctg tcccgaagct gctgttctgg   1440
ggcaccccag gcgttctgat cccaccggcc gaagccgctc gcctggccaa agcctgcct    1500 aactgcaagg ctgtggacat cggcccgggt ctgaatctgc tgcaagaaga caacccggac   1560
ctgatcggca gcgagatcgc gcgctggctg tcgacgctcg agatttccgg cgagccaacc   1620
actaagagta gaatcacaag cgaaggcgag tacatccccc tggatcaaat agacataaat   1680
gtaggtggat tttgttatga gaatgaagta taa                                1713
```

<210> SEQ ID NO 36
<211> LENGTH: 570
<212> TYPE: PRT
<213> ORGANISM: Artificial Sequence
<220> FEATURE:
<223> OTHER INFORMATION: Synthetic

<400> SEQUENCE: 36

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Ser Gly Ile Ala Ser
        50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
```

-continued

```
            145                 150                 155                 160
        Val Leu Ala Thr Ser Leu Arg Ser Ala Ala Lys Glu Arg Gly Pro Glu
                        165                 170                 175
        Val Ala Ser Thr Phe Asn Thr Leu Thr Ala Leu Val Leu Val Leu Trp
                        180                 185                 190
        Thr Ala Tyr Pro Ile Leu Trp Ile Ile Gly Thr Glu Gly Ala Gly Val
                        195                 200                 205
        Val Gly Leu Gly Ile Glu Thr Leu Leu Phe Met Val Leu Asp Val Thr
                        210                 215                 220
        Ala Lys Val Gly Phe Gly Phe Ile Leu Arg Ser Arg Ala Ile Leu
        225                 230                 235                 240
        Gly Asp Thr Ile Gly Thr Gly Phe Pro Phe Asp Pro His Tyr Val Glu
                        245                 250                 255
        Val Leu Gly Glu Arg Met His Tyr Val Asp Val Gly Pro Arg Asp Gly
                        260                 265                 270
        Thr Pro Val Leu Phe Leu His Gly Asn Pro Thr Ser Ser Tyr Val Trp
                        275                 280                 285
        Arg Asn Ile Ile Pro His Val Ala Pro Thr His Arg Cys Ile Ala Pro
                        290                 295                 300
        Asp Leu Ile Gly Met Gly Lys Ser Asp Lys Pro Asp Leu Gly Tyr Phe
        305                 310                 315                 320
        Phe Asp Asp His Val Arg Phe Met Asp Ala Phe Ile Glu Ala Leu Gly
                        325                 330                 335
        Leu Glu Glu Val Val Leu Val Ile His Asp Trp Gly Ser Ala Leu Gly
                        340                 345                 350
        Phe His Trp Ala Lys Arg Asn Pro Glu Arg Val Lys Gly Ile Ala Phe
                        355                 360                 365
        Met Glu Phe Ile Arg Pro Ile Pro Thr Trp Asp Glu Trp Pro Glu Phe
                        370                 375                 380
        Ala Arg Glu Thr Phe Gln Ala Phe Arg Thr Thr Asp Val Gly Arg Lys
        385                 390                 395                 400
        Leu Ile Ile Asp Gln Asn Val Phe Ile Glu Gly Thr Leu Pro Met Gly
                        405                 410                 415
        Val Val Arg Pro Leu Thr Glu Val Glu Met Asp His Tyr Arg Glu Pro
                        420                 425                 430
        Phe Leu Asn Pro Val Asp Arg Glu Pro Leu Trp Arg Phe Pro Asn Glu
                        435                 440                 445
        Leu Pro Ile Ala Gly Glu Pro Ala Asn Ile Val Ala Leu Val Glu Glu
                        450                 455                 460
        Tyr Met Asp Trp Leu His Gln Ser Pro Val Pro Lys Leu Leu Phe Trp
        465                 470                 475                 480
        Gly Thr Pro Gly Val Leu Ile Pro Pro Ala Glu Ala Ala Arg Leu Ala
                        485                 490                 495
        Lys Ser Leu Pro Asn Cys Lys Ala Val Asp Ile Gly Pro Gly Leu Asn
                        500                 505                 510
        Leu Leu Gln Glu Asp Asn Pro Asp Leu Ile Gly Ser Glu Ile Ala Arg
                        515                 520                 525
        Trp Leu Ser Thr Leu Glu Ile Ser Gly Glu Pro Thr Thr Lys Ser Arg
                        530                 535                 540
        Ile Thr Ser Glu Gly Glu Tyr Ile Pro Leu Asp Gln Ile Asp Ile Asn
        545                 550                 555                 560
        Val Gly Gly Phe Cys Tyr Glu Asn Glu Val
                        565                 570
```

<210> SEQ ID NO 37
<211> LENGTH: 1707
<212> TYPE: DNA
<213> ORGANISM: Artificial Sequence
<220> FEATURE:
<223> OTHER INFORMATION: Synthetic

<400> SEQUENCE: 37

| | |
|---|---|
| atggtaagta tcgctctgca ggctggttac gacctactgg gtgacggcag acctgaaacc | 60 |
| ctgtggctgg gcatcggcac tctgctgatg ctgattggaa ccttctactt tctggtccgc | 120 |
| ggatggggag tcaccgataa ggatgcccgg gaatattacg ctgtgactat cctggtgtcc | 180 |
| ggaatcgcat ccgccgcata tctgtctatg ttctttggta tcgggcttac tgaggtgtcc | 240 |
| gtcggggcg aaatgttgga tatctattat gccaggtacg cccagtggct gtttaccacc | 300 |
| ccacttctgc tgctgcacct ggcccttctc gctaaggtgg atcgggtgac catcggcacc | 360 |
| ctggtgggtg tggacgccct gatgatcgtc actggcctca tcggagcctt gagccacacg | 420 |
| gccatagcca gatacagttg gtggttgttc tctacaattt gcatgatagt ggtgctctat | 480 |
| gttctggcta catccctgcg atctgctgca aaggagcggg ccccgaggt ggcatctacc | 540 |
| tttaacaccc tgacagctct ggtcttggtg ctgtggaccg cttaccctat cctgtggatc | 600 |
| ataggcactg agggcgctgg cgtggtgggc ctgggcatcg aaactctgct gtttatggtg | 660 |
| ttggacgtga ctgccaaggt cggctttggc tttatcctgt tgagatcccg ggctattctg | 720 |
| ggcgacacca ctggctttcc attcgacccc cattatgtgg aagtcctggg cgagcgcatg | 780 |
| cactacgtcg atgttggtcc gcgcgatggc acccctgtgc tgttcctgca cggtaacccg | 840 |
| acctcctcct acgtgtggcg caacatcatc ccgcatgttg caccgaccca tcgctgcatt | 900 |
| gctccagacc tgatcggtat gggcaaatcc gacaaaccag acctgggtta tttcttcgac | 960 |
| gaccacgtcc gcttcatgga tgccttcatc gaagccctgg gtctggaaga ggtcgtcctg | 1020 |
| gtcattcacg actgggctc cgctctgggt ttccactggg ccaagcgcaa tccagagcgc | 1080 |
| gtcaaaggta ttgcatttat ggagttcatc cgccctatcc gacctggga cgaatggcca | 1140 |
| gaatttgccc gcgagacctt ccaggccttc cgcaccaccc acgtcggccg caagctgatc | 1200 |
| atcgatcaga acgttttat cgagggtacg ctgccgatgg tgtcgtccg cccgctgact | 1260 |
| gaagtcgaga tggaccatta ccgcgagccg ttcctgaatc ctgttgaccg cgagccactg | 1320 |
| tggcgcttcc caaacgagct gccaatcgcc ggtgagccag cgaacatcgt cgcgctggtc | 1380 |
| gaagaataca tggactggct gcaccagtcc cctgtcccga gctgctgtt ctggggcacc | 1440 |
| ccaggcgttc tgatcccacc ggccgaagcc gctcgcctgg ccaaaagcct gcctaactgc | 1500 |
| aaggctgtgg acatcggccc gggtctgaat ctgctgcaag aagacaaccc ggacctgatc | 1560 |
| ggcagcgaga tcgcgcgctg gctgtcgacg ctcgagattt ccggcgagcc aaccactaag | 1620 |
| agtagaatca aagcgaagg cgagtacatc cccctggatc aaatagacat aaatgtaggt | 1680 |
| ggatttttgtt atgagaatga agtataa | 1707 |

<210> SEQ ID NO 38
<211> LENGTH: 568
<212> TYPE: PRT
<213> ORGANISM: Artificial Sequence
<220> FEATURE:
<223> OTHER INFORMATION: Synthetic

<400> SEQUENCE: 38

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
50                      55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
            100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
            130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Thr Gly Phe Pro Phe Asp Pro His Tyr Val Glu Val Leu
            245                 250                 255

Gly Glu Arg Met His Tyr Val Asp Val Gly Pro Arg Asp Gly Thr Pro
            260                 265                 270

Val Leu Phe Leu His Gly Asn Pro Thr Ser Ser Tyr Val Trp Arg Asn
            275                 280                 285

Ile Ile Pro His Val Ala Pro Thr His Arg Cys Ile Ala Pro Asp Leu
            290                 295                 300

Ile Gly Met Gly Lys Ser Asp Lys Pro Asp Leu Gly Tyr Phe Phe Asp
305                 310                 315                 320

Asp His Val Arg Phe Met Asp Ala Phe Ile Glu Ala Leu Gly Leu Glu
            325                 330                 335

Glu Val Val Leu Val Ile His Asp Trp Gly Ser Ala Leu Gly Phe His
            340                 345                 350

Trp Ala Lys Arg Asn Pro Glu Arg Val Lys Gly Ile Ala Phe Met Glu
            355                 360                 365

Phe Ile Arg Pro Ile Pro Thr Trp Asp Glu Trp Pro Glu Phe Ala Arg
            370                 375                 380

Glu Thr Phe Gln Ala Phe Arg Thr Thr Asp Val Gly Arg Lys Leu Ile
385                 390                 395                 400

Ile Asp Gln Asn Val Phe Ile Glu Gly Thr Leu Pro Met Gly Val Val
            405                 410                 415

Arg Pro Leu Thr Glu Val Glu Met Asp His Tyr Arg Glu Pro Phe Leu
```

```
                420           425           430
Asn Pro Val Asp Arg Glu Pro Leu Trp Arg Phe Pro Asn Glu Leu Pro
            435                 440                 445

Ile Ala Gly Glu Pro Ala Asn Ile Val Ala Leu Val Glu Glu Tyr Met
    450                 455                 460

Asp Trp Leu His Gln Ser Pro Val Pro Lys Leu Leu Phe Trp Gly Thr
465                 470                 475                 480

Pro Gly Val Leu Ile Pro Pro Ala Glu Ala Arg Leu Ala Lys Ser
                485                 490                 495

Leu Pro Asn Cys Lys Ala Val Asp Ile Gly Pro Gly Leu Asn Leu Leu
                500                 505                 510

Gln Glu Asp Asn Pro Asp Leu Ile Gly Ser Glu Ile Ala Arg Trp Leu
                515                 520                 525

Ser Thr Leu Glu Ile Ser Gly Glu Pro Thr Thr Lys Ser Arg Ile Thr
            530                 535                 540

Ser Glu Gly Glu Tyr Ile Pro Leu Asp Gln Ile Asp Ile Asn Val Gly
545                 550                 555                 560

Gly Phe Cys Tyr Glu Asn Glu Val
                565
```

<210> SEQ ID NO 39
<211> LENGTH: 1701
<212> TYPE: DNA
<213> ORGANISM: Artificial Sequence
<220> FEATURE:
<223> OTHER INFORMATION: Synthetic

<400> SEQUENCE: 39

```
atggtaagta tcgctctgca ggctggttac gacctactgg gtgacggcag acctgaaacc    60
ctgtggctgg gcatcggcac tctgctgatg ctgattggaa ccttctactt tctggtccgc   120
ggatggggag tcaccgataa ggatgcccgg gaatattacg ctgtgactat cctggtgtcc   180
ggaatcgcat ccgccgcata tctgtctatg ttctttggta tcgggcttac tgaggtgtcc   240
gtcgggggcg aaatgttgga tatctattat gccaggtacg cccagtggct gtttaccacc   300
ccacttctgc tgctgcacct ggcccttctc gctaaggtgg atcgggtgac catcggcacc   360
ctggtgggtg tggacgccct gatgatcgtc actggcctca tcggagcctt gagccacacg   420
gccatagcca gatacagttg gtggttgttc tctacaattt gcatgatagt ggtgctctat   480
gttctggcta catccctgcg atctgctgca aggagcgggg ccccgaggt ggcatctacc   540
tttaacaccc tgacagctct ggtcttggtg ctgtggaccg cttaccctat cctgtggatc   600
ataggcactg agggcgctgg cgtggtgggc ctgggcatcg aaactctgct gtttatggtg   660
ttggacgtga ctgccaaggt cggctttggc tttatcctgt tgagatcccg ggctattctg   720
ggcgacacct ttccattcga cccccattat gtggaagtcc tgggcgagcg catgcactac   780
gtcgatgttg gtccgcgcga tgcacccct gtgctgttcc tgcacggtaa cccgacctcc   840
tcctacgtgt ggcgcaacat catcccgcat gttgcaccga cccatcgctg cattgctcca   900
gacctgatcg gtatgggcaa atccgacaaa ccagacctgg ttatttcttc gacgaccac   960
gtccgcttca tggatgcctt catcgaagcc tgggtctggg agaggtcgt cctggtcatt  1020
cacgactggg gctccgctct gggtttccac tgggccaagc gcaatccaga gcgcgtcaaa  1080
ggtattgcat ttatggagtt catccgcct atcccgacct gggacgaatg ccagaatttt  1140
gcccgcgaga ccttccaggc cttccgcacc accgacgtcg ccgcaagct gatcatcgat  1200
```

```
cagaacgttt ttatcgaggg tacgctgccg atgggtgtcg tccgcccgct gactgaagtc    1260
gagatggacc attaccgcga gccgttcctg aatcctgttg accgcgagcc actgtggcgc    1320
ttcccaaacg agctgccaat cgccggtgag ccagcgaaca tcgtcgcgct ggtcgaagaa    1380
tacatggact ggctgcacca gtcccctgtc ccgaagctgc tgttctgggg cacccccaggc   1440 gttctgatcc caccggccga agccgctcgc ctggccaaaa gcctgcctaa ctgcaaggct    1500
gtggacatcg gcccgggtct gaatctgctg caagaagaca accggacct gatcggcagc     1560 gagatcgcgc gctggctgtc gacgctcgag atttccggcg agccaaccac taagagtaga    1620
atcacaagcg aaggcgagta catccccctg gatcaaatag acataaatgt aggtggattt    1680
tgttatgaga atgaagtata a                                              1701
```

<210> SEQ ID NO 40
<211> LENGTH: 566
<212> TYPE: PRT
<213> ORGANISM: Artificial Sequence
<220> FEATURE:
<223> OTHER INFORMATION: Synthetic

<400> SEQUENCE: 40

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Phe Pro Phe Asp Pro His Tyr Val Glu Val Leu Gly Glu
                245                 250                 255

Arg Met His Tyr Val Asp Val Gly Pro Arg Asp Gly Thr Pro Val Leu
            260                 265                 270
```

-continued

```
Phe Leu His Gly Asn Pro Thr Ser Ser Tyr Val Trp Arg Asn Ile Ile
            275                 280                 285
Pro His Val Ala Pro Thr His Arg Cys Ile Ala Pro Asp Leu Ile Gly
            290                 295                 300
Met Gly Lys Ser Asp Lys Pro Asp Leu Gly Tyr Phe Phe Asp His
305                 310                 315                 320
Val Arg Phe Met Asp Ala Phe Ile Glu Ala Leu Gly Leu Glu Glu Val
                325                 330                 335
Val Leu Val Ile His Asp Trp Gly Ser Ala Leu Gly Phe His Trp Ala
                340                 345                 350
Lys Arg Asn Pro Glu Arg Val Lys Gly Ile Ala Phe Met Glu Phe Ile
            355                 360                 365
Arg Pro Ile Pro Thr Trp Asp Glu Trp Pro Glu Phe Ala Arg Glu Thr
    370                 375                 380
Phe Gln Ala Phe Arg Thr Thr Asp Val Gly Arg Lys Leu Ile Ile Asp
385                 390                 395                 400
Gln Asn Val Phe Ile Glu Gly Thr Leu Pro Met Gly Val Val Arg Pro
                405                 410                 415
Leu Thr Glu Val Glu Met Asp His Tyr Arg Glu Pro Phe Leu Asn Pro
                420                 425                 430
Val Asp Arg Glu Pro Leu Trp Arg Phe Pro Asn Glu Leu Pro Ile Ala
            435                 440                 445
Gly Glu Pro Ala Asn Ile Val Ala Leu Val Glu Glu Tyr Met Asp Trp
    450                 455                 460
Leu His Gln Ser Pro Val Pro Lys Leu Leu Phe Trp Gly Thr Pro Gly
465                 470                 475                 480
Val Leu Ile Pro Pro Ala Glu Ala Ala Arg Leu Ala Lys Ser Leu Pro
                485                 490                 495
Asn Cys Lys Ala Val Asp Ile Gly Pro Gly Leu Asn Leu Leu Gln Glu
            500                 505                 510
Asp Asn Pro Asp Leu Ile Gly Ser Glu Ile Ala Arg Trp Leu Ser Thr
            515                 520                 525
Leu Glu Ile Ser Gly Glu Pro Thr Thr Lys Ser Arg Ile Thr Ser Glu
    530                 535                 540
Gly Glu Tyr Ile Pro Leu Asp Gln Ile Asp Ile Asn Val Gly Gly Phe
545                 550                 555                 560
Cys Tyr Glu Asn Glu Val
                565
```